United States Patent
Caughey et al.

(10) Patent No.: US 11,906,530 B2
(45) Date of Patent: Feb. 20, 2024

(54) METHODS FOR THE DETECTION OF TAU PROTEIN AGGREGATES

(71) Applicant: THE UNITED STATES OF AMERICA, as represented by the Secretary, Department of Health and Human Services, Bethesda, MD (US)

(72) Inventors: Byron Winslow Caughey, Hamilton, MT (US); Eri Saijo, Hamilton, MT (US); Allison Lindsey Kraus, Hamilton, MT (US); Michael Anthony Metrick, II, Hamilton, MT (US)

(73) Assignee: The United States of America, as represented by the Secretary Department of Health and Human Services, Bethesda, MD (US)

(*) Notice: Subject to any disclaimer, the term of this patent is extended or adjusted under 35 U.S.C. 154(b) by 171 days.

(21) Appl. No.: 16/474,040

(22) PCT Filed: Dec. 29, 2017

(86) PCT No.: PCT/US2017/069024
§ 371 (c)(1),
(2) Date: Jun. 26, 2019

(87) PCT Pub. No.: WO2018/126180
PCT Pub. Date: Jul. 5, 2018

(65) Prior Publication Data
US 2020/0249245 A1    Aug. 6, 2020

Related U.S. Application Data

(60) Provisional application No. 62/440,885, filed on Dec. 30, 2016.

(51) Int. Cl.
*G01N 33/68* (2006.01)

(52) U.S. Cl.
CPC . *G01N 33/6896* (2013.01); *G01N 2800/2821* (2013.01)

(58) Field of Classification Search
None
See application file for complete search history.

(56) References Cited

U.S. PATENT DOCUMENTS

| 2010/0063250 A1* | 3/2010 | Kontsekova ....... C07K 14/4711 530/324 |
| 2013/0251731 A1 | 9/2013 | Lee et al. |
| 2013/0288389 A1 | 10/2013 | Orru et al. |

FOREIGN PATENT DOCUMENTS

| WO | WO 2001/018546 A2 | 3/2001 |
| WO | WO 2016/123401 A1 | 8/2016 |

OTHER PUBLICATIONS

Dinkel et al., Variations in Filament Conformation Dictate Seeding Barrier between Three- and Four-Repeat Tau. Biochemistry 2011 50 (20), 4330-4336 DOI: 10.1021/bi2004685 (Year: 2011).*

(Continued)

*Primary Examiner* — Aurora M Fontainhas
(74) *Attorney, Agent, or Firm* — Klarquist Sparkman, LLP

(57) ABSTRACT

Methods are disclosed herein for determining whether a subject has a Tauopathy, such as Pick disease, Alzheimer disease, progressive supranuclear palsy (PSP), corticobasal degeneration (CBD) or argyrophilic grain disease (AGD). These methods utilize an amyloid seeding assay.

35 Claims, 55 Drawing Sheets

Specification includes a Sequence Listing.

(56) References Cited

OTHER PUBLICATIONS

Sadik et al., Phosphorylation of tau at Ser214 mediated its interaction with 14-3-3 protein: implications for the mechanism of tau aggregation. Journal of Neurochemistry, 2009, 108, 33-43. (Year: 2009).*
Colby et al., Prion detection by an amyloid seeding assay. PNAS Dec. 26, 2007 104 (52) 20914-20919; https://doi.org/10.1073/pnas.0710152105 (Year: 2007).*
Omran, Ahmed, "The Effects of Molecular Chaperones on Tau Fibril Assembly" (2015). Electronic Theses and Dissertations. 1045. https://digitalcommons.du.edu/etd/1045 91pages (Year: 2015).*
Cramm et al., Stability and Reproducibility Underscore Utility of RT-QuIC for Diagnosis of Creutzfeldt-Jakob Disease. Mol Neurobiol. Apr. 2016;53(3):1896-1904. doi: 10.1007/s12035-015-9133-2. Epub Apr. 1, 2015. PMID: 25823511; PMCID: PMC4789202. (Year: 2016).*
Haque, et al., (2014) Inhibition of tau aggregation by a rosamine derivative that blocks tau intermolecular disulfide cross-linking, Amyloid, 21:3, 185-190 (Year: 2014).*
Holmes et al., "Proteopathic tau seeding predicts tauopathy in vivo," PNAS E4376-E4385 (e-Pub Sep. 26, 2014).
International Search Report and Written Opinion from parent PCT Application No. PCT/US2017/069024, 10 pages (dated Mar. 19, 2018).
Irwin et al., "Deep clinical and neuropathological phenotyping of pick disease," *Annuals of Neurology* 79:272-287 (2016).
Meyer et al., "Amplification of tau fibrils from minute quantities of seeds," *Biochemistry* 53: 5804-5809 (2014).
Morozova et al., "Conformational features of tau fibrils from Alzheimer's disease brain are faithfully propagated by unmodified recombinant protein," *Biochemistry* 52: 6960-6967 (Sep. 13, 2013).
Saijo et al., "Ultrasensitive and selective detection of 3-repeat tau seeding activity in pick disease brain and cerebrospinal fluid," *Acta Neuropathologica* 133(5): 751-765 (Supplemental materials 8 pages)(e-Pub Mar. 17, 2017).
Schmitz et al., "The real-time quaking-induced conversion assay for detection of human prion disease and study of other protein misfolding diseases," Nat. Protoc. 11(11):2233-2242 (e-Pub Oct. 13, 2016).
Stang et al., "Distinct differences in prion-like seeding and aggregation between tau protein variants provide mechanistic insights into tauopathies," *J. Biol. Chem.* 293(7): 2408-2421 (e-Pub Dec. 19, 2017).
Takeda et al., "Seed-competent high-molecular-weight tau species accumulates in the cerebrospinal fluid of Alzheimer's disease mouse model and human patients," *Annals of Neurology* 80: 355-367 (2016).
Llorens et al., "CSF Biomarkers in Neurodegenerative and Vascular Dementias," *Prog. Neurobiol.*, vol. 138-140:36-53, 2016.
Mackenzie et al., "Molecular Neuropathology of Frontotemporal Dementia: Insights into Disease Mechanisms from Postmortem Studies," *J. Neurochem.*, vol. 138:54-70, 2016.
Kraus et al., "Seeding selectivity and ultrasensitive detection of tau aggregate conformers of Alzheimer disease," *Acta Neuropathol* 137(4):585-598, 2019.
Tennant et al., "RT-QuIC detection of tauopathies using full-length tau substrates," *Prion* 14(1):249-256, 2020.
Wu et al., "Selective Detection of Misfolded Tau from Postmortem Alzheimer's Disease Brains," *Front Aging Neurosci* 14:945875, 2022.

* cited by examiner

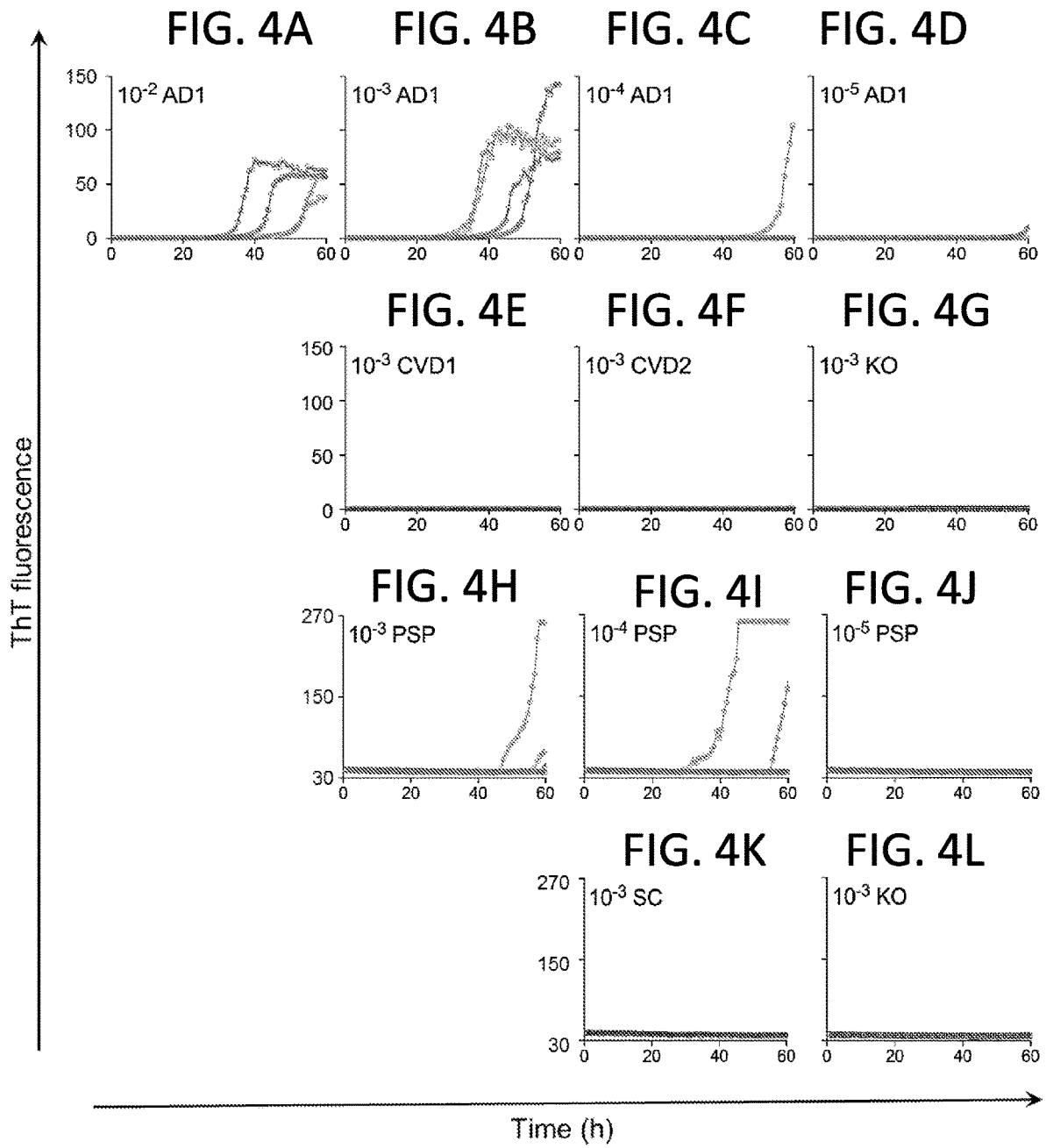

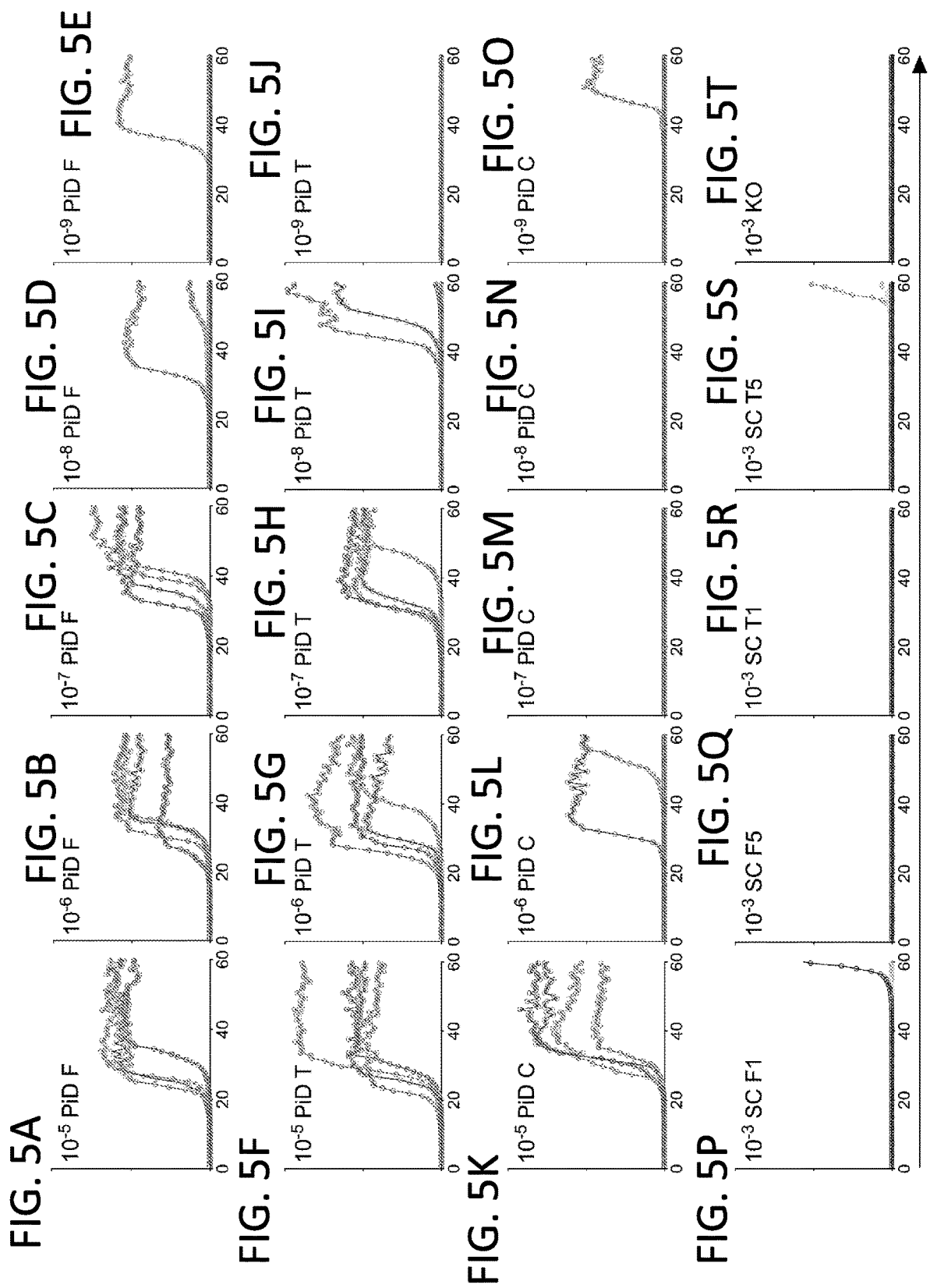

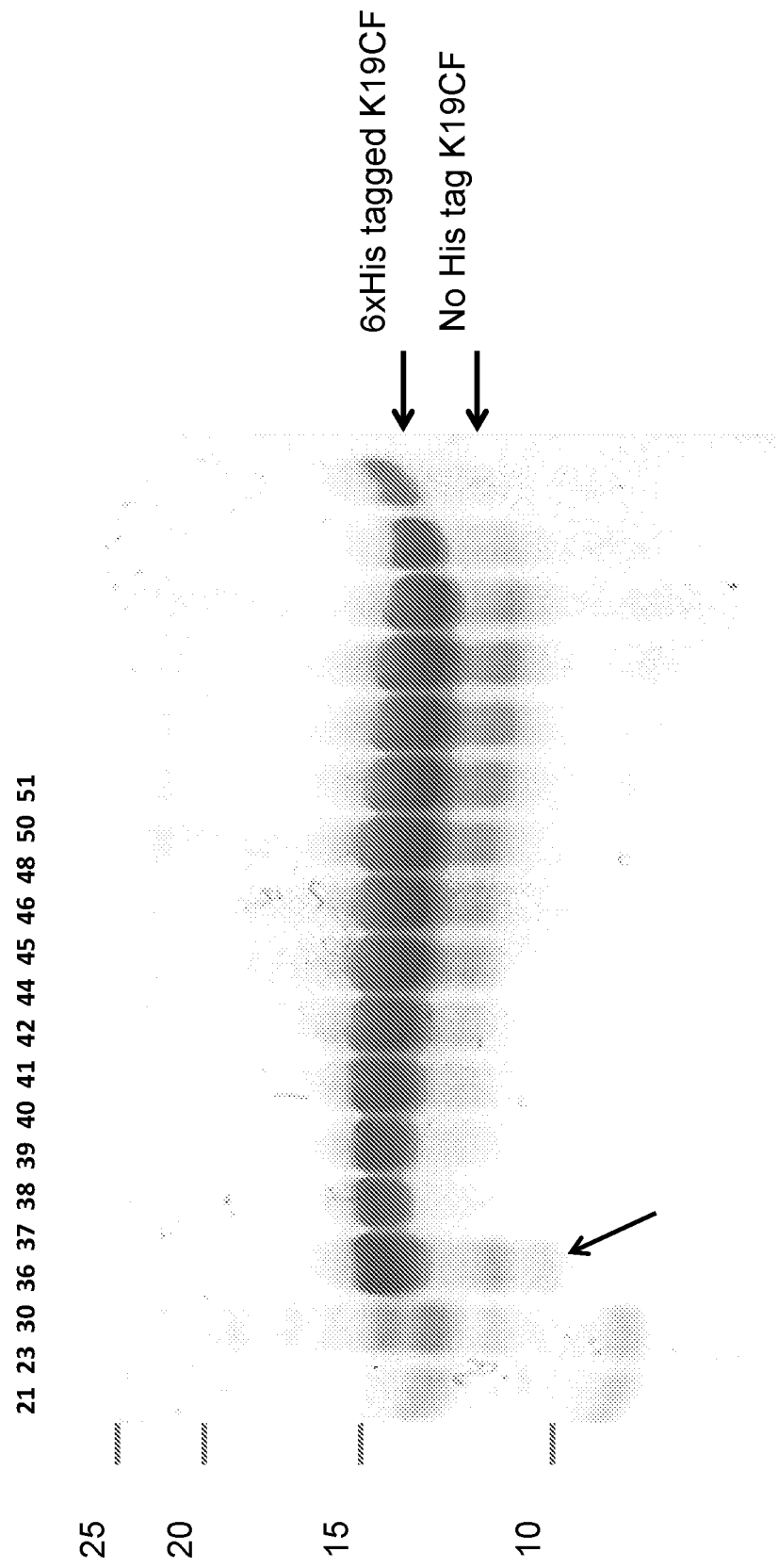

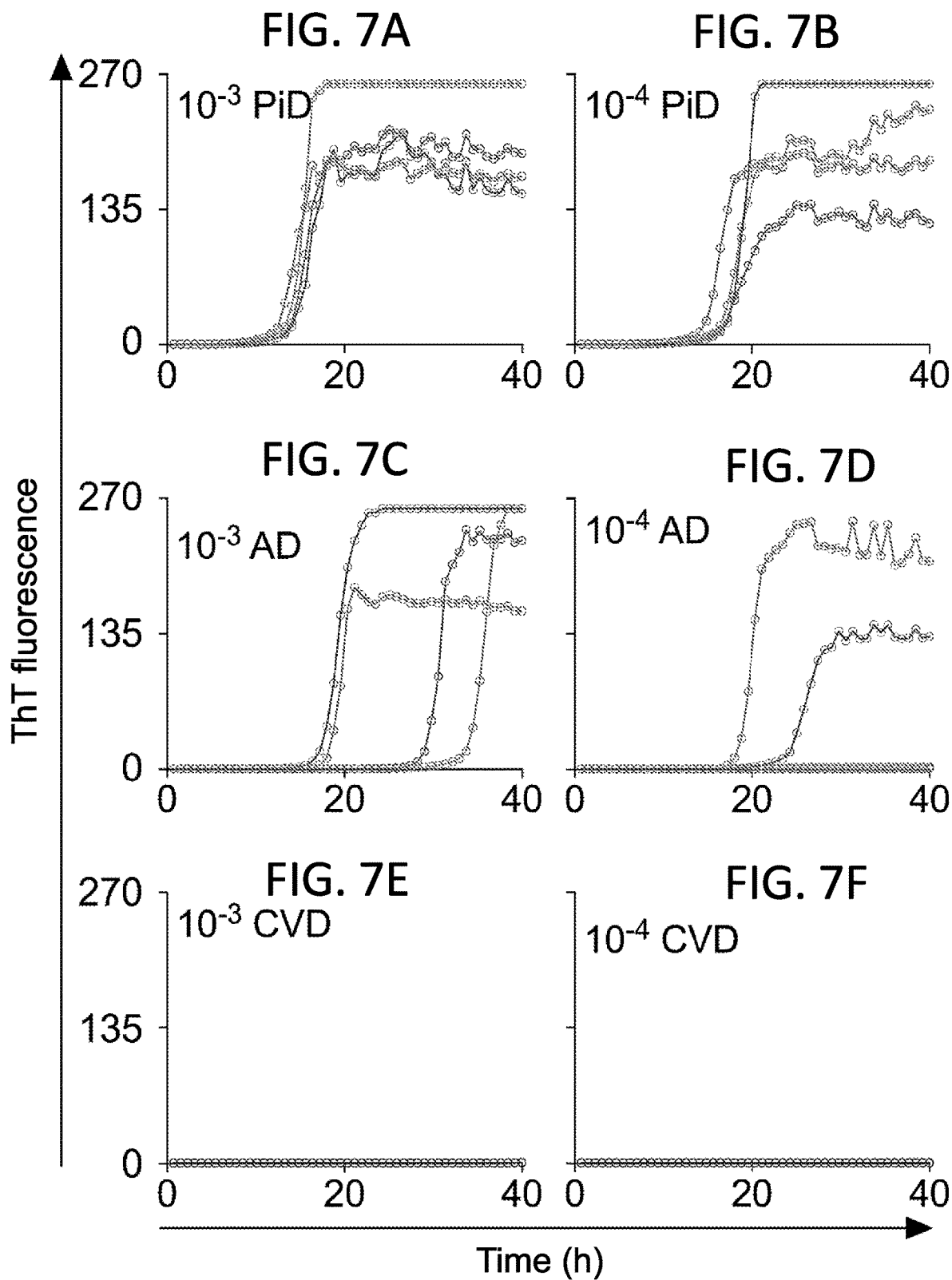

FIG. 8

6xHis K19 Cysteine-Free (K19CFh)

MGSSHHHHHH SSGLVPRGSH MQTAPVPMPD
Start       Poly-histidine            Start
codon       tag (6XHis)               codon

LKNVKSKIGS TENLKHQPGG GKVQIVYKPV

DLSKVTSKSG SLGNIHHKPG GGQVEVKSEK
         ↳ Mutation was introduced Cysteine to Serine at residue 322

LDFKDRVQSK IGSDNITHV PGGGNKKIE Stop

FIG. 9

6xHis K18 Cysteine-free (K18CFh)

<u>MGSSHHHHHH</u> SSGLVPRGSH MQTAPVPMPD

Start — Poly-histidine     Start
codon    tag (6xHis)     codon

LKNVKSKIGS TENLKHQPGG GKVQIINKKL

DLSNVQSKSG SKDNIKHVPG GGSVQIVYKP

↳ Mutation was introduced Cysteine to Serine at residue 291

VDLSKVTSKS GSLGNIHHKP GGGQVEVKSE

↳ Mutation was introduced Cysteine to Serine at residue 322

KLDFKDRVQS KIGSLDNITH VPGGGNKKIE Stop

FIG. 10

6xHis K12A322 (K12A322h)

MGSSHHHHHH SSGLVPRGSH MQTAPVPMPD

Start codon — Poly-histidine tag (6xHis) — Start codon

LKNVKSKIGS TENLKHQPGG GKVQIVYKPV

DLSKVTSKAG SLGNIHHKPG GGQVEVKSEK

↳ Mutation was introduced Cysteine to Alanine at reside 322

LDFKDRVQSK IGSLDNITHV PGGGNKKIET

HKLTFRENAK AKTDHGAEIV YKSPVVS Stop

FIG. 11  Alignment of his-tagged tau substrates

```
                10         20         30         40         50         60
                 |          |          |          |          |          |
K19CFh    MGSSHHHHHHSSGLVPRGSHMQTAPVPMPDLKNVKSKIGSTENLKHQPGGGK-----------
K18CFh    MGSSHHHHHHSSGLVPRGSHMQTAPVPMPDLKNVKSKIGSTENLKHQPGGGK-----------
K12A322h  MGSSHHHHHHSSGLVPRGSHMQTAPVPMPDLKNVKSKIGSTENLKHQPGGGKVQIINKKL 70         80         90        100        110        120
                 |          |          |          |          |          |
K19CFh    ------------------------VQIVYKPVDLSKVTSKSGSLGNIHHKPGGGQVEVKSE
K18CFh    DLSNVQSKSGSKDNIKHVPGGGSVQIVYKPVDLSKVTSKSGSLGNIHHKPGGGQVEVKSE
K12A322h  ------------------------VQIVYKPVDLSKVTSKAGSLGNIHHKPGGGQVEVKSE 130        140        150        160        170
                 |          |          |          |          |
K19CFh    KLDFKDRVQSKIGSLDNITHVPGGGNKKIE-------------------------
K18CFh    KLDFKDRVQSKIGSLDNITHVPGGGNKKIE-------------------------
K12A322h  KLDFKDRVQSKIGSLDNITHVPGGGNKKIETHKLTFRENAKAKTDHGAEIVYKSPVVS
```

FIG. 13A
Tau substrate with poly-histidine tag

| Current/potential substrate | Tau classification | | Number of Amino acids | Mass (Da) |
|---|---|---|---|---|
| 6xHis K19 Cys-free (S322) | 3R | truncated | 119 | 12714.4 |
| 6xHis K19 | 3R | truncated | 119 | |
| 6xHis K18 Cys-free (S291, S322) | 4R | truncated | 150 | |
| 6xHis K18 | 4R | truncated | 150 | |
| 6xHis K12 | 3R | truncated | 147 | |
| 6xHisK12A322 | 3R | truncated | 147 | |
| 6xHis K12S322 | 3R | truncated | 147 | |
| 6xHis human tau 40 (htau40) | 4R | Full-length | 461 | |
| 6xHis human tau 34 (htau34) | 4R | Full-length | 432 | |
| 6xHis human tau 24 (htau24) | 4R | Full-length | 403 | |
| 6xHis human tau 39 (htau39) | 3R | Full-length | 430 | |
| 6xHis human tau 37 (htau37) | 3R | Full-length | 401 | |
| 6xHis human tau 23 (htau23) | 3R | Full-length | 372 | |

FIG. 13B Tau substrate without poly-histidine tag

| Current/potential substrate | Tau classification | | Number of Amino acids | Mass (kDa) |
|---|---|---|---|---|
| K19 Cys-free (S322) | 3R | truncated | 99 | 10551.1 |
| K19 | 3R | truncated | 99 | 10567.1 |
| K18 Cys-free (S291, S322) | 4R | truncated | 130 | 13781.8 |
| K18 | 4R | truncated | 130 | 13813.9 |
| K12 | 3R | truncated | 127 | |
| K12A322 | 3R | truncated | 127 | 13644.6 |
| K12S322 | 3R | truncated | 127 | |
| human tau 40 (htau40) | 4R | Full-length | 441 | 46 |
| human tau 34 (htau34) | 4R | Full-length | 412 | 43 |
| human tau 24 (htau24) | 4R | Full-length | 383 | 40 |
| human tau 39 (htau39) | 3R | Full-length | 410 | 43 |
| human tau 37 (htau37) | 3R | Full-length | 381 | 40 |
| human tau 23 (htau23) | 3R | Full-length | 352 | 37 |

FIG. 18A

```
                 10         20         30         40         50         60
                  |          |          |          |          |          |
K12A322    ------------------------------------------------------------
K12S322    ------------------------------------------------------------
K12        ------------------------------------------------------------
hTau40     MAEPRQEFEVMEDHAGTYGLGDRKDQGGYTMHQDQEGDTDAGLKESPLQTPTEDGSEEPG
K19        ------------------------------------------------------------
K19CF      ------------------------------------------------------------
K18CF      ------------------------------------------------------------
K18        ------------------------------------------------------------

70         80         90        100        110        120
                  |          |          |          |          |          |
K12A322    ------------------------------------------------------------
K12S322    ------------------------------------------------------------
K12        ------------------------------------------------------------
hTau40     SETSDAKSTPTAEDVTAPLVDEGAPGKQAAAQPHTEIPEGTTAEEAGIGDTPSLEDEAAG
K19        ------------------------------------------------------------
K19CF      ------------------------------------------------------------
K18CF      ------------------------------------------------------------
K18        ------------------------------------------------------------

130        140        150        160        170        180
                  |          |          |          |          |          |
K12A322    ------------------------------------------------------------
K12S322    ------------------------------------------------------------
K12        ------------------------------------------------------------
hTau40     HVTQARMVSKSKDGTGSDDKKAKGADGKTKIATPRGAAPPGQKGQANATRIPAKTPPAPK
K19        ------------------------------------------------------------
K19CF      ------------------------------------------------------------
K18CF      ------------------------------------------------------------
K18        ------------------------------------------------------------

190        200        210        220        230        240
                  |          |          |          |          |          |
K12A322    ------------------------------------------------------------
K12S322    ------------------------------------------------------------
K12        ------------------------------------------------------------
hTau40     TPPSSGEPPKSGDRSGYSSPGSPGTPGSRSRTPSLPTPPTREPKKVAVVRTPPKSPSSAK
K19        ------------------------------------------------------------
K19CF      ------------------------------------------------------------
K18CF      ------------------------------------------------------------
K18        ------------------------------------------------------------
```

FIG. 18B

```
                 250        260        270        280        290        300
                  |          |          |          |          |          |
K12A322    --MQTAPVPMPDLKNVKSKIGSTENLKHQPGGGK--------------------------
K12S322    --MQTAPVPMPDLKNVKSKIGSTENLKHQPGGGK--------------------------
K12        --MQTAPVPMPDLKNVKSKIGSTENLKHQPGGGK--------------------------
hTau40     SRLQTAPVPMPDLKNVKSKIGSTENLKHQPGGGKVQIINKKLDLSNVQSKCGSKDNIKHV
K19        --MQTAPVPMPDLKNVKSKIGSTENLKHQPGGGK--------------------------
K19CF      --MQTAPVPMPDLKNVKSKIGSTENLKHQPGGGK--------------------------
K18CF      --MQTAPVPMPDLKNVKSKIGSTENLKHQPGGGKVQIINKKLDLSNVQSKSGSKDNIKHV
K18        --MQTAPVPMPDLKNVKSKIGSTENLKHQPGGGKVQIINKKLDLSNVQSKCGSKDNIKHV 310        320        330        340        350        360
                  |          |          |          |          |          |
K12A322    -----VQIVYKPVDLSKVTSKAGSLGNIHHKPGGGQVEVKSEKLDFKDRVQSKIGSLDNI
K12S322    -----VQIVYKPVDLSKVTSKSGSLGNIHHKPGGGQVEVKSEKLDFKDRVQSKIGSLDNI
K12        -----VQIVYKPVDLSKVTSKCGSLGNIHHKPGGGQVEVKSEKLDFKDRVQSKIGSLDNI
hTau40     PGGGSVQIVYKPVDLSKVTSKCGSLGNIHHKPGGGQVEVKSEKLDFKDRVQSKIGSLDNI
K19        -----VQIVYKPVDLSKVTSKCGSLGNIHHKPGGGQVEVKSEKLDFKDRVQSKIGSLDNI
K19CF      -----VQIVYKPVDLSKVTSKSGSLGNIHHKPGGGQVEVKSEKLDFKDRVQSKIGSLDNI
K18CF      PGGGSVQIVYKPVDLSKVTSKSGSLGNIHHKPGGGQVEVKSEKLDFKDRVQSKIGSLDNI
K18        PGGGSVQIVYKPVDLSKVTSKCGSLGNIHHKPGGGQVEVKSEKLDFKDRVQSKIGSLDNI 370        380        390        400        410        420
                  |          |          |          |          |          |
K12A322    THVPGGGNKKIETHKLTFRENAKAKTDHGAEIVYKSPVVS---------------------
K12S322    THVPGGGNKKIETHKLTFRENAKAKTDHGAEIVYKSPVVS---------------------
K12        THVPGGGNKKIETHKLTFRENAKAKTDHGAEIVYKSPVVS---------------------
hTau40     THVPGGGNKKIETHKLTFRENAKAKTDHGAEIVYKSPVVSGDTSPRHLSNVSSTGSIDMV
K19        THVPGGGNKKIE-----------------------------------------------
K19CF      THVPGGGNKKIE-----------------------------------------------
K18CF      THVPGGGNKKIE-----------------------------------------------
K18        THVPGGGNKKIE-----------------------------------------------

430        440
                  |          |
K12A322    --------------------
K12S322    --------------------
K12        --------------------
hTau40     DSPQLATLADEVSASLAKQGL
K19        --------------------
K19CF      --------------------
K18CF      --------------------
K18        --------------------
```

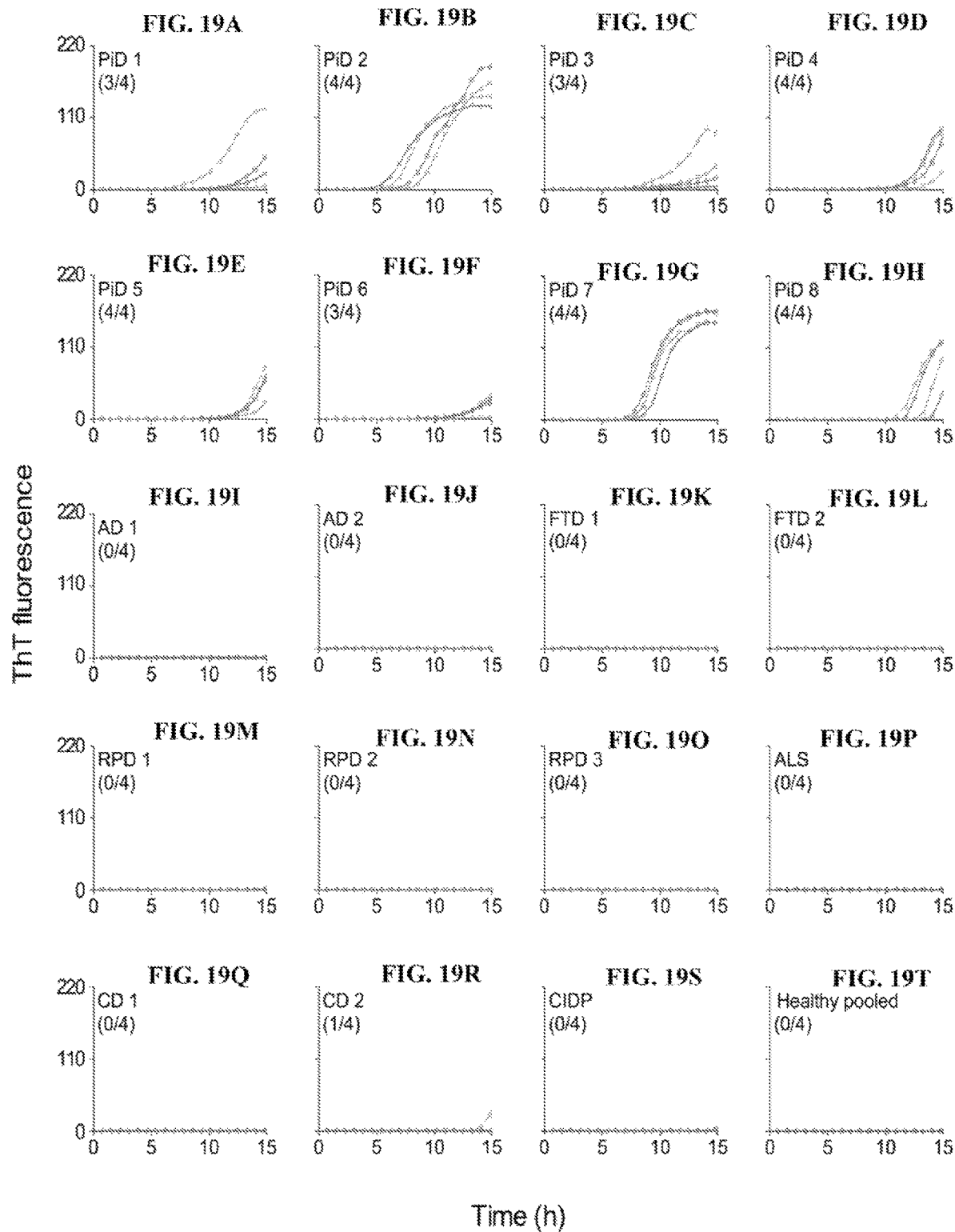

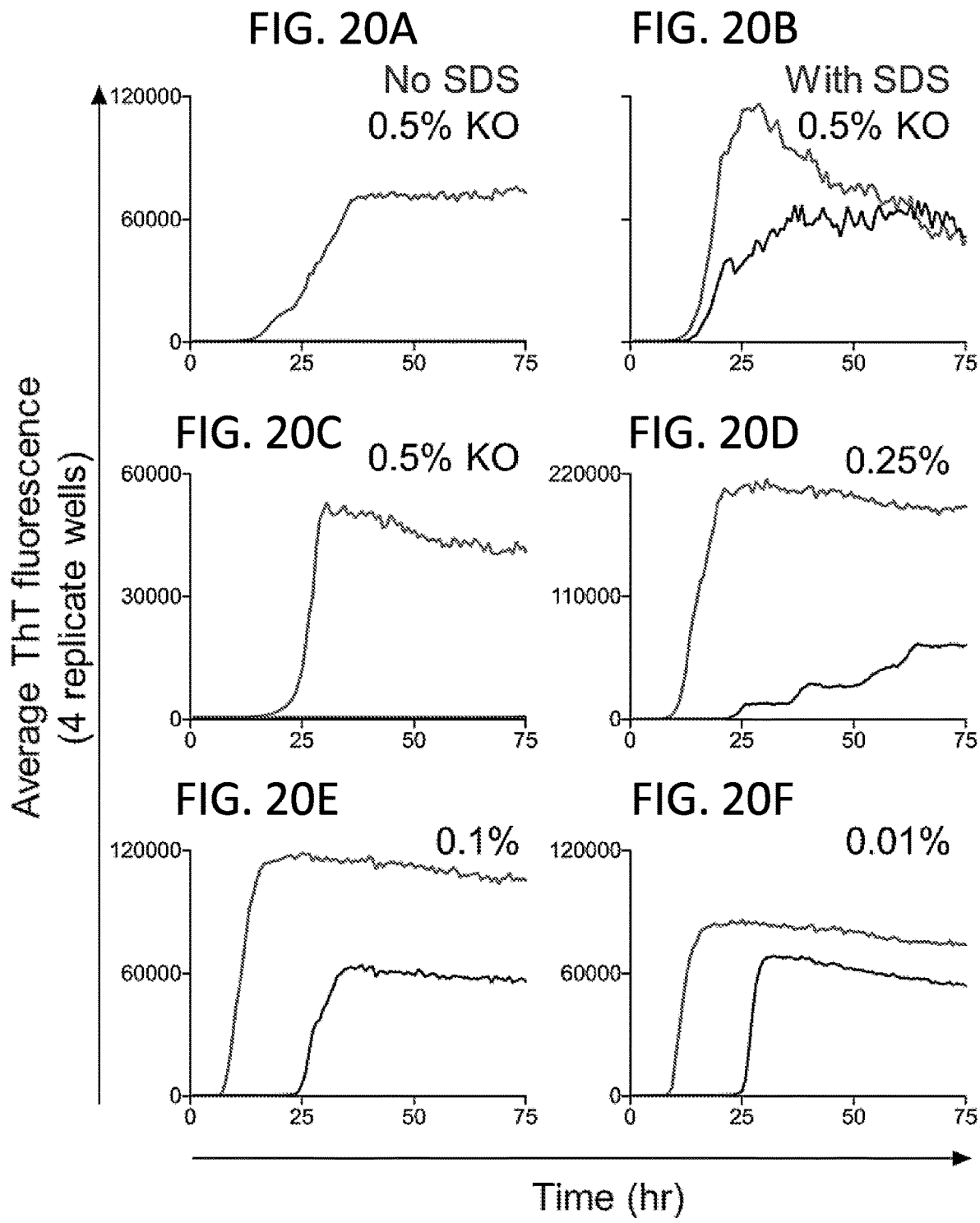

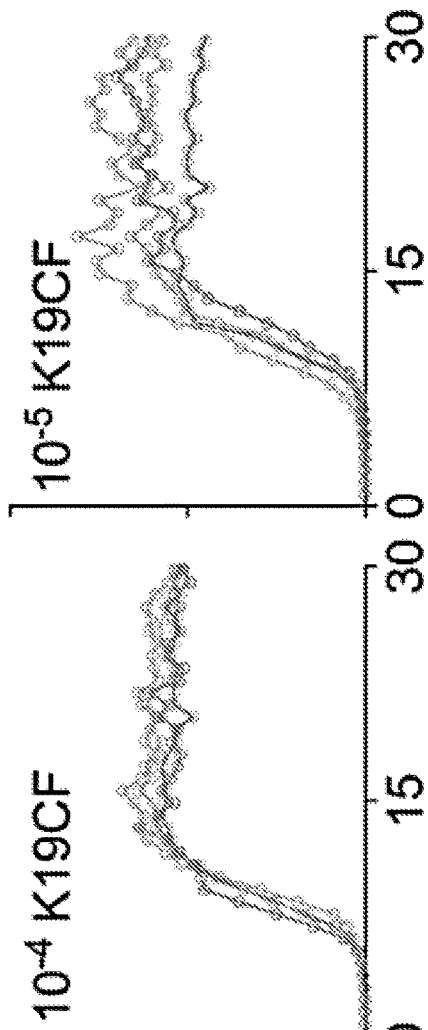

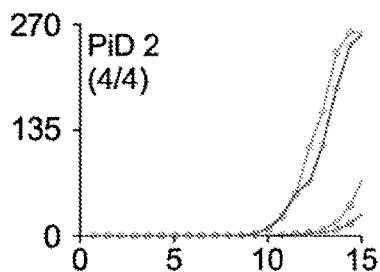
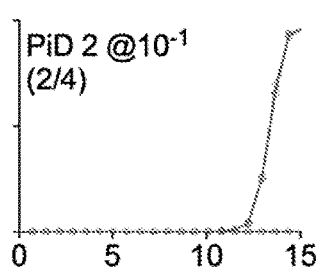
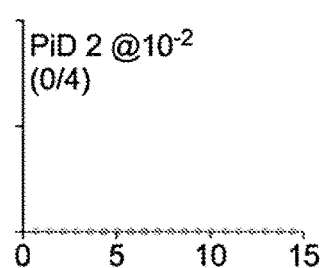
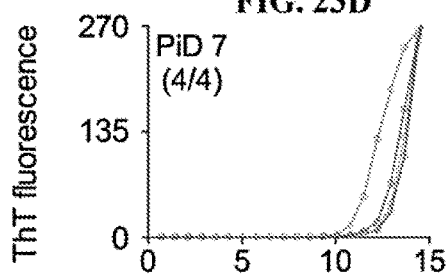
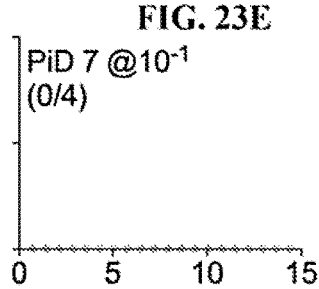
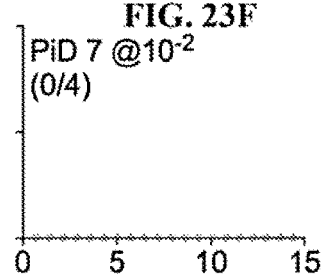
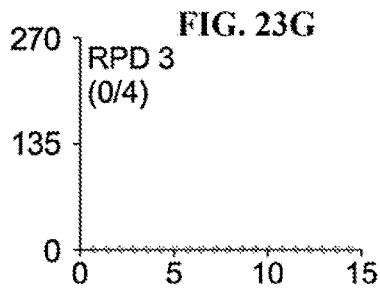
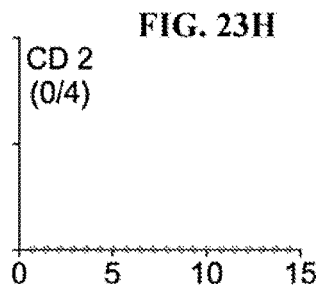
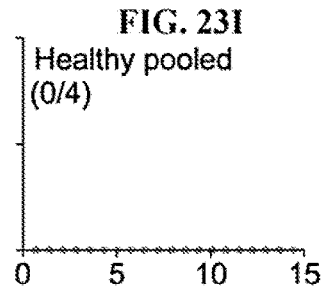

Discrimination of PiD from non-PiD cases

Discrimination of PiD and OND from Healthy cases

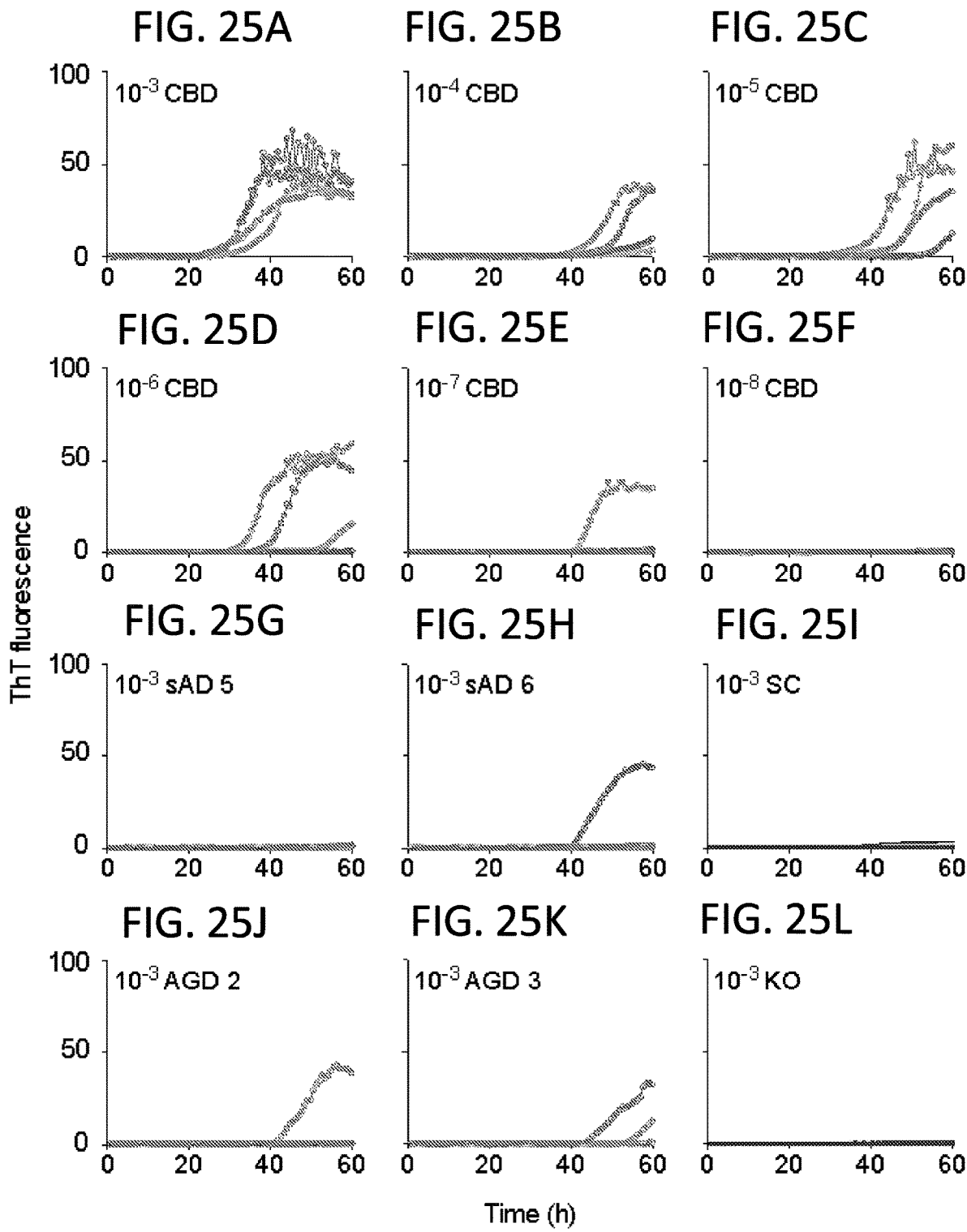

Table 1. End-point quantification of tau seeding activity in brain tissue

| Tauopathy classification | 1° (2°, 3°, 4°) Diagnosis | Brain region | Sex | AOD | PMI | Brain Weight | Tau RT-QuIC Seed concentration (log SD₅₀/mg tissue) ||||||||||
|---|---|---|---|---|---|---|---|---|---|---|---|---|---|---|---|---|
| | | | | | | | Heparin + poly-D-glutamate |||| Heparin only ||||
| | | | | | | | Expt 1 | Expt 2 | Expt 3 | Avg ± SD | Expt 1 | Expt 2 | Expt 3 | Expt 4 | Avg ± SD |
| | PSP 1 | F | M | 86 | 7 | 1530 | 2.5 | | | | 4.7 | | | | |
| | PSP 2 (CVD) | F | M | 71 | 13 | 1143 | 5.0 | 4.5 | | | | 5.0 | | | |
| | PSP 3 (CVD) | F | M | 65 | 8 | 1175 | 5.2 | 5.2 | | | 4.7 | | | | |
| | PSP 4 (SC) | F | M | 67 | 4 | 1480 | 3.0 | | | | | 3.5 | | | |
| | PSP 5 (CVD) | F | M | 76 | 6 | 1381 | 9.0 | | | | 10.0 | 9.0 | 8.5 | | 9.2 ± 0.8 |
| | PSP 6 | F | F | 71 | 7 | 1043 | 5.0 | | | | 5.2 | | | | |
| | PSP 7 (MSA) | F | M | 84 | 48 | NA | 2.5 | | | | | | | | |
| 4R | CBD 1 | F | F | 51 | 10 | NA | 4.5 | 4.7 | 4.7 | 4.6 ± 0.1 | 3.0 | | | | |
| | CBD 2 (CVD, SC) | F | F | 75 | 51 | 1120 | 4.2 | 5.2 | 6.5 | 5.3 ± 1.2 | 3.2 | | | | |
| | CBD 3 (CVD) | F | M | 65 | 17 | 1200 | 4.7 | | | | 3.0 | | | | |
| | CBD 4 (CVD, SC) | F | F | 69 | 5 | 1000 | 5.2 | 5.5 | 5.7 | 5.5 ± 0.3 | | | | | |
| | AGD 1 | F | F | 82 | 19 | 1049 | 5 | 3.2 | | | 2.7 | | | | |
| | AGD 2 (CVD) | F | M | 91 | 2 | 1175 | < 2.2 | | | | < 2.2 | | | | |
| | AGD 3 (HS) | F | M | 86 | 110 | 1330 | 2.5 | | | | 2.5 | | | | |
| | FTLD-TDP-Type B 2 (PSP, SC, CVD) | F | F | 73 | 23 | 979 | 3.5 | | | | | | | | |
| | AD 1 | F | M | 58 | 13 | NA | < 2.2 | | | | 2.7 | | | | |
| | AD 2 | F | F | 80 | 26 | 1007 | 2.5 | | | | < 2.2 | | | | |
| | AD 3 | F | M | 70 | 9 | 1390 | < 2.2 | | | | < 2.2 | | | | |
| 3R/4R | AD 4 | F | F | 87 | 8 | 854 | 3.2 | | | | 2.5 | | | | |
| | AD 5 | F | M | 71 | 2 | 1032 | 2.5 | < 2.2 | | | 2.5 | | | | |
| | AD 6 | F | F | 84 | 33 | 851 | | | | | 2.5 | | | | |
| | SC 3 | F | F | 81 | 25 | 1100 | < 2.2 | < 2.2 | < 2.2 | < 2.2 ± 0 | 2.5 | < 2.2 | | | |
| | CVD 2 | F | F | 66 | 17 | 1072 | | | | | | | | | |
| | CVD 4 (sub-arachnoid hemorrhage, SC) | F | F | 86 | NA | 1050 | 3.0 | | | | 3.0 | 2.7 | | | 2.6 ± 0.4 |
| | DLBD 1 (SC, CVD) | F | M | 80 | 12 | 1285 | | | | | 2.5 | | | | |
| Nodow | DLBD 2 (SC, CM, CVD) | F | M | 81 | 20 | 1294 | | | | | < 2.2 | | | | |
| | DLBD 3 (SC, CVD) | F | M | 73 | 14 | 1072 | < 2.2 | | | | < 2.2 | < 2.2 | | | |
| | DLBD 4 (CVD, SC) | F | M | 71 | 8 | 1395 | | | | | < 2.2 | | | | |
| | ALS 1 (SC, CVD) | F | M | 72 | 2 | 1376 | < 2.2 | | | | < 2.2 | < 2.2 | | | |
| | tau KO | Whole | NA | NA | NA | NA | < 2.2 | < 2.2 | < 2.2 | < 2.2 ± 0 | < 2.2 | < 2.2 | < 2.2 | < 2.2 | < 2.2 ± 0 |

| | | | |
|---|---|---|---|
| AGD | Argyrophilic grain disease | HS | Hippocampal sclerosis | Brain region |
| AD | Alzheimer's disease | IVH | Intraventricular hemorrhage | F Frontal cortex |
| ALS | Amyotrophic lateral sclerosis | MSA | Multi-system atrophy | Brain weight (g) |
| AOD | Age of death | NA | Not available | |
| CBD | Corticobasal degeneration | PMI | Post-mortem interval | *Two more experiments were performed |
| CM | Cerebral malformation | PSP | Progrsive supranuclear palsy | Numbers in red indicate no ThT-positive reaction out of four technical replicates |
| CVD | Cerebrovascular disease | SC | Senile change | |
| DLBD | Diffuse Lewy body disease | tau KO | Human and mouse tau knockout mouse | |
| FTLD-TDP | Frontotemporal lobar degeneration with TDP-43 | | | |

FIG. 28

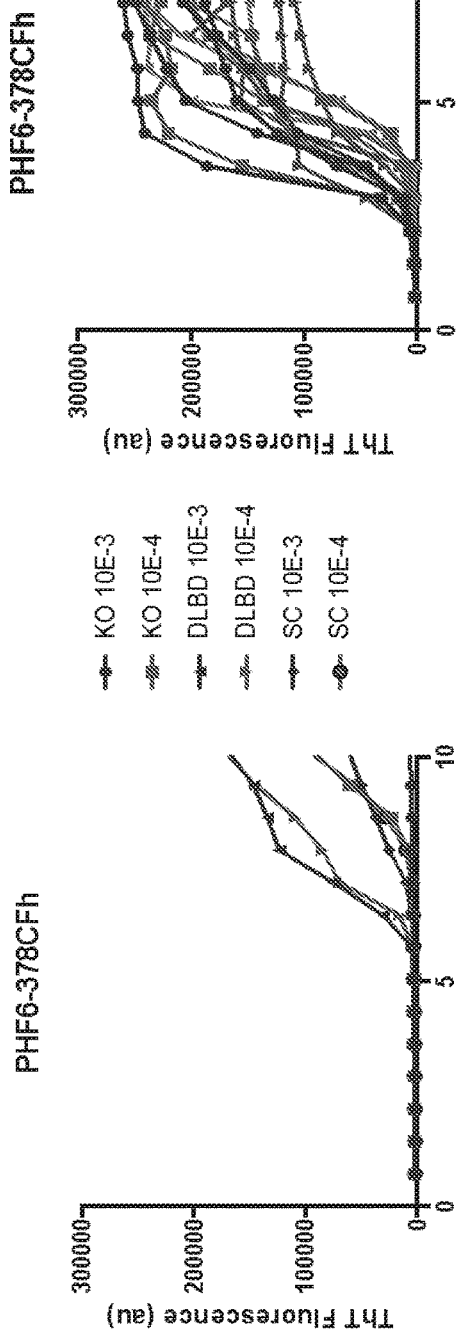
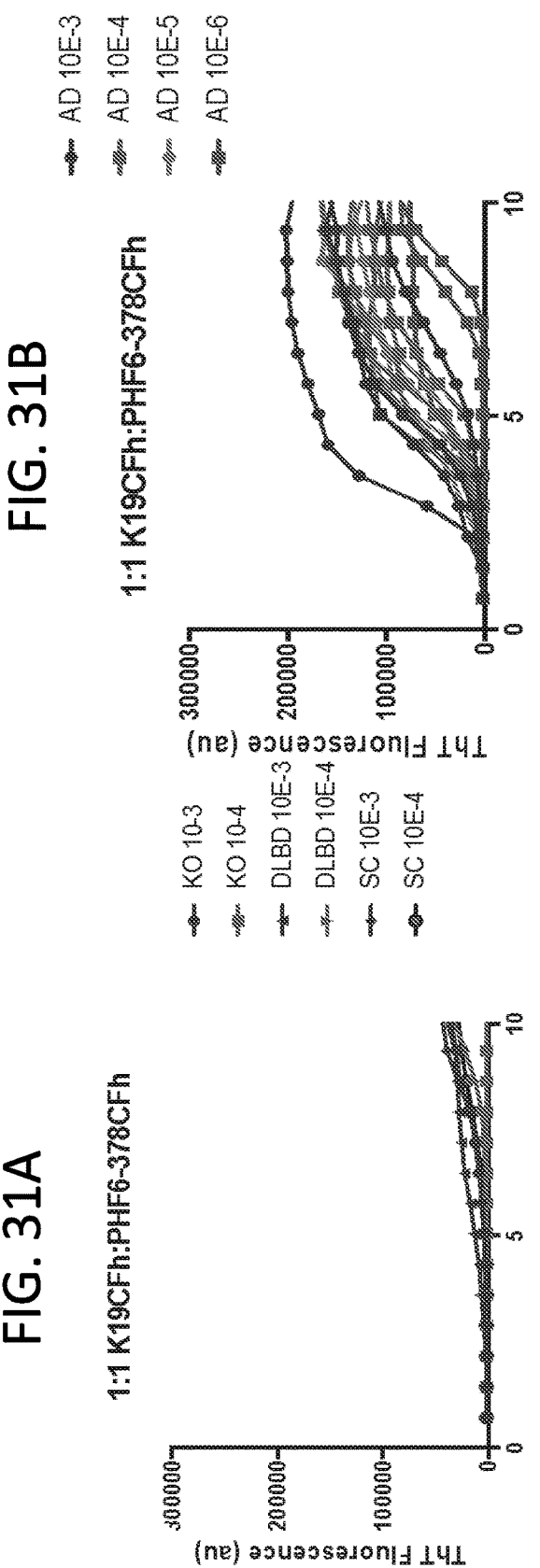
FIG. 31A
FIG. 31B
FIG. 31C
FIG. 31D

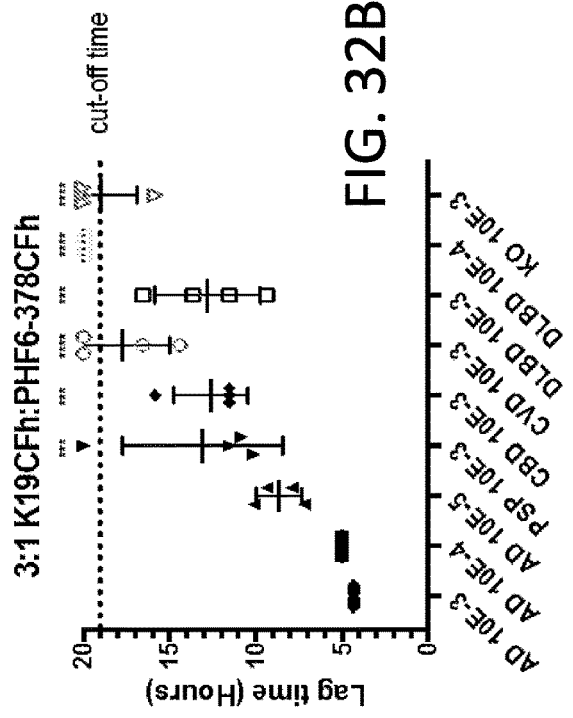
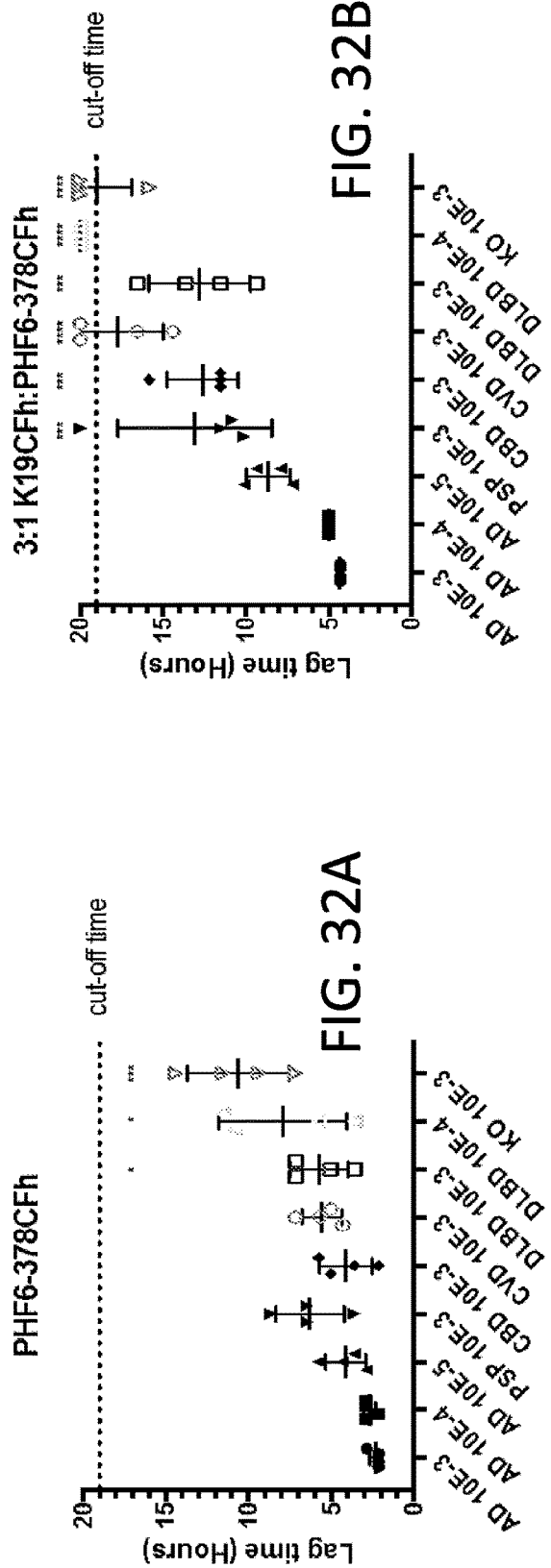
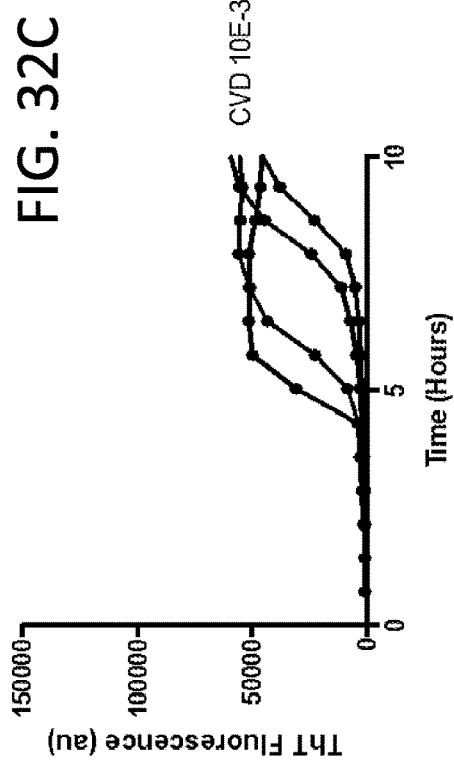
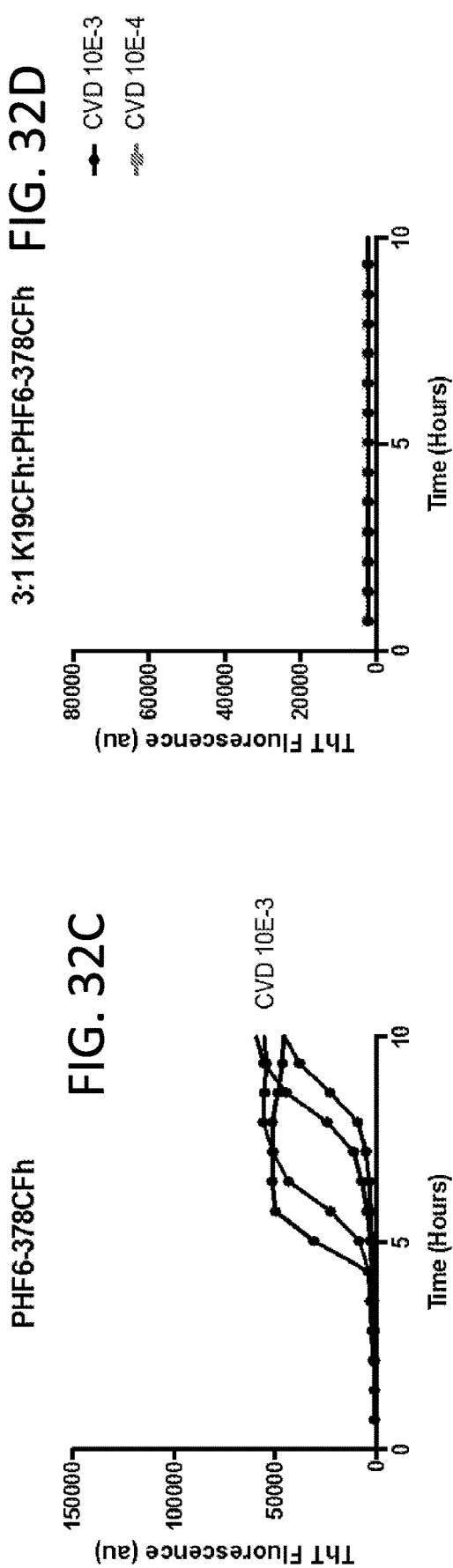
FIG. 32A
FIG. 32B
FIG. 32C
FIG. 32D

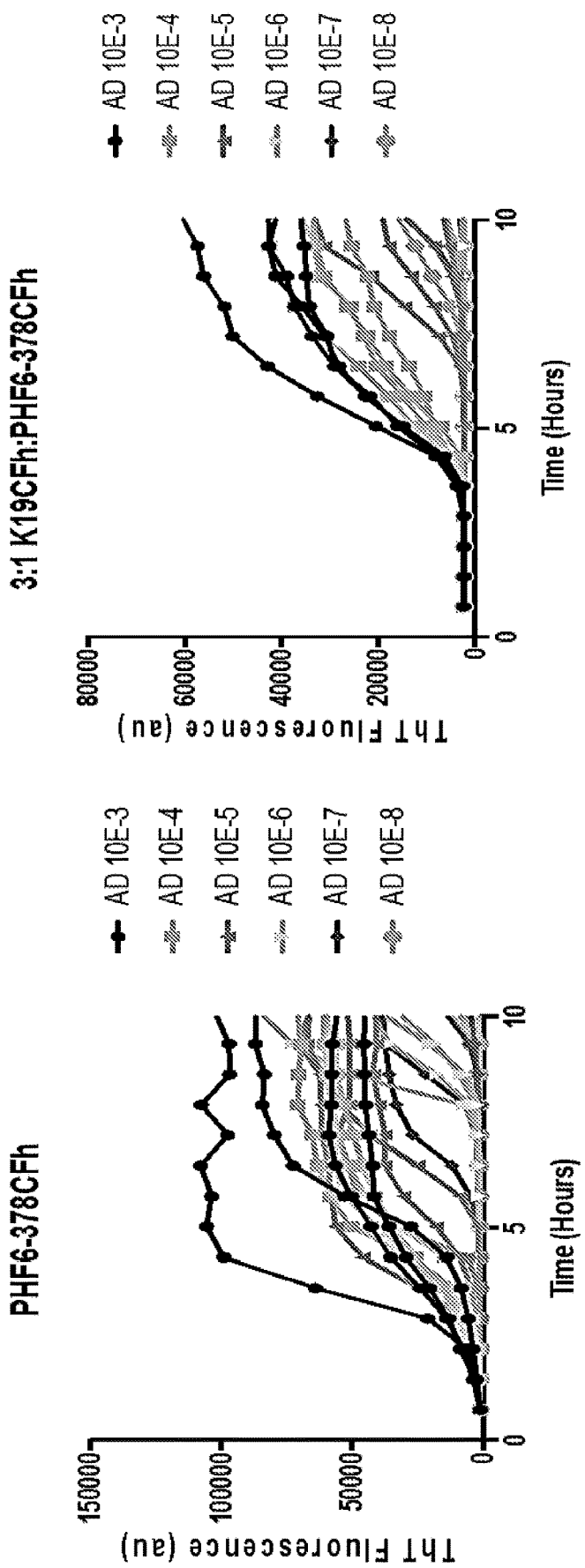

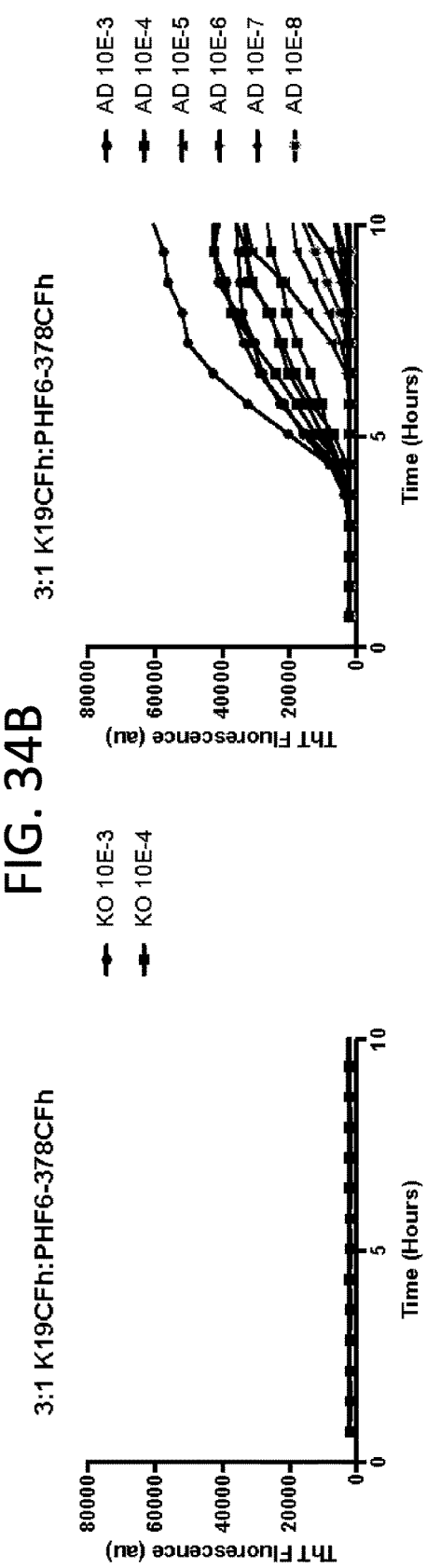
FIG. 34A
FIG. 34B
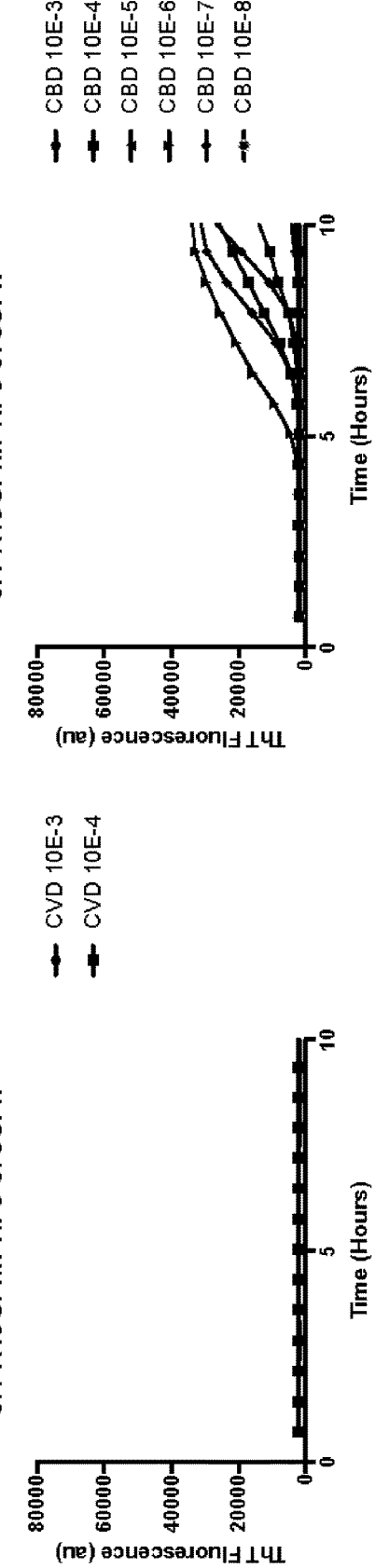
FIG. 34C
FIG. 34D

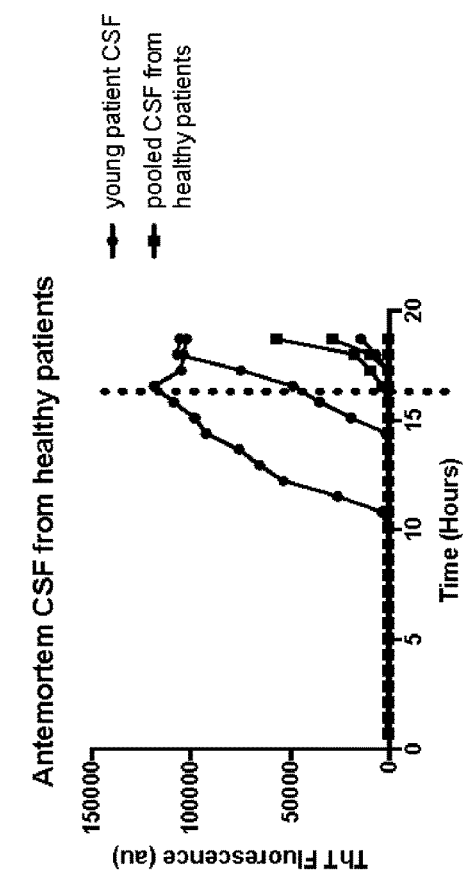
FIG. 35A salt: CaCl$_2$
FIG. 35B salt: NaCl
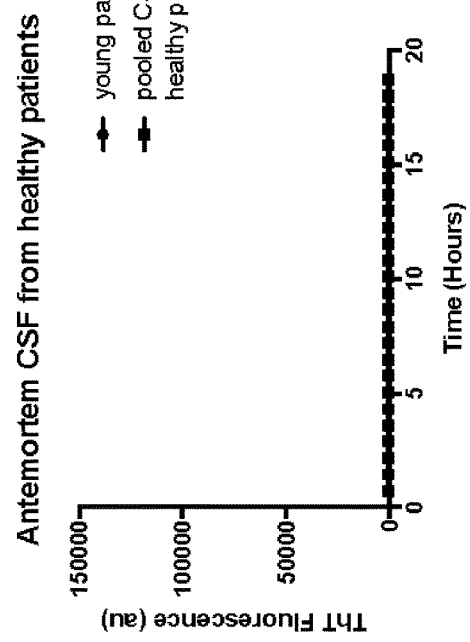
FIG. 35C
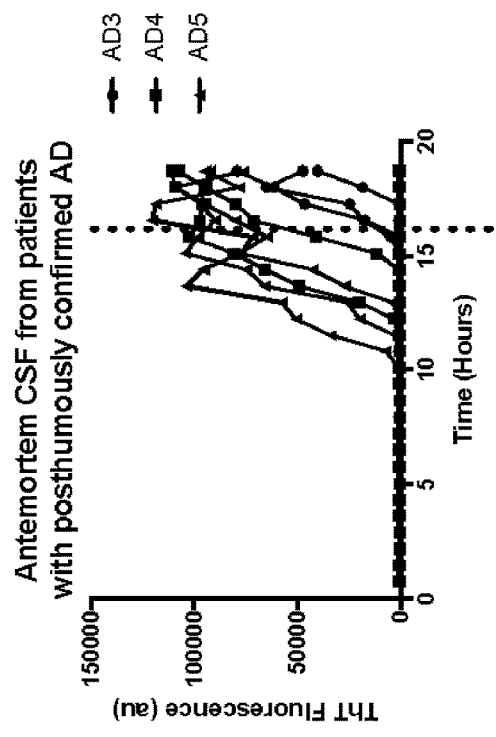
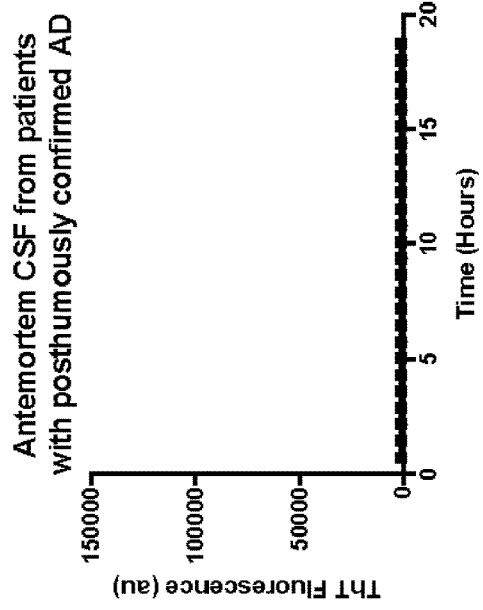
FIG. 35D

METHODS FOR THE DETECTION OF TAU PROTEIN AGGREGATES

CROSS REFERENCE TO RELATED APPLICATION

This is a § 371 U.S. national stage of International Application No. PCT/US2017/069024, filed Dec. 29, 2017, which was published in English under PCT Article 21(2), which claims the benefit of U.S. Provisional Application No. 62/440,885, filed on Dec. 30, 2016, which is incorporated by reference herein.

FIELD OF THE DISCLOSURE

This relates to the field of Tauopathies, specifically to method for detecting a Tauopathy using a seeded polymerization assay.

BACKGROUND

Many neurodegenerative diseases involve the pathological accumulation of specific proteins such as Tau, Aβ or α-synuclein in the form of self-seeding filaments or sub-filamentous deposits. It is often difficult or impossible to diagnose and differentiate many of such neurodegenerative diseases prior to post-mortem pathological analysis, especially those of sporadic rather than genetic origin. This is due in part to the inability to detect the given misfolded proteins, which represent disease-associated biomarkers, with sufficient sensitivity and specificity. The same problem hampers the assessment of therapeutic trials which are aimed at blocking the accumulation of specific misfolded proteins and, consequently, disease progression.

In contrast, considerable progress has been made in the ultrasensitive detection of prions and the diagnosis and differentiation of prion diseases based on the in vitro amplification of misfolded, self-propagating forms of prion protein (see Castillaet al., *Methods Enzymol.* 412, 3-21 (2006); Atarashi et al. *Nat. Med.* 17, 175-178 (2011); Orru et al., *Prion* 6, 147-152 (2012); Zanusso et al., *Nat Rev Neurol* 12, 325-333 (2016).=; and Schmitz, M. et al., *Nat Protoc* 11, 2233-2242 (2016)). These tests are based on the ability of oligomeric prions to seed or template the conversion of monomeric forms of PrP into amyloid fibrils or proteinase K-resistant aggregates with seed amplifications of up to ~$10^{12}$. Among the most practical and broadly applied of these prion tests is the real time quaking-induced conversion (RT-QuIC). This assay is performed in multi-well plates with an amyloid-sensing thioflavin T (ThT) fluorescence readout. RT-QuIC assays can directly detect as little as $10^{-9}$ dilutions of brain homogenates from human Creutzfeldt-Jakob disease patients, and when coupled with immunoprecipitation, as little as $10^{-14}$ dilutions (Orru et al., *mBio* 2, e00078-00011 (2011)). Prion RT-QuIC assays are sensitive enough to detect seeding activity in cerebrospinal fluid (Atarashi et al., *Nat. Med.* 17, 175-178 (2011); McGuire et al., *Ann. Neurol.* 72, 278-285 (2012); Cramm et al., *Mol. Neurobiol.* 51, 396-405 (2015): and Orru et al., *MBio* 6 e02451-14 (2015)) and nasal brushings (Orru et al., *New Engl. J. Med.* 371, 519-529 (2014); Zanusso et al., *N Engl J Med* 371, 1842-1843 (2014); Bongianni et al., JAMA Neurol. 74(2): 155-162 (2017).) obtained from live patients, providing intra vitam diagnostic testing that can be virtually 100% sensitive and specific. Moreover, by varying the recombinant PrP substrates and the reaction conditions RT-QuIC reactions can detect most, if not all, of the known prions of mammalian species and discriminate major prion strains of humans, cattle and sheep (Orru et al., *PLoS Path.* 11, e1004983 (2015); Masujin et al., *J. Clin. Microbiol.* 54, 676-686 (2016); Orru et al., *J. Clin. Microbiol.* 53, 1115-1120 (2015)).

Humans normally express six isoforms of Tau which contain either 3 or 4 microtubule binding repeats (3R and 4R Tau, respectively). Pick disease (PiD) is a form of fronto-temporal degeneration with preferential accumulation of 3R Tau isoforms whereas other Tauopathies tend to accumulate either predominantly 4R Tau assemblies or mixtures of 4R and 3R isoforms (Williams, *Intern. Med. J.* 36, 652-660 (2006)); Irwin et al., *Ann. Neurol.* 79, 272-287 (2016); Goedert et al., Cold Spring Harb Perspect Med. February; 2(2):a006254. doi: 10.1101/cshperspect.a006254 (2012); Makenzie et al., J Neurochem. 138 Suppl 1:54-70. doi: 10.1111/jnc.13588, Epub 2016 Jun. 15; Simoes and Lityan, "Tauopathies" in Encyclopedia of Movement Disorders, Academic Press, NY, pages 219-226 (2010)). Some Tauopathies, such as Alzheimer disease, result in the pathological accumulation of roughly equal proportions of 3R and 4R isoforms of Tau. Others are due to predominant aggregation and deposition of the 4R isoform (e.g., corticobasal degeneration (CBD), progressive supranuclear palsy (PSP), and argyrophilic grain disease (AGD)). CBD is a progressive neurological disorder with symptoms similar to those of Parkinson's disease. It develops over 6-8 years in patients that are usually between 45-77 years old and is difficult to diagnose. The incidence is estimated to be between 4.9 to 7.3 per 100,000, but recent studies suggest that it might be more common. PSP is a movement disorder involving difficulties in the control of eye movement, walking (gait) and balance, speech, swallowing, vision, mood and behavior, and thinking. Although originally estimated to have an incidence similar to that of CBD, recent evidence suggests that it is much more common than that, with PSP pathology detected in 2.9% of generalized forensic autopsy cases (ages 0-101) in Japan, with a majority of those cases reported to also have clinical signs consistent with PSP, despite dying of some other more proximal cause (Yoshida et al., *Acta Neuropath* 2017).

The ultrastructure and biochemical characteristics of the Tau aggregates can vary between the different Tauopathies (Spillantini and Goedert, *Lancet Neurol* 12, 609-622 (2013; Taniguchi-Watanabe S et al. 2015 Acta. Neuropathol. 131 (2):267-80. doi: 10.1007/s00401-015-1503-3, Epub 2015 November; Irwin et al., *Ann. Neurol.* 79, 272-287 (2016); Simoes and Lityan , "Tauopathies" in Encyclopedia of Movement Disorders, Academic Press, NY, pages 219-226 (2010); Goedert et al., Cold Spring Harb Perspect Med. February; 2(2):a006254. doi: 10.1101/cshperspect.a006254 (2012); Makenzie et al., J Neurochem. 138 Suppl 1:54-70. doi: 10.1111/jnc.13588, Epub 2016 Jun. 15).

Studies have shown the detection of Tau seeding activity in Alzheimer brain extracts using cell cultures expressing fluorescently tagged Tau constructs (Holmes et al., *Proc Natl Acad Sci USA* 111, E4376-4385 (2014); Sanders al. Neuron 82, 1271-1288 (2014); Takeda et al., *Ann. Neurol.* 80, 355-367 (2016)). These cell-based assays can be highly sensitive and quantitative, especially in combination with flow cytometry based analysis of the cells. However, the practicality of the previously described assays for routine diagnostic purposes is limited because of one or more of the following: unknown or insufficient sensitivity and specificity, the need for complex tissue extractions and/or the use of tissue cell cultures followed by flow cytometry. Thus, a need remains for other assays that can detect Tau, such as a seeded Tau polymerization assay.

SUMMARY OF THE DISCLOSURE

Methods are disclosed herein for determining whether a subject has a Tauopathy. In some embodiments, the methods include a) performing a seeded Tau polymerization assay on a biological sample from the subject, wherein the assay includes (i) contacting the biological sample with a purified recombinant truncated Tau protein, wherein the truncated Tau protein includes two, three or four microtubule binding domains, and optionally a human Tau-free carrier to form a reaction mixture; (ii) incubating the reaction mixture to permit coaggregation of disease-associated Tau protein ($T^D$) present in the biological sample with the recombinant truncated Tau protein; (iii) maintaining incubation conditions that promote coaggregation of the recombinant truncated Tau protein with the $T^D$ to result in a conversion of the recombinant truncated Tau protein to amyloid Tau protein aggregates while inhibiting development of spontaneously forming Tau protein aggregates ($rT^{(spon)}$); and (iv) agitating amyloid Tau protein aggregates formed during step (iii), wherein the agitating includes shaking the reaction mixture in a shaking cycle, wherein each shaking cycle includes a period of rest and a period of shaking. Amyloid Tau protein present in the reaction mixture is then detected. The detection of amyloid Tau protein in the reaction mixture indicates that the subject has the Tauopathy. In some embodiments, an amyloid sensitive dye is used to detect the presence of amyloid Tau protein.

In additional embodiments, methods are disclosed for determining whether a subject has 3R Tauopathy, such as Pick disease. The methods include performing an amyloid seeding assay on a biological sample from the subject, wherein the biological sample comprises brain tissue and/or cerebrospinal fluid. The amyloid seeding assay includes: (i) contacting the biological sample with a purified recombinant truncated Tau protein, wherein the recombinant truncated Tau protein comprises three microtubule binding domains, a Tau-free brain homogenate, an effective amount of N2, and an amyloid-sensing dye to form a reaction mixture; (ii) incubating the reaction mixture to permit coaggregation of disease-associated Tau protein ($T^D$) present in the biological sample with the recombinant truncated Tau protein; (iii) maintaining incubation conditions that promote coaggregation of the recombinant truncated Tau protein with the $T^D$ to result in a conversion of the recombinant truncated Tau protein to amyloid Tau protein aggregates while inhibiting development of spontaneously forming Tau protein aggregates ($rT^{(spon)}$); (iv) agitating amyloid Tau protein aggregates formed during step (iii), wherein the agitating comprises shaking the reaction mixture in a shaking cycle, wherein each shaking cycle comprises a period of rest and a period of shaking. Aggregated Tau protein present in the reaction mixture is detected, such as using an amyloid-sensing dye. In some non-limiting examples, steps (a)-(b) are performed in the absence of an anionic detergent, and detection of the amyloid sensing dye indicates that the subject has Pick disease.

Methods are also provided for determining whether a subject has a 4R Tauopathy, such as progressive supranuclear palsy (PSP), corticobasal degeneration (CBD) or argyrophilic grain disease (AGD). These methods include: a) performing an amyloid seeding assay on a biological sample from the subject, wherein the biological sample includes brain tissue and/or cerebral spinal fluid. The amyloid seeding assay includes: (i) contacting the biological sample with a purified recombinant truncated Tau protein, wherein the recombinant truncated Tau protein has four microtubule binding domains, and an amyloid-sensing dye to form a reaction mixture; (ii) incubating the reaction mixture to permit coaggregation of disease-associated Tau protein ($T^D$) present in the biological sample with the recombinant truncated Tau protein; (iii) maintaining incubation conditions that promote coaggregation of the recombinant truncated Tau protein with the $T^D$ to result in a conversion of the recombinant truncated Tau protein to amyloid Tau protein aggregates while inhibiting development of spontaneously forming recombinant amyloid protein ($rT^{(spon)}$); (iv) agitating amyloid Tau protein aggregates formed during step (iii), wherein the agitating includes shaking the reaction mixture in a shaking cycle, wherein each shaking cycle comprises a period of rest and a period of shaking. These methods also include: b) detecting amyloid Tau protein present in the reaction mixture, wherein detection of amyloid Tau protein in the reaction mixture comprises detecting fluorescence of the amyloid sensing dye, and wherein detecting fluorescence indicates that the subject has a 4R Tauopathy.

In some embodiments, the reaction mixture further includes a second purified recombinant truncated Tau protein, wherein the second purified recombination Tau protein has three microtubule binding domains. Thus methods are also provided for determining whether a subject has a 4R Tauopathy. These methods include: a) performing an amyloid seeding assay on a biological sample from the subject, wherein the biological sample includes brain tissue and/or cerebral spinal fluid. The amyloid seeding assay includes: (i) contacting the biological sample with a first purified recombinant truncated Tau protein, wherein the first recombinant truncated Tau protein has four microtubule binding domains, and a second purified recombinant truncated Tau protein, wherein the second purified recombinant truncated Tau protein comprises three microtubule binding domains, respectively and an amyloid-sensing dye to form a reaction mixture; (ii) incubating the reaction mixture to permit coaggregation of disease-associated Tau protein ($T^D$) present in the biological sample with the first recombinant truncated Tau protein and the second recombinant truncated Tau protein; (iii) maintaining incubation conditions that promote coaggregation of the first recombinant truncated Tau protein and the second recombinant truncated Tau protein with the $T^D$ to result in a conversion of the first recombinant truncated Tau protein and the second recombinant truncated Tau protein to amyloid Tau protein aggregates while inhibiting development of spontaneously forming recombinant amyloid protein ($rT^{(spon)}$); (iv) agitating amyloid Tau protein aggregates formed during step (iii), wherein the agitating includes shaking the reaction mixture in a shaking cycle, wherein each shaking cycle comprises a period of rest and a period of shaking. These methods also include: b) detecting amyloid Tau protein present in the reaction mixture, wherein detection of amyloid Tau protein in the reaction mixture comprises detecting fluorescence of the amyloid sensing dye, and wherein detecting fluorescence indicates that the subject has a 4R Tauopathy.

In further embodiments, methods are disclosed for detecting a 3R/4R Tauopathy such as Alzheimer disease. These methods include: a) performing an amyloid seeding assay on a biological sample from the subject, wherein the biological sample comprises brain tissue and/or cerebral spinal fluid, wherein the amyloid seeding assay includes: (i) contacting the biological sample with a first purified recombinant truncated Tau protein, wherein the first recombinant truncated Tau protein comprises at least two microtubule binding domains and further comprises amino acids 306 to amino acid 378 of SEQ ID NO: 8 to form a reaction mixture; (ii) incubating the reaction mixture to permit coaggregation of disease-associated Tau protein ($T^D$) present in the biological sample with the first recombinant truncated Tau protein; (iii) maintaining incubation conditions that promote coaggregation of the first recombinant truncated Tau protein with the $T^D$ to result in a conversion of the first recombinant truncated Tau protein to amyloid Tau protein aggregates while inhibiting development of spontaneously forming Tau protein aggregates ($rT^{(spon)}$); and (iv) agitating amyloid Tau protein aggregates formed during step (iii), wherein the agitating comprises shaking the reaction mixture in a shaking cycle, wherein each shaking cycle comprises a period of rest and a period of shaking. These methods also include b) detecting amyloid Tau protein present in the reaction mixture, wherein detection of amyloid Tau protein in the reaction mixture comprises detecting fluorescence of the amyloid sensing dye, and wherein detecting fluorescence indicates that the subject has a 3R/4R Tauopathy. In some embodiments, the first purified recombinant truncated Tau protein has two, three or four microtubule binding domains.

In more embodiments, methods for detecting a 3R/4R Tauopathy such as Alzheimer disease include a) performing an amyloid seeding assay on a biological sample from the subject, wherein the biological sample comprises brain tissue and/or cerebral spinal fluid, wherein the amyloid seeding assay includes: (i) contacting the biological sample with a first purified recombinant truncated Tau protein, wherein the first recombinant truncated Tau protein comprises at least two (such as two, three or four microtubule binding domains) and amino acid 306 to amino acid 378 of SEQ ID NO: 8 and second recombinant truncated Tau protein comprising three or four microtubule binding domains to form a reaction mixture; (ii) incubating the reaction mixture to permit coaggregation of disease-associated Tau protein ($T^D$) present in the biological sample with the first recombinant truncated Tau protein and the second recombinant truncated Tau protein; (iii) maintaining incubation conditions that promote coaggregation of the first recombinant truncated Tau protein and the second recombinant truncated Tau protein with the $T^D$ to result in a conversion of the first recombinant truncated Tau protein and the second recombinant truncated Tau protein to amyloid Tau protein aggregates while inhibiting development of spontaneously forming Tau protein aggregates ($rT^{(spon)}$); and (iv) agitating amyloid Tau protein aggregates formed during step (iii), wherein the agitating comprises shaking the reaction mixture in a shaking cycle, wherein each shaking cycle comprises a period of rest and a period of shaking. These methods also include b) detecting amyloid Tau protein present in the reaction mixture, wherein detection of amyloid Tau protein in the reaction mixture comprises detecting fluorescence of the amyloid sensing dye, and wherein detecting fluorescence indicates that the subject has a 3R/4R Tauopathy.

Protein amino acid residues are referred to throughout by their amino acid identity and/or the position number in the human Tau 40 protein isoform (SEQ ID NO: 8). As one non-limiting example, with regard to SEQ ID NO: 3, "S291, S322" refers to the serine corresponding to position 291 of the human Tau 40 protein of SEQ ID NO: 8 and "S322" refers to the serine at position 322 of the human Tau 40 protein of SEQ ID NO:8.

The foregoing and other features and advantages of the invention will become more apparent from the following detailed description of several embodiments which proceeds with reference to the accompanying figures.

BRIEF DESCRIPTION OF THE FIGURES

FIGS. 2A-2H show individual ThT fluorescence traces for replicate wells (n=4) at the designated dilutions of a frontal lobe sample from a human PiD case. FIG. 2I. A Tau knockout mouse (KO) was used as a Tau-negative control at a $10^{-3}$ dilution. FIG. 2J. A human brain sample with senile changes (SC) but no immunohistological evidence of Tau deposits was also included at a $10^{-3}$ dilution. The recombinant truncated Tau substrate was K19CFh.

FIGS. 4A-4L. End-point Tau RT-QuIC dilution analysis of select AD and PSP cases using Pick disease-optimized (3R) RT-QuIC with the 6× His-tagged K19CF recombinant Tau substrate (SEQ ID NO:14). Primary data are shown from an AD case (FIGS. 4A-4D) and a PSP case (FIGS. 4H-4J), each corresponding to a data pointed encircled in black in FIG. 3. Quadruplicate reactions were run for each 10-fold dilution of brain homogenate. Human cases with CVD (n=2, FIGS. 4E-4F) or senile changes (SC; FIG. 4K) without apparent Tau immunohistopathology were tested concurrently at the $10^{-3}$ dilution. Mouse KO (FIGS. 4G, L) brain was used as a Tau-free control at $10^{-3}$. Traces from individual replicate wells are plotted with ThT fluorescence units are indicated in thousands.

FIGS. 5A-5T. 3R Tau RT-QuIC end-point dilution analyses of PiD brain regions with [frontal (F) and temporal (T) cortices] or without [cerebellar cortex (C)] apparent Tau immunohistopathology. SC and KO brains were used as a negative control at the lowest dilution of $10^{-3}$ as in previous figures. Traces from individual quadruplicate wells are plotted with ThT fluorescence units indicated in thousands. The recombinant truncated Tau substrate was K19CFh.

FIGS. 6A-6B. Imidazole washes prior to the elution of K19CFh removed impurities that might inhibit 3R Tau RT-QuIC reactions. Recombinant Tau K19CFh was purified by nickel affinity chromatography with sequential 30 and 46 mM imidazole washes followed by a linear gradient from 46 to 200 mM imidazole.

Figure 6A:
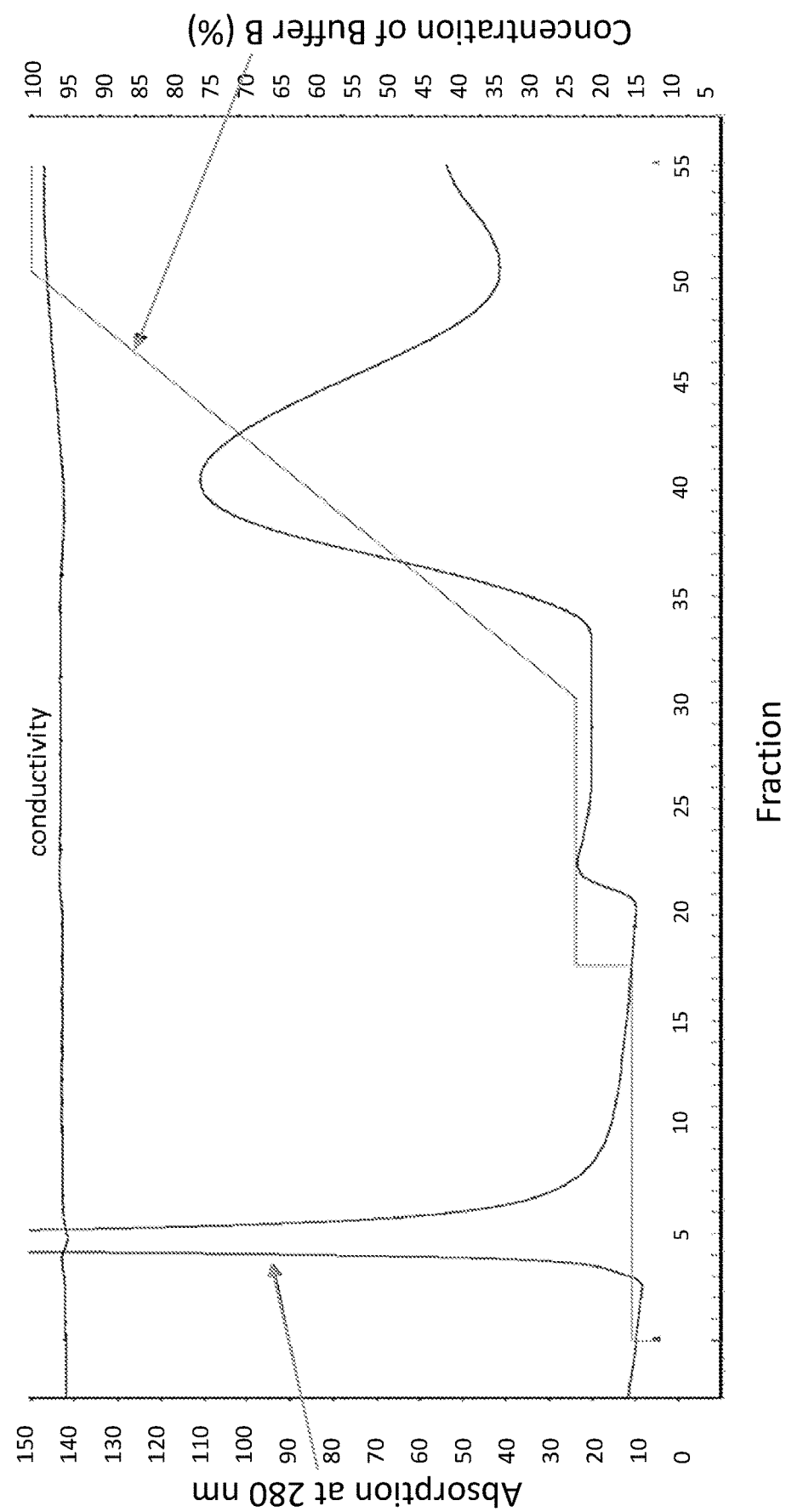

Fractions from the second step and linear gradient were analyzed on SDS-PAGE with Coomassie blue staining for protein (FIG. 6B). Major impurities were eluted with 30 mM imidazole, and minor impurities approximately 10 kDa in size (dark arrow) were eluted with 46 mM imidazole. Lighter arrows indicate recombinant Tau K19CF that either contained or lacked the 6-histidine tag.

FIG. 7A-F. 3R Tau RT-QuIC seeding activity in Sarkosyl-insoluble extracts from PiD and AD brains. The designated dilutions of Sarkosyl-insoluble (Tau filament) extracts from PiD (FIGS. 2A, 2B), AD (FIGS. 2C, 2D) and CVD (FIGS. 2E, 2F). Each of the undiluted extracts contained 5 g wet brain tissue equivalents per ml. Traces from individual quadruplicate wells are plotted in different colors with ThT fluorescence units indicated in thousands.

FIG. 8. 6×His K19 Cysteine-free (K19CFh) (SEQ ID NO: 14). This sequence represents an N-terminally 6× histidine-tagged fragment of the human Tau sequence that contains microtubule binding repeats 1, 3 and 4, a cysteine to serine mutation at residue 322 (residue numbering according to the full-length hTau40 sequence (SEQ ID NO:8) and a C-terminal extension to residue 372. The sequence contains two potential methionine start codons as designated, with the second start codon immediately preceding the beginning of Tau sequence corresponding to residue 244 of hTau40.

FIG. 9. 6×His K18 Cysteine-free (K18CFh) (SEQ ID NO: 16). This sequence represents an N-terminally 6× histidine-tagged fragment of the human Tau sequence that contains microtubule binding repeats 1-4, two cysteine-to-serine mutations at residues 291 and 322 (residue numbering according to the full-length hTau40 sequence (SEQ ID NO:8) and a C-terminal extension to residue 372. The sequence contains two potential methionine start codons as designated, with the second start codon immediately preceding the beginning of Tau sequence corresponding to residue 244 of hTau40.

FIG. 10. 6×His K12A322 (K12A322h) (SEQ ID NO: 19). This sequence represents an N-terminally 6× histidine-tagged fragment of the human Tau sequence that contains microtubule binding repeats 1, 3 and 4, a cysteine to alanine mutation at residue 322 (residue numbering according to the full-length hTau40 sequence (SEQ ID NO:8)) and a C-terminal extension to residue 400. The sequence contains two potential methionine start codons as designated, with the second start codon immediately preceding the beginning of Tau sequence corresponding to residue 244 of hTau40.

FIG. 11. Alignment of his-tagged Tau substrates. In this alignment, SEQ ID NO: 14, SEQ ID NO: 16 and SEQ ID NO: 19 are shown.

Figure 12:
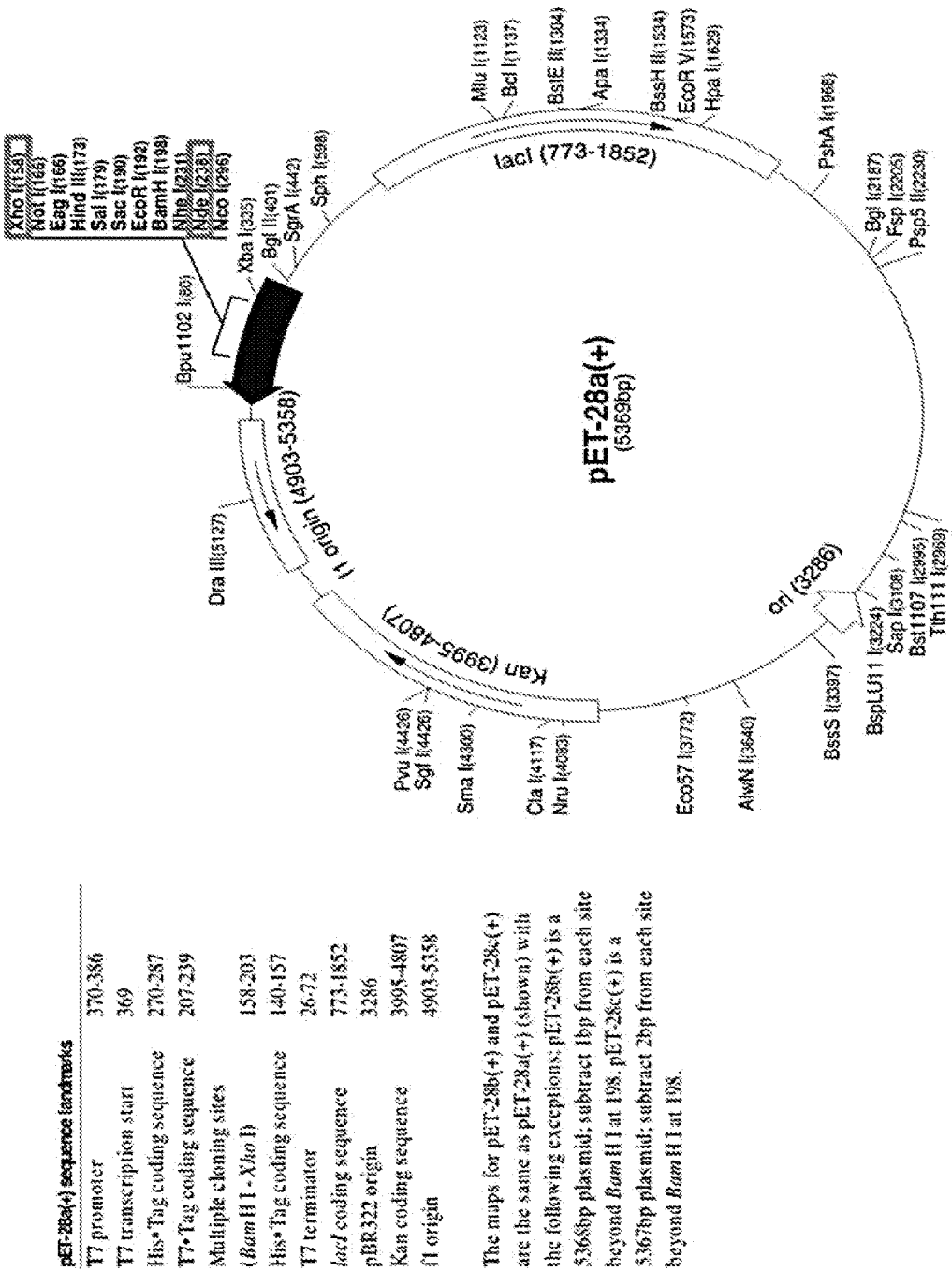

FIG. 12. Map of bacterial expression vector pET-28a. Tau (e.g. K19Cys-free) encoding sequence was designed between two restriction endonuclease enzyme sites NdeI at the 5' and XhoI at the 3' end in pET-28a. A poly-histidine tag is expressed at the N-terminal of Tau recombinant protein. The diagram is modified from the published description of the pET28 vector (Novagen, Cat. No. 69864-3).

FIGS. 13A-13B. Lists of Tau substrates. FIG. 13A is a list of Tau substrates with a polyhistidine tag. FIG. 13B is a list of Tau substrates without a polyhistidine tag.

Figure 14A:
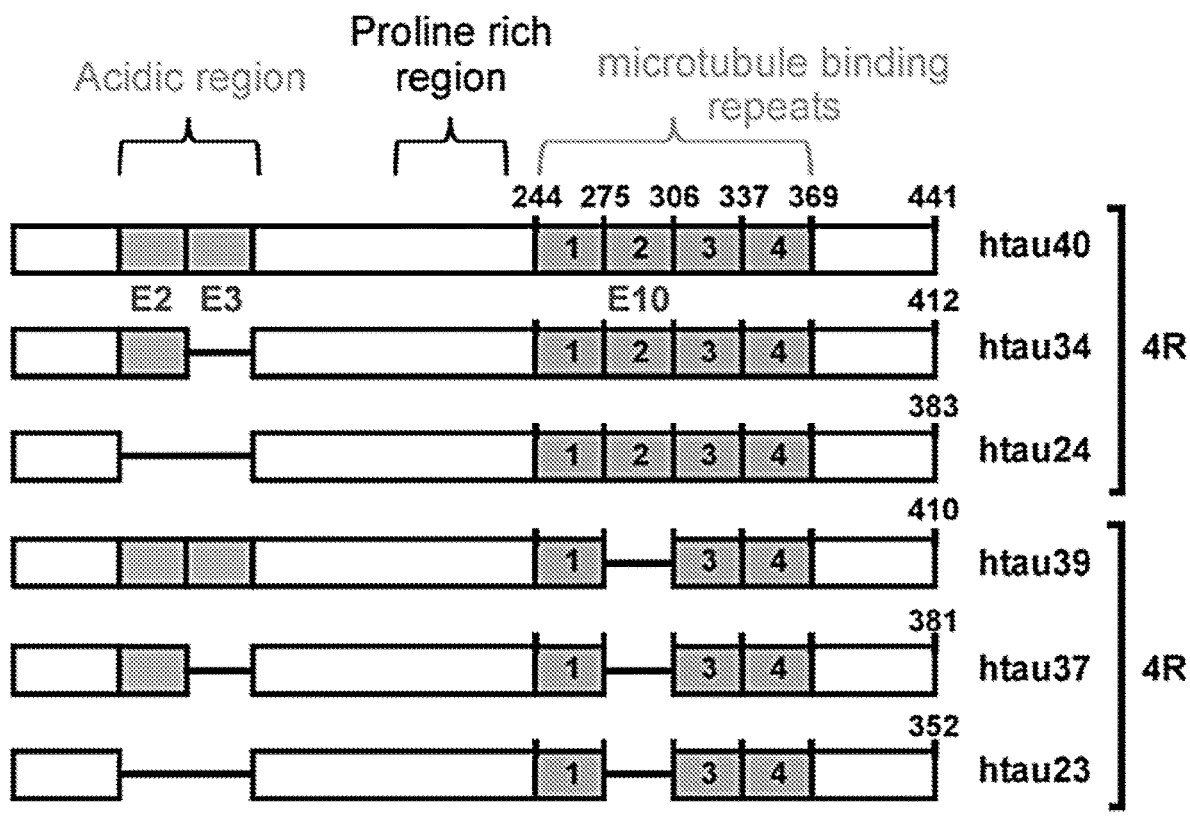
Figure 14B:
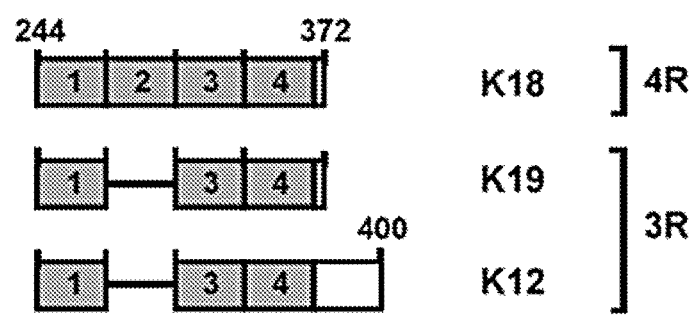

FIG. 14A-14B. Diagram of Tau isoforms and truncated forms. FIG. 14A Tau isoforms are defined by the presence or absence of two inserts (grey: exon 2 (E2) and/or exon 3 (E3)) in the N-terminal half and the inclusion or exclusion of the second microtubule binding repeat (marked as 2; exon 10 (E10)) in the C-terminal half. FIG. 14B constructs K18 and K19 encompass the repeat region. 4R=4-repeat, 3R=3-repeat. (Modified from Dinkel, P D, et al. Variations in Filament Conformation Dictate Seeding Barrier between Three- and Four-Repeat Tau. Biochemistry. 2011; 50(20)).

Figure 15:
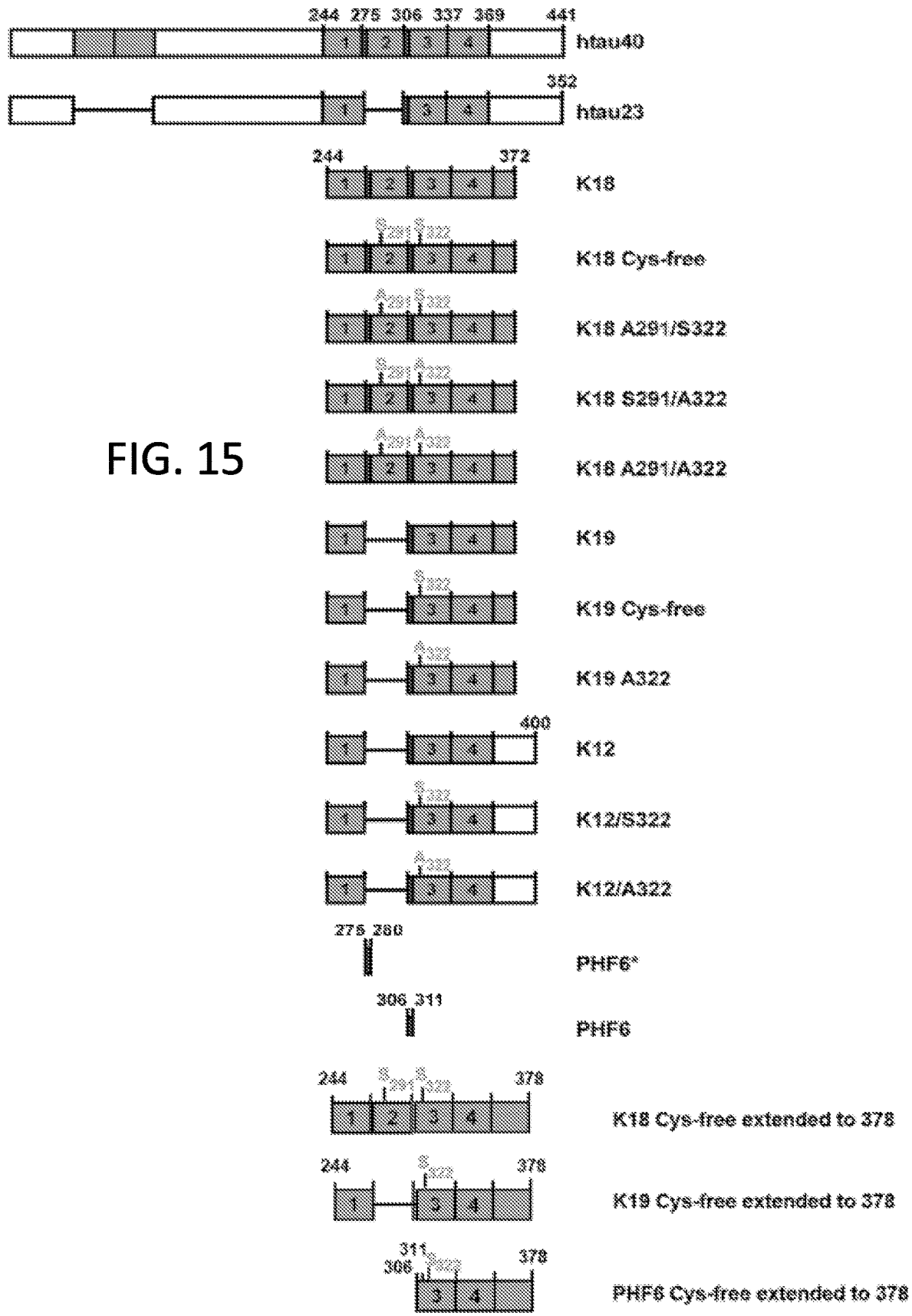

FIG. 15. Bar diagram of Tau isoforms and constructs.

Figure 16:
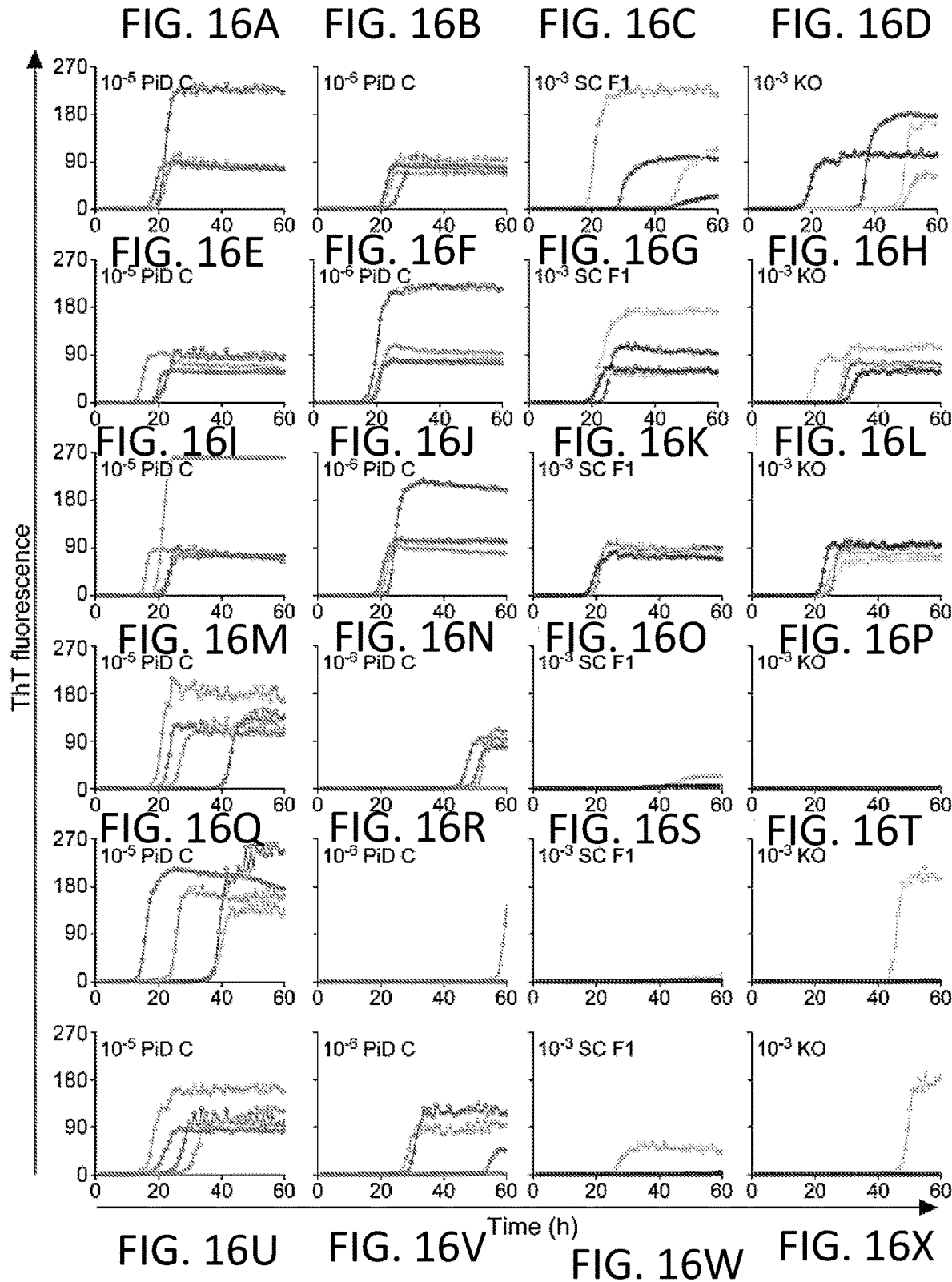

FIG. 16A-16X. Importance of KCl in KO brain homogenate preparation when assaying brain (but not CSF) specimens by Tau RT-QuIC. Tau knockout (KO) brain homogenate prepared in Tris-buffered saline (TBS) with 2.7 mM potassium chloride (KCl) delayed PiD-independent K19CFh amyloid formation when KO brain homogenate was used in the brain sample dilution buffer for Tau RT-QuIC. KO brain homogenate was used to maintain consistent overall biomass in serial dilutions of brain homogenate (but not CSF) test samples (see FIG. 20 for need of Tau KO in brain seed dilutions). When the KO brain tissue was homogenized in 137 mM NaCl, 2.7 mM KCl, 25 mM Tris-HCl, pH 7.4 with an EDTA-free protease inhibitor cocktail, the formation of K19CFh fibrils in Tau RT-QuIC reactions treated with non-Tauopathy (SC and KO) brain samples treated was delayed relative to PiD-seeded reactions (FIG. 16M-P). However, this delaying effect was not observed when: the KO brain homogenate was prepared in TBS lacking KCl (FIG. 16A-16D); the equivalent or 2-3 times the amount of KCl was added to the Tau RT-QuIC reaction only after the test brain homogenate was diluted in KO brain homogenate made with TBS lacking KCl (FIG. 16E-H and FIG. 16I-L); KCl was supplemented in both the QuIC reaction buffer and brain seed dilution buffer [a total final concentration of 5.3 µM KCl per reaction (2.3 µM KCl in Tau KO brain homogenate and 3 µM KCl in Tau RT-QuIC reaction buffer (FIG. 16Q-T) or a total of 8.3 µM KCl (2.3 µM KCl in Tau KO brain homogenate and 6 µM KCl in Tau RT-QuIC reaction buffer (FIG. 16U-X)]. Panels FIGS. 16A-16X show individual ThT fluorescence traces for replicate wells (n=4) at the designated dilutions of the cerebellar cortex sample from human PiD case. A Tau knockout mouse (KO) was used as a Tau-negative control at a $10^{-3}$ dilution (FIGS. 16D, H, L, P, T, X). A human brain sample (the frontal cortex) with senile change (SC) but no immunohistological evidence of Tau deposition was also included at a $10^{-3}$ dilution (FIGS. 16C, 16G, 16K, 16O, 16S, 16W). ThT fluorescence units are indicated in thousands.

Figure 17:
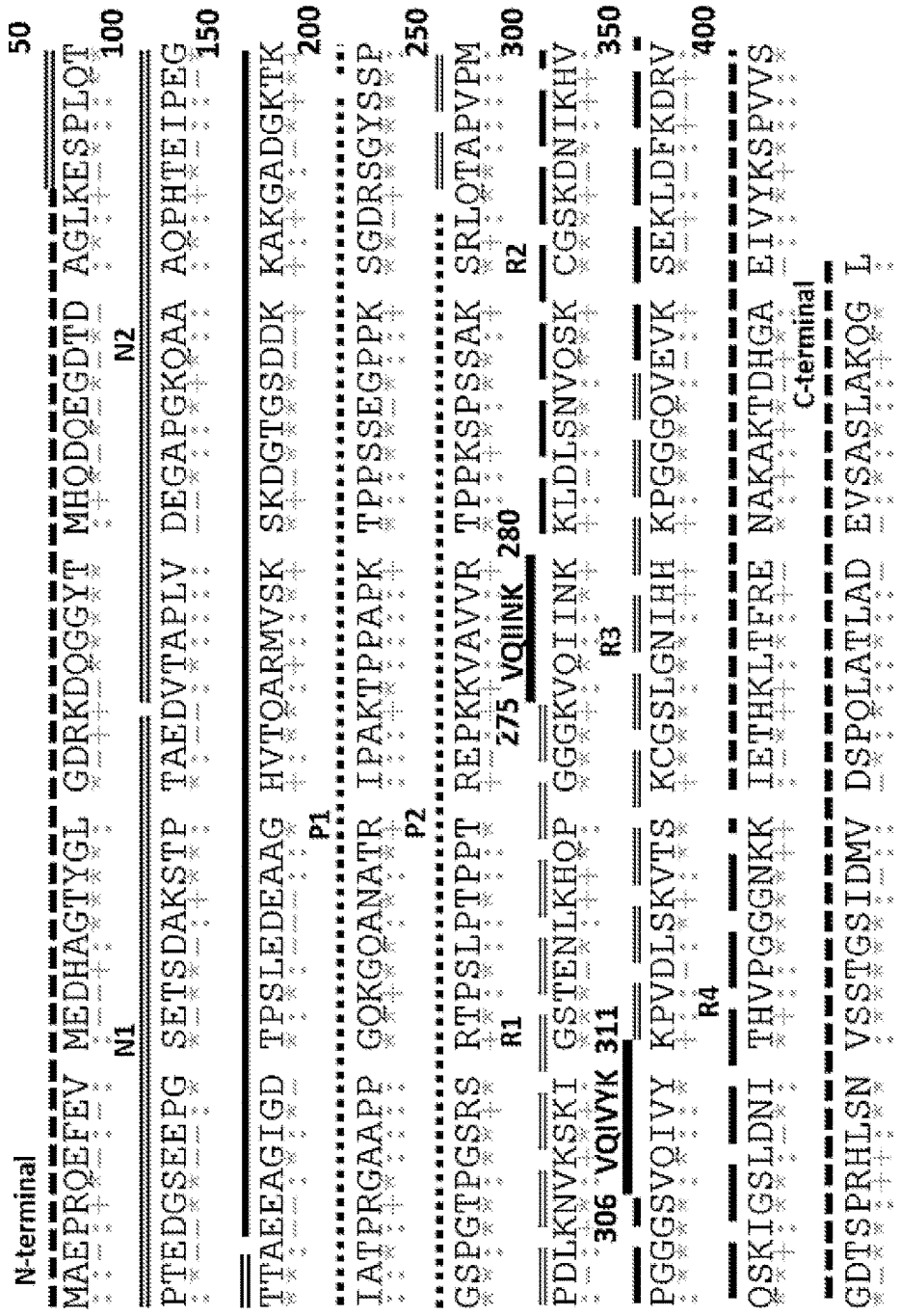

FIG. 17. Amino acid sequence of the longest Tau isoform (441 amino acids) (SEQ ID NO: 8). N1 and N2: the polypeptide sequences encoded by exons 2 and 3; P1 and P2: proline-rich regions; R1-R4: microtubule-binding domains encoded by exons 9-12; $^{275}$VQIINK$^{280}$ and $^{306}$VQIVYK$^{311}$: sequences with β-structure (modified from Mukrasch M D, Bibow S, Korukottu J, et al. Structural polymorphism of 441-residue Tau at single residue resolution. *PLoS Biology*. 2009; 7(2)).

FIGS. 18A-18B. Alignment of Tau substrates (without histidine-tag). From top to bottom, SEQ ID NO: 6, SEQ ID NO: 7, SEQ ID NO: 5, SEQ ID NO: 8, SEQ ID NO: 2, SEQ ID NO: 1, SEQ ID NO: 3, and SEQ ID NO: 4 are shown. Residue numbering corresponds to that of hTau 40 (SEQ ID NO: 8).

FIGS. 19A-19T. 3R Tau RT-QuIC analyses of CSF from PiD and OND cases. CSF samples (5 µl) from PiD (n=8; postmortem) and the designated other neurological disease (OND; n=11) cases including Alzheimer disease (AD; n=2), frontotemporal dementia (FTD; n=2), rapidly progress dementia (RPD; n=3), amyotrophic lateral sclerosis (ALS; n=1), cognitive decline (CD; n=2), and chronic inflammatory demyelinating polyneuropathy (CIDP; n=1) were analyzed by 3R Tau RT-QuIC. Pooled CSF samples from healthy individuals was used as a negative control. Traces from individual quadruplicate wells are plotted with ThT fluorescence units indicated in thousands. The fraction of the quadruplicate reaction wells with fluorescence readings exceeding the threshold is shown in parentheses.

FIGS. 20A-20F. The absence of SDS and presence of 0.5% KO brain homogenate in brain seed dilution buffer delayed tauopathy seed-independent (spontaneous) fibril formation of tau K19CFh substrate. Panels FIG. 20A-F show an average ThT fluorescence of four technical replicate wells with the designated concentration of TauKO brain homogenate in the dilution buffer with, or without, the addition of $10^{-3}$ dilution of PiD brain homogenate seed. Positive responses from the PiD sample were seen in all panels, while responses with TauKO brain homogenate alone were seen only in panels B, D, E and F, in which case they are the right trace in the panel. Comparison of the presence (FIG. 20B) and absence (FIG. 20A) of SDS in brain seed dilution buffer are shown. The results show that, of these concentrations, 0.5% KO was optimal for detecting the PiD-seeded reaction without spontaneous fibrillization of the K19CFh substrate in the presence of TauKO brain homogenate alone (FIG. 20C).

Figure 21A:
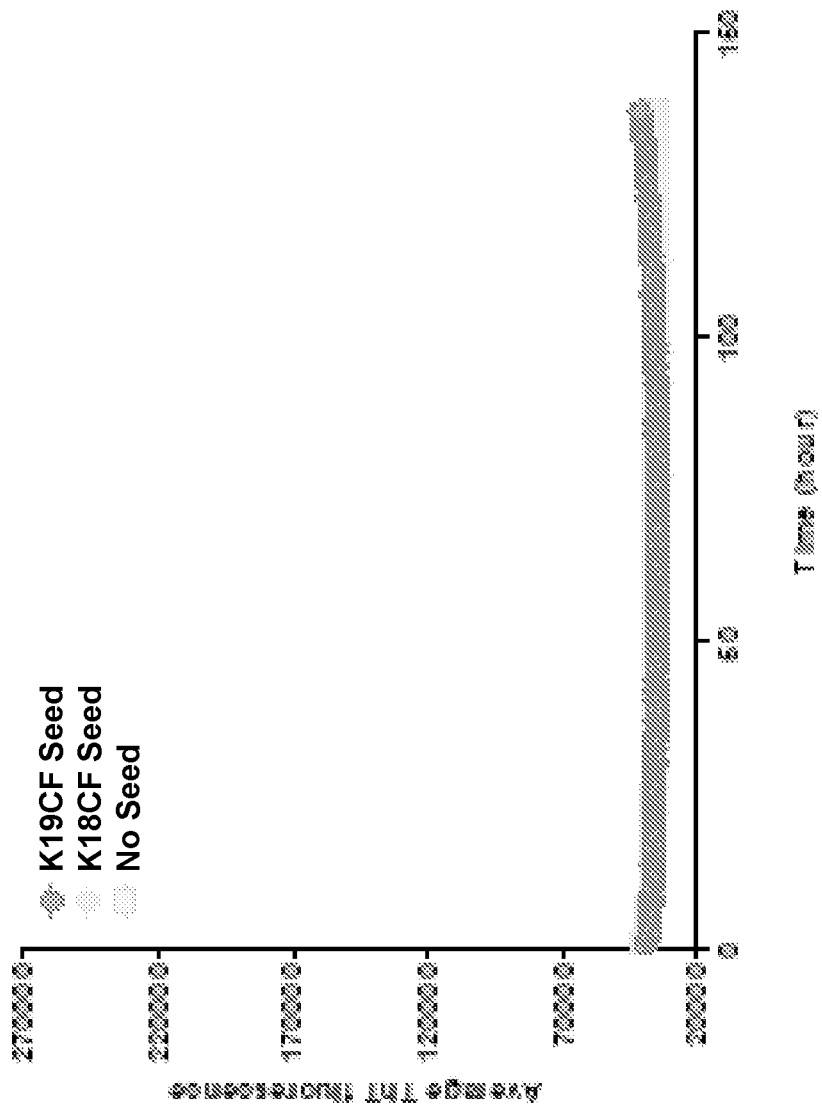
Figure 21B:
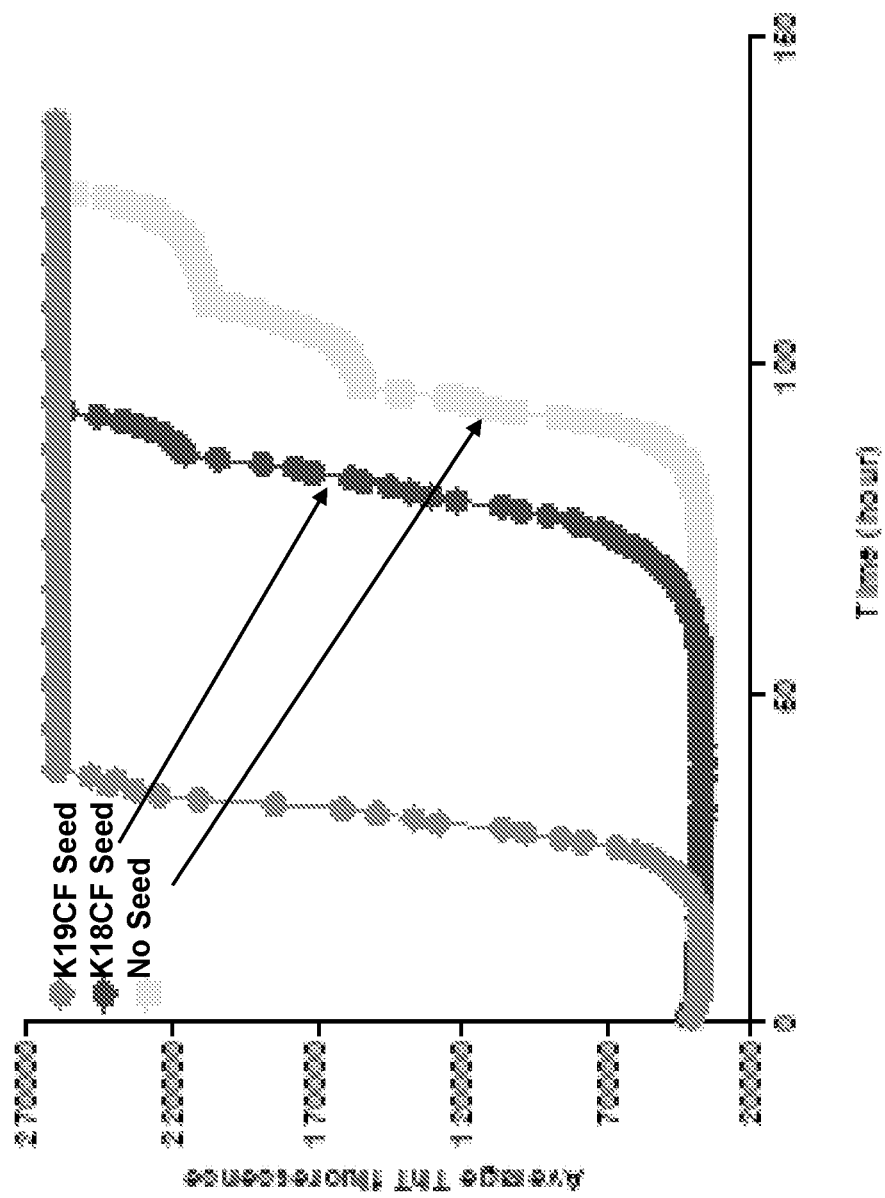
Figure 21C:
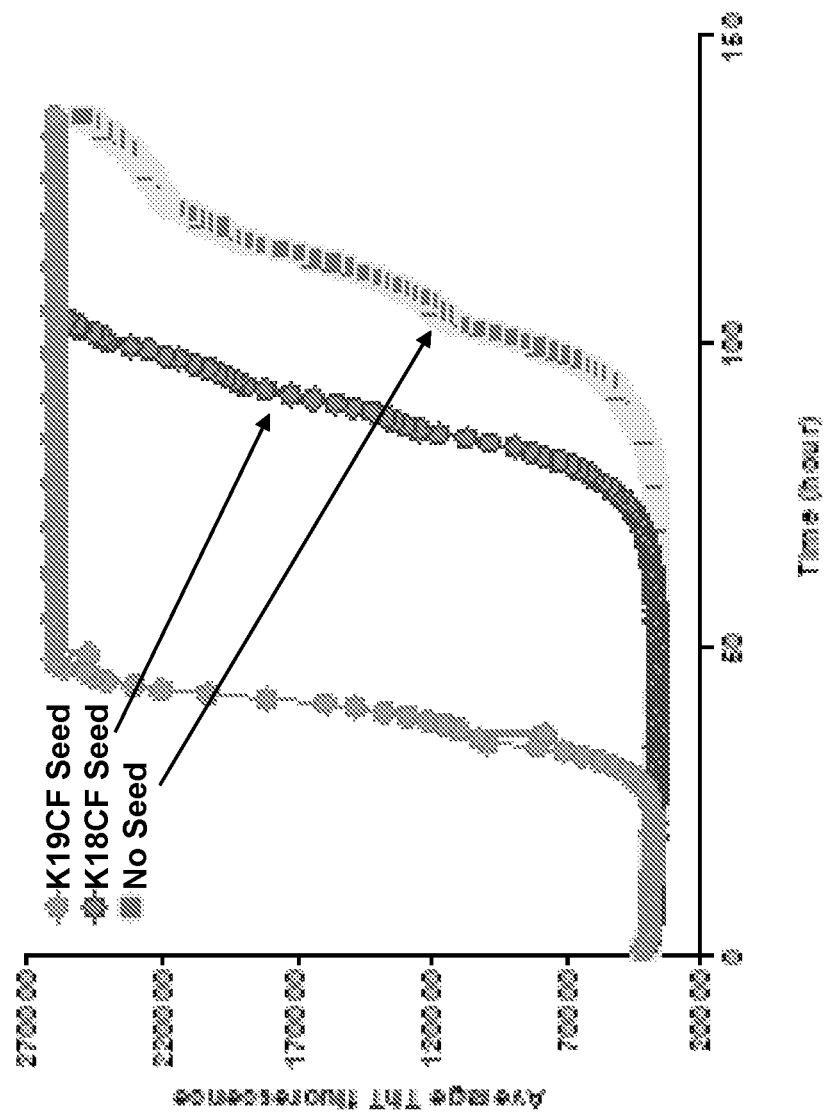
Figure 21D:
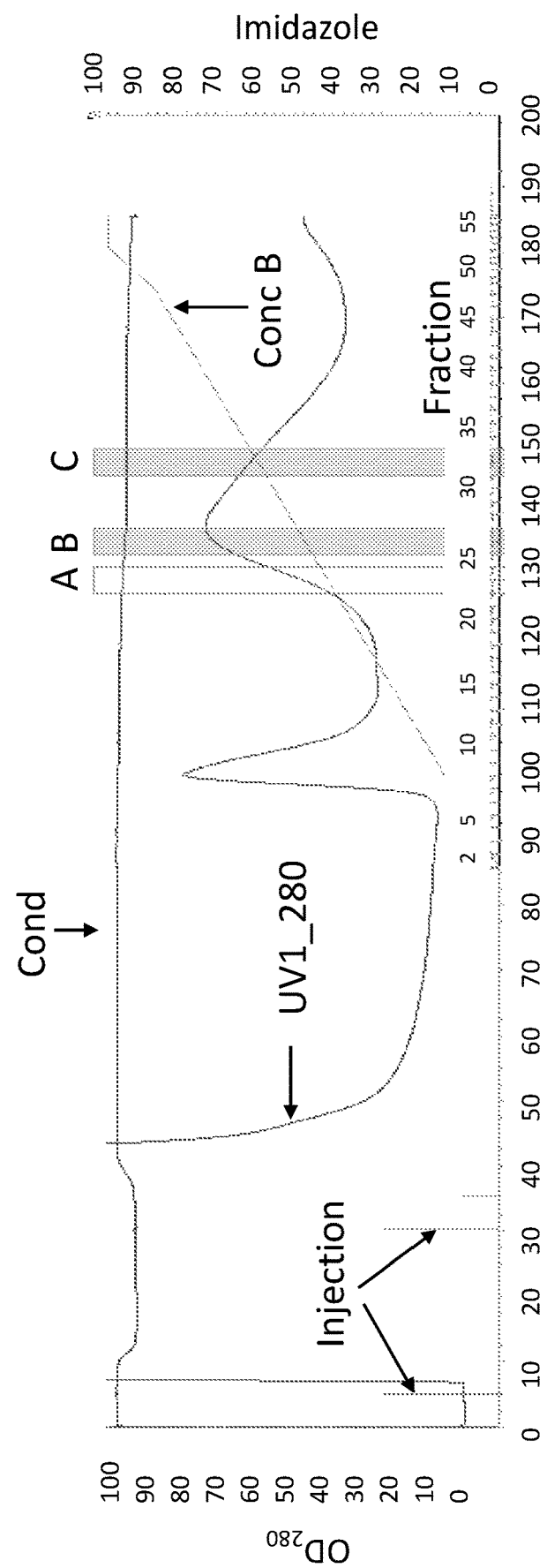
Figure 21E:
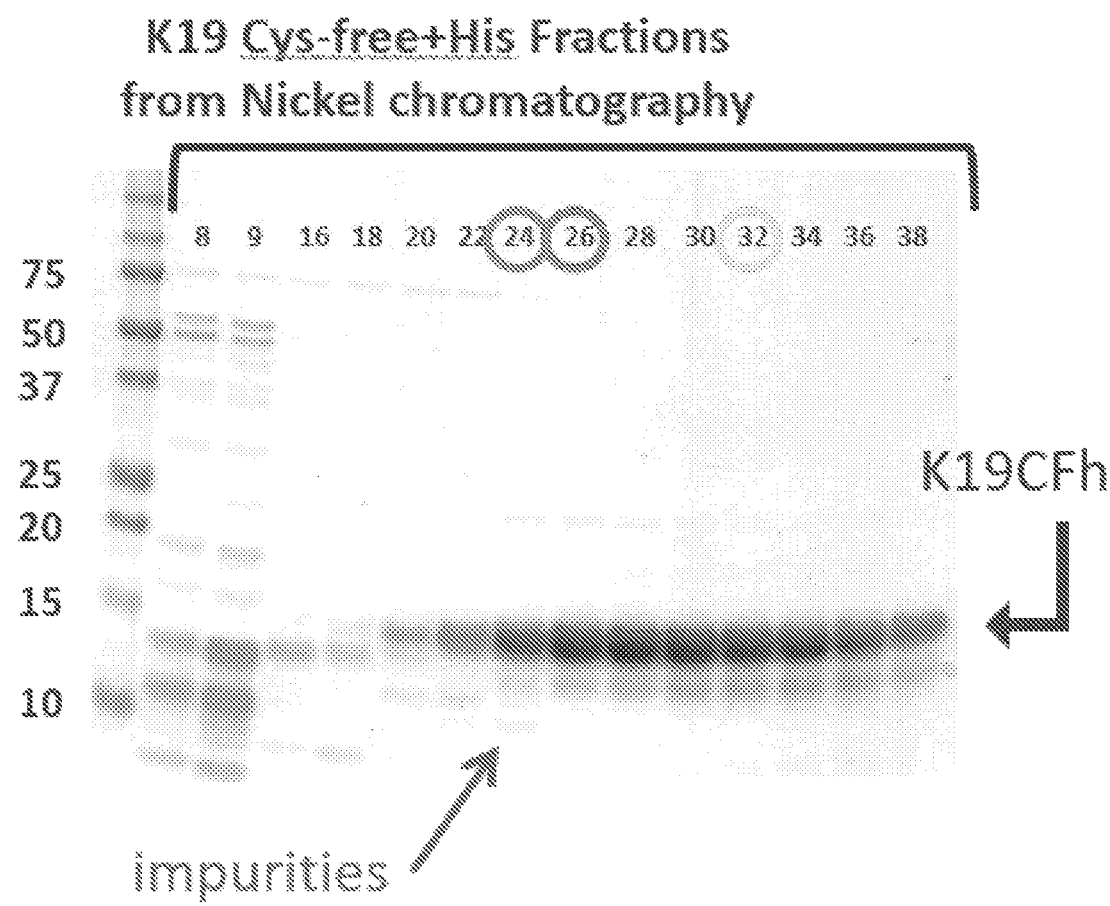

FIGS. 21A-21E. Purification of K19CFh with a nickel chromatography protocol. Recombinant Tau K19CFh was purified by nickel affinity chromatography with a standard linear gradient from 5 to 200 mM imidazole (FIG. 21D). Fractions were analyzed on SDS-PAGE with Coomassie blue staining for protein, and a blue arrow indicates recombinant Tau K19CF that either contained or lacked the 6-histidine tag (FIG. 21E). FIG. 21A-C show data of Tau RT-QuIC using different fractions from the K19CFh elution peak. FIG. 21A shows no detection of Tau seeding activity by Tau RT-QuIC with K19CFh fraction A (yellow in FIG. 21D; fraction 24 in FIG. 21E), including impurities (red arrow in FIG. 21E). However, Tau RT-QuIC was able to detect Tau seeding activity with either K19CFh fraction B (pink in FIG. 21D and fraction 26 in FIG. 21E) or C (blue in FIG. 21D and fraction 32 in FIG. 21E). These results demonstrated that the standard nickel affinity chromatography protocol was improved to consistently provide adequate supplies of K19CFh to perform Tau RT-QuIC.

FIGS. 22A-22F. 3R Tau RT-QuIC seeding activity in synthetic K19CF amyloid. The designated dilutions of a 25 μM (monomer equivalent) preparation of K19CF amyloid fibrils formed in vitro were used to seed quadruplicate Tau RT-QuIC reactions with each reaction at a given seed dilution shown as a separate trace (FIG. 22A-C). Simultaneous negative control reactions were given KO (FIG. 22D) or SC (FIG. 22E) brain homogenates and positive control reactions were seeded with a PiD (FIG. 22F) brain homogenate. ThT fluorescence units are indicated in thousands. Synthetic Tau seed was generated in HEPES-buffered saline solutions containing low molecular weight heparin (methods disclosed in Dinkel et al., *Biochemistry* 50, 4330-4336 (2011), incorporated herein by reference).

FIG. 23A-23I. End-point dilution 3R Tau RT-QuIC analysis of two PiD CSF samples. To assess the concentration of seeding activity in two cases of PiD CSF samples, 5 μl of neat CSF and $10^{-1}$ and $10^{-2}$ dilutions thereof were tested in 3R Tau RT-QuIC (PiD 2; FIG. 23A-C and PiD 7; FIG. 23D-F). Neat CSF samples from rapidly progress dementia (RPD), cognitive decline (CD) and healthy (blue) cases were included as negative controls. Traces from individual quadruplicate wells are plotted with ThT fluorescence units indicated in thousands. The fraction of the quadruplicate reaction wells with fluorescence readings exceeding the threshold described in the Examples section is shown in parentheses.

Figure 24A:
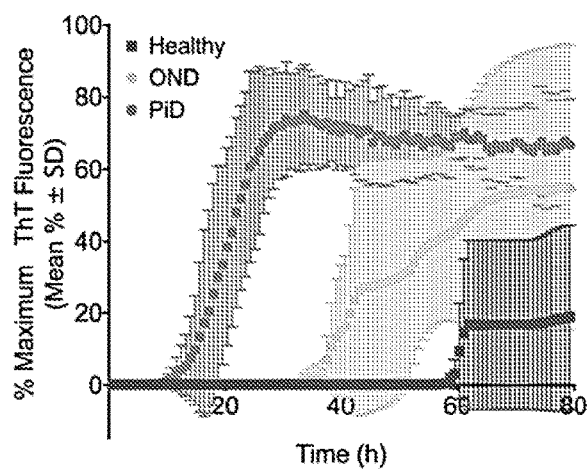
Figure 24B:
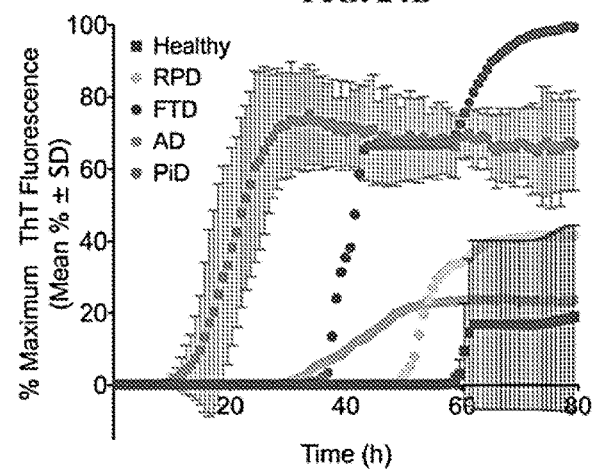
Figure 24C:
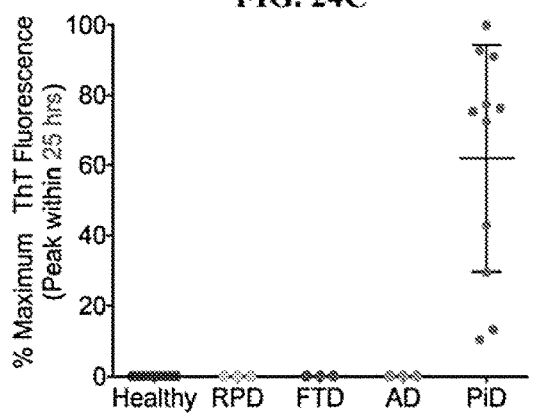
Figure 24D:
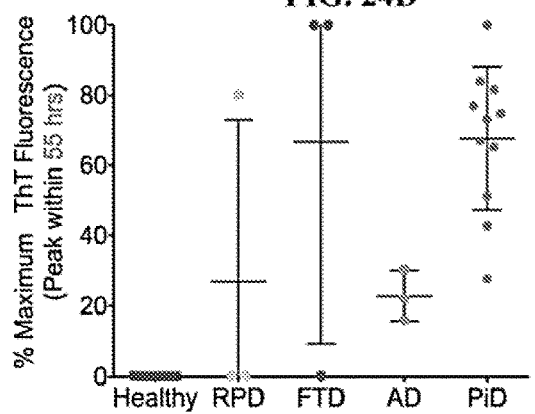

FIG. 24A-24D. Combined 3R Tau RT-QuIC data from two experiments analyzing CSF samples from PiD, OND and healthy cases. CSF samples (20 μl) from PiD (n=3) and other neurological disease (OND, n=3) cases including single cases of rapidly progressive dementia (RPD), frontotemporal dementia (FTD) and Alzheimer disease (AD) were analyzed by Tau RT-QuIC. Pooled CSF samples from healthy individuals was used as a negative control. FIGS. 24A, 24B show the overall mean (+/−SD) of the individual mean fluorescent readings from triplicate or quadruplicate reactions obtained from two experiments as a function of reaction time. FIGS. 24C, D shows relative % maximum fluorescence values (normalized between experiments against a positive control as described in Materials and Methods, +/−SD) for each specimen tested in the designated experiments. At the 25-h time point (FIG. 24C), the differences between the PiD and non-PiD (OND and healthy) responses were highly significant [p<0.0001, unpaired t tests], thus it discriminates PiD from non-PiD cases. At the 55-h time point (FIG. 24D), the differences between the healthy and PiD or AD responses were highly significant [p<0.0001, unpaired t tests]; further, the differences between the healthy and FTD is also significant [p<0.01, an unpaired t test]. Statistical analysis was performed using values from each individual replicate in each experiment.

FIG. 25A-L. 4R Tau RT-QuIC analysis of Tau seeding activity in designated dilutions ($10^{-3}$-$10^{-8}$) of a corticobasal degeneration (CBD) brain specimen. For comparison, $10^{-3}$ dilutions of sporadic Alzheimer (sAD, n=2), argyrophilic grain disease (AGD, n=2), non-Tauopathy senile change (SC) and Tau-free (KO). All but KO brain samples are from human patients. KO is from a Tau knockout mouse. Traces from individual quadruplicate reactions are shown. For CBD, the end-point dilution containing a seeding dose eliciting positive responses in half of replicate reactions ($SD_{50}$) is between $10^{-6}$ and $10^{-7}$ dilution of this CBD brain tissue.

Figure 26:
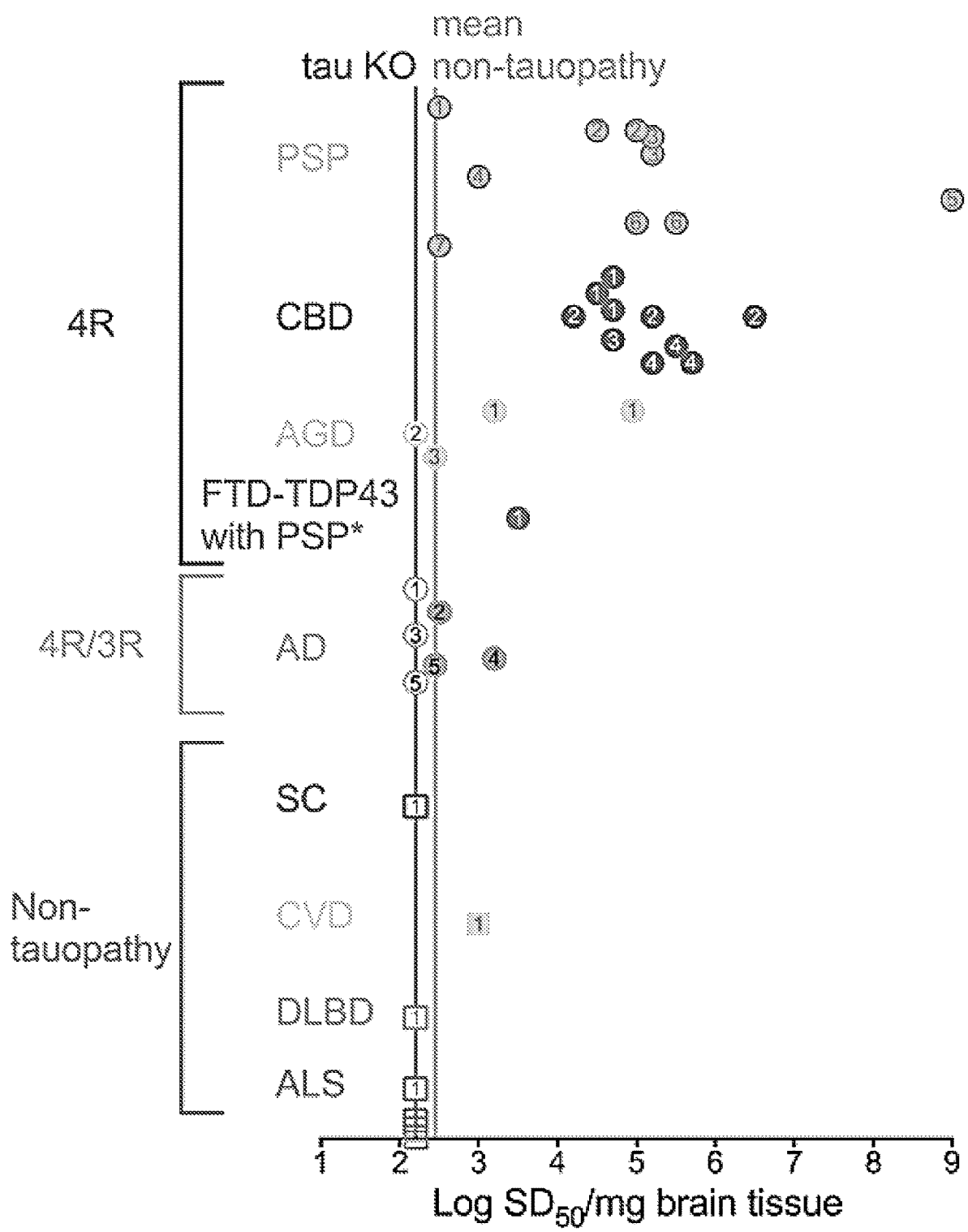

FIG. 26. End-point dilution quantitation of Tau seeding activity using 4R RT-QuIC (H+PLG). Data points indicate $SD_{50}$ concentration determinations from individual end-point dilution series with 4 replicate reactions at each brain tissue dilution (like the CBD example shown in FIG. 25A-25F). Numbers corresponding to individual patients is given within each symbol. Filled symbols indicate samples giving positive Tau RT-QuIC reactions. Open symbols indicate samples giving no positive reactions. *Designated as a 4R Tauopathy based on a secondary diagnosis of PSP. The left Tau KO vertical line indicates the detection limit established by analysis of Tau-free mice. The right line (labeled "mean non-Tauopathy") indicates the mean of the mean log $SD_{50}$/mg values obtained from cases that were negative for Tau pathology by immunohistochemical analysis of brain.

Figure 27:
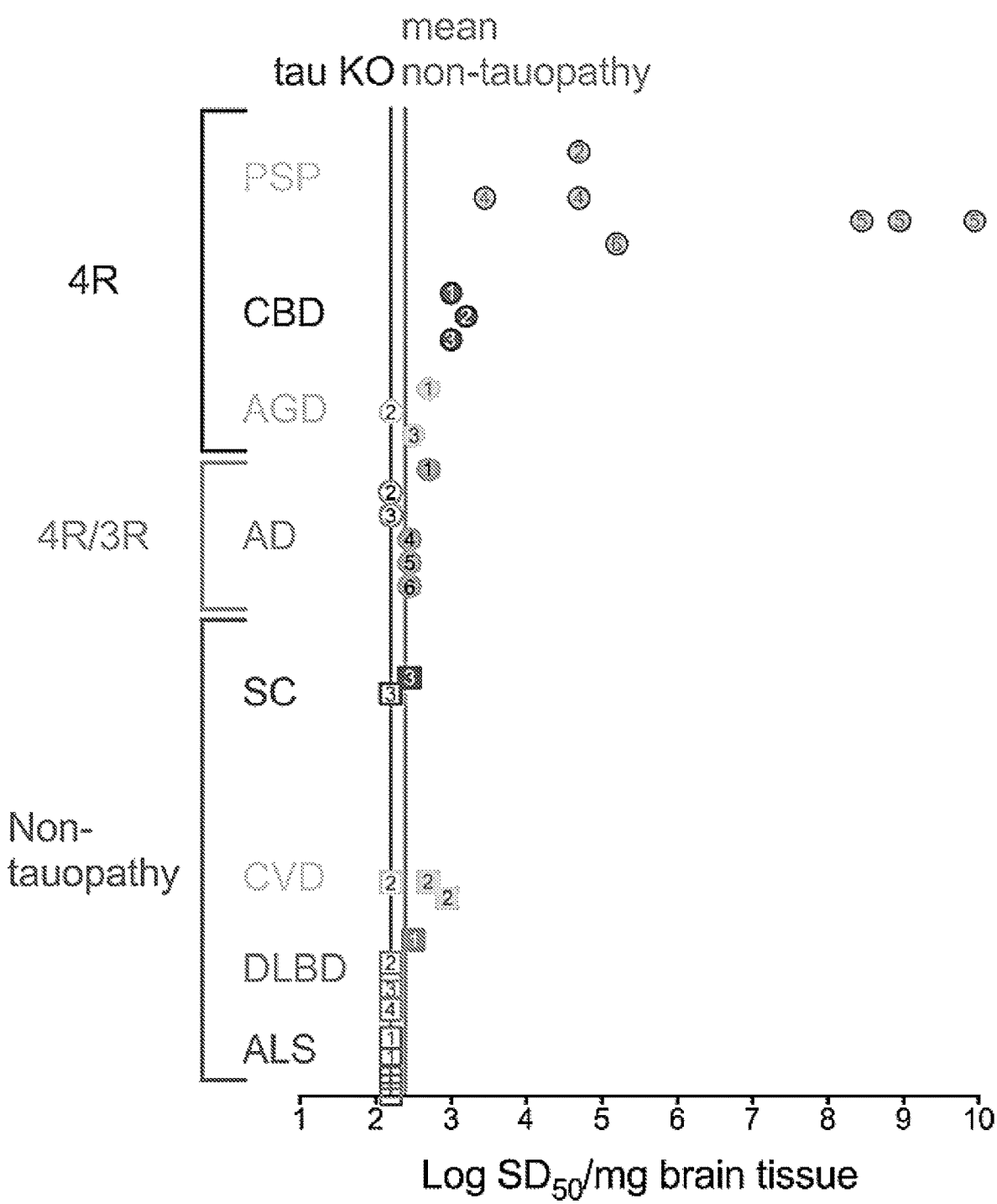
Figure 29A:
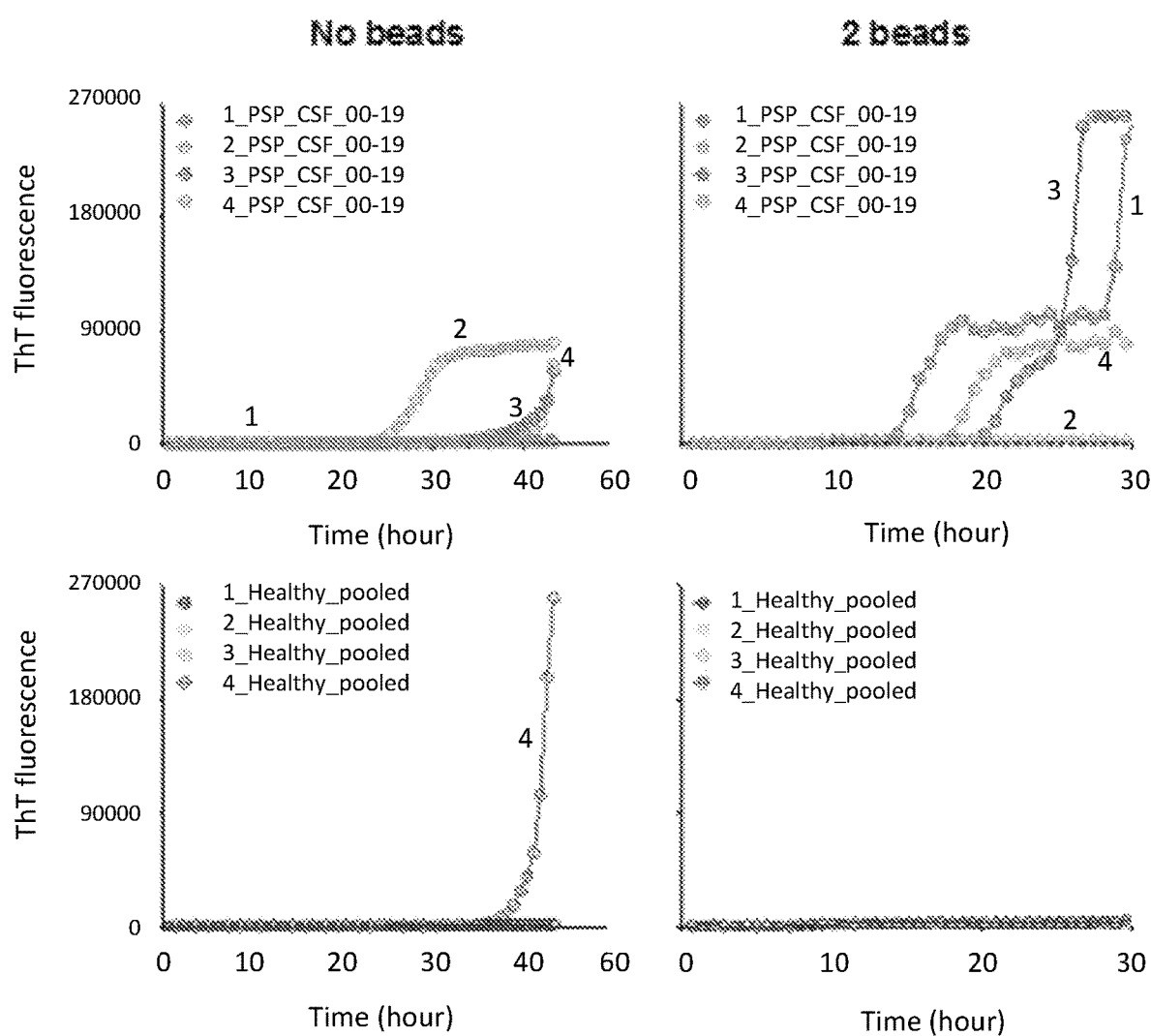
Figure 29B:
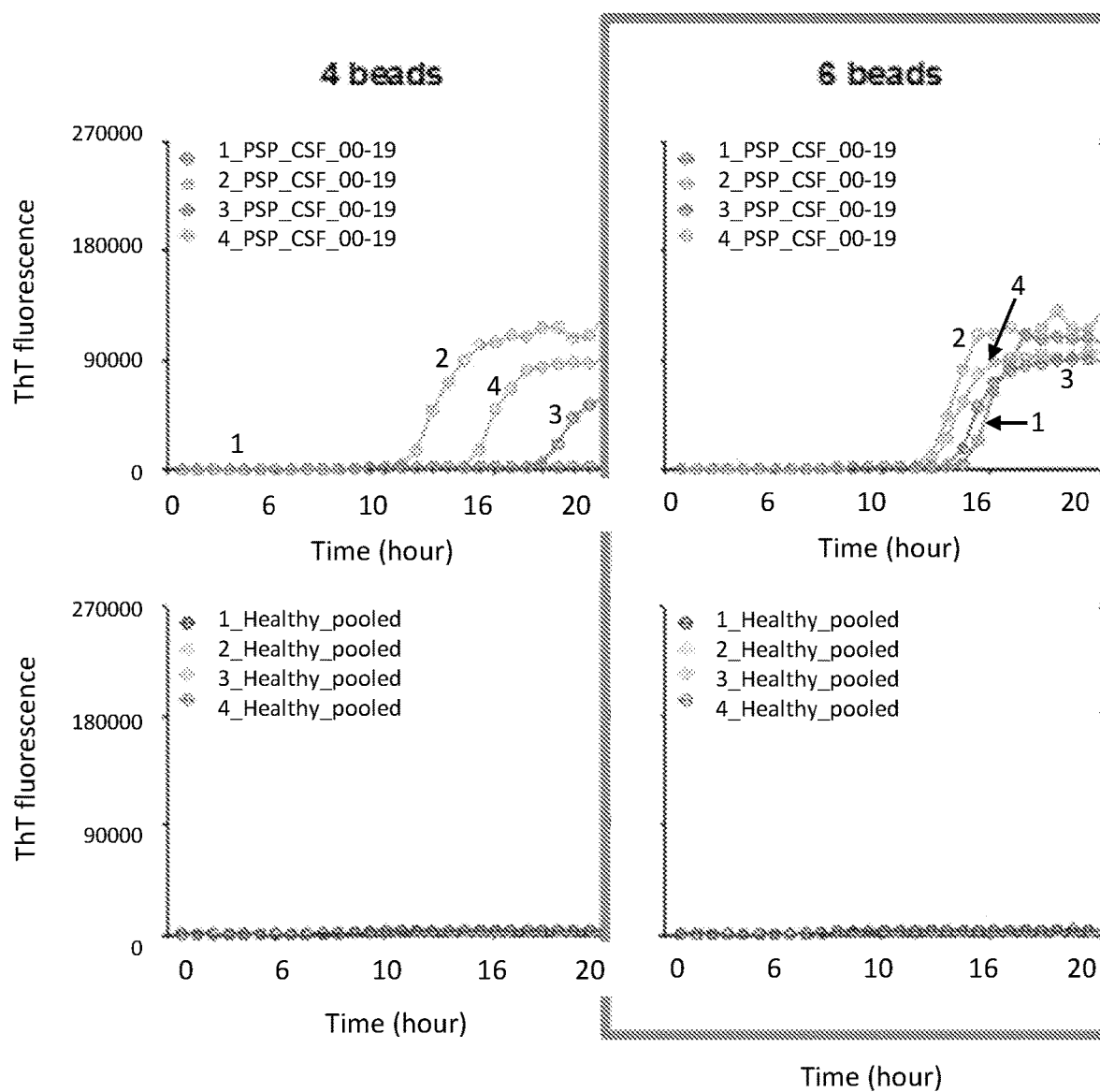
Figure 29C:
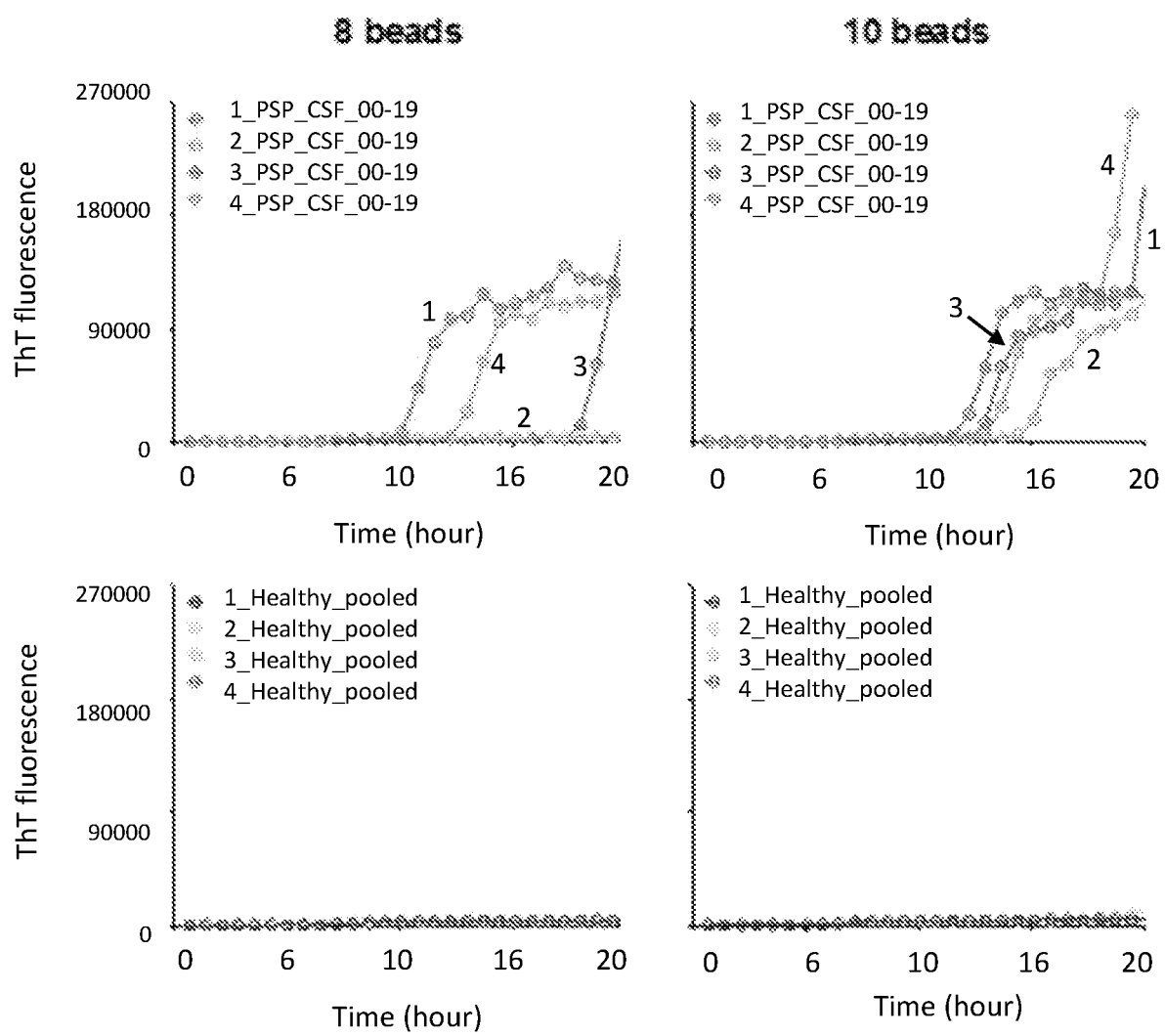
Figure 29D:
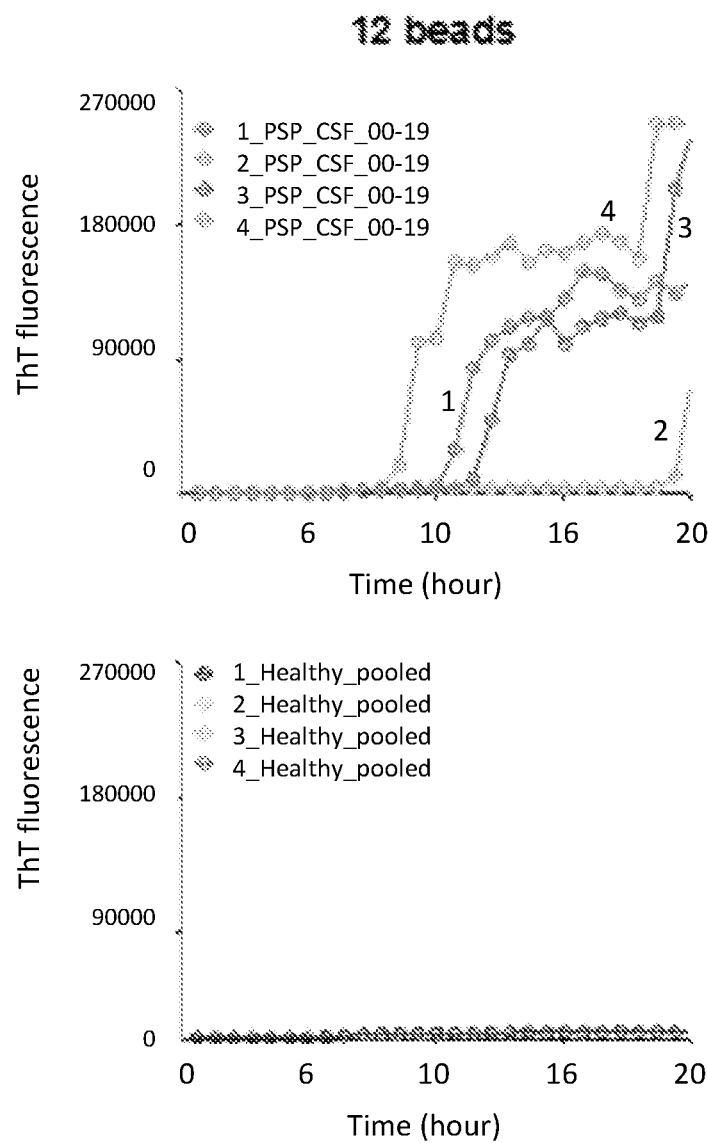
Figure 30A:
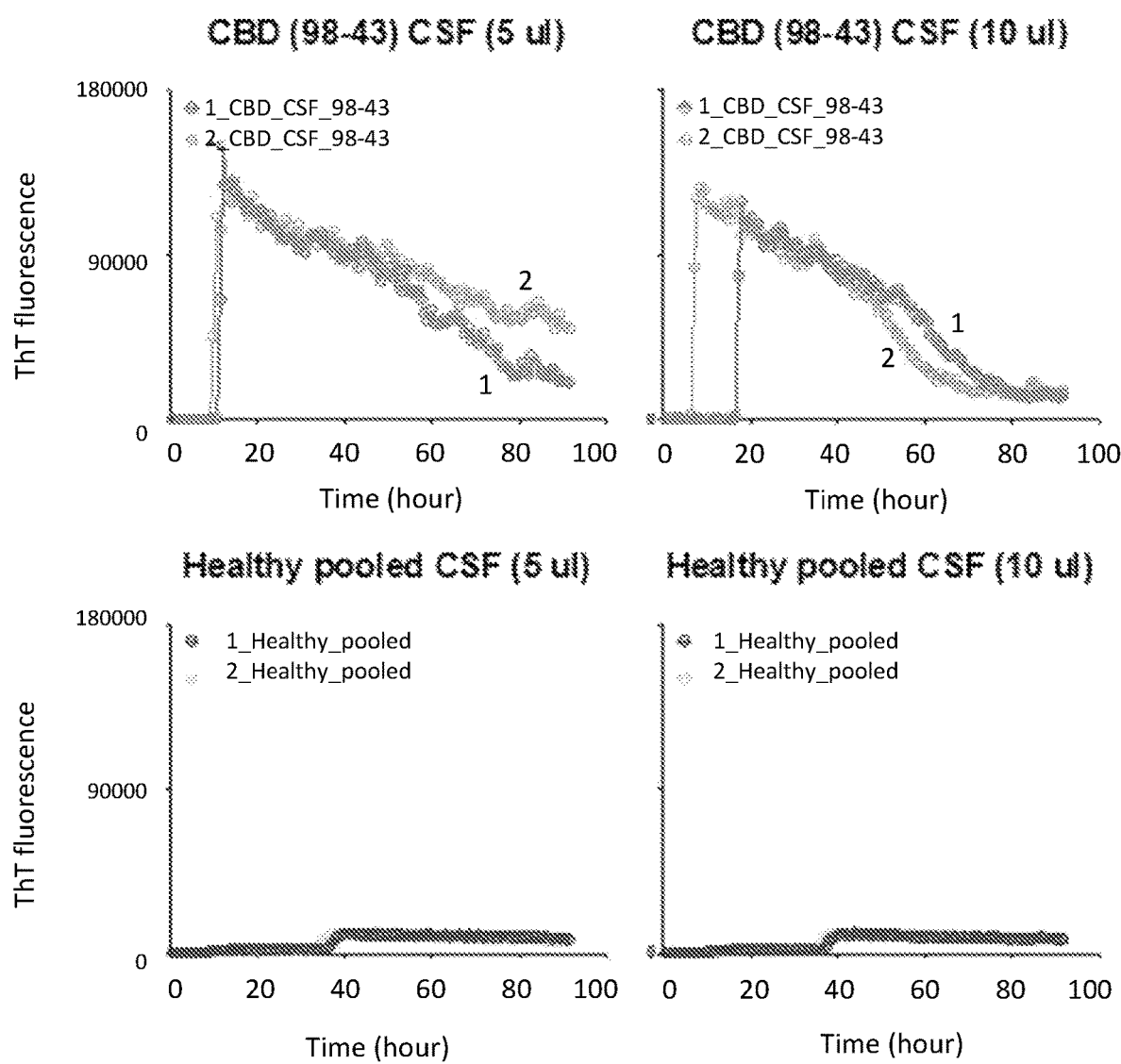
Figure 30B:
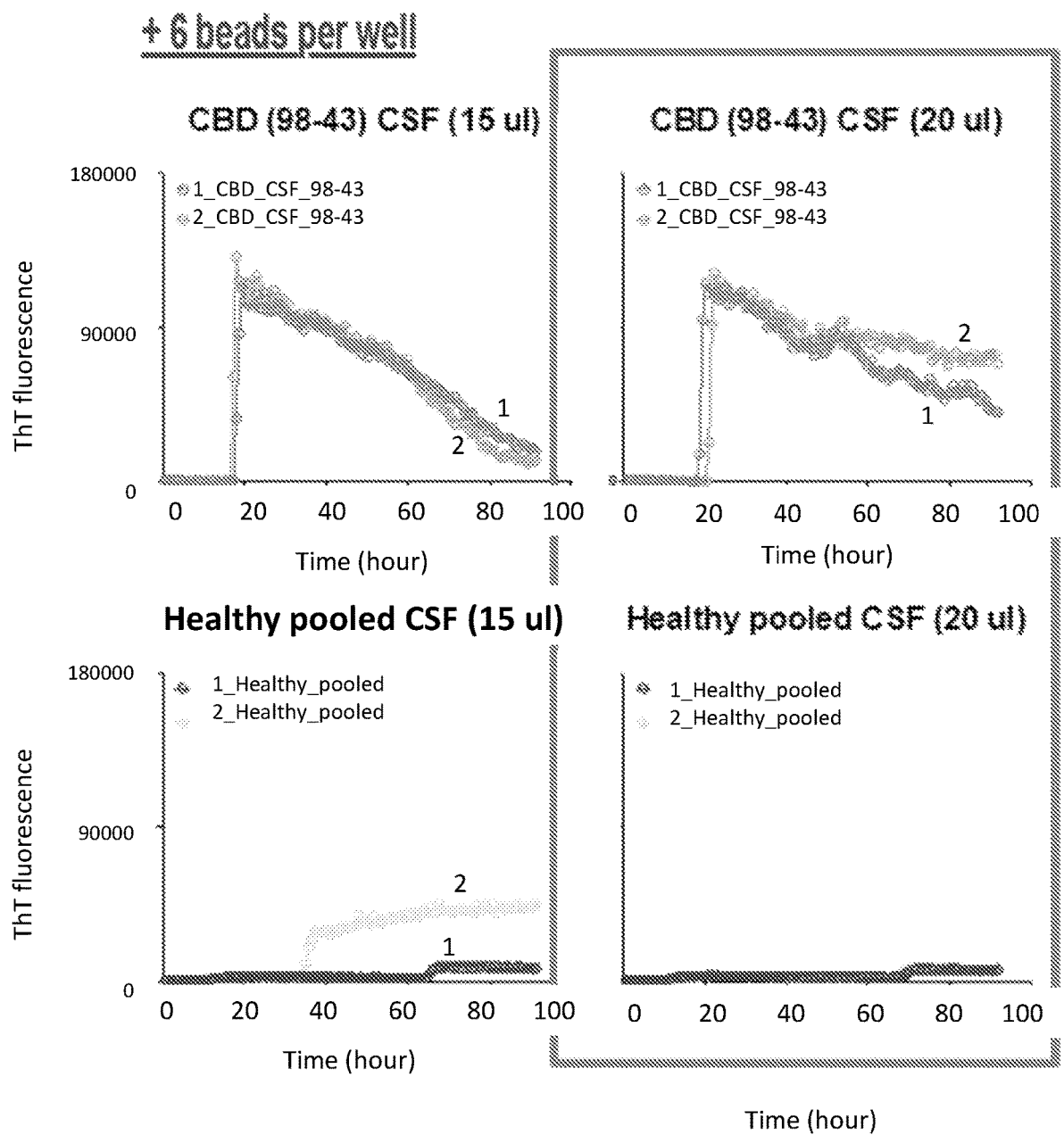
Figure 30C:
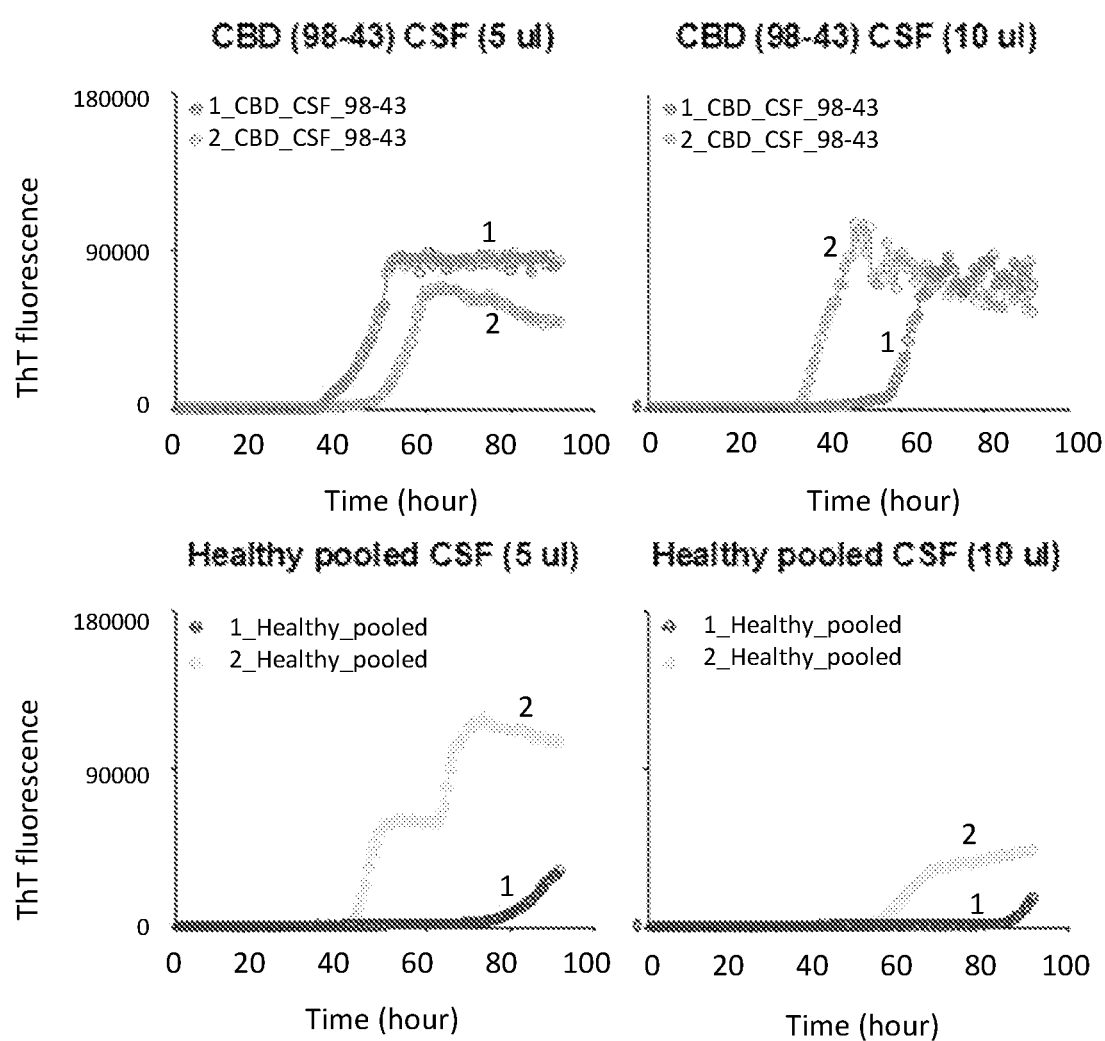
Figure 30D:
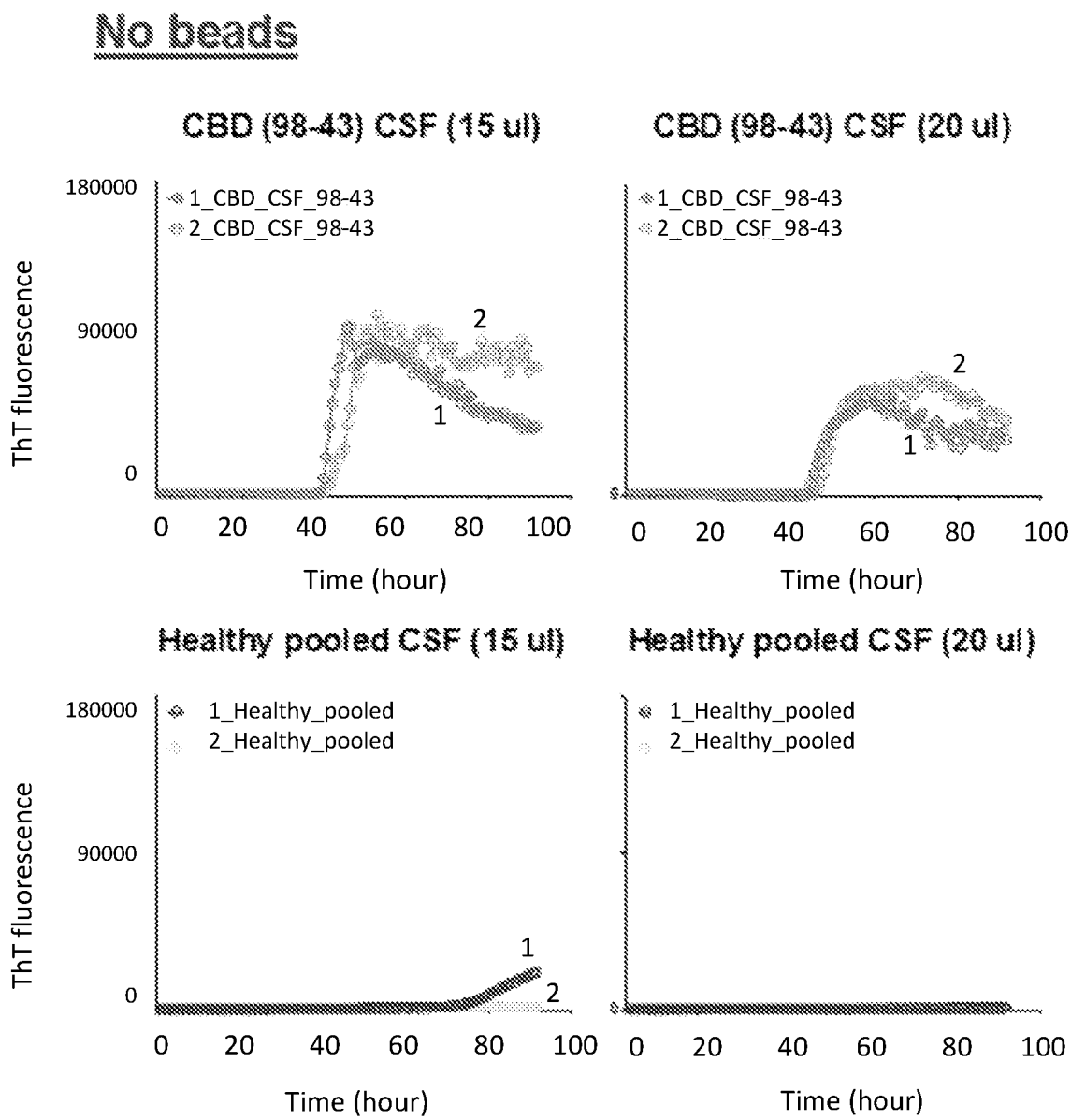
Figure 31E:
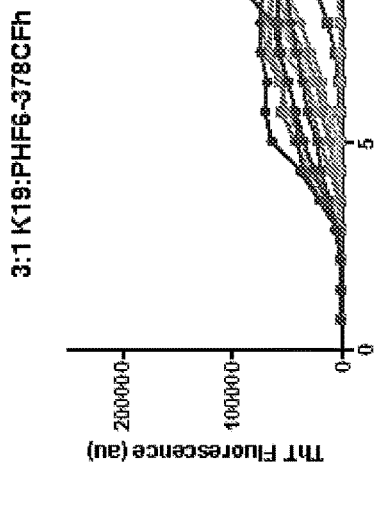
Figure 31F:
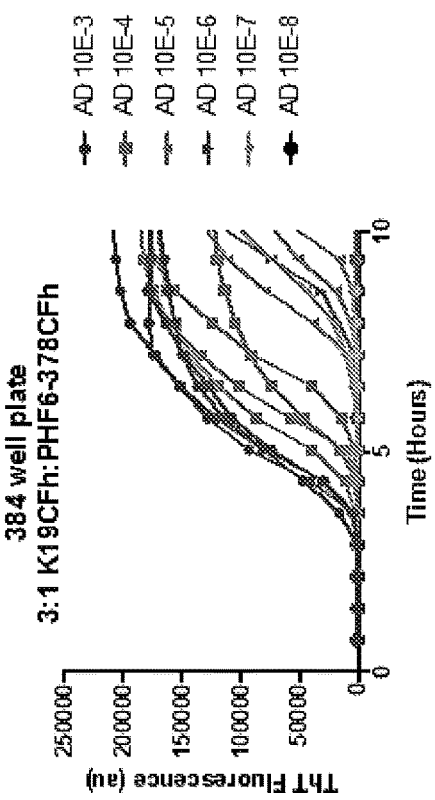
Figure 31G:
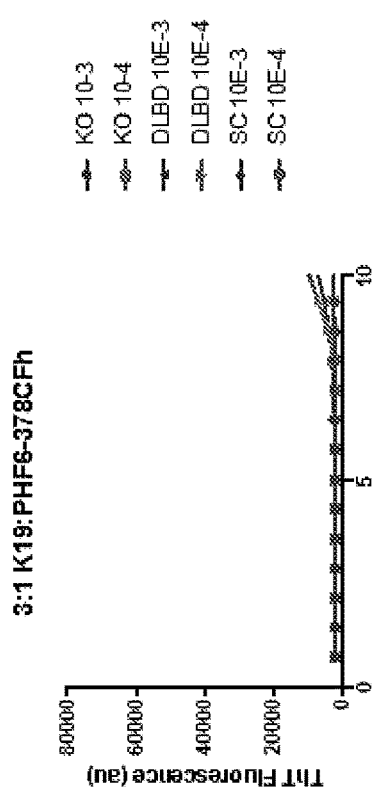
Figure 31H:
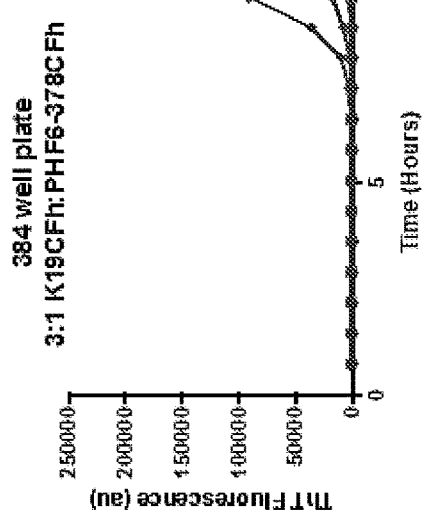
Figure 31I:
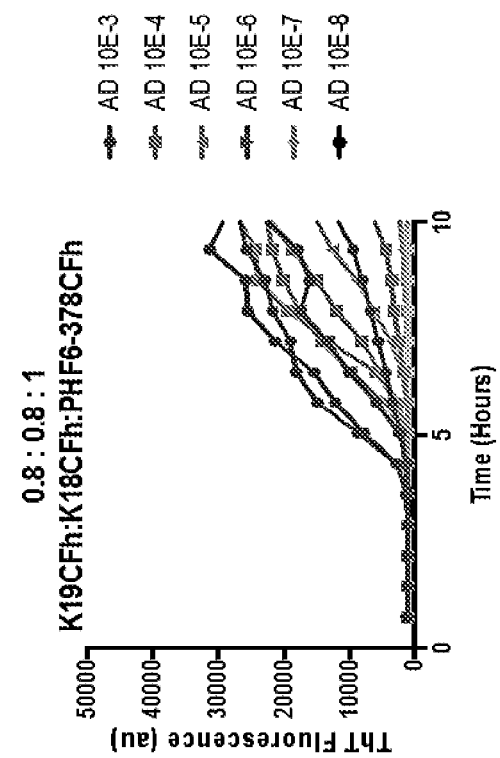
Figure 31J:
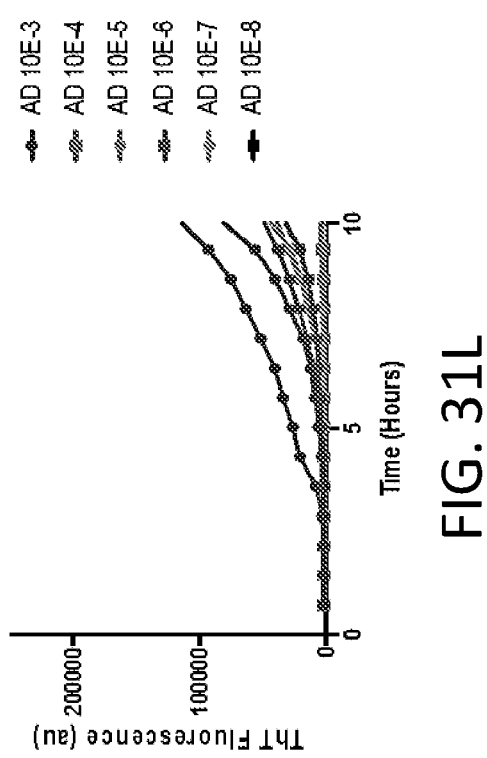
Figure 31K:
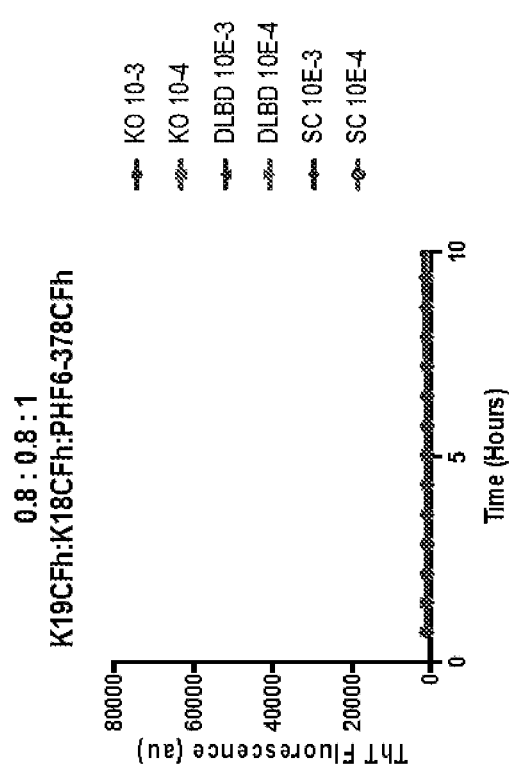
Figure 31L:
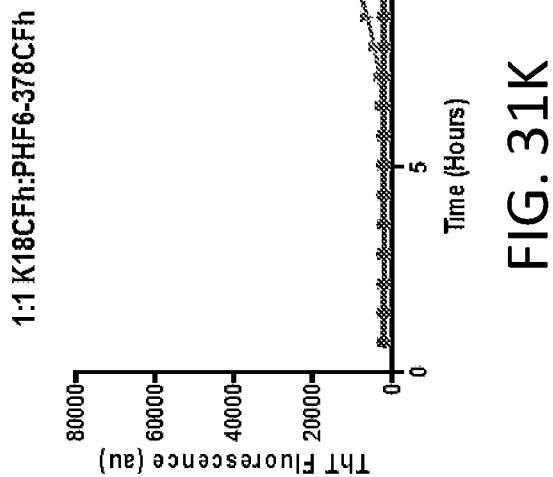

FIG. 27. End-point dilution quantitation of Tau seeding activity using 4R RT-QuIC (H). Data points indicate $SD_{50}$ concentration determinations from individual end-point dilution series with 4 replicate reactions at each brain tissue dilution (for example, the CBD experiments shown in FIG. 25A-25F). Numbers corresponding to individual patients is given within each symbol. Filled symbols indicate samples giving positive RT-QuIC reactions. Open symbols indicate samples giving no positive reactions.

FIG. 28. Table providing the endpoint quantification of Tau seeding assay in brain tissue.

FIGS. 29A-29D. Effect of glass beads on 4R Tau RT-QuIC assay with heparin. Traces from individual quadruplicate reactions are plotted with ThT fluorescence units. Top row: Seeded with PSP postmortem CSF (5 µl per reaction). Bottom row: Seeded with healthy (non-Tauopathy) pooled antemortem CSF.

FIGS. 30A-30D. Effect of glass beads on 4R Tau RT-QuIC assay with heparin+polyglutamate seeded with 5-20 µl CSF per reaction. Traces from individual quadruplicate reactions are plotted with ThT fluorescence units. Top row: Seeded with CBD postmortem CSF. Bottom row: Seeded with healthy (non-Tauopathy) pooled antemortem CSF.

FIG. 31A-31L. Alzheimer disease brain-seeded Tau RT-QuIC reactions using PHF6-378CFh alone (A & B) or with different molar ratios of K19CFh and/or K18CFh (C-L). Quadruplicate reactions were given the designated dilutions of brain tissue (in the form of homogenates) from Alzheimer disease (AD) (B, D, F, H, J, L) or control decedents (A, C, E, G, I, K), the latter including those derived from mice completely lacking all Tau isoforms (KO), and humans with diffuse Lewy body disease (DLBD), a synucleinopathy, or senile change (SC), with neuropathological lesions but no histologically apparent Tau pathology. The substrate molecules and their molar ratios are indicated above each graph. These results demonstrate that under each of these reaction conditions, there are more rapid ThT fluorescence increases in reactions seeded with dilutions of AD brain tissue, in some cases as low as $10^{-5}$-$10^{-6}$. Assay cutoff times are established when ThT-fluorescence is significantly increased above starting values with control decedent samples, with a positive AD sample giving ThT fluorescence increases before the assay cutoff time determined with controls. Assay conditions in E-L show nearly comparable results in 96 well (E, F, I-L) or 384 well plates (G&H), the latter containing half the total reaction volume. Traces from individual quadruplicate reactions are shown. PHF6-378CFh is an N-terminal 6× histidine tag on a fragment of the human Tau sequence spanning from the PHF6 domain to residue 378, Cys-free, see SEQ ID NO: 43.

FIG. 32A-32F. Mixed substrate ratios (3:1 K19CFh:PHF6-378CFh) improve the detection of AD. A&B) The lag time between ThT fluorescence increases in the presence of AD brain homogenates versus non-Tauopathy controls (CVD, DLBD, KO) is significantly increased when a 3:1 K19CFh:PHF6-378CFh mixed substrate ratio is used (B, D, F) compared to the use of PHF6-378CFh alone (A, C, E). *p<0.05, *p<0.001, **p<0.0001. p values were determined by one-way ANOVA with Tukey's post hoc analysis.

Figure 33A:
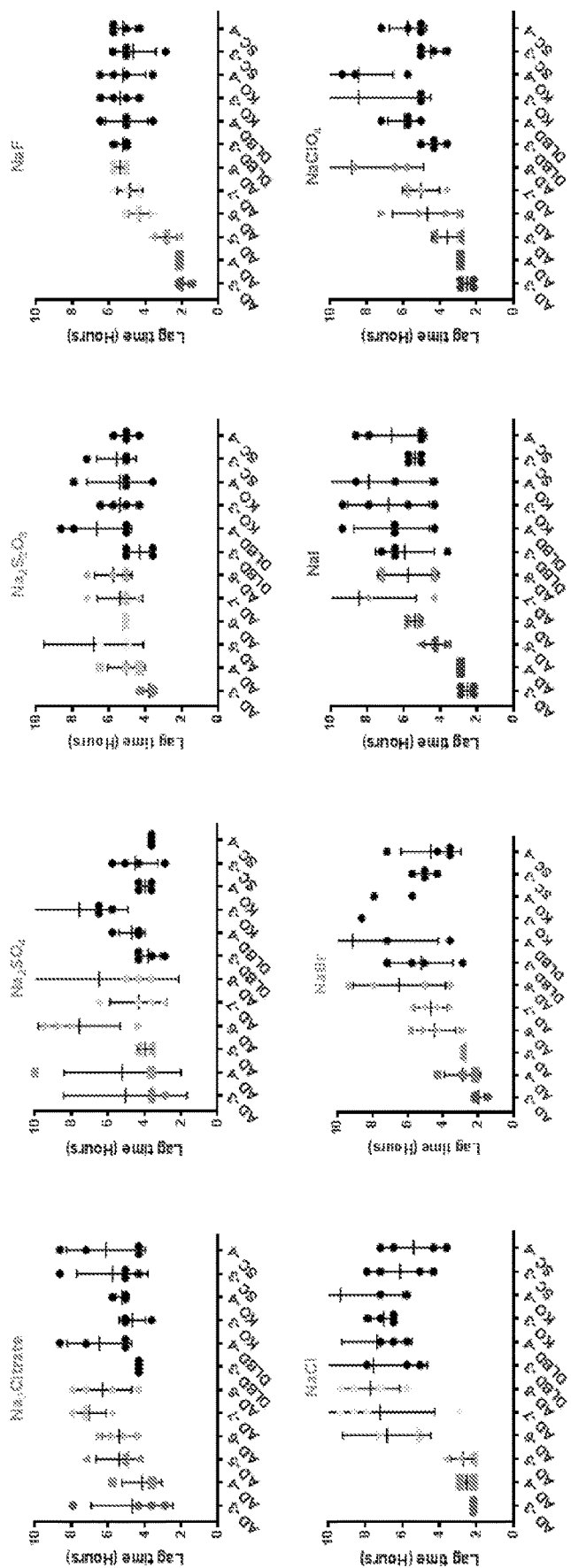
Figure 33B:
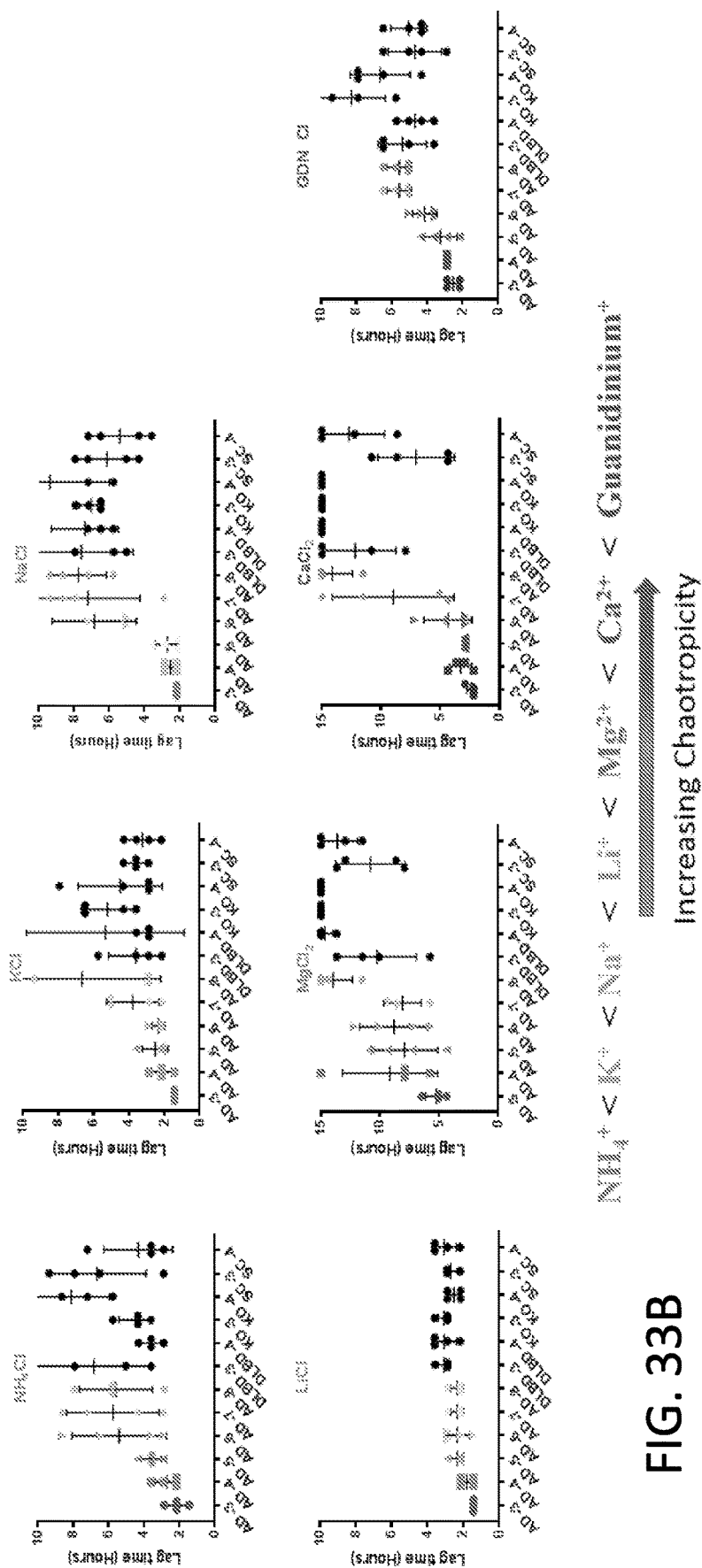
Figure 34E:
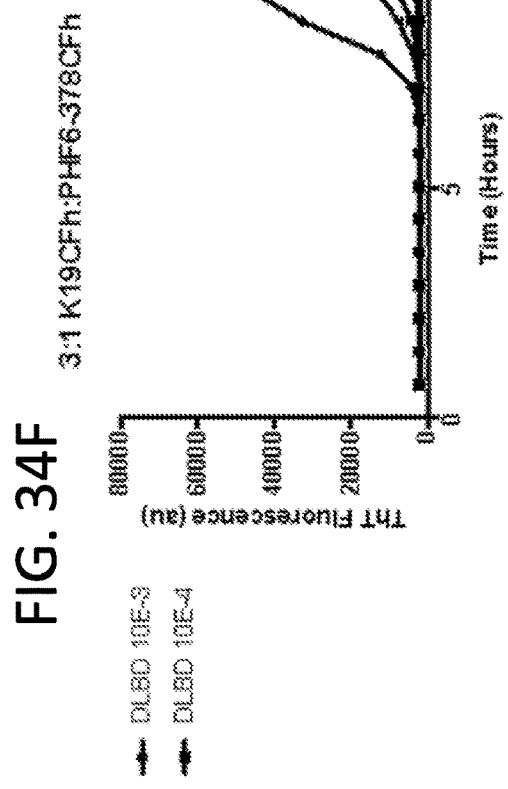
Figure 34F:
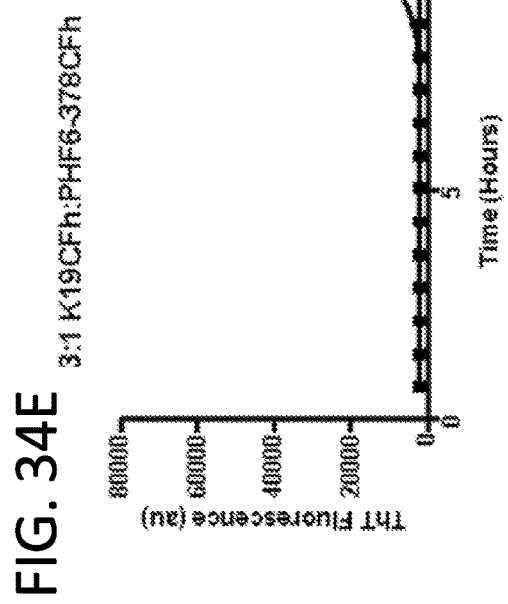
Figure 34G:
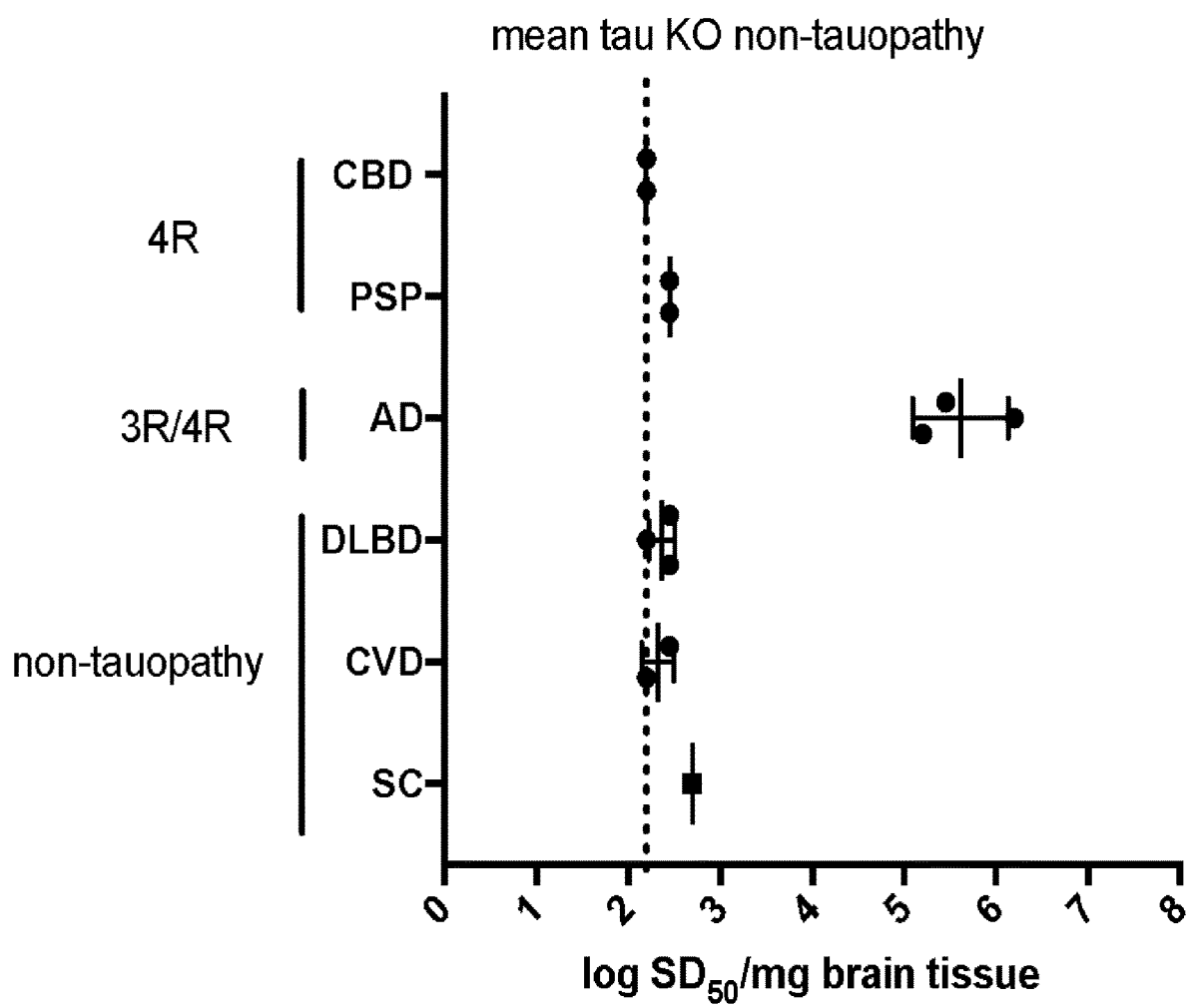
Figure 35E:
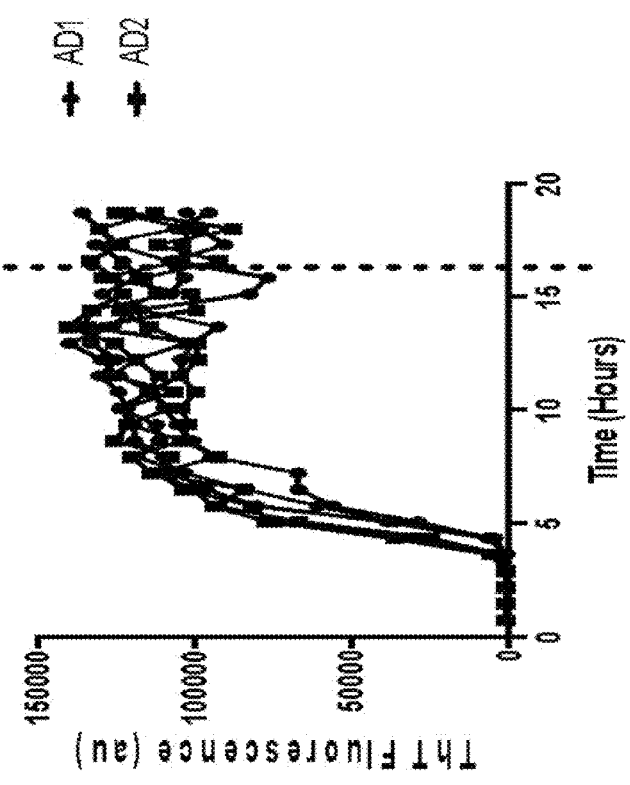
Figure 35F:
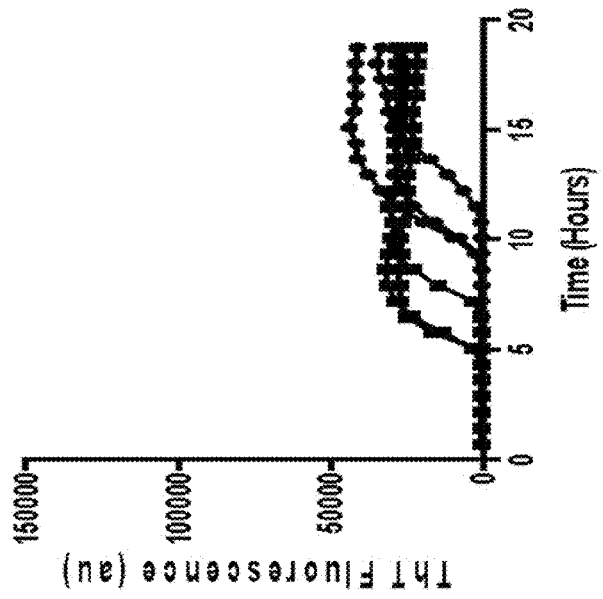

FIG. 33A-33B. Use of different salts to enhance the differentiation between Tau RT-QuIC reactions in the presence AD brain homogenate samples compared to reactions in the presence of non-Tauopathy controls (DLBD, KO, SC). Data points represent individual wells in a 50 µL reaction, 384-well Tau RT-QuIC experiment (500 rpm orbital shaking, 1 mM shake, 1 min rest, with fluorescence reads every 45 mM) containing 4 µM PHF6-378CFh substrate, 200 mM salts, 80 µM heparin, 10 mM ThT, 10 mM HEPES buffer at pH 7.4. Lag time was calculated as the time at which ThT fluorescence values exceeded a threshold equal to 100× standard deviation of the baseline of quadruplicate wells. Reactions in the presence of AD brain homogenates are grey while reactions with non-Tauopathy samples are black. Differentiation between AD-seeded and non-AD-seeded fibrillization is enhanced in the presence of chaotropic salts. Specific chaotropic salts (NaF, GDN-Cl) enhance the fidelity of the reactions in the presence of AD brain homogenates (i.e. decrease the standard deviation, compare NaF, GDN-Cl error bars versus NaCl, NaI, NaClO$_4$). Overall, the use of a chaotropic salt (one containing Cl$^-$, F$^-$, Br$^-$, I$^-$, ClO$_4^-$, Mg$^{2+}$, Ca$^{2+}$) and not a kosmotropic salt (one containing Citrate$^{3-}$, SO$_4^{2-}$, S$_2$O$_3^{2-}$, NH$_4^+$, K$^+$) enhances distinction of AD-seeded versus non-AD-seeded reactions. Note the scale difference of MgCl$_2$ and CaCl$_2$ as these salts prolonged negative controls beyond 15 hours.

FIG. 34A-34G. Mixed substrate ratios (3:1 K19CFh:PHF6-378CFh) allow differentiation of AD (a 3R/4R Tauopathy) from 4R Tauopathies (including PSP and CBD). These results demonstrate that under each of these reaction conditions, there are more rapid ThT fluorescence increases in reactions seeded with dilutions of AD brain tissue (B), in some cases as low as $10^{-5}$, compared to any increases in ThT fluorescence with non-Tauopathy brain homogenates (A,C, E) and 4R brain homogenates (D, F). Each curve is an individual replicate well in a 96 well plate, with each sample being run in quadruplicate. G) Using mixed ratios of K19CFh:PHF6-378CFh, we can detect $10^{-5}$-$10^{-6}$ dilutions from AD, but not from 4R diseased (CBD, PSP) or non-Tauopathy (DLBD, CVD, SC, KO). Responses from knock-out mouse (KO) brains at a $10^{-3}$ dilution provided Tau-free controls to establish a Tau-negative baseline (black dotted line). Data points represent the $\log_{10}$ SD$_{50}$/mg brain tissue for each case as estimated by Spearman-Karber analysis of a series (if necessary) of 10-fold dilutions, with 4 technical replicate reactions performed at each dilution. Data points for DLBD and KO were obtained from a single biological replicate, from quadruplicate wells with three independent experiments. The rest of the data points were determined from individual decedent samples, with each sample run in quadruplicate.

FIG. 35A-35F. CSF collected postmortem from AD decedents and antemortem from patients who were posthumously confirmed with AD gives more rapid increases in ThT fluorescence than antemortem CSF from healthy individuals. A) Analysis of antemortem CSF from a young patient (without detectable misfolded Tau, confirmed posthumously) and pooled CSF from healthy individuals using CaCl$_2$ as the salt. B) Analysis of antemortem CSF from a young patient and pooled CSF from healthy individuals using NaCl as the salt. The dotted line indicates the cut-off time of the assay. C) In the presence of CaCl$_2$, antemortem CSF from patient with posthumously confirmed AD does not result in increases in ThT fluorescence. By contrast, the use of NaCl salt D) allows antemortem CSF from patient with posthumously confirmed AD to give more rapid ThT fluorescence increases compared to healthy individuals in B). Post-mortem CSF from AD decedent results in more rapid ThT fluorescence increases in the presence of both E) CaCl$_2$ and F) NaCl compared to CSF from healthy individuals in A&B. The numbering indicates CSF samples from different patients/decedents, with each reaction run in triplicate. Traces from individual triplicate reactions are shown. The assay was set up in a 384 well plate, with one 800 µM silica bead per well.

SEQUENCE LISTING

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file Sequence_Listing.txt, Jun. 10, 2019, 109 KB, which is incorporated by reference herein. Tau residues specified in the sequence titles are numbered according to the full hTau40 sequence (SEQ ID NO:8).

One letter amino acid code is utilized in the listing below.

```
SEQ ID NO: 1 is the amino acid sequence of K19 Cys-Free (S322).
MQTAPVPMPD LKNVKSKIGS TENLKHQPGG GKVQIVYKPV DLSKVTSKSG

SLGNIHHKPG GGQVEVKSEK LDFKDRVQSK IGSLDNITHV PGGGNKKIE

SEQ ID NO: 2 is the amino acid sequence of K19.
MQTAPVPMPD LKNVKSKIGS TENLKHQPGG GKVQIVYKPV DLSKVTSKCG

SLGNIHHKPG GGQVEVKSEK LDFKDRVQSK IGSLDNITHV PGGGNKKIE

SEQ ID NO: 3 is the amino acid sequence of K18 Cys-Free (S291, S322 in bold).
MQTAPVPMPD LKNVKSKIGS TENLKHQPGG GKVQIINKKL DLSNVQSKSG

SKDNIKHVPG GGSVQIVYKP VDLSKVTSKS GSLGNIHHKP GGGQVEVKSE

KLDFKDRVQS KIGSLDNITH VPGGGNKKIE

SEQ ID NO: 4 is the amino acid sequence of K18 (cysteines in bold).
MQTAPVPMPD LKNVKSKIGS TENLKHQPGG GKVQIINKKL DLSNVQSKCG

SKDNIKHVPG GGSVQIVYKP VDLSKVTSKC GSLGNIHHKP GGGQVEVKSE

KLDFKDRVQS KIGSLDNITH VPGGGNKKIE

SEQ ID NO: 5 is the amino acid sequence of K12 (cysteine in bold).
MQTAPVPMPD LKNVKSKIGS TENLKHQPGG GKVQIVYKPV DLSKVTSKCG

SLGNIHHKPG GGQVEVKSEK LDFKDRVQSK IGSLDNITHV PGGGNKKIET

HKLTFRENAK AKTDHGAEIV YKSPVVS

SEQ ID NO: 6 is the amino acid sequence of K12A322 (A322 in bold).
MQTAPVPMPD LKNVKSKIGS TENLKHOPGG GKVQIVYKPV DLSKVTSKAG

SLGNIHHKPG GGQVFVKSEK LDFKDRVQSY IGSLDNITHV PGGGNKKIET

HKLTFRENAK AKTDHGAEIV YKSPVVS

SEQ ID NO: 7 is the amino acid sequence of K12S322 (S322 in bold).
MQTAPVPMPD LKNVKSKIGS TENLKHQPGG GKVQIVYKPV DLSKVISKSG

SLGNIHHKPG GGQVEVKSEK LDFKDRVQSK IGSLDNITHV PGGGNKKIET

HKLTFRENAK AKTDHGAEIV YKSPVVS

SEQ ID NO: 8 is the amino acid sequence of human Tau 40 (hTau40).
MAEPRQEFEVMEDHAGTYGLGDRKDQGGYTMHQDQEGDTDAGLKESPLQTPTEDGSEEPGSETSDA

KSTPTAEDVTAPLVDEGAPGKQAAAQPHTEIPEGTTAEEAGIGDTPSLEDEAAGHVTQARMVSKSK

DGTGSDDKKAKGADGKTKIATPRGAAPPGQKGQANATRIPAKTPPAPKTPPSSGEPPKSGDRSGYS

SPGSPGTPGSRSRTPSLPTPPTREPKKVAVVRTPPKSPSSAKSRLQTAPVPMPDLKNVKSKIGSTE

NLKHQPGGGKVQIINKKLDLSNVQSKCGSKDNIKHVPGGGSVQIVYKPVDLSKVTSKCGSLGNIHH

KPGGGQVEVKSEKLDFKDRVQSKIGSLDNITHVPGGGNKKIETHKLTFRENAKAKTDHGAEIVYKS

PVVSGDTSPRHLSNVSSTGSIDMVDSPQLATLADEVSASLAKQGL

SEQ ID NO: 9 is the amino acid sequence of human Tau 34 (hTau34).
MAEPRQEFEV MEDHAGTYGL GDRKDQGGYT MHQDQEGDTD AGLKESPLQT PTEDGSEEPG

SETSDAKSTP TAEDEEAGIGD TPSLEDEAAG HVTQARMVSK SKDGTGSDDK KAKGADGKTK

IATPRGAAPP GQKGQANATR IPAKTPPAPK TPPSSGEPPK SGDRSGYSSP GSPGTPGSRS

RTPSLPTPPT REPKKVAVVR TPPKSPSSAK SRLQTAPVPM PDLKNVKSKI GSTENLKHQP

GGGKVQIINK KLDLSNVQSK CGSKDNIKHV PGGGSVQIVY KPVDLSKVTS KCGSLGNIHH

KPGGGQVEVK SEKLDFKDRV QSKIGSLDNI THVPGGGNKK IETHKLTFRE NAKAKTDHGA

EIVYKSPVVS GDTSPRHLSN VSSTGSIDMV DSPQLATLAD EVSASLAKQG L
```

SEQ ID NO: 10 is the amino acid sequence of human Tau 24 (hTau24).
MAEPRQEFEV MEDHAGTYGL GDRKDQGGYT MHQDQEGDTD AGLKAEEAGI GDTPSLEDEA

AGHVTQARMV SKSKDGTGSD DKKAKGADGK TKIATPRGAA PPGQKGQANA TRIPAKTPPA

PKTPPSSGEP PKSGDRSGYS SPGSPGTPGS RSRTPSLPTP PTREPKKVAV VRTPPKSPSS

AKSRLQTAPV PMPDLKNVKS KIGSTENLKH QPGGGKVQII NKKLDLSNVQ SKCGSKDNIK

HVPGGGSVQI VYKPVDLSKV TSKCGSLGNI HHKPGGGQVE VKSEKLDFKD RVQSKIGSLD

NITHVPGGGN KKIETHKLTF RENAKAKTDH GAEIVYKSPV VSGDTSPRHL SNVSSTGSID

MVDSPQLATL ADEVSASLAK QGL

SEQ ID NO: 11 is the amino acid sequence of human Tau 39 (hTau39).
MAEPRQEFEV MEDHAGTYGL GDRKDQGGYT MHQDQEGDTD AGLKESPLQT PTEDGSEEPG

SETSDAKSTP TAEDVTAPLV DEGAPGKQAA AQPHTEIPEG TTAEEAGIGD TPSLEDEAAG

HVTQARMVSK SKDGTGSDDK KAKGADGKTK IATPRGAAPP GQKGQANATR IPAKTPPAPK

TPPSSGEPPK SGDRSGYSSP GSPGTPGSRS RTPSLPTPPT REPKKVAVVR TPPKSPSSAK

SRLQTAPVPM PDLKNVKSKI GSTENLKHQP GGGKVQIVYK PVDLSKVTSK CGSLGNIHHK

PGGGQVEVKS EKLDFKDRVQ SKIGSLDNIT HVPGGGNKKI ETHKLTFREN AKAKTDHGAE

IVYKSPVVSG DTSPRHLSNV SSTGSIDMVD SPQLATLADE VSASLAKQGL

SEQ ID NO: 12 is the amino acid sequence of human Tau 37 (hTau37).
MAEPRQEFEV MEDHAGTYGL GDRKDQGGYT MHQDQEGDTD AGLKESPLQT PTEDGSEEPG

SETSDAKSTP TAEDEEAGIG DTPSLEDEAA GHVTQARMVS KSKDGTGSDD KKAKGADGKT

KIATPRGAAP PGQKGQANAT RIPAKTPPAP KTPPSSGEPP KSGDRSGYSS PGSPGTPGSR

SRTPSLPTPP TREPKKVAVV RTPPKSPSSA KSRLQTAPVP MPDLKNVKSK IGSTENLKHQ

PGGGKVQIVY KPVDLSKVTS KCGSLGNIHH KPGGGQVEVK SEKLDFKDRV QSKIGSLDNI

THVPGGGNKK IETHKLTFRE NAKAKTDHGA EIVYKSPVVS GDTSPRHLSN VSSTGSIDMV

DSPQLATLAD EVSASLAKQG L

SEQ ID NO: 13 is the amino acid sequence of human Tau 23 (hTau23).
MAEPRQEFEV MEDHAGTYGL GDRKDQGGYT MHQDQEGDTD AGLKAEEAGI GDTPSLEDEA

AGHVTQARMV SKSKDGTGSD DKKAKGADGK TKIATPRGAA PPGQKGQANA TRIPAKTPPA

PKTPPSSGEP PKSGDRSGYS SPGSPGTPGS RSRTPSLPTP PTREPKKVAV VRTPPKSPSS

AKSRLQTAPV PMPDLKNVKS KIGSTENLKH QPGGGKVQIV YKPVDLSKVT SKCGSLGNIH

HKPGGGQVEV KSEKLDFKDR VQSKIGSLDN ITHVPGGGNK KIETHKLTFR ENAKAKTDHG

AEIVYKSPVV SGDTSPRHLS NVSSTGSIDM VDSPQLATLA DEVSASLAKQ GL

SEQ ID NO: 14 is the amino acid sequence of 6XHis K19 Cys-Free (S322).
MGSSHHHHHH SSGLVPRGSH MQTAPVPMPD LKNVKSKIGS TENLKHQPGG

GKVQIVYKPV DLSKVTSKSG SLGNIHHKPG GGQVEVKSEK LDFKDRVQSK

IGSLDNITHV PGGGNKKIE

SEQ ID NO: 15 is the amino acid sequence of 6XHis K19.
MGSSHHHHHH SSGLVPRGSH MQTAPVPMPD LKNVKSKIGS TENLKHQPGG

GKVQIVYKPV DLSKVTSKCG SLGNIHHKPG GGQVEVKSEK LDFKDRVQSK

IGSLDNITHV PGGGNKKIE

SEQ ID NO: 16 is the amino acid sequence of 6XHis K18 Cys-Free (S291, S322).
MGSSHHHHHH SSGLVPRGSH MQTAPVPMPD LKNVKSKIGS TENLKHQPGG

GKVQIINKKL DLSNVQSKSG SKDNIKHVPG

GGSVQIVYKP VDLSKVTSKS GSLGNIHHKP GGGQVEVKSE KLDFKDRVQS

KIGSLDNITH VPGGGNKKIE

-continued

SEQ ID NO: 17 is the amino acid sequence of 6XHis K18 (cysteines in bold).
MGSSHHHHHH SSGLVPRGSH MQTAPVPMPD LKNVKSKIGS TENLKHQPGG

GKVQIINKKL DLSNVQSKCG SKDNIKHVPG

GGSVQIVYKP VDLSKVTSKC GSLGNIHHKP GGGQVEVKSE KLDFKDRVQS

KIGSLDNITH VPGGGNKKIE

SEQ ID NO: 18 is the amino acid sequence of 6XHis K12 (cysteine in bold and underlined).
MGSSHHHHHH SSGLVPRGSH MQTAPVPMPD LKNVKSKIGS TENLKHQPGG GKVQIVYKPV DLSKVISK<u>C</u>G SLGNIHHKPG GGQVEVKSEK LDFKDRVQSK

IGSLDNITHV PGGGNKKIET HKLTFRENAK AKTDHGAEIV YKSPVVS

SEQ ID NO: 19 is the amino acid sequence of 6XHis K12A322 (A322 in bold and underlined).
MGSSHHHHHH SSGLVPRGSH MQTAPVPMPD LKNVKSKIGS TENLKHQPGG GYVQIVYKPV DLSKVTSK<u>A</u>G SLGNIHHKPG GGQVEVKSEK LDFKDRVQSK

IGSLDNITHV PGGGNKKIET HKLTFRENAK AKTDHGAEIV YKSPVVS

SEQ ID NO: 20 is the amino acid sequence of 6XHis K12S322 (S322 in bold and underlined).
MGSSHHHHHH SSGLVPRGSH MQTAPVPMPD LKNVKSKIGS TENLKHQPGG GKVQIVYKPV DLSKVTSK<u>S</u>G SLGNIHHKPG GGQVEVKSEK LDFKDRVQSK

IGSLDNITHV PGGGNKKIET HKLTFRENAK AKTDHGAEIV YKSPVVS

SEQ ID NO: 21 is the amino acid sequence of 6XHis human Tau 40 (hTau40).
MGSSHHHHHH SSGLVPRGSH MAEPRQEFEV MEDHAGTYGL GDRKDQGGYT MHQDQEGDTD

AGLKESPLQT PTEDGSEEPG SETSDAKSTP TAEDVTAPLV DEGAPGKQAA AQPHTEIPEG

TTAEEAGIGD TPSLEDEAAG HVTQARMVSK SKDGTGSDDK KAKGADGKTK IATPRGAAPP

GQKGQANATR IPAKTPPAPK TPPSSGEPPK SGDRSGYSSP GSPGTPGSRS RTPSLPTPPT

REPKKVAVVR TPPKSPSSAK SRLQTAPVPM PDLKNVKSKI GSTENLKHQP GGKVQIINK

KLDLSNVQSK CGSKDNIKHV PGGGSVQIVY KPVDLSKVTS KCGSLGNIHH KPGGGQVEVK

SEKLDFKDRV QSKIGSLDNI THVPGGGNKK IETHKLTFRE NAKAKTDHGA EIVYKSPVVS

GDTSPRHLSN VSSTGSIDMV DSPQLATLAD EVSASLAKQG L

SEQ ID NO: 22 is the amino acid sequence of 6XHis human Tau 34 (hTau34).
MGSSHHHHHH SSGLVPRGSH MAEPRQEFEV MEDHAGTYGL GDRKDQGGYT MHQDQEGDTD

AGLKESPLQT PTEDGSEEPG SETSDAKSTP TAEDEEAGIG DTPSLEDEAA GHVTQARMVS

KSKDGTGSDD KKAKGADGKT KIATPRGAAP PGQKGQANAT RIPAKTPPAP KTPPSSGEPP

KSGDRSGYSS PGSPGTPGSR SRTPSLPTPP TREPKKVAVV RTPPKSPSSA KSRLQTAPVP

MPDLKNVKSK IGSTENLKHQ PGGGKVQIIN KKLDLSNVQS KCGSKDNIKH VPGGGSVQIV

YKPVDLSKVT SKCGSLGNIH HKPGGGQVEV KSEKLDFKDR VQSKIGSLDN ITHVPGGGNK

KIETHKLTFR ENAKAKTDHG AEIVYKSPVV SGDTSPRHLS NVSSTGSIDM VDSPQLATLA

DEVSASLAKQ GL

SEQ ID NO: 23 is the amino acid sequence of 6XHis human Tau 24 (hTau24).
MGSSHHHHHH SSGLVPRGSH MAEPRQEFEV MEDHAGTYGL GDRKDQGGYT MHQDQEGDTD

AGLKAEEAGI GDTPSLEDEA AGHVTQARMV SKSKDGTGSD DKKAKGADGK TKIATPRGAA

PPGQKGQANA TRIPAKTPPA PKTPPSSGEP PKSGDRSGYS SPGSPGTPGS RSRTPSLPTP

PTREPKKVAV VRTPPKSPSS AKSRLQTAPV PMPDLKNVKS KIGSTENLKH QPGGGKVQII

NKKLDLSNVQ SKCGSKDNIK HVPGGGSVQI VYKPVDLSKV TSKCGSLGNI HHKPGGGQVE

VKSEKLDFKD RVQSKIGSLD NITHVPGGGN KKIETHKLTF RENAKAKTDH GAEIVYKSPV

VSGDTSPRHL SNVSSTGSID MVDSPQLATL ADEVSASLAK QGL

```
SEQ ID NO: 24 is the amino acid sequence of 6XHis human Tau 39 (hTau39).
MGSSHHHHHH SSGLVPRGSH MAEPRQEFEV MEDHAGTYGL GDRKDQGGYT MHQDQEGDTD

AGLKESPLQT PTEDGSEEPG SETSDAKSTP TAEDVTAPLV DEGAPGKQAA AQPHTEIPEG

TTAEEAGIGD TPSLEDEAAG HVTQARMVSK SKDGTGSDDK KAKGADGKTK IATPRGAAPP

GQKGQANATR IPAKTPPAPK TPPSSGEPPK SGDRSGYSSP GSPGTPGSRS RTPSLPTPPT

REPKKVAVVR TPPKSPSSAK SRLQTAPVPM PDLKNVKSKI GSTENLKHQP GGGKVQIVYK

PVDLSKVTSK CGSLGNIHHK PGGGQVEVKS EKLDFKDRVQ SKIGSLDNIT HVPGGGNKKI

ETHKLTFREN AKAKTDHGAE IVYKSPVVSG DTSPRHLSNV SSTGSIDMVD SPQLATLADE

VSASLAKQGL

SEQ ID NO: 25 is the amino acid sequence of 6XHis human Tau 37 (hTau37).
MGSSHHHHHH SSGLVPRGSH MAEPRQEFEV MEDHAGTYGL GDRKDQGGYT MHQDQEGDTD

AGLKESPLQT PTEDGSEEPG SETSDAKSTP TAEDEEAGIG DTPSLEDEAA GHVTQARMVS

KSKDGTGSDD KKAKGADGKT KIATPRGAAP PGQKGQANAT RIPAKTPPAP KTPPSSGEPP

KSGDRSGYSS PGSPGTPGSR SRTPSLPTPP TREPKKVAVV RTPPKSPSSA KSRLQTAPVP

MPDLKNVKSK IGSTENLKHQ PGGGKVQIVY KPVDLSKVTS KCGSLGNIHH KPGGGQVEVK

SEKLDFKDRV QSKIGSLDNI THVPGGGNKK IETHKLTFRE NAKAKTDHGA EIVYKSPVVS

GDTSPRHLSN VSSTGSIDMV DSPQLATLAD EVSASLAKQG L

SEQ ID NO: 26 is the amino acid sequence of 6XHis human Tau 23 (hTau23).
MGSSHHHHHH SSGLVPRGSH MAEPRQEFEV MEDHAGTYGL GDRKDQGGYT MHQDQEGDTD

AGLKAEEAGI GDTPSLEDEA AGHVTQARMV SKSKDGTGSD DKKAKGADGK TKIATPRGAA

PPGQKGQANA TRIPAKTPPA PKTPPSSGEP PKSGDRSGYS SPGSPGTPGS RSRTPSLPTP

PTREPKKVAV VRTPPKSPSS AKSRLQTAPV PMPDLKNVKS KIGSTENLKH QPGGGKVQIV

YKPVDLSKVT SKCGSLGNIH HKPGGGQVEV KSEKLDFKDR VQSKIGSLDN ITHVPGGGNK

KIETHKLTFR ENAKAKTDHG AEIVYKSPVV SGDTSPRHLS NVSSTGSIDM VDSPQLATLA

DEVSASLAKQ GL

SEQ ID NO: 27 is the amino acid sequence of hexapeptide PHF6.
VQIVYK

SEQ ID NO: 28 is the amino acid sequence of hexapeptide PHF6*.
VQIINK

SEQ ID NO: 29 is the amino acid sequence of K19 A322.
MQTAPVPMPD LKNVKSKIGS TENLKHQPGG GKVQIVYKPV DLSKVTSKAG

SLGNIHHKPG GGQVEVKSEK LDFKDRVQSK IGSLDNITHV PGGGNKKIE

SEQ ID NO: 30 is the amino acid sequence of K18 A291/S322.
MQTAPVPMPD LKNVKSKIGS TENLKHQPGG GKVQIINKKL DLSNVQSKAG

SKDNIKHVPG GGSVQIVYKP VDLSKVISKS GSLGNIHHKP GGGQVEVKSE

KLDFKDRVQS KIGSLDNITH VPGGGNKKIE

SEQ ID NO: 31 is the amino acid sequence of K18 5291/A322.
MQTAPVPMPD LKNVKSKIGS TENLKHQPGG GKVQIIMKKL DLSNVQSKSG

SKDNIKHVPG GGSVQIVYKP VDLSKVTSKA GSLGNIHHKP GGGQVEVKSE

KLDFKDRVQS KIGSLDNITH VPGGGNKKIE

SEQ ID NO: 32 is the amino acid sequence of K18 A291/A322.
MQTAPVPMPD LKNVKSKIGS TENLKHQPGG GKVQIINKKL DLSNVQSKAG

SKDNIKHVPG GGSVQIVYKP VDLSKVTSKA GSLGNIHHKP GGGQVEVKSE

KLDFKDRVQS KIGSLDNITH VPGGGNKKIE
```

SEQ ID NO: 33 is the amino acid sequence of 6XHis K19 A322.
MGSSHHHHHH SSGLVPRGSH MQTAPVPMPD LKNVKSKIGS TENLKHQPGG

GKVQIVYKPV DLSKVTSKAG SLGNIHHKPG GGQVEVKSEK LDFKDRVQSK

IGSLDNITHV PGGGNKKIE

SEQ ID NO: 34 is the amino acid sequence of 6XHis K18 A291/S322.
MGSSHHHHHH SSGLVPRGSH MQTAPVPMPD LKNVKSKIGS TENLKHQPGG

GKVQIINKKL DLSNVQSKAG SKDNIKHVPG GGSVQIVYKP VDLSKVTSKS

GSLGNIHHKP GGGQVEVKSE KLDFKDRVQS KIGSLDNITH VPGGGNKKIE

SEQ ID NO: 35 is the amino acid sequence of 6XHis K18 S291/A322.
MGSSHHHHHH SSGLVPRGSH MQTAPVPMPD LKNVKSKIGS TENLKHQPGG

GKVQIINKKL DLSNVQSKSG SKDNIKHVPG GGSVQIVYKP VDLSKVTSKA

GSLGNIHHKP GGGQVEVKSE KLDFKDRVQS KIGSLDNITH VPGGGNKKIE

SEQ ID NO: 36 is the amino acid sequence of 6XHis K18 A291/A322.
MGSSHHHHHH SSGLVPRGSH MQTAPVPMPD LKNVKSKIGS TENLKHQPGG

GKVQIINKKL DLSNVQSKAG SKDNIKHVPG GGSVQIVYKP VDLSKVTSKA

GSLGNIHHKP GGGQVEVKSE KLDFKDRVQS KIGSLDNITH VPGGGNKKIE

SEQ ID NO: 37 is a microtubule binding domain in 4-repeat Tau protein
(amino acids 244-370)
QTAPVPMPD LYNVKSKIGS TENLKHQPGG GKVQIINKKL DLSNVQSKCG

SKDNIKHVPG GGSVQIVYKP VDLSKVTSKG SLGNIHHKP GGGQVEVKSE

KLDFKDRVQS KIGSLDNITH VPGGGNKK

SEQ ID NO: 38 is a microtubule binding domain in 3-repeat Tau protein
(amino acids 244-274 and 306-370 lacking the second repeat (amino acids 275-305))
QTAPVPMPD LKNVKSKIGS TENLKHQPGG GKVQIVYKP VDLSKVTSKC

GSLGNIHHKP GGGQVEVKSE KLDFKDRVQS KIGSLDNITH VPGGGNKK

In the following sequences, the 6× His tag+linker is indicated, where relevant, with underlining at the beginning of the protein sequence. In the case of Cysteine-free mutant sequences (Cys-free) the location of the mutation is indicated as in a bold "S".

SEQ ID NO: 39 is the amino acid sequence of 6XHis K19 Cys-Free (S322) extended to residue 378
(244-274, 306-378).
<u>MGSSHHHHHH SSGLVPRGSH</u> MQTAPVPMPD LKNVKSKIGS TENLKHQPGG

GKVQIVYKPV DLSKVISKSG SLGNIHHKPG GGQVEVKSEK LDFKDRVQSK

IGSLDNITHV PGGGNKKIETH KLTF

SEQ ID NO: 40 is the amino acid sequence of K19 Cys-Free (S322) extended to residue 378
(244-274, 306-378).
QTAPVPMPD LKNVKSKIGS TENLKHQPGG GKVQIVYKPV DLSKVTSKSG

SLGNIHHKPG GGQVEVKSEK LDFKDRVQSK IGSLDNITHV PGGGNKKIETH KLTF

SEQ ID NO: 41 is the amino acid sequence of 6XHis K18 Cys-Free (S291, S322) extended to
residue 378 (244-378).
<u>MGSSHHHHHH SSGLVPRGSH</u> MQTAPVPMPD LKNVKSKIGS TENLKHQPGG

GKVQIINKKL DLSNVQSKSG SKDNIKHVPG GGSVQIVYKP VDLSKVTSKS

GSLGNIHHKP GGGQVEVKSE KLDFKDRVQS KIGSLDNITH VPGGGNKKIET HKLTF

SEQ ID NO: 42 is the amino acid sequence of K18 Cys-Free (S291, S322) extended to residue 378
(244-378).
QTAPVPMPD LKNVKSKIGS TENLKHQPGG GKVQIINKKL DLSNVQSKSG

SKDNIKHVPG GGSVQIVYKP VDLSKVTSKS GSLGNIHHKP GGGQVEVKSE

KLDFKDRVQS KIGSLDNITH VPGGGNKKIET HKLTF

-continued

SEQ ID NO: 43 is the amino acid sequence of 6XHis PHF6 Cys-Free (S322) extended to residue 378 (306-378).
<u>MGSSHHHHHH SSGLVPRGSH</u> VQIVYKPVDL SKVTSKSGSL GNIHHKPGGG

QVEVKSEKLD FKDRVQSKIG SLDNITHVPG GGNKKIETHK LTF

SEQ ID NO: 44 is the amino acid sequence of PHF6 Cys-Free (S322) extended to residue 378 (306-378).
VQIVYKPVDL SKVISKSGSL GNIHHKPGGG QVEVKSEKLD FKDRVQSKIG

SLDNITHVPG GGNKKIETHK LTF

SEQ ID NO: 45 is the amino acid sequence of 6XHis R1:R3 (244-274, 306-346).
<u>MGSSHHHHHH SSGLVPRGSH</u> QTAPVPMPDL KNVKSKIGST ENLKHQPGGG

KVQIVYKPVD LSKVTSKCGS LGNIHHKPGG GQVEVKSEKL DF

SEQ ID NO: 46 is the amino acid sequence of R1:R3 (244-274, 306-346).
QTAPVPMPDL KNVKSKIGST ENLKHQPGGG KVQIVYKPVD LSKVTSKCGS

LGNIHHKPGG GQVEVKSEKL DF

SEQ ID NO: 47 is the amino acid sequence of 6XHis R1:R3 Cys-free (S322) (244-274, 306-346).
<u>MGSSHHHHHH SSGLVPRGSH</u> QTAPVPMPDL KNVKSKIGST ENLKHQPGGG

KVQIVYKPVD LSKVISKSGS LGNIHHKPGG GQVEVKSEKL DF

SEQ ID NO: 48 is the amino acid sequence of R1:R3 Cys-free (S322) (244-274, 306-346).
QTAPVPMPDL KNVKSKIGST ENLKHQPGGG KVQIVYKPVD LSKVTSKSGS

LGNIHHKPGG GQVEVKSEKL DF

SEQ ID NO: 49 is the amino acid sequence of 6XHis R1:R2 (244-315).
<u>MGSSHHHHHH SSGLVPRGSH</u> QTAPVPMPDL KNVKSKIGST ENLKHQPGGG

KVQIVYKPVD LSKVQSKCGS LDNIKHVPGG GSVQIVYKPV DL

SEQ ID NO: 50 is the amino acid sequence of R1:R2 (244-315).
QTAPVPMPDL KNVKSKIGST ENLKHQPGGG KVQIINKKLD LSNVQSKCGS

KDNIKHVPGG GSVQIVYKPV DL

SEQ ID NO: 51 is the amino acid sequence of 6XHis R1:R2 Cys-free (S291) (244-315).
<u>MGSSHHHHHH SSGLVPRGSH</u> QTAPVPMPDL KNVKSKIGST ENLKHQPGGG

KVQIINKKLD LSNVQSKSGS KDNIKHVPHG GSVQIVYKPV DL

SEQ ID NO: 52 is the amino acid sequence of R1:R2 Cys-free (244-315, S291).
QTAPVPMPDL KNVKSKIGST ENLKHQPGGG KVQIINKKLD LSNVQSKSGS

KDNIKHVPGG GSVQIVYKPV DL

SEQ ID NO: 53 is the amino acid sequence of 6XHis R2:R3 (275-346).
<u>MGSSHHHHHH SSGLVPRGSH</u> VQIINKKLDL SNVQSKCGSK DNIKHVPGGG

SVQIVYYPVD LSKVTSKCGSL GNIHHKPGGG QVEVKSEKLD F

SEQ ID NO: 54 is the amino acid sequence of R2:R3 (275-346).
VQIINKKLDL SNVQSKCGSK DNIKHVPGGG SVQIVYKPVD LSKVTSKCGSL

GNIHHKPGGG QVEVKSEKLD F

SEQ ID NO: 55 is the amino acid sequence of 6XHis R2:R3 Cys-free (S291) (275-346).
<u>MGSSHHHHHH SSGLVPRGSH</u> VQIINKKLDL SNVQSKSGSK DNIKHVPGGG

SVQIVYKPVD LSKVTSKSGSL GNIHHKPGGG QVEVKSEKLD F

SEQ ID NO: 56 is the amino acid sequence of R2:R3 Cys-free (S291) (275-346).
VQIINKKLDL SNVQSKSGSK DNIKHVPGGG SVQIVYKPVD LSKVTSKSGSL

GNIHHKPGGG QVEVKSEKLD F

SEQ ID NO: 57 is the amino acid sequence of 6XHis R2:R3:R4 (275-368).
<u>MGSSHHHHHH SSGLVPRGSH</u> VQIINKKLDL SNVQSKCGSK DNIKHVPGGG

SVQIVYKPVD LSKVTSKCGS LGNIHHKPGG GQVEVKSEKL DFKDRVQSKI

GSLDNITHVP GGGN

-continued

SEQ ID NO: 58 is the amino acid sequence of R2:R3:R4 (275-368).
VQIINKKLDL SNVQSKCGSK DNIKHVPGGG SVQIVYKPVD LSKVTSKCGS

LGNIHHKPGG GQVEVKSEKL DFKDRVQSKI GSLDNITHVP GGGN

SEQ ID NO: 59 is the amino acid sequence of 6XHis R2:R3:R4 Cys-free (S291, S322) (275-368).
MGSSHHHHHH SSGLVPRGSH VQIINKKLDL SNVQSKCGSK DNIKHVPGGG

SVQIVYKPVD LSKVTSKSGS LGNIHHKPGG GQVEVKSEKL DFKDRVQSKI

GSLDNITHVP GGGN

SEQ ID NO: 60 is the amino acid sequence of R2:R3:R4 Cys-free (S291, S322) (275-368).
VQIINKKLDL SNVQSKSGSK DNIKHVPGGG SVQIVYKPVD LSKVTSKSGS

LGNIHHKPGG GQVEVKSEKL DFKDRVQSKI GSLDNITHVP GGGN

SEQ ID NO: 61 is the amino acid sequence of 6XHis R1:R4 (244-277, 347-378).
MGSSHHHHHH SSGLVPRGSH QTAPVPMPDL KNVKSKIGST ENLKHQPGGG

KVQIKDRVQS KIGSLDNITH VPGGGNKKIE THKLTF

SEQ ID NO: 62 is the amino acid sequence of R1:R4 (244-277, 347-378).
QTAPVPMPDL KNVKSKIGST ENLKHQPGGG KVQIKDRVQS KIGSLDNITH

VPGGGNKKIE THKLTF

SEQ ID NO: 63 is the amino acid sequence of 6XHis R1 (244-274).
MGSSHHHHHH SSGLVPRGSH QTAPVPMPDL KNVKSKIGST ENLKHQPGGG K SEQ ID NO: 64 is the amino acid sequence of R1 (244-274).
QTAPVPMPDL KNVKSKIGST ENLKHQPGGG K SEQ ID NO: 65 is the amino acid sequence of 6XHis R2 (275-305).
MGSSHHHHHH SSGLVPRGSH VQIINKKLDL SNVQSKCGSK DNILKHVPGGG S SEQ ID NO: 66 is the amino acid sequence of R2 (275-305).
VQIINKKLDL SNVQSKCGSK DNIKHVPGGG S SEQ ID NO: 67 is the amino acid sequence of 6XHis R2 Cys-free (5291) (275-305).
MGSSHHHHHH SSGLVPRGSH VQIINKKLDL SNVQSKSGSK DNIKHVPGGG S SEQ ID NO: 68 is the amino acid sequence of R2 Cys-free (5291) (275-305).
VQIINKKLDL SNVQSKSGSK DNIKHVPGGG S SEQ ID NO: 69 is the amino acid sequence of 6XHis R3 (306-336).
MGSSHHHHHH SSGLVPRGSH VQIVYKPVDL SKVTSKCGSL GNIHHKPGGG Q SEQ ID NO: 70 is the amino acid sequence of R3 (306-336).
VQIVYKPVDL SKVTSKCGSL GNIHHKPGGG Q SEQ ID NO: 71 is the amino acid sequence of 6XHis R3 Cys-free (S322) (306-336).
MGSSHHHHHH SSGLVPRGSH VQIVYKPVDL SKVISKSGSL GNIHHKPGGG Q SEQ ID NO: 72 is the amino acid sequence of R3 Cys-free (S322) (306-336) .
VQIVYKPVDL SKVISKSGSL GNIHHKPGGG Q SEQ ID NO: 73 is the amino acid sequence of 6XHis R4 (337-368).
MGSSHHHHHH SSGLVPRGSH VEVKSEKLDF KDRVQSKIGS LDNITHVPGG GN SEQ ID NO: 74 is the amino acid sequence of R4 (337-368).
VEVKSEKLDF KDRVQSKIGS LDNITHVPGG GN SEQ ID NO: 75 is the amino acid sequence of 6XHis R4 extended to 378 (337-378).
MGSSHHHHHH SSGLVPRGSH VEVKSEKLDF KDRVQSKIGS LDNITHVPGG

GNKKIETHKL IF

SEQ ID NO: 76 is the amino acid sequence of R4 extended to 378 (337-378).
VEVKSEKLDF KDRVQSKIGS LDNITHVPGG GNKKIETHKL TF SEQ ID NO: 77 is the amino acid sequence of 373-378 (sequence alone, and with N-Terminal Acetylation and C-Terminal Amidation)
THKLTF SEQ ID NO: 78 is the amino acid sequence of 368-378 (sequence alone, and with N-Terminal Acetylation and C-Terminal Amidation)
NKKIETHKLTF -continued SEQ ID NO: 79 is the amino acid sequence of 354-369 (sequence alone, and with N-Terminal Acetylation and C-Terminal Amidation)
IGSLDNITHVPGGNK SEQ ID NO: 80 is the amino acid sequence of 6XHis R2:R3:R4 extended to 378 (275-378).
MGSSHHHHHH SSGLVPRGSH VQIINKKLDL SNVQSKCGSK DNIKHVPGGG

SVQIVYKPVD LSKVTSKCGS LGNIHHKPGG GQVEVKSEKL DFKDRVQSKI

GSLDNITHVP GGGNKKIETH KLTF

SEQ ID NO: 81 is the amino acid sequence of R2:R3:R4 (275-378).
VQIINKKLDL SNVQSKCGSK DNIKHVPGGG SVQIVYKPVD LSKVTSKCGS

LGNIHHKPGG GQVEVKSEKL DFKDRVQSKI GSLDNITHVP GGGNKKIETH KLTF

SEQ ID NO: 82 is the amino acid sequence of 6XHis R2:R3:R4 Cys-free (S291, S322) (275-378).
MGSSHHHHHH SSGLVPRGSH VQIINKKLDL SNVQSKSGSK DNIKHVPGGG

SVQIVYKPVD LSKVTSKSGS LGNIHHKPGG GQVEVKSEKL DFKDRVQSKI

GSLDNITHVP GGGNKKIETH KLTF

SEQ ID NO: 83 is the amino acid sequence of R2:R3:R4 Cys-free (S291, S322) (275-378).
VQIINKKLDL SNVQSKSGSK DNIKHVPGGG SVQIVYKPVD LSKVTSKSGS

LGNIHHKPGG GQVEVKSEKL DFKDRVQSKI GSLDNITHVP GGGNKKIETH KLTF

SEQ ID NO: 84 is the amino acid sequence of 6XHis R3 extended to residues 346 (306-346).
MGSSHHHHHH SSGLVPRGSH VQIVYKPVDL SKVTSKCGSL GNIHHKPGGG

QVEVKSEKLD F

SEQ ID NO: 85 is the amino acid sequence of R3 extended to residues 346 (306-346).
VQIVYKPVDL SKVTSKCGSL GNIHHKPGGG QVEVKSEKLD F SEQ ID NO: 86 is the amino acid sequence of 6XHis R3 Cys-free (S322) extended to residues 346 (306-346).
MGSSHHHHHH SSGLVPRGSH VQIVYKPVDL SKVISKSGSL GNIHHKPGGG

QVEVKSEKLD F

SEQ ID NO: 87 is the amino acid sequence of R3 Cys-free (S322) extended to residues 346 (306-346).
VQIVYKPVDL SKVISKSGSL GNIHHKPGGG QVEVKSEKLD F SEQ ID NO: 88 is the R1 sequence
[244]QTAPVPMPDLK-NVKSKIGSTENLKHQPGGGK[274]

SEQ ID NO: 89 is the R2 sequence
[275]VQIINKKLDLS-NVQSKCGSKDNIKHVPGGGS[305]

SEQ ID NO: 90 is the R3 sequence
[306]VQIVYKPVDLS-KVTSKCGSLGNIHHKPGGGQ[336]

SEQ ID NO: 91 is the R4 sequence
[337]VEVKSEKLDFKDRVQSKIGSLDNITHVPGGGN[368]

SEQ ID NO: 92 is the amino acid sequence of 6XHis PHF6 extended to residue 378 (306-378).
MGSSHHHHHH SSGLVPRGSH VQIVYKPVDL SKVTSKCGSL GNIHHKPGGG

QVEVKSEKLD FKDRVQSKIG SLDNITHVPG GGNKKIETHK LIF

SEQ ID NO: 93 is the amino acid sequence of PHF6 extended to residue 378 (306-378).
VQIVYKPVDL SKVTSKCGSL GNIHHKPGGG QVEVKSEKLD FKDRVQSKIG

SLDNITHVPG GGNKKIETHK LIF

The sequence MGSS (SEQ ID NO: 94) is a leader sequence used before the six histidine residues. In some embodiments, this sequence (SEQ ID NO: 94) can be modified or removed. For any recombinant truncated tau protein is referred to by SEQ ID NO below, when the recombinant truncated Tau protein begins with M or MGSS (SEQ ID NO: 94), the M or the MGSS (SEQ ID NO: 94) can be removed.

DETAILED DESCRIPTION OF SEVERAL EMBODIMENTS

Like prions, hyper-phosphorylated Tau assembled into filaments can seed the in vitro assembly of amyloid fibrils from recombinant Tau, or fragments thereof. A highly sensitive assay was developed that was applicable to detection of Tau related neurodegenerative disorders, and is disclosed herein. The assays disclosed herein can be used to detect, without limitation, Pick disease (PiD), frontotemporal degeneration, corticobasal degeneration (CBD), argyrophilic grain disease (AGD), progressive supranuclear palsy (PSP), chronic traumatic encephalopathy, Alzheimer disease (AD), a Tauopathy associated with Parkinson disease, and Gerstmann-Straussler-Scheinker syndrome.

Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

Aggregate: More than one molecule in association, such as dimers, multimers, and polymers of Tau proteins, for instance aggregates, dimers, multimers, polymers and amyloid fibrils. Co-aggregates are aggregates of more than one type of molecule, such as, but not limited to, disease-associated Tau protein ($T^D$) and the recombinant truncated Tau protein.

Agitation: Introducing any type of turbulence or motion into a mixture or reaction mix, for examples by sonication, stirring, or shaking. In some embodiments, agitation includes the use of force sufficient to fragment amyloid aggregates or amyloids, which disperses amyloid aggregates and/or polymers to facilitate further amplification. In some examples fragmentation includes complete fragmentation, whereas in other examples, fragmentation is only partial, for instance, a population of aggregates can be about 1%, 2%, 5%, 10%, 20%, 30%, 40%, 50%, 60%, 70%, 80%, 90%, or 100% fragmented by agitation. Exemplary agitation methods are described in the Examples section below.

Argyrophilic Grain Disease (AGD): A Tauopathy characterized by an abundance of argyrophilic grains and coiled bodies in the entorhinal cortex, hippocampus, amygdala and the temporal cortex. These patients have pathological aggregation of Tau protein in neurofibrillary or gliofibrillary tangles. Lewy bodies are frequent in the amygdala. The disease is a late-onset dementing disorder clinically characterized by amnesia, with other cognitive functions relatively spared, and prominent neuropsychiatric features.

Alzheimer disease: A chronic neurodegenerative disease that is the cause of 60% to 70% of cases of dementia that is a 3R/4R Tauopathy. The most common early symptom is difficulty in remembering recent events (short-term memory loss). As the disease advances, symptoms can include problems with language, disorientation (including easily getting lost), mood swings, loss of motivation, not managing self-care, and behavioral issues. Although the speed of progression can vary, the average life expectancy following diagnosis is three to nine years.

Alzheimer disease is characterized by loss of neurons and synapses in the cerebral cortex and certain subcortical regions of the brain. This loss results in gross atrophy of the affected regions, including degeneration in the temporal lobe and parietal lobe, and parts of the frontal cortex and cingulate gyrus. Degeneration is also present in brainstem nuclei like the locus coeruleus. Both amyloid plaques and neurofibrillary tangles are clearly visible by microscopy in brains of patients. The plaques are dense, mostly insoluble deposits of beta-amyloid peptide and cellular material outside and around neurons. Tangles (neurofibrillary tangles) are aggregates of the microtubule-associated protein Tau that accumulate inside the cells themselves.

Amyloid: Fibrillar protein aggregates that contains cross-beta structure and typically stains in characteristic ways with certain dyes such as thioflavin T (ThT). The term amyloid includes protein aggregates that have one or more typical features of amyloid such as fibrillar ultrastructure, insolubility, protease-resistant cores, or staining with amyloid-selective dyes that results in alterations in fluorescence, birefringence or other optical properties. Amyloid is often found in Tauopathies and is called disease-associated Tau protein ($T^D$) when it is present in diseased brains from subjects with a Tauopathy. Many different proteins can form amyloids in association with a wide variety of diseases.

Antibody: A polypeptide ligand comprising at least a light chain or heavy chain immunoglobulin variable region which specifically recognizes and binds an epitope of an antigen or a fragment thereof. An antibody can specifically bind a Tau protein. Antibodies can be composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody.

The term antibody includes intact immunoglobulins and the variants and portions of them well known in the art, such as Fab' fragments, F(ab)'$_2$ fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (for example, humanized antibodies), heteroconjugate antibodies (such as, bispecific antibodies). See also, *Pierce Catalog and Handbook*, 1994-1995 (Pierce Chemical Co., Rockford, Ill.); Kuby, J., *Immunology*, 3$^{rd}$ Ed., W. H. Freeman & Co., New York, 1997.

Typically, a naturally occurring immunoglobulin has heavy (H) chains and light (L) chains interconnected by disulfide bonds. There are two types of light chain, lambda (λ) and kappa (k). There are five main heavy chain classes (or isotypes) which determine the functional activity of an antibody molecule: IgM, IgD, IgG, IgA and IgE.

Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs". The extent of the framework region and CDRs have been defined (see, Kabat et al., *Sequences of Proteins of Immunological Interest*, U.S. Department of Health and Human Services, 1991, which is hereby incorporated by reference). The Kabat database is now maintained online. The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. An antibody that binds an antigen of interest has a specific $V_H$ region and the $V_L$ region sequence, and thus specific CDR sequences. Antibodies with different specificities (due to different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

References to "$V_H$" or "VH" refer to the variable region of an immunoglobulin heavy chain, including that of an Fv, scFv, dsFv or Fab. References to "$V_L$" or "VL" refer to the variable region of an immunoglobulin light chain, including that of an Fv, scFv, dsFv or Fab.

A "monoclonal antibody" is an antibody produced by a single clone of B-lymphocytes or by a cell into which the light and heavy chain genes of a single antibody have been transfected, or a progeny thereof. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

Antibody binding affinity: Affinity of an antibody for an antigen, such as a Tau protein. In one embodiment, affinity is calculated by a modification of the Scatchard method described by Frankel et al., *Mol. Immunol.*, 16:101-106, 1979. In another embodiment, binding affinity is measured by an antigen/antibody dissociation rate. In yet another embodiment, a high binding affinity is measured by a competition radioimmunoassay. In several examples, a high binding affinity is at least about $1 \times 10^{-8}$ M. In other embodiments, a high binding affinity is at least about $1.5 \times 10^{-8}$ M, at least about $2.0 \times 10^{-8}$ M, at least about $2.5 \times 10^{-8}$ M, at least about $3.0 \times 10^{-8}$ M, at least about $3.5 \times 10^{-8}$ M, at least about $4.0 \times 10^{-8}$ M, at least about $4.5 \times 10^{-8}$ M, or at least about $5.0 \times 10^{-8}$ M.

Antigen: A compound, composition, or substance that can stimulate the production of antibodies or a T-cell response in an animal, including compositions that are injected or absorbed into an animal. An antigen reacts with the products of specific humoral or cellular immunity, including those induced by heterologous immunogens. The term "antigen" includes all related antigenic epitopes. "Epitope" or "antigenic determinant" refers to a site on an antigen to which B and/or T-cells respond. In one embodiment, T-cells respond to the epitope, when the epitope is presented in conjunction with an MHC molecule. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5, about 9, or about 8-10 amino acids in a unique spatial conformation. Methods of determining spatial conformation of epitopes include, for example, x-ray crystallography and 2-dimensional nuclear magnetic resonance. An antigen can be a Tau protein.

Conservative variant: In the context of a prion protein, refers to a peptide or amino acid sequence that deviates from another amino acid sequence only in the substitution of one or several amino acids for amino acids having similar biochemical properties (so-called conservative substitutions). Conservative amino acid substitutions are likely to have minimal impact on the activity of the resultant protein. Further information about conservative substitutions can be found, for instance, in Ben Bassat et al. (*J. Bacteriol.*, 169:751-757, 1987), O'Regan et al. (*Gene*, 77:237-251, 1989), Sahin-Toth et al. (*Protein Sci.*, 3:240-247, 1994), Hochuli et al. (*Bio/Technology*, 6:1321-1325, 1988) and in widely used textbooks of genetics and molecular biology. In some examples, prion protein variants can have no more than 1, 2, 3, 4, 5, 10, 15, 30, 45 conservative amino acid changes.

In one example, a conservative variant prion protein is one that functionally performs substantially like a similar base component, for instance, a Tau protein having variations in the sequence as compared to a reference Tau protein, but that can also perform a similar function, such as in an assay for a Tauopathy. In this example, the Tau protein and the conservative variant Tau protein do not have the same amino acid sequences. The conservative variant can have, for instance, one variation, two variations, three variations, four variations, or five or more variations in sequence, as long as the conservative variant is still complementary to the corresponding Tau protein.

Conditions sufficient to detect: Any environment that permits the desired activity, for example, that permits an interaction to be detected, or such as conditions that allow ThT to be detected. For example, such conditions include appropriate temperatures, buffer solutions, and detection means such as and digital imaging equipment.

Corticobasal Degeneration: A rare, progressive neurodegenerative disease involving the cerebral cortex and the basal ganglia. CBD symptoms typically begin in people from 50-70 years of age, and the average disease duration is six years. The Gallyas-Braak staining method, which is effective in identifying the presence of astroglial inclusions and coincidental Tauopathy, can be used to diagnose CBD. PSP and CBD result in similar symptoms, and both display Tauopathies upon histological inspection. However, Tauopathy in PSP results in tuft-shaped astrocytes in contrast with the doughnut-shaped astrocytic plaques found as a result of CBD.

Detect: To determine if an agent (such as a signal or protein, for example $T^D$) is present or absent. In some examples, this can further include quantification, for example the quantification of the amount of $T^D$ in a sample.

Diagnostic: Identifying the presence or nature of a pathologic condition, such as, but not limited to, identifying the presence of $T^D$. Diagnostic methods differ in their sensitivity and specificity. The "sensitivity" of a diagnostic assay is the percentage of diseased individuals who test positive (percent of true positives). The "specificity" of a diagnostic assay is 1 minus the false positive rate, where the false positive rate is defined as the proportion of those without the disease who test positive. While a particular diagnostic method may not provide a definitive diagnosis of a condition, it suffices if the method provides a positive indication that aids in diagnosis. "Prognostic" is the probability of development (for example severity) of a pathologic condition.

Disaggregate: To partially or completely disrupt an aggregate, such as an aggregate of a recombinant truncated Tau protein.

Encode: Any process whereby the information in a polymeric macromolecule or sequence is used to direct the production of a second molecule or sequence that is different from the first molecule or sequence. As used herein, the term is construed broadly, and can have a variety of applications. In some aspects, the term "encode" describes the process of semi-conservative DNA replication, wherein one strand of a double-stranded DNA molecule is used as a template to encode a newly synthesized complementary sister strand by a DNA-dependent DNA polymerase.

In another aspect, the term "encode" refers to any process whereby the information in one molecule is used to direct the production of a second molecule that has a different chemical nature from the first molecule. For example, a DNA molecule can encode an RNA molecule (for instance, by the process of transcription incorporating a DNA-dependent RNA polymerase enzyme). Also, an RNA molecule can encode a peptide, as in the process of translation. When used to describe the process of translation, the term "encode" also extends to the triplet codon that encodes an amino acid. In some aspects, an RNA molecule can encode a DNA molecule, for instance, by the process of reverse transcription incorporating an RNA-dependent DNA polymerase. In another aspect, a DNA molecule can encode a peptide, where it is understood that "encode" as used in that case incorporates both the processes of transcription and translation.

Fluorophore: A chemical compound, which when excited by exposure to a particular stimulus, such as a defined wavelength of light, emits light (fluoresces), for example at a different wavelength (such as a longer wavelength of light). Fluorophores are part of the larger class of luminescent compounds. Luminescent compounds include chemiluminescent molecules, which do not require a particular wavelength of light to luminesce, but rather use a chemical source of energy. Therefore, the use of chemiluminescent molecules (such as aequorin) can eliminate the need for an external source of electromagnetic radiation, such as a laser. Thioflavin T is a fluorophore of use for the detection of amyloid.

Examples of particular fluorophores that can attached to antibodies are provided in U.S. Pat. No. 5,866,366 to Nazarenko et al., such as 4-acetamido-4'-isothiocyanatostilbene-2,2'disulfonic acid, acridine and derivatives such as acridine and acridine isothiocyanate, 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, Brilliant Yellow, coumarin and derivatives such as coumarin, 7-amino-4-methylcoumarin (AMC, Coumarin 120), 7-amino-4-trifluoromethylcouluarin (Coumaran 151); cyanosine; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino] naphthalene-1-sulfonyl chloride (DNS, dansyl chloride); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), and QFITC (XRITC); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (Cibacron™ Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid and terbium chelate derivatives; LightCycler Red 640; Cy5.5; and Cy56-carboxyfluorescein; 5-carboxyfluorescein (5-FAM); boron dipyrromethene difluoride (BODIPY); N,N,N',N'-tetramethyl-6-carboxyrhodamine (TAMRA); acridine, stilbene, -6-carboxy-fluorescein (HEX), TET (Tetramethyl fluorescein), 6-carboxy-X-rhodamine (ROX), Texas Red, 2',7'-dimethoxy-4',5'-dichloro-6-carboxyfluorescein (JOE), Cy3, CyS, VIC® (Applied Biosystems), LC Red 640, LC Red 705, Yakima yellow amongst others.

Other suitable fluorophores include those known to those skilled in the art, for example those available from Molecular Probes (Eugene, Oreg.). In particular examples, a fluorophore is used as a donor fluorophore or as an acceptor fluorophore. In some examples, a fluorophore is detectable label, such as a detectable label attached to an antibody.

Gerstmann-Sträussler-Scheinker syndrome (GSS): A very rare, usually familial, fatal neurodegenerative disease caused by prions that affects patients from 20 to 60 years in age. Many symptoms are associated with GSS, such as progressive ataxia, pyramidal signs, and even adult-onset dementia; the symptoms progress as the disease progresses. GSS can be caused by a substitution at codon 102 from proline to leucine (P102L) in the prion protein gene (PRNP), encoded on chromosome 20, although other mutations are associated with GSS. However, it can also be caused by F198S, A117V and H187R mutations, and other point PRNP mutations. The trait is an autosomal-dominant trait. There is no cure for GSS, nor is there any known treatment to slow the progression of the disease. GSS is the slowest to progress among human prion diseases. The duration of GSS ranges from 3 months to 13 years, with an average duration of 5 or 6 years.

Microtubule: A component of the cytoskeleton, found in the cytoplasm of eukaryotic cells and some bacteria. Microtubules are formed by polymerization of polymers of a dimer of two globular proteins, alpha and beta tubulin, and can be as long as 50 micrometres. The outer diameter of a microtubule is about 24 nm while the inner diameter is about 12 nm formed by the polymerization. In vivo, microtubules are involved in maintaining the structure of the cell and, together with microfilaments and intermediate filaments, they form the cytoskeleton.

Immunoassay: A biochemical test that measures the presence or concentration of a substance in a sample, such as a biological sample obtained from a subject, using the reaction of an antibody to its cognate antigen, for example the specific binding of an antibody to a protein, such as $T^D$. Both the presence of antigen or the amount of antigen present can be measured. In some examples, the amount of $T^D$ is measured.

Immunoprecipitation (IP): The technique of precipitating a protein antigen out of solution using an antibody or peptides that specifically binds to that particular protein. These solutions will often be in the form of a crude lysate of an animal tissue. Other sample types could be body fluids or other samples of biological origin. Generally, in IP the antibody or peptides are coupled to a solid substrate at some point in the procedure.

Isolated: An "isolated" biological component, such as a peptide or assembly of polypeptides (for example Tau protein), cell, nucleic acid, or serum samples has been substantially separated, produced apart from, or purified away from other biological components in the cell of the organism in which the component naturally occurs, for instance, other chromosomal and extrachromosomal DNA and RNA, and proteins. Nucleic acids, peptides and proteins that have been "isolated" thus include nucleic acids and proteins purified by standard purification methods. The term also embraces nucleic acids, peptides and proteins prepared by recombinant expression in a cell as well as chemically synthesized peptide and nucleic acids. The term "isolated" or "purified" does not require absolute purity; rather, it is intended as a relative term. Thus, for example, an isolated peptide preparation is one in which the peptide or protein is more enriched than the peptide or protein is in its natural environment within a cell. Preferably, a preparation is purified such that the protein or peptide represents at least 50% of the total peptide or protein content of the preparation, such as at least 50%, at least 60%, at least 70%, at least 80%, at least 90%, at least 95%, or even at least 99% of the peptide or protein concentration.

Nucleic acid molecule: A polymeric form of nucleotides, which can include both sense and anti sense strands of RNA, cDNA, genomic DNA, and synthetic forms and mixed polymers of the above. A nucleotide refers to a ribonucleotide, deoxynucleotide or a modified form of either type of nucleotide. A "nucleic acid molecule" as used herein is synonymous with "nucleic acid" and "polynucleotide." A nucleic acid molecule is usually at least 10 bases in length, unless otherwise specified. The term includes single and double stranded forms of DNA. A nucleic acid molecule can include either or both naturally occurring and modified nucleotides linked together by naturally occurring and/or non-naturally occurring nucleotide linkages.

Parkinson disease: A degenerative disorder of the central nervous system that impairs motor skills, cognitive processes, and other functions. Parkinson disease is also referred to as Parkinson disease, Parkinson, PD and primary parkinsonism. The most obvious symptoms of Parkinson disease are motor-related, including tremor, rigidity, slowness of movement and postural instability. Among non-motor symptoms are autonomic dysfunction and sensory and sleep difficulties. Cognitive and neurobehavioral problems, including dementia, are common in the advanced stages of the disease.

In subjects that develop Parkinson disease, symptoms typically begin around the age of 60, although there are young-onset cases. Symptoms result from insufficient formation and action of dopamine produced in the dopaminergic neurons of the midbrain (specifically the substantia nigra). Pathologically the disease is characterized by the accumulation of alpha-synuclein protein forming inclusions called Lewy bodies. Such pathology can only be demonstrated at autopsy so diagnosis is mainly clinical (based on symptoms). Some tests such as neuroimaging techniques can also aid in diagnosis.

Pick Disease: A type of frontotemporal degeneration that is a rare neurodegenerative disease that causes progressive destruction of neurons in the brain. Symptoms include loss of language (aphasia), movement disorders and/or dementia. While some of the symptoms can initially be alleviated, the disease progresses and patients often die within two to ten years. A defining characteristic of the disease is build-up of Tau proteins in neurons, accumulating into silver-staining, spherical aggregations known as "Pick bodies." Pick bodies are almost always found in several regions in the brain, including the dentate gyms, the pyramidal cells of the CA1 sector and subiculum of the hippocampus, the neocortex, AND a plurality of other nuclei. Changes in personality allow Pick disease to be distinguished from Alzheimer disease. Symptoms include difficulty in language and thinking, efforts to dissociate from family, behavioral changes, unwarranted anxiety, irrational fears, impaired regulation of social conduct (e.g., breaches of etiquette, vulgar language, tactlessness, disinhibition, misperception), passivity, low motivation (aboulia), inertia, over-activity, pacing and wandering.

PMCA or Protein Misfolding Cyclic Amplification: A method for amplifying a protein, such as $T^D$, in a sample by mixing a substrate with the sample, incubating the reaction mix to permit the substrate to initiate the conversion of a Tau protein to aggregates, fragmenting any aggregates formed during the incubation step by sonication, and repeating one or more cycles of the incubation and fragmentation steps.

Polypeptide: A polymer in which the monomers are amino acid residues that are joined together through amide bonds. When the amino acids are alpha-amino acids, either the L-optical isomer or the D-optical isomer can be used, the L-isomers being preferred. Generally, a polypeptide has an amino (N) and a carboxy (C) terminus. The terms "polypeptide" or "protein" as used herein is intended to encompass any amino acid sequence and include modified sequences such as glycoproteins. The term "polypeptide" is specifically intended to cover naturally occurring proteins, as well as those that are recombinantly or synthetically produced.

The term "polypeptide fragment" refers to a portion of a polypeptide which exhibits at least one useful epitope or domain, such as a microtubule binding domain. The term "domain of a polypeptide" refers to a domain of a polypeptide that retains an activity of the polypeptide. Biological domains, for example, can vary in size from a polypeptide fragment as small as an epitope capable of binding an antibody molecule to a larger polypeptide capable of participating in a characteristic phenotype, such as binding to microtubules.

Progressive supranuclear palsy (PSP): A degenerative 4R Tauopathy also known as Steele-Richardson-Olszewski syndrome. The initial symptoms in two-thirds of cases are loss of balance, lunging forward when mobilizing, fast walking, bumping into objects or people, and falls. Later symptoms and signs are dementia, slurring of speech, difficulty swallowing, and difficulty moving the eyes, particularly vertically. The ophthalmoparesis experienced by these patients mainly concerns voluntary eye movement and the inability to make vertical saccades, which is often worse with downward saccades. Patients tend to have difficulty looking down (a downgaze palsy) followed by the addition of an up-gaze palsy. A variant in the gene encoding Tau protein called the H1 haplotype, located on chromosome 17, has been linked to PSP.

QuIC or Quaking Induced Conversion: A particular type of $T_D$ seeded Tau polymerization assay, in which shaking of the reaction vessels is performed to agitate the reaction. An "amyloid seeding assay" or a "seeded Tau polymerization assay" is an assay for $T^D$ seeds that induce amyloid formation form from a recombinant truncated Tau protein.

Real Time (RT)-QuIC: A type of QuIC assay that includes intermittent shaking without sonication to agitate the reaction and includes the use of a fluorescent readout, such as the fluorescent dye thioflavin T (ThT) to detect amyloid produced by a protein amyloid seeding reaction. Exemplary protocols are disclosed, for example, in Wilham et al., PLOS Pathog. 6(12): e1001217, pages 1-15. In this disclosure, this assay uses a recombinant truncated Tau protein as a substrate, intermittently shaken reactions, and can be predominantly detergent-free (such as ≤0.003% of SDS) or detergent-free. The assay includes fluorescent detection of $T^D$-seeded recombinant amyloid fibrils. Both QuIC and RT-QuIC can be used to detect $T^D$ with amyloid seeding activity. In some examples, $T^D$ is detected by the production of ThT-reactive amyloid in this assay. Tau RT-QuIC assay conditions that can detect Tau seeds associated with 3R, 4R or 3R/4R Tauopathies are called 3R, 4R and 3R/4R Tau RT-QuIC assays, respectively. Some examples of these Tau RT-QuIC assays can detect seeds from multiple types of Tauopathies while others only detect seeds associated with a subset of 3R, 4R or 3R/4R Tauopathies.

Recombinant: Prepared artificially through molecular genetic techniques. A recombinant protein does not occur in nature.

Sample: A biological sample obtained from a subject, such as a human or veterinary subject, which contains for example nucleic acids and/or proteins. As used herein, biological samples include all clinical samples useful for detection of $T^D$ in subjects, including, but not limited to, brain samples, cerebral spinal fluid, nasal brushings (including swabs), saliva, cells, tissues, and bodily fluids, such as: blood, its derivatives and fractions, such as serum; extracted galls; biopsied or surgically removed tissue, including tissues that are, for example, unfixed, frozen, fixed in formalin and/or embedded in paraffin; tears; milk; skin scrapes; skin punches; surface washings; urine; sputum; cerebrospinal fluid; prostate fluid; pus; muscle; lymphoid tissues; olfactory mucosa; urine; feces; or bone marrow aspirates. The tissue can be any tissue of interest. In specific non-limiting examples, the tissue can be brain tissue. In some embodiments, a sample may be contacted in solution with an agent, such as but not limited to purified recombinant truncated Tau protein or an antibody that specifically binds purified recombinant truncated Tau protein or $T^D$. In other embodiments, a sample may be contacted in solid phase with an agent, such as but not limited to purified recombinant truncated Tau protein or an antibody that specifically binds purified recombinant truncated Tau protein or $T^D$. In other embodiments, a sample may be contacted in solution and in solid phase with an agent, such as but not limited to purified recombinant truncated Tau protein or an antibody that specifically binds purified recombinant truncated Tau protein or $T^D$.

Sequence identity: The similarity between two nucleic acid sequences or between two amino acid sequences is expressed in terms of the level of sequence identity shared between the sequences. Sequence identity is typically expressed in terms of percentage identity; the higher the percentage, the more similar the two sequences. Methods for aligning sequences for comparison are described in detail below, in section IV E of the Detailed Description.

Single Round: Performing a method wherein serial amplification is not performed. For example, $T^D$ can be amplified in a sample, by mixing the sample with purified recombinant truncated Tau protein to make a reaction mix; performing an amplification reaction that includes (i) incubating the reaction mix to permit coaggregation of the recombinant truncated Tau protein with the $T^D$ that may be present in the reaction mix, and maintaining incubation conditions that promote coaggregation of the recombinant truncated Tau protein with the $T^D$ and results in a conversion of the recombinant truncated Tau protein to amyloid while inhibiting development of spontaneous amyloid $T^{(spon)}$ (amyloid that is generated spontaneously in the absence of $T^D$) (ii) agitating aggregates formed during step (i); (iii) optionally repeating steps (i) and (ii) one or more times. Amyloid is detected in the reaction mix, wherein detection of amyloid in the reaction mix indicates that $T^D$ was present in the sample. In a single round reaction, a portion of the reaction mix is not removed and incubated with additional recombinant truncated Tau protein in a separate reaction mixture.

Sonication: The process of disrupting or dispersing biological materials using sound wave energy.

Specific binding agent: An agent that binds substantially only to a defined target. In some embodiments, a specific binding agent is an antibody that specifically binds $T^D$.

The term "specifically binds" refers to the preferential association of an antibody or other ligand, in whole or part, with an antigen. Specific binding may be distinguished as mediated through specific recognition of the antigen. Although selectively reactive antibodies bind antigen, they may do so with low affinity. On the other hand, specific binding results in a much stronger association between the antibody (or other ligand) and antigen (or cells bearing the antigen) than between the bound antibody (or other ligand) and another protein (or cells lacking the antigen). Specific binding typically results in greater than 2-fold, such as greater than 5-fold, greater than 10-fold, or greater than 100-fold increase in amount of bound antibody or other ligand (per unit time) to a cell or tissue expressing the target epitope as compared to a cell or tissue lacking this epitope. A variety of immunoassay formats are appropriate for selecting antibodies or other ligands specifically immunoreactive with a particular protein. For example, solid-phase ELISA immunoassays are routinely used to select monoclonal antibodies specifically immunoreactive with a protein. See Harlow & Lane, *Antibodies, A Laboratory Manual*, Cold Spring Harbor Publications, New York (1988), for a description of immunoassay formats and conditions that can be used to determine specific immunoreactivity.

Tau: Proteins that are the product of alternative splicing from the microtubule-associated protein Tau (MAPT) gene in humans. Tau proteins include to full-length and truncated forms of any of Tau's isoforms. In humans, the Tau gene on chromosome 17q21 contains a total of 16 exons with the major Tau protein isoforms being encoded by 11 of these exons. Alternative mRNA splicing of exons 2, 3, and 10 a set of six isoforms ranging from 352 to 441 amino acids are generated in adult human brain. Exons 9-12 encode four microtubule binding motifs which are imperfect repeats of 31 or 32 amino acids in the carboxy-terminal half of the Tau molecule, and through which the interaction between Tau and microtubules is mediated. Three of the isoforms (hTau39, hTau37 and hTau23) have three microtubule binding domains and the other three isoforms (hTau40, hTau34, and hTau24) have four microtubule binding domains. These isoforms are shown diagrammatically in FIG. 14A. The microtubule binding domain is an 18 amino acid sequence that binds microtubules in vivo. Misfolded Tau is present in subjects with Tauopathies. The microtubule binding domains in 4-repeat Tau proteins is 127 amino acids, and in 3-repeat Tau proteins is 96 amino acids, see FIG. 14, residues 244-370. SEQ ID NO; 37 is an exemplary microtubule binding domain.

The microtubule binding domain binds microtubules and promotes microtubule assembly in neurons. Misfolded Tau is present in subjects with Tauopathies. The microtubule binding domains in 4-repeat Tau proteins is 127 amino acids, and in 3-repeat Tau proteins is 96 amino acids, see FIG. 14A, amino acids 244-370. SEQ ID NO; 37 is an exemplary microtubule binding domain in 4-repeat Tau protein. SEQ ID NO; 38 is an exemplary microtubule binding domain in 3-repeat Tau protein.

Tauopathy: A class of neurodegenerative diseases clinically characterized by dementia and/or motor syndromes, present morphologically with abundant neurofibrillary lesions (NFL) including intracellular accumulations of abnormal filaments that are composed of the microtubule-associated protein Tau in a hyperphosphorylated state. Neurofibrillary lesions that are positive for thioflavin-S, and thioflavin-T, silver stains, and anti-Tau antibodies are observed in the brains of individuals with a Tauopathy. Tauopathies are divided into the 3 repeat (3R), 4 repeat (4R) and combination of three and four repeat (3R/4R) forms. A table listing exemplary Tauopathies is provided below, showing the classification. Exemplarily Tauopathies include Alzheimer disease, Parkinson disease, Pick disease, primary age-related Tauopathy, demenial pugilstica, progressive supranucelar palsy, corticobasal degeneration, chronic traumatic encephalopathy, Lytico-Bodig disease, Parkinson-dementia complex of Guam Ganglioglioma, gangliocytoma Meningioangiomatosis, postencephalitic parkinsonism, subacute sclerosing panencephalitis, and Hallervorden-Spatz disease. A listing of Tauopathies is provided below.

Truncated: A protein that is not the full length native sequence, and thus includes fewer amino acids than the native protein. In some embodiments, a truncated protein, such as a Tau protein, does not include N-terminal and/or C-terminal domains.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Suitable methods and materials for the practice or testing of the disclosure are described below. However, the provided materials, methods, and examples are illustrative only and are not intended to be limiting. Accordingly, except as otherwise noted, the methods and techniques of the present disclosure can be performed according to methods and materials similar or equivalent to those described and/or according to conventional methods well known in the art and as described in various general and more specific references that are cited and discussed throughout the present specification (see, for instance, Sambrook et al., Molecular Cloning: A Laboratory Manual, 2d ed., Cold Spring Harbor Laboratory Press, 1989; Sambrook et al., Molecular Cloning: A Laboratory Manual, 3d ed., Cold Spring Harbor Press, 2001; Ausubel et al., Current Protocols in Molecular Biology, Greene Publishing Associates, 1992 (and Supplements to 2000); Ausubel et al., Short Protocols in Molecular Biology: A Compendium of Methods from Current Protocols in Molecular Biology, 4th ed., Wiley & Sons, 1999).

I. Overview of Several Embodiments

Methods are disclosed herein for determining whether a subject has a Tauopathy. In some embodiments, the methods include a) performing a seeded Tau polymerization assay on a biological sample from the subject, wherein the assay includes (i) contacting the biological sample with a purified recombinant truncated Tau protein, wherein the truncated Tau protein includes two, three or four microtubule binding domains, and optionally a human Tau-free carrier to form a reaction mixture; (ii) incubating the reaction mixture to permit coaggregation of disease-associated Tau protein ($T^D$) present in the biological sample with the recombinant truncated Tau protein; (iii) maintaining incubation conditions that promote coaggregation of the recombinant truncated Tau protein with the $T^D$ to result in a conversion of the recombinant truncated Tau protein to amyloid Tau protein aggregates while inhibiting development of spontaneously forming Tau protein aggregates ($rT^{(spon)}$); and (iv) agitating amyloid Tau protein aggregates formed during step (iii), wherein the agitating includes shaking the reaction mixture in a shaking cycle, wherein each shaking cycle includes a period of rest and a period of shaking. Amyloid Tau protein present in the reaction mixture is then detected. The detection of amyloid Tau protein in the reaction mixture indicates that the subject has the Tauopathy.

In further embodiments, the method can determine if the subject has a 3R Tauopathy, a 4R Tauopathy, or a 3R/4R Tauopathy. In yet other embodiments, the methods can distinguish the type of 4R Tauopathy, such as to determine if the subject has PSP, CBD, or AGD. In further embodiments, the method can be used to detect if a subject has Alzheimer disease.

For any recombinant truncated tau protein is referred to by SEQ ID NO below, wherein the recombinant truncated Tau protein begins with M or MGSS (SEQ ID NO: 94), the M or the MGSS can be removed.

In some non-limiting examples, the recombinant truncated Tau protein comprises or consists of one of SEQ ID NO: 1, SEQ ID NO: 2, SEQ ID NO: 14, SEQ ID NO: 15, SEQ ID NO: 29, SEQ ID NO: 39, or SEQ ID NO: 40 and the Tauopathy is Pick disease. In other non-limiting examples, the recombinant truncated Tau protein comprises or consists of SEQ ID NO: 3, SEQ ID NO: 4, SEQ ID NO: 16, SEQ ID NO: 17, SEQ ID NO: 30, SEQ ID NO: 31, SEQ ID NO: 32, and the Tauopathy is Tauopathy associated with Parkinson disease. In further non-limiting examples, the recombinant truncated Tau protein comprises or consists of the amino acid sequence set forth as SEQ ID NOs: 1-7, SEQ ID NOs: 29-32 and SEQ ID NOs: 39-87. In yet other non-limiting examples, the recombinant Tau protein comprises at least six consecutive histidine residues at or near the N-terminus or the C-terminus. Exemplary substrates are shown, for example, in SEQ ID NOs: 14-26. SEQ ID NOs: 33-36, SEQ ID NOs: 39, 41, 43, 45, 47, 49, 51, 53, 55, 57, 59, 61, 63, 65, 67, 69, 7, 73, 75, 80, 82, 84 and 86. Additional exemplary substrates are provided as SEQ ID NOs: 40, 42, 44, 46, 48, 50, 52, 54, 56, 58, 60, 64, 68, 70, 72, 74, 76-79, 83, 85, and 87. In further examples, a full length Tau protein is used in the assays, such as a Tau protein that includes or consists of SEQ ID NO: 8. In other non-limiting the recombinant truncated Tau protein includes only one microtubule binding domain. Exemplary substrates are shown, for example, in SEQ ID NO: 76 and SEQ ID NOs: 84-91.

In some embodiments, the recombinant truncated Tau protein comprises or consists of one of SEQ ID NO: 3, SEQ ID NO: 4, SEQ ID NO: 16, SEQ ID NO: 17, SEQ ID NO: 30, SEQ ID NO: 31, SEQ ID NO: 32, SEQ ID NO: 34, SEQ ID NO: 35, SEQ ID NO: 36, SEQ ID NO: 37, SEQ ID NO: 41, SEQ ID NO: 42, SEQ ID NO: 57, SEQ ID NO: 58, SEQ ID NO: 59, SEQ ID NO: 60, SEQ ID NO: 61, SEQ ID NO: 62, SEQ ID NO: 73, SEQ ID NO: 74, SEQ ID NO: 75, or SEQ ID NO: 91 and the Tauopathy is AGD.

In some embodiments, the recombinant truncated Tau protein comprises or consists of one of SEQ ID NO: 3, SEQ ID NO: 4, SEQ ID NO: 16, SEQ ID NO: 17, SEQ ID NO: 30, SEQ ID NO: 31, SEQ ID NO: 32, SEQ ID NO: 34, SEQ ID NO: 35, SEQ ID NO: 36, SEQ ID NO: 37, SEQ ID NO: 41, SEQ ID NO: 42, SEQ ID NO: 57, SEQ ID NO: 58, SEQ ID NO: 59, SEQ ID NO: 60, SEQ ID NO: 61, SEQ ID NO: 62, SEQ ID NO: 73, SEQ ID NO: 74, SEQ ID NO: 75, or SEQ ID NO: 91 and the Tauopathy is CBD. In some non-limiting examples, to detect CBD, the reaction mixture includes a second recombinant truncated Tau protein that comprises or consists of one of SEQ ID NO: 1, SEQ ID NO: 2, SEQ ID NO: 5, SEQ ID NO: 6, SEQ ID NO: 7, SEQ ID NO: 11, SEQ ID NO: 12, SEQ ID NO: 13, SEQ ID NO: 14, SEQ ID NO: 15, SEQ ID NO: 18, SEQ ID NO: 19, SEQ ID NO: 20, SEQ ID NO: 21, SEQ ID NO: 24, SEQ ID NO: 25, SEQ ID NO: 26, SEQ ID NO: 29, SEQ ID NO: 33, or SEQ ID NO: 39, SEQ ID NO: 40.

In some embodiments, the recombinant truncated Tau protein comprises or consists of one of SEQ ID NO: 3, SEQ ID NO: 4, SEQ ID NO: 16, SEQ ID NO: 17, SEQ ID NO: 30, SEQ ID NO: 31, SEQ ID NO: 32, SEQ ID NO: 34, SEQ ID NO: 35, SEQ ID NO: 36, SEQ ID NO: 37, SEQ ID NO: 41, SEQ ID NO: 42, SEQ ID NO: 57, SEQ ID NO: 58, SEQ ID NO: 59, SEQ ID NO: 60, SEQ ID NO: 61, SEQ ID NO: 62, SEQ ID NO: 73, SEQ ID NO: 74, SEQ ID NO: 75, or SEQ ID NO: 91 and the Tauopathy is PSP. In some non-limiting examples, to detect PSP, the reaction mixture includes a second recombinant truncated Tau protein that comprises or consists of one of SEQ ID NO: 1, SEQ ID NO: 2, SEQ ID NO: 5, SEQ ID NO: 6, SEQ ID NO: 7, SEQ ID NO: 11, SEQ ID NO: 12, SEQ ID NO: 13, SEQ ID NO: 14, SEQ ID NO: 15, SEQ ID NO: 18, SEQ ID NO: 19, SEQ ID NO: 20, SEQ ID NO: 21, SEQ ID NO: 24, SEQ ID NO: 25, SEQ ID NO: 26, SEQ ID NO: 29, SEQ ID NO: 33, or SEQ ID NO: 39, SEQ ID NO: 40.

In some embodiments, the recombinant truncated Tau protein comprises or consists of one of SEQ ID NO: 39, SEQ ID NO: 40, SEQ ID NO: 41, SEQ ID NO: 42, SEQ ID NO: 43, SEQ ID NO: 44, SEQ ID NO: 92, SEQ ID NO: 93, SEQ ID NO: 5, SEQ ID NO: 6, SEQ ID NO: 7, SEQ ID NO: 18, SEQ ID NO: 19, SEQ ID NO: 20, SEQ ID NO: 61, SEQ ID NO: 62, SEQ ID NO: 75, SEQ ID NO: 76, SEQ ID NO: 77, SEQ ID NO: 91 and the Tauopathy is Alzheimer disease. In some non-limiting examples, to detect Alzheimer disease, the reaction mixture includes a second recombinant truncated Tau protein that comprises or consists of one of SEQ ID NO: 1, SEQ ID NO: 2, SEQ ID NO: 5, SEQ ID NO: 6, SEQ ID NO: 7, SEQ ID NO: 11, SEQ ID NO: 12, SEQ ID NO: 13, SEQ ID NO: 14, SEQ ID NO: 15, SEQ ID NO: 18, SEQ ID NO: 19, SEQ ID NO: 20, SEQ ID NO: 21, SEQ ID NO: 24, SEQ ID NO: 25, SEQ ID NO: 26, SEQ ID NO: 29, SEQ ID NO: 33, or SEQ ID NO: 39, SEQ ID NO: 40. In other non-limiting examples, to detect Alzheimer disease, the reaction mixture includes a second recombinant truncated Tau protein that comprises or consists of one of SEQ ID NO: 3, SEQ ID NO: 4, SEQ ID NO: 16, SEQ ID NO: 17, SEQ ID NO: 30, SEQ ID NO: 31, SEQ ID NO: 32, SEQ ID NO: 34, SEQ ID NO: 35, SEQ ID NO: 36, SEQ ID NO: 37, SEQ ID NO: 41, SEQ ID NO: 42, SEQ ID NO: 57, SEQ ID NO: 58, SEQ ID NO: 59, SEQ ID NO: 60, SEQ ID NO: 61, SEQ ID NO: 62, SEQ ID NO: 73, SEQ ID NO: 74, SEQ ID NO: 75, or SEQ ID NO: 91.

When the recombinant truncated Tau protein includes at least six histidines, the recombinant truncated Tau protein can be purified using immobilized metal ion affinity chromatography, such as, but not limited to, nickel ion affinity chromatography. The recombinant truncated Tau protein can be purified by elution from a column comprising an immobilized metal ion using between about 46 mM and about 200 mM imidazole, such as about 46 mM imidazole to about 100 mM imidazole, such as 46 to 50 mM imidazole or 150 mM imidazole to about 200 mM imidazole. One suitable, non-limiting buffer includes about 10 mM Tris, pH 8.0, 500 mM NaCl, and 200 mM imidazole.

The biological sample can be any sample taken from the subject of interest, such as a subject that has, or is suspected to have, a Tauopathy. In some embodiments, the biological sample is a brain tissue sample or a cerebral spinal fluid sample. In other embodiments, the biological sample is a nasal brushing, saliva, blood (including whole blood and components thereof), serum, plasma, cerebral spinal fluid, skin, feces, urine or tissue sample.

In some embodiments, the presence of Tau amyloid in the biological sample can be detected using an amyloid-sensing dye. The dye can be, for example, thioflavin T or thioflavin S. Thus, the reaction mix can include thioflavin T (ThT), and detecting amyloid Tau protein can include detecting fluorescence.

In some embodiments, the step (iv) comprises agitating aggregates in the absence of sonication. In further embodiments, the shaking cycle in step (iv) comprises a period of rest that precedes the period of shaking, and wherein the period of rest and the period of shaking are equal. In yet other embodiments, the shaking cycle in step (iv) includes a period of rest and the period of shaking at a ratio of about 1:2 to about 2:1. In specific non-limiting examples, the shaking cycle in step (iv) is 20 to 180 seconds in length, such as the shaking cycle in step (iv) is 120 seconds in length. In specific non-limiting examples, each shaking cycle is 60 seconds of shaking and 60 seconds of rest; 45 seconds of shaking and 45 seconds of rest; or 30 seconds of shaking and 30 seconds of rest.

In further embodiments, a human Tau-free carrier is included in the reaction mixture. The human Tau-free carrier in the reaction mixture can be a brain homogenate lacking human Tau, such as, but not limited to, a murine brain homogenate. The human Tau-free murine brain homogenate can be from a mouse deficient for the production of murine Tau protein. In yet other embodiments, the reaction mixture further comprises an effective amount of N2.

In some embodiments, the biological sample is contacted with more than one purified recombinant truncated Tau protein. The biological sample can be contacted with 1, 2, 3, 4, 5, 6, 7, 8, 9, or 10 different truncated Tau proteins. A first recombinant truncated Tau protein and a second recombinant truncated Tau protein can be utilized at a ratio of 1:100 to 100:1, for example, 1:10 to 10:1, or from 1:3 to 3:1. Exemplary non-limiting ratios for any assays using a first and a second recombinant truncated Tau protein are 1:1, 1:2, 1:3, 1:4, 1:5, 1:10, 1:20, 1:30, 1:40, 1:50: 50:1, 40:1, 30:1, 20:1, 10:1, 4: 1, 3:1, or 2: 1.

In any of the disclosed embodiments, the reaction mixture can include 1 to 10 beads per 50 µl of reaction mixture, such as wherein the reaction mixture comprises 1 bead per 50 µl of reaction mixture. The beads can be about 0.5 mm to about 3 mm in diameter, such as about 0.8 mm or about 1 mm in diameter. In some embodiments, the beads are glass.

In additional embodiments, methods (a 3R Tau RT-QuIC) are disclosed for of determining whether a subject has a Pick disease. The methods include performing an amyloid seeding assay on a biological sample from the subject, wherein the biological sample comprises brain tissue and/or cerebral spinal fluid. The amyloid seeding assay includes: (i) contacting the biological sample with a purified recombinant truncated Tau protein, wherein the recombinant truncated Tau protein comprises three microtubule binding domains, an amyloid-sensing dye, optionally an effective amount of N2, and optionally a brain homogenate lacking human Tau, to form a reaction mixture; (ii) incubating the reaction mixture to permit coaggregation of disease-associated Tau protein ($T^D$) present in the biological sample with the recombinant truncated Tau protein; (iii) maintaining incubation conditions that promote coaggregation of the recombinant truncated Tau protein with the $T^D$ to result in a conversion of the recombinant truncated Tau protein to amyloid Tau protein aggregates while inhibiting development of spontaneously forming recombinant amyloid protein ($rT^{(spon)}$); (iv) agitating amyloid Tau protein aggregates formed during step (iii), wherein the agitating comprises shaking the reaction mixture in a shaking cycle, wherein each shaking cycle comprises a period of rest and a period of shaking. Amyloid Tau protein present in the reaction mixture is detected, such as using an amyloid-sensing dye. In some non-limiting examples, steps (a)-(b) are performed in the absence of an anionic detergent, and detection of the amyloid sensing dye indicates that the subject has Pick disease. In specific non-limiting examples, the recombinant truncated Tau protein comprises one of SEQ ID NO: 1, SEQ ID NO: 2, SEQ ID NO: 14, SEQ ID NO: 15, SEQ ID NO: 29, SEQ ID NO: 39, or SEQ ID NO: 40.

Methods are also provided for determining whether a subject has a 4R Tauopathy. These methods include: a) performing an amyloid seeding assay on a biological sample from the subject, wherein the biological sample includes brain tissue and/or cerebral spinal fluid. The amyloid seeding assay includes: (i) contacting the biological sample with a purified recombinant truncated Tau protein, wherein the recombinant truncated Tau protein has four microtubule binding domains, and an amyloid-sensing dye to form a reaction mixture; (ii) incubating the reaction mixture to permit coaggregation of disease-associated Tau protein ($T^D$) present in the biological sample with the recombinant truncated Tau protein; (iii) maintaining incubation conditions that promote coaggregation of the recombinant truncated Tau protein with the $T^D$ to result in a conversion of the recombinant truncated Tau protein to amyloid Tau protein aggregates while inhibiting development of spontaneously forming recombinant amyloid protein ($rT^{(spon)}$); (iv) agitating amyloid Tau protein aggregates formed during step (iii), wherein the agitating includes shaking the reaction mixture in a shaking cycle, wherein each shaking cycle comprises a period of rest and a period of shaking. These methods also include: b) detecting amyloid Tau protein present in the reaction mixture, wherein detection of amyloid Tau protein in the reaction mixture comprises detecting fluorescence of the amyloid sensing dye, and wherein detecting fluorescence indicates that the subject has a 4R Tauopathy.

In some embodiments, the reaction mixture further includes a second purified recombinant truncated Tau protein, wherein the second purified recombination Tau protein has three microtubule binding domains, respectively. These methods include: a) performing an amyloid seeding assay on a biological sample from the subject, wherein the biological sample includes brain tissue and/or cerebral spinal fluid. The amyloid seeding assay includes: (i) contacting the biological sample with a first purified recombinant truncated Tau protein, wherein the first recombinant truncated Tau protein has four microtubule binding domains, and a second purified recombinant truncated Tau protein, wherein the second purified recombinant truncated Tau protein comprises three microtubule binding domains, respectively and an amyloid-sensing dye to form a reaction mixture; (ii) incubating the reaction mixture to permit coaggregation of disease-associated Tau protein ($T^D$) present in the biological sample with the first recombinant truncated Tau protein and the second recombinant truncated Tau protein; (iii) maintaining incubation conditions that promote coaggregation of the first recombinant truncated Tau protein and the second recombinant truncated Tau protein with the $T^D$ to result in a conversion of the first recombinant truncated Tau protein and the second recombinant truncated Tau protein to amyloid Tau protein aggregates while inhibiting development of spontaneously forming recombinant amyloid protein ($rT^{(spon)}$); (iv) agitating amyloid Tau protein aggregates formed during step (iii), wherein the agitating includes shaking the reaction mixture in a shaking cycle, wherein each shaking cycle comprises a period of rest and a period of shaking. These methods also include: b) detecting amyloid Tau protein present in the reaction mixture, wherein detection of amyloid Tau protein in the reaction mixture comprises detecting fluorescence of the amyloid sensing dye, and wherein detecting fluorescence indicates that the subject has a 4R Tauopathy.

In some embodiments, the first recombinant truncated Tau protein comprises one of SEQ ID NO: 3, SEQ ID NO: 4, SEQ ID NO: 16, SEQ ID NO: 17, SEQ ID NO: 30, SEQ ID NO: 31, SEQ ID NO: 32, SEQ ID NO: 34, SEQ ID NO: 35, SEQ ID NO: 36, SEQ ID NO: 37, SEQ ID NO: 41 or SEQ ID NO: 42 for the detection of a 4R tauopathy, such as AGD, CBD or PSP.

In some embodiments, the recombinant truncated Tau protein comprises or consists of one of SEQ ID NO: 3, SEQ ID NO: 4, SEQ ID NO: 16, SEQ ID NO: 17, SEQ ID NO:

30, SEQ ID NO: 31, SEQ ID NO: 32, SEQ ID NO: 34, SEQ ID NO: 35, SEQ ID NO: 36, SEQ ID NO: 37, SEQ ID NO: 41, SEQ ID NO: 42, SEQ ID NO: 57, SEQ ID NO: 58, SEQ ID NO: 59, SEQ ID NO: 60, SEQ ID NO: 61, SEQ ID NO: 62, SEQ ID NO: 73, SEQ ID NO: 74, SEQ ID NO: 75, or SEQ ID NO: 91 and the Tauopathy is AGD.

In some embodiments, the recombinant truncated Tau protein comprises or consists of one of SEQ ID NO: 3, SEQ ID NO: 4, SEQ ID NO: 16, SEQ ID NO: 17, SEQ ID NO: 30, SEQ ID NO: 31, SEQ ID NO: 32, SEQ ID NO: 34, SEQ ID NO: 35, SEQ ID NO: 36, SEQ ID NO: 37, SEQ ID NO: 41, SEQ ID NO: 42, SEQ ID NO: 57, SEQ ID NO: 58, SEQ ID NO: 59, SEQ ID NO: 60, SEQ ID NO: 61, SEQ ID NO: 62, SEQ ID NO: 73, SEQ ID NO: 74, SEQ ID NO: 75, or SEQ ID NO: 91 and the Tauopathy is CBD. In some non-limiting examples, to detect CBD, the reaction mixture includes a second recombinant truncated Tau protein that comprises or consists of one of SEQ ID NO: 1, SEQ ID NO: 2, SEQ ID NO: 5, SEQ ID NO: 6, SEQ ID NO: 7, SEQ ID NO: 11, SEQ ID NO: 12, SEQ ID NO: 13, SEQ ID NO: 14, SEQ ID NO: 15, SEQ ID NO: 18, SEQ ID NO: 19, SEQ ID NO: 20, SEQ ID NO: 21, SEQ ID NO: 24, SEQ ID NO: 25, SEQ ID NO: 26, SEQ ID NO: 29, SEQ ID NO: 33, or SEQ ID NO: 39, SEQ ID NO: 40.

In some embodiments, the recombinant truncated Tau protein comprises or consists of one of SEQ ID NO: 3, SEQ ID NO: 4, SEQ ID NO: 16, SEQ ID NO: 17, SEQ ID NO: 30, SEQ ID NO: 31, SEQ ID NO: 32, SEQ ID NO: 34, SEQ ID NO: 35, SEQ ID NO: 36, SEQ ID NO: 37, SEQ ID NO: 41, SEQ ID NO: 42, SEQ ID NO: 57, SEQ ID NO: 58, SEQ ID NO: 59, SEQ ID NO: 60, SEQ ID NO: 61, SEQ ID NO: 62, SEQ ID NO: 73, SEQ ID NO: 74, SEQ ID NO: 75, or SEQ ID NO: 91 and the Tauopathy is PSP. In some non-limiting examples, to detect PSP, the reaction mixture includes a second recombinant truncated Tau protein that comprises or consists of one of SEQ ID NO: 1, SEQ ID NO: 2, SEQ ID NO: 5, SEQ ID NO: 6, SEQ ID NO: 7, SEQ ID NO: 11, SEQ ID NO: 12, SEQ ID NO: 13, SEQ ID NO: 14, SEQ ID NO: 15, SEQ ID NO: 18, SEQ ID NO: 19, SEQ ID NO: 20, SEQ ID NO: 21, SEQ ID NO: 24, SEQ ID NO: 25, SEQ ID NO: 26, SEQ ID NO: 29, SEQ ID NO: 33, or SEQ ID NO: 39, SEQ ID NO: 40.

In additional embodiments, the first recombinant truncated Tau protein and/or the second recombinant truncated Tau protein comprises six consecutive histidine residues at or near the N-terminus or the C-terminus. In more embodiments, the first recombinant truncated Tau protein and/or the second recombinant truncated Tau protein is purified by elution from a column comprising an immobilized metal ion using between about 46 mM and about 200 mM imidazole.

In other embodiments, the first recombinant truncated Tau protein and or the second recombinant truncated Tau protein is purified using immobilized metal ion affinity chromatography.

In more embodiments, the sample comprises brain tissue or cerebral spinal fluid, and wherein the reaction mixture further comprises a brain homogenate lacking human Tau, such as a murine brain homogenate, for example from a mouse deficient for the production of murine Tau protein.

Any of these methods can include agitating amyloid Tau protein aggregates formed during step (iii) comprises shaking in the absence of sonication. In more embodiments, steps (a)-(b) are performed in the absence of added anionic detergent. In some embodiments, agitating amyloid Tau protein aggregates formed during step (iii) is performed for at least about 10 hours or about 15 hours. In further embodiments, the amyloid sensing dye is thioflavin T or thioflavin S.

In specific non-limiting examples, the first recombinant truncated Tau protein comprises SEQ ID NO: 3, SEQ ID NO: 4, SEQ ID NO: 16, or SEQ ID NO: 17, and wherein the second recombinant truncated Tau protein comprises SEQ ID NO: 1 or SEQ ID NO: 2, SEQ ID NO: 14 or SEQ ID NO: 15.

In more non-limiting examples, the reaction mixture comprises heparin, and wherein the Tauopathy is progressive supranuclear palsy (PSP), corticobasal degeneration (CBD) or argyrophilic grain disease (AGD). In additional non-limiting examples, the reaction mixture comprises both heparin and poly-glutamate, and wherein the Tauopathy is AGD, PSP or CBD. In more non-limiting examples, the reaction mixture comprises heparin but does not comprise polyglutamate, and wherein the tauopathy is AGD or PSP.

In further embodiments, methods are disclosed for detecting a 3R/4R Tauopathy such as Alzheimer disease. These methods include: a) performing an amyloid seeding assay on a biological sample from the subject, wherein the biological sample comprises brain tissue and/or cerebral spinal fluid, wherein the amyloid seeding assay includes: (i) contacting the biological sample with a first purified recombinant truncated Tau protein, wherein the first recombinant truncated Tau protein comprises at least two microtubule binding domains (such as two, three or four microtubule binding domains and further comprises amino acid 306 to amino acid 378 of SEQ ID NO: 8 to form a reaction mixture; (ii) incubating the reaction mixture to permit coaggregation of disease-associated Tau protein ($T^D$) present in the biological sample with the first recombinant truncated Tau protein; (iii) maintaining incubation conditions that promote coaggregation of the first recombinant truncated Tau protein with the $T^D$ to result in a conversion of the first recombinant truncated Tau protein to amyloid Tau protein aggregates while inhibiting development of spontaneously forming Tau protein aggregates ($rT^{(spon)}$); and (iv) agitating amyloid Tau protein aggregates formed during step (iii), wherein the agitating comprises shaking the reaction mixture in a shaking cycle, wherein each shaking cycle comprises a period of rest and a period of shaking. These methods also include b) detecting amyloid Tau protein present in the reaction mixture, wherein detection of amyloid Tau protein in the reaction mixture comprises detecting fluorescence of the amyloid sensing dye, and wherein detecting fluorescence indicates that the subject has a 3R/4R Tauopathy. The Tauopathy can be Alzheimer disease. In some embodiments, the first purified recombinant truncated Tau protein includes two microtubule binding domains, and amino acids 306-378 of human Tau 40.

In more embodiments, methods for detecting a 3R/4R Tauopathy such as Alzheimer disease include a) performing an amyloid seeding assay on a biological sample from the subject, wherein the biological sample comprises brain tissue and/or cerebral spinal fluid, wherein the amyloid seeding assay includes: (i) contacting the biological sample with a first purified recombinant truncated Tau protein, wherein the first recombinant truncated Tau protein comprises two, three or four microtubule binding domains and further comprises amino acid 306 to amino acid 378 of SEQ ID NO: 8 and a second recombinant truncated Tau protein comprising three or four microtubule binding domains to form a reaction mixture; (ii) incubating the reaction mixture to permit coaggregation of disease-associated Tau protein ($T^D$) present in the biological sample with the first recombinant truncated Tau protein and the second recombinant truncated Tau protein; (iii) maintaining incubation conditions that promote coaggregation of the first recombinant truncated Tau protein and the second recombinant truncated Tau protein with the $T^D$ to result in a conversion of the first recombinant truncated Tau protein and the second recombinant truncated Tau protein to amyloid Tau protein aggregates while inhibiting development of spontaneously forming Tau protein aggregates ($rT^{(spon)}$); and (iv) agitating amyloid Tau protein aggregates formed during step (iii), wherein the agitating comprises shaking the reaction mixture in a shaking cycle, wherein each shaking cycle comprises a period of rest and a period of shaking. These methods also include b) detecting amyloid Tau protein present in the reaction mixture, wherein detection of amyloid Tau protein in the reaction mixture comprises detecting fluorescence of the amyloid sensing dye, and wherein detecting fluorescence indicates that the subject has a 3R/4R Tauopathy. The Tauopathy can be Alzheimer disease.

In some non-limiting examples, the first recombinant truncated Tau protein comprises two, three or four microtubule binding domains and further includes amino acid 306 to amino acid 378 of SEQ ID NO: 8. In other non-limiting examples, the first recombinant truncated Tau protein includes one of SEQ ID NO: 6, SEQ ID NO: 7, SEQ ID NO: 18, SEQ ID NO: 19, SEQ ID NO: 20, SEQ ID NO: 39, SEQ ID NO: 40, SEQ ID NO: 41, SEQ ID NO: 42, SEQ ID NO: 43, SEQ ID NO: 44, SEQ ID NO: 92 or SEQ ID NO: 93. In more non-limiting examples, the second recombinant truncated Tau protein comprises one of SEQ ID NO: 1, SEQ ID NO: 2, SEQ ID NO: 14, SEQ ID NO: 15, or SEQ ID NO: 29. In further non-limiting examples, the second recombinant truncated Tau protein comprises one of SEQ ID NO: 3, SEQ ID NO: 4, SEQ ID NO: 16, SEQ ID NO: 17, SEQ ID NO: 30, SEQ ID NO: 31, SEQ ID NO: 32, SEQ ID NO: 39, SEQ ID NO: 40, SEQ ID NO: 41, or SEQ ID NO: 42.

In yet other non-limiting examples: a) the first recombinant truncated Tau protein comprises SEQ ID NO: 43 and the second recombinant truncated Tau protein comprises SEQ ID NO: 14; b) the first recombinant truncated Tau protein comprises SEQ ID NO: 43 and the second recombinant truncated Tau protein comprises SEQ ID NO: 16; c) the first recombinant truncated Tau protein comprises SEQ ID NO: 43 and the second recombinant truncated Tau protein comprises SEQ ID NO: 41; or d) the first recombinant truncated Tau protein comprises SEQ ID NO: 39 and the second recombinant truncated Tau protein comprises SEQ ID NO: 41.

In more embodiments, the reaction mixture includes heparin.

In any of the disclosed methods, a recombinant truncated Tau protein can include at least six consecutive histidine residues at or near the N-terminus or the C-terminus. In further embodiments, the recombinant truncated Tau protein is purified using immobilized metal ion affinity chromatography. The recombinant truncated Tau protein can be purified by elution from a column comprising an immobilized metal ion using about 46 mM and about 200 mM imidazole.

In some embodiments, the Tau-free brain homogenate is a murine brain homogenate, such as mouse deficient for the production of murine Tau protein.

In further embodiments, agitating amyloid Tau protein aggregates formed during step (iii) comprises shaking in the absence of sonication For any of the disclosed methods, the amyloid seeding assay can be performed in the absence of added anionic detergent. Furthermore, for any of the disclosed methods agitating amyloid Tau protein aggregates formed during step (iii) is performed for at least about 10 hours, 11 hour, 12 hours, 13 hours, 14 hours, or 15 hours. In addition, for any of the disclosed methods, the amyloid sensing dye can be thioflavin T or thioflavin S.

The biological sample can be contacted with 1, 2, 3, 4, 5, 6, 7, 8, 9, or 10 different truncated tau proteins. A first recombinant truncated tau protein and a second recombinant truncated tau protein can be utilized at a ratio of 1:100 to 100:1, for example, 1:10 to 10:1, or from 1:3 to 3:1. Exemplary non-limiting ratios for any assays using a first and a second recombinant truncated tau protein are 1:1, 1:2, 1:3, 1:4, 1:5, 1:10, 1:20, 1:30, 1:40, 1:50: 50:1, 40:1, 30:1, 20:1, 10:1, 4:1, 3:1 and 2:1 in any of the assays disclosed herein.

In further embodiments, in any of the disclosed methods, the reaction mixture can include 1 to 10 beads per 50 µl of reaction mixture. In some non-limiting examples, the beads are about 0.5 mm to about 3 mm in diameter, such as, but not limited to, 0.8 mm in diameter or 1 mm in diameter. In additional non-limiting examples, the reaction mixture comprises 1 bead per 50 µl of reaction mixture.

In some embodiments, the method can include a comparison to a control. The control can be a reaction performed on a biological sample, such as brain tissue or CSF, from a subject known not to have a Tauopathy. Thus, the control can be a negative control. The control can be a reaction performed on a biological sample, such as brain tissue or CSF, from a subject known to have a particular Tauopathy. Thus, the control can be a positive control.

II. Substrates

Disclosed herein are methods for determining whether a subject has a Tauopathy using a seeded Tau polymerization assay, which is performed on a biological sample from the subject. In these assays, the sample is contacted with a purified recombinant truncated Tau protein. In some embodiments, the truncated Tau protein comprises two, three or four microtubule binding domains. In other embodiments, the recombinant truncated Tau protein includes only one microtubule binding domain.

A truncated Tau protein does not include a full-length Tau sequence. For example, a truncated Tau protein can include one, two, three or four microtubule binding domains, but not include the N terminal amino acid sequence and/or the C-terminal amino acid sequence of the corresponding native Tau protein. The substrate can be a truncated Tau protein that includes two microtubule binding domains. The substrate can be a truncated Tau protein that includes three microtubule binding domains. The substrate can be a truncated Tau protein that includes four microtubule binding domains. The microtubule binding domains in Tau protein are R1, R2, R3 and R4. In a truncated Tau protein that includes two microtubule binding domains, at most two of R1, R2, R3 and R4 are present. In a truncated Tau protein that includes three microtubule binding domains, at most three of R1, R2, R3 and R4 are present. Thus, in non-limiting examples, these microtubule binding domain can include R1, R2 and R3; R1, R2 and R4; R2, R3 and R4; R1, R2 and R4, etc. A Tau protein with two microtubule binding domains can include two of the same microtubule binding domains, to two different microtubule binding domains. Similarly, and Tau protein with three microtubule binding domains can have three different microtubule binding domains, two of the same and one different microtubule binding domains, or all three of the same microtubule binding domains. A Tau protein with four different microtubule binding domains can have all different microtubule binding domains, two of the same and two different microtubule binding domains, two sets of the same microtubule binding domain, three of the same and one different microtubule biding domains, or all four of the same microtubule binding domains. One of skill in the art readily understands combinations of use.

In some embodiments, the N-terminal amino acid sequence is not present in the truncated Tau protein. In specific non-limiting examples, up to the first 244 amino acids can be removed. Thus, in some non-limiting examples, the initial 100, 125, 150, 175, 200, 225 or 244 consecutive N-terminal amino acids can be deleted, so they are not present in the recombinant truncated Tau protein. In further embodiments, the C-terminal amino acid sequence is not included in the truncated Tau protein. In specific non-limiting examples, amino acids after amino acid 366 are deleted so they are not present in the recombinant truncated Tau protein. Thus, in some non-limiting examples, amino acids 366-441, amino acids 375-441, amino acids 400-441, or amino acids 441 are not present in the recombinant truncated Tau protein. In other specific non-limiting examples, amino acids after amino acid 378 are deleted so they are not present in the recombinant truncated Tau protein. Thus, in some non-limiting examples, amino acids 378-441, amino acids 379-441, amino acids 380-441, are not present in the recombinant truncated Tau protein.

In yet other embodiments, the substrate includes residues 300, 301, 202, 303, 304, 305, 306, 307, 308, 309 or 310 to residue 378 of human Tau protein (e.g., SEQ ID NO: 8). In one non-limiting example, the substrate includes residue 306-378 of a human Tau protein (e.g., SEQ ID NO: 8).

For any recombinant truncated tau protein is referred to by SEQ ID NO below, when the recombinant truncated Tau protein beings with M or MGSS (SEQ ID NO: 94), the M or the MGSS (SEQ ID NO: 94) can be removed.

In other embodiments, the first recombinant truncated Tau protein comprises two, three or four microtubule binding domains and further comprises at least 6, 7, 8, 9, 10, 20, 30, 40, 50, 60, or 70 consecutive amino acids from the amino acid sequence of amino acid 306 to amino acid 378 of SEQ ID NO: 8. Exemplary substrates include, but are not limited to, SEQ ID NO: 5, SEQ ID NO: 6, SEQ ID NO: 7, SEQ ID NO: 18, SEQ ID NO: 19, SEQ ID NO: 20, SEQ ID NO: 39, SEQ ID NO: 40, SEQ ID NO: 41, SEQ ID NO: 42, SEQ ID NO: 43, SEQ ID NO: 44, SEQ ID NO: 92 or SEQ ID NO: 93.

FIGS. 8, 9, 10, 11, 17, 18A-18B provide exemplary sequences. FIGS. 14-15 show domains that can be removed in a truncated Tau protein. FIGS. 13A-13B provide additional information about substrates. In some embodiments, the projection domains including the acidic region (for example, E2 and E3) and/or proline rich region are not included in the recombinant truncated Tau protein. The N-terminal portion of a Tau protein is the projection domain; this domain projects from the microtubule surface when the microtubule binding domain binds to microtubules. As shown in FIG. 17, N1 and N2 (amino acids 45-103) and FIG. 17, P1 and P2 (amino acids 151-243). In some embodiments, the C-terminal portion after the microtubule binding domain (amino acids 371-444 in grey in FIG. 17) is partially or entirely not included in the recombinant truncated Tau protein.

In other embodiments the substrate includes PHF6* (amino acids 275-280, SEQ ID NO: 28) or PHF6 (amino acids 306-311, SEQ ID NO: 27) which are a hexapeptide in Tau protein and part of the microtubule binding region (see FIG. 15 and FIG. 17). PHF6* is located between the 1st and 2nd microtubule binding domains. PHF6 is located between the 2nd and 3rd microtubule binding domains. PHF6 is capable of forming β-sheet fibrils. Thus, these molecules can also be used as substrates in the disclosed Tau RT-QuIC assays.

In some embodiments, a truncated Tau protein is mutated to remove one or more cysteines found in the corresponding position in the wild-type full-length Tau protein, such as using molecular techniques. In some embodiments, one or more cysteines present in the truncated Tau protein are substituted for another amino acid. In particular embodiments, in K18, another amino acid can be substituted for the cysteine at position 291 and/or 322. In specific non-limiting examples, a serine and/or an alanine can be substituted for the cysteine at position 291 and/or a serine or an alanine can be substituted for the cysteine at 322. In other embodiments, in K19, another amino acid can be substituted for the cysteine at position 322. In specific non-limiting examples, an alanine or a serine can be substituted for cysteine at position 322. Exemplary embodiments are shown graphically in FIG. 15, and exemplary sequences for these substrates are listed above. As noted above, the number (291, 322, etc.) refers to the position in SEQ ID NO: 8.

In further embodiments, the truncated Tau protein includes at least six histidines at or near the N or the C terminus. By "near" the C-terminus is meant within five amino acids, from the N-terminus. In some embodiments, the truncated Tau protein can include MGSS (SEQ ID NO: 94) prior to the histidines. The truncated Tau protein can include for example, 6, 7, 8, 9 or 10 histidines at or near either the N or the C terminus. Thus, histidines can be added to the N or C-terminus of the recombinant truncated Tau proteins of SEQ ID NOs: 1-7 or SEQ ID NO: 29-32. Exemplary truncated Tau proteins that include at least six histidines are SEQ ID NOs: 14-20 and SEQ ID NO: 33-36. Additional substrates are shown as SEQ ID NOs: 39-81. Further exemplary truncated Tau proteins that include at least six histidines, and are of use in the disclosed assays, are provided in SEQ ID NOs: 39, 41, 43, 45, 47, 49, 51, 53, 55, 57, 59, 61, 63, 65, 67, 69, 71, 73, 75, 80, 82, 84 and 86.

Substrates can include only three microtubule binding domains. In some embodiments, the recombinant truncated Tau protein is one of SEQ ID NO: 1, SEQ ID NO: 2, SEQ ID NO: 14, SEQ ID NO: 15, SEQ ID NO: 29, SEQ ID NO: 39, or SEQ ID NO: 40. These recombinant truncated Tau proteins can be used for the detection Pick disease.

Substrates can include four microtubule binding domains. In other embodiments, the recombinant truncated Tau protein is one of SEQ ID NO: 3, SEQ ID NO: 4, SEQ ID NO: 16, SEQ ID NO: 17, SEQ ID NO: 30, SEQ ID NO: 31, SEQ ID NO: 32, SEQ ID NO: 41 or SEQ ID NO: 42. In other embodiments, the recombinant truncated Tau protein comprises or consists of one of SEQ ID NO: 3, SEQ ID NO: 4, SEQ ID NO: 16, SEQ ID NO: 17, SEQ ID NO: 30, SEQ ID NO: 31, SEQ ID NO: 32, SEQ ID NO: 34, SEQ ID NO: 35, SEQ ID NO: 36, SEQ ID NO: 37, SEQ ID NO: 41, SEQ ID NO: 42, SEQ ID NO: 57, SEQ ID NO: 58, SEQ ID NO: 59, SEQ ID NO: 60, SEQ ID NO: 61, SEQ ID NO: 62, SEQ ID NO: 73, SEQ ID NO: 74, SEQ ID NO: 75, or SEQ ID NO: 91. These recombinant truncated Tau proteins are of use for the detection of a 4R Tauopathy, such as a Tauopathy associated with Parkinson disease, CBD, AGD or PSP.

In further embodiments, the recombinant truncated Tau protein includes two, three or four microtubule binding domains and further comprises amino acid 306 to amino acid 378 of SEQ ID NO: 8. The recombinant truncated Tau protein can include one of SEQ ID NO: 39, SEQ ID NO: 40, SEQ ID NO: 41, SEQ ID NO: 42, SEQ ID NO: 43, SEQ ID NO: 44, SEQ ID NO: 92 or SEQ ID NO: 93. In other embodiments, the recombinant truncated Tau protein comprises or consists of one of SEQ ID NO: 39, SEQ ID NO: 40, SEQ ID NO: 41, SEQ ID NO: 42, SEQ ID NO: 43, SEQ ID NO: 44, SEQ ID NO: 92, SEQ ID NO: 93, SEQ ID NO: 5, SEQ ID NO: 6, SEQ ID NO: 7, SEQ ID NO: 18, SEQ ID NO: 19, SEQ ID NO: 20, SEQ ID NO: 61, SEQ ID NO: 62, SEQ ID NO: 75, SEQ ID NO: 76, SEQ ID NO: 77, SEQ ID NO: 91. These substrates are of use for detecting a 3R/4R Tauopathy, such as Alzheimer disease.

In some embodiments, the biological sample is contacted with more than one purified recombinant truncated Tau protein. The biological sample can be contacted with 1, 2, 3, 4, 5, 6, 7, 8, 9, or 10 different truncated Tau proteins.

A first recombinant truncated Tau protein and a second recombinant truncated Tau protein can be utilized at a ratio of 1:100 to 100:1, for example, 1:10 to 10:1, or from 1:3 to 3:1. Exemplary non-limiting ratios for any assays using a first and a second recombinant truncated Tau protein are 1:1, 1: 2, 1:3, 1: 4, 1:5, 1:10, 1:20, 1:30, 1:40, 1:50: 50:1, 40:1, 30:1, 20:1, 10:1, 5:1, 4:1, 3:1 or 2:1.

In some embodiments, two recombinant truncated Tau proteins are utilized in the reaction mixture. For the detection of a 4R Tauopathy, such as AGD, CBD, or PSP, a first recombinant truncated Tau protein can include four microtubule binding domain and a second recombinant truncated Tau protein can include three microtubule binding domains. In some embodiments, a first recombinant truncated Tau protein includes one of SEQ ID NO: 3, SEQ ID NO: 4, SEQ ID NO: 16, SEQ ID NO: 17, SEQ ID NO: 30, SEQ ID NO: 31, SEQ ID NO: 32, SEQ ID NO: 34, SEQ ID NO: 35, SEQ ID NO: 36, SEQ ID NO: 37, SEQ ID NO: 41 or SEQ ID NO: 42. In other embodiments, the first recombinant truncated Tau protein includes SEQ ID NO: 3 SEQ ID NO: 4, SEQ ID NO: 16, or SEQ ID NO: 17, and wherein the second recombinant truncated Tau protein comprises SEQ ID NO: 1, SEQ ID NO: 2, SEQ ID NO: 14 or SEQ ID NO: 15.

In some embodiments, the recombinant truncated Tau protein comprises or consists of one of SEQ ID NO: 3, SEQ ID NO: 4, SEQ ID NO: 16, SEQ ID NO: 17, SEQ ID NO: 30, SEQ ID NO: 31, SEQ ID NO: 32, SEQ ID NO: 34, SEQ ID NO: 35, SEQ ID NO: 36, SEQ ID NO: 37, SEQ ID NO: 41, SEQ ID NO: 42, SEQ ID NO: 57, SEQ ID NO: 58, SEQ ID NO: 59, SEQ ID NO: 60, SEQ ID NO: 61, SEQ ID NO: 62, SEQ ID NO: 73, SEQ ID NO: 74, SEQ ID NO: 75, or SEQ ID NO: 91 and the Tauopathy is AGD.

In some embodiments, the recombinant truncated Tau protein comprises or consists of one of SEQ ID NO: 3, SEQ ID NO: 4, SEQ ID NO: 16, SEQ ID NO: 17, SEQ ID NO: 30, SEQ ID NO: 31, SEQ ID NO: 32, SEQ ID NO: 34, SEQ ID NO: 35, SEQ ID NO: 36, SEQ ID NO: 37, SEQ ID NO: 41, SEQ ID NO: 42, SEQ ID NO: 57, SEQ ID NO: 58, SEQ ID NO: 59, SEQ ID NO: 60, SEQ ID NO: 61, SEQ ID NO: 62, SEQ ID NO: 73, SEQ ID NO: 74, SEQ ID NO: 75, or SEQ ID NO: 91 and the Tauopathy is CBD. In some non-limiting examples, to detect CBD, the reaction mixture includes a second recombinant truncated Tau protein that comprises or consists of one of SEQ ID NO: 1, SEQ ID NO: 2, SEQ ID NO: 5, SEQ ID NO: 6, SEQ ID NO: 7, SEQ ID NO: 11, SEQ ID NO: 12, SEQ ID NO: 13, SEQ ID NO: 14, SEQ ID NO: 15, SEQ ID NO: 18, SEQ ID NO: 19, SEQ ID NO: 20, SEQ ID NO: 21, SEQ ID NO: 24, SEQ ID NO: 25, SEQ ID NO: 26, SEQ ID NO: 29, SEQ ID NO: 33, or SEQ ID NO: 39, SEQ ID NO: 40.

In some embodiments, the recombinant truncated Tau protein comprises or consists of one of SEQ ID NO: 3, SEQ ID NO: 4, SEQ ID NO: 16, SEQ ID NO: 17, SEQ ID NO: 30, SEQ ID NO: 31, SEQ ID NO: 32, SEQ ID NO: 34, SEQ ID NO: 35, SEQ ID NO: 36, SEQ ID NO: 37, SEQ ID NO: 41, SEQ ID NO: 42, SEQ ID NO: 57, SEQ ID NO: 58, SEQ ID NO: 59, SEQ ID NO: 60, SEQ ID NO: 61, SEQ ID NO: 62, SEQ ID NO: 73, SEQ ID NO: 74, SEQ ID NO: 75, or SEQ ID NO: 91 and the Tauopathy is PSP. In some non-limiting examples, to detect PSP, the reaction mixture includes a second recombinant truncated Tau protein that comprises or consists of one of SEQ ID NO: 1, SEQ ID NO: 2, SEQ ID NO: 5, SEQ ID NO: 6, SEQ ID NO: 7, SEQ ID NO: 11, SEQ ID NO: 12, SEQ ID NO: 13, SEQ ID NO: 14, SEQ ID NO: 15, SEQ ID NO: 18, SEQ ID NO: 19, SEQ ID NO: 20, SEQ ID NO: 21, SEQ ID NO: 24, SEQ ID NO: 25, SEQ ID NO: 26, SEQ ID NO: 29, SEQ ID NO: 33, or SEQ ID NO: 39, SEQ ID NO: 40.

For detection of a 3R/4R Tauopathy, such as Alzheimer disease, the first recombinant truncated Tau protein can include one of SEQ ID NO: 39, SEQ ID NO: 40, SEQ ID NO: 41, SEQ ID NO: 42, SEQ ID NO: 43, SEQ ID NO: 44, SEQ ID NO: 92 or SEQ ID NO: 93. SEQ ID NO: 39, SEQ ID NO: 40, SEQ ID NO: 41, SEQ ID NO: 42, SEQ ID NO: 43, SEQ ID NO: 44, SEQ ID NO: 92, SEQ ID NO: 93, SEQ ID NO: 5, SEQ ID NO: 6, SEQ ID NO: 7, SEQ ID NO: 18, SEQ ID NO: 19, or SEQ ID NO: 20. For detection of a 3R/4R Tauopathy, such as Alzheimer disease, the first recombinant truncated Tau protein can include one of SEQ ID NO: 61, SEQ ID NO: 62, SEQ ID NO: 75, SEQ ID NO: 76, SEQ ID NO: 77, or SEQ ID NO: 91.

In some embodiments, the recombinant truncated Tau protein comprises or consists of one of SEQ ID NO: 39, SEQ ID NO: 40, SEQ ID NO: 41, SEQ ID NO: 42, SEQ ID NO: 43, SEQ ID NO: 44, SEQ ID NO: 92, SEQ ID NO: 93, SEQ ID NO: 5, SEQ ID NO: 6, SEQ ID NO: 7, SEQ ID NO: 18, SEQ ID NO: 19, SEQ ID NO: 20, SEQ ID NO: 61, SEQ ID NO: 62, SEQ ID NO: 75, SEQ ID NO: 76, SEQ ID NO: 77, SEQ ID NO: 91 and the Tauopathy is Alzheimer disease. In some non-limiting examples, to detect Alzheimer disease, the reaction mixture includes a second recombinant truncated Tau protein that comprises or consists of one of SEQ ID NO: 1, SEQ ID NO: 2, SEQ ID NO: 5, SEQ ID NO: 6, SEQ ID NO: 7, SEQ ID NO: 11, SEQ ID NO: 12, SEQ ID NO: 13, SEQ ID NO: 14, SEQ ID NO: 15, SEQ ID NO: 18, SEQ ID NO: 19, SEQ ID NO: 20, SEQ ID NO: 21, SEQ ID NO: 24, SEQ ID NO: 25, SEQ ID NO: 26, SEQ ID NO: 29, SEQ ID NO: 33, or SEQ ID NO: 39, SEQ ID NO: 40. In other non-limiting examples, to detect Alzheimer disease, the reaction mixture includes a second recombinant truncated Tau protein that comprises or consists of one of SEQ ID NO: 3, SEQ ID NO: 4, SEQ ID NO: 16, SEQ ID NO: 17, SEQ ID NO: 30, SEQ ID NO: 31, SEQ ID NO: 32, SEQ ID NO: 34, SEQ ID NO: 35, SEQ ID NO: 36, SEQ ID NO: 37, SEQ ID NO: 41, SEQ ID NO: 42, SEQ ID NO: 57, SEQ ID NO: 58, SEQ ID NO: 59, SEQ ID NO: 60, SEQ ID NO: 61, SEQ ID NO: 62, SEQ ID NO: 73, SEQ ID NO: 74, SEQ ID NO: 75, or SEQ ID NO: 91.

In more non-limiting examples, the second recombinant truncated Tau protein can include one of SEQ ID NO: 1, SEQ ID NO: 2, SEQ ID NO: 14, SEQ ID NO: 15, or SEQ ID NO: 29. In further non-limiting examples, the second recombinant truncated Tau protein includes one of SEQ ID NO: 3, SEQ ID NO: 4, SEQ ID NO: 16, SEQ ID NO: 17, SEQ ID NO: 30, SEQ ID NO: 31, SEQ ID NO: 32, SEQ ID NO: 39, SEQ ID NO: 40, SEQ ID NO: 41, or SEQ ID NO: 42. In yet other non-limiting examples, a) the first recombinant truncated Tau protein comprises SEQ ID NO: 43 and the second recombinant truncated Tau protein comprises SEQ ID NO: 14; b) the first recombinant truncated Tau protein comprises SEQ ID NO: 43 and the second recombinant truncated Tau protein comprises SEQ ID NO: 16; c) the first recombinant truncated Tau protein comprises SEQ ID NO: 43 and the second recombinant truncated Tau protein comprises SEQ ID NO: 41; or d) the first recombinant truncated Tau protein comprises SEQ ID NO: 39 and the second recombinant truncated Tau protein comprises SEQ ID NO: 41.

In more embodiments, methods for detecting a 3R/4R Tauopathy such as Alzheimer disease include a) performing an amyloid seeding assay on a biological sample from the subject, wherein the biological sample comprises brain tissue and/or cerebral spinal fluid, wherein the amyloid seeding assay includes: (i) contacting the biological sample with a first purified recombinant truncated Tau protein, wherein the first recombinant truncated Tau protein comprises at least two (such as two, three or four microtubule binding domains) and amino acid 306 to amino acid 378 of SEQ ID NO: 8, second recombinant truncated Tau protein comprising three or four microtubule binding domains, and a third recombinant truncated Tau protein to form a reaction mixture; (ii) incubating the reaction mixture to permit coaggregation of disease-associated Tau protein ($T^D$) present in the biological sample with the first recombinant truncated Tau protein, the second recombinant truncated Tau protein, and the third recombinant truncated Tau protein; (iii) maintaining incubation conditions that promote coaggregation of the first recombinant truncated Tau protein, the second recombinant truncated Tau protein, and the third recombinant truncated Tau protein with the $T^D$ to result in a conversion of the first recombinant truncated Tau protein, the second recombinant truncated Tau protein, and the third recombinant truncated Tau protein to amyloid Tau protein aggregates while inhibiting development of spontaneously forming Tau protein aggregates ($rT^{(spon)}$); and (iv) agitating amyloid Tau protein aggregates formed during step (iii), wherein the agitating comprises shaking the reaction mixture in a shaking cycle, wherein each shaking cycle comprises a period of rest and a period of shaking. These methods also include b) detecting amyloid Tau protein present in the reaction mixture, wherein detection of amyloid Tau protein in the reaction mixture comprises detecting fluorescence of the amyloid sensing dye, and wherein detecting fluorescence indicates that the subject has a 3R/4R Tauopathy. In some non-limiting examples, the first recombinant truncated Tau protein comprises or consists of SEQ ID NO: 43, the second recombinant truncated Tau protein comprises of consists of SEQ ID NO: 16, and the third recombinant truncated Tau protein comprises or consists of SEQ ID NO: 14.

Recombinant truncated Tau polypeptides may be obtained by methods well-known in the art for recombinant peptide expression and purification. A DNA molecule encoding a recombinant truncated Tau polypeptide can be generated. The DNA sequence is deduced from the protein sequence based on known codon usage. See, e.g., Old and Primrose, Principles of Gene Manipulation $3^{rd}$ ed., Blackwell Scientific Publications, 1985; Wada et al., Nucleic Acids Res. 20: 2111-2118 (1992). In some embodiments, the DNA molecule includes additional sequence, for example recognition sites for restriction enzymes which facilitate its cloning into a suitable cloning vector, such as a plasmid. Nucleic acids are provided including the coding regions, non-coding regions, or both, either alone or cloned in a recombinant vector, as well as oligonucleotides and related primer and primer pairs corresponding thereto. Nucleic acids may be DNA, RNA, or a combination thereof. Vectors can be expression vectors, see, for example, FIG. 12. Nucleic acids encoding Tau polypeptides may be obtained by any method known within the art (e.g., by PCR amplification using synthetic primers hybridizable to the 3'- and 5'-termini of the sequence and/or by cloning from a cDNA or genomic library using an oligonucleotide sequence specific for the given gene sequence, or the like). Nucleic acids can also be generated by chemical synthesis.

Any of the methodologies known within the relevant art regarding the insertion of nucleic acid fragments into a vector may be used to construct expression vectors that contain a chimeric gene comprised of the appropriate transcriptional/translational control signals and peptide-coding sequences. Promoter/enhancer sequences within expression vectors can be plant, animal, insect, or fungus regulatory sequences. An inducible or constitutive promoter can be operably linked to a nucleic acid encoding an engineered chloride channel receptor. In some embodiments the expression of the polypeptides encoded by the vectors are controlled by a constitutive promoter. Suitable promoters include, but are not limited to, the T7 promoter. In other embodiments the expression of the polypeptides encoded by the vectors are controlled by an inducible or repressible promoter. Typically, the promoter is a constitutive promoter that results in high levels of transcription upon introduction into a host cell in the absence of additional factors. Optionally, the transcription control sequences include one or more enhancer elements, which are binding recognition sites for one or more transcription factors that increase transcription above that observed for the minimal promoter alone.

It may be desirable to include a polyadenylation signal to effect proper termination and polyadenylation of the gene transcript. Exemplary polyadenylation signals have been isolated from bovine growth hormone, SV40 and the herpes simplex virus thymidine kinase genes. Any of these or other polyadenylation signals can be utilized in the context of the adenovirus vectors described herein.

Thus, in one embodiment, the polynucleotide encoding a recombinant truncated Tau is included in a vector for expression. Suitable viral vectors include retrovirus vectors, orthopox vectors, avipox vectors, fowlpox vectors, capripox vectors, suipox vectors, adenoviral vectors, herpes virus vectors, alpha virus vectors, baculovirus vectors, Sindbis virus vectors, vaccinia virus vectors and poliovirus vectors. Specific exemplary vectors are poxvirus vectors such as vaccinia virus, fowlpox virus and a highly attenuated vaccinia virus (MVA), adenovirus, baculovirus, yeast and the like. A vector can also be used for expression in bacterial cells. Such vectors are known in the art, and include, for example, plasmids such as pBR322.

Any of the disclosed vectors can be expressed in suitable host cells. Following expression in host cells, such as eukaryotic or prokaryotic host cell, the recombinant truncated Tau protein is purified. The inclusion of at least six histidines facilitates purification by immobilized metal ion affinity chromatography. Immobilized metal affinity chromatography (IMAC), also known as metal chelate affinity chromatography (MCAC), is a specialized aspect of affinity chromatography. The principle behind IMAC lies in the fact that many metal ions, i.e., nickel, zinc, cobalt and copper, can coordinate to the amino acids histidine, cysteine, and tryptophan via electron donor groups on the amino acid side chains. To utilize this interaction for chromatographic purposes, the metal ion must be immobilized onto an insoluble support. This can be done by attaching a chelating group to the chromatographic matrix. The most common chelating group used in this technique is iminodiacetic acid (IDA). It coupled to a matrix such as SEPHAROSE 6B, via a long hydrophilic spacer arm. The spacer arm ensures that the chelating metal is fully accessible to all available binding sites on a protein. Another chelating group is tris(carboxymethyl)-ethylenediamine (TED). $Cu^{++}$, $Ni^{++}$, and $Co^{++}$ are also applied for certain proteins. Interactions between immobilized metals and tryptophan, tyrosine, or cysteine residues of proteins have been reported, however, these are generally weaker interactions. In some embodiments, a solution including the protein of interest, such as a recombinant truncated Tau protein, is used at a pH of about 6.75 to 7.2. The solution is applied to an IMAC column, so that the protein binds to the column, and eluting the protein from the column, see U.S. Pat. No. 5,932,102, incorporated herein by reference. In some embodiments, the resin is washed with phosphate buffer to remove proteins that do not specifically interact with the metal, such as a nickel ion. With nickel chromatography methods, washing efficiency can be improved by the addition of imidazole. One of skill in the art can readily use metal ion chromatography for the purification of proteins.

In some embodiments, the column is washed, and then eluted with, for example, with about 46 mM and about 200 mM imidazole, such as about 46 mM imidazole and 100 mM imidazole, for example about 46 mM imidazole to about 50 mM imidazole or 150 mM imidazole to about 200 mM imidazole. One suitable, non-limiting buffer includes about 10 mM Tris, pH 8.0, 500 mM NaCl, and 200 mM imidazole.

III. Tau RT-QuIC

Methods are disclosed herein for determining if a subject has a Tauopathy. Tauopathies include, but are not limited to, the 3R, 4R and 3R/4R forms of the disease listed in the table below:

| Biochemical classification of tauopathy | Diseases with tau inclusions (tauopathies) |
| --- | --- |
| 3-repeat | Pick disease<br>Frontotemporal dementia and parkinsonism linked to chromosome 17<br>(FTDP-17) (K257T, G389R)* |
| 4-repeat | Progressive supranuclear palsy (PSP)<br>Corticobasal degeneration (CBD)<br>Argyrophilic grain disease (AGD)<br>Globular glial tauopathy (GGT)<br>Guadeloupean parkinsonism (GP)<br>Sporadic multisystem tauopathy with dementia<br>Pallido-nigral-luysial atrophy<br>Neurofibrillary degeneration of CA2<br>FTDP-17 (V337M, R406W)* |
| 3-repeat/4-repeat | Alzheimer disease (AD)<br>Post-encephalitic parkinsonism (PEP)<br>Amyotrophic lateral sclerosis-parkinsonism-dementia complex<br>Neurofibrillary tangle dementia/tangle only dementia<br>Diffuse neurofibrillary tangles with calcification<br>Familial British dementia<br>Familial Danish dementia<br>FTDP-17 (P301L)*<br>Gerstmann-Straussler-Scheinker disease (GSS) with F198S mutation in human prion protein (PRNP) |
| Not biochemically classified | GSS with D202N mutation in PRNP<br>GSS with Q217R mutation in PRNP<br>Chronic traumatic encephalopathy (dementia pugilistica)<br>Primary age-related tauopathy<br>Creutzfeldt-Jakob disease (CJD)<br>Down syndrome<br>Ganglioglioma and gangliocytoma<br>Meningioangiomatosis<br>Corticobasal ganglionic degeneration<br>Myotonic dystrophy<br>Hallevorden-Spatz disease<br>Niemann Pick type C<br>Postencephalitic parkinsonism<br>Subacute sclerosing panencephalitis<br>Lead encephalopathy<br>Tuberous sclerosis<br>Lipofuscinosis<br>Huntington disease<br>Neurodegeneration with brain iron accumulation<br>Non-Guamanian motor neuron disease with neurofibrillary tangles<br>Prion protein cerebral amyloid angiopathy<br>SLC9A6-related mental retardation<br>Tangle-only dementia<br>White matter tauopathy with globular glial inclusions |

In some embodiments, the Tauopathy is a 4-repeat Tauopathy. In other embodiments, the Tauopathy is a 3-repeat/4-repeat Tauopathy. In particular non-limiting examples, the Tauopathy is Pick Disease, Alzheimer disease or a Tauopathy associated with Parkinson disease.

These methods are of use with any sample of interest. The methods disclosed herein include the use of a sample from a subject, such as, but not limited to, a brain homogenate and/or a cerebral spinal fluid sample. In some embodiments, the sample is a nasal brushing, saliva, cerebral spinal fluid, blood, fecal, tissue, urine, or serum sample. If the sample is a tissue sample, such as a brain sample, the tissue can be fresh tissue or fixed tissue, such as formalin-fixed tissue. In some specific non-limiting examples, the same is a cerebral spinal fluid sample. The sample can be diluted, such as in a buffer. In some embodiments, serial dilutions of the sample are tested. The sample can be diluted, for example, at $10^{-2}$, $10^{-3}$, $10^{-4}$, $10^{-5}$, $10^{-6}$, $10^{-7}$, $10^{-8}$, $10^{-9}$ or $10^{-10}$ dilution.

QuIC and RT-QuIC methods generally involve mixing a sample, that can include disease associated Tau protein ($T^D$) with a purified recombinant truncated Tau protein to make a reaction mix, and performing a primary reaction to form and amplify specific forms of Tau protein the mixture, by using incubation conditions that promote coaggregation of the recombinant truncated Tau protein with the $T^D$ to result in a conversion of the recombinant truncated Tau protein to amyloid Tau protein aggregates. In these reactions, the development of spontaneously amyloid Tau protein (rT$^{(spon)}$) is inhibited. The purified recombinant truncated Tau protein is selected so that a particular disease is detected. For example, substrates are selected to identify a 3-repeat Tauopathy, such as Pick disease, or a 3-repeat/4-repeat Tauopathy, such as Alzheimer disease or to detect a Tauopathy associated with Parkinson disease. Exemplary substrates are disclosed above.

The substrate can be a truncated Tau protein that includes one microtubule binding domain. The substrate can be a truncated Tau protein that includes two microtubule binding domains. The substrate can be a truncated Tau protein that includes three microtubule binding domains. The substrate can be a truncated Tau protein that includes four microtubule binding domains. In some embodiments, a truncated Tau protein is mutated to remove one or more cysteines found in the corresponding position in the wild-type full-length Tau protein. In some embodiments, the truncated Tau protein includes at least six histidines at or near the N or the C terminus.

In some embodiments additional substrate is added to the reaction mix. In other embodiments, additional substrate is not added to the reaction mix.

This primary reaction includes incubating the reaction mix to permit the $T^D$ to initiate the conversion of recombinant truncated Tau protein to amyloid Tau protein, fragmenting any amyloid formed during the incubation step; and repeating the incubation and fragmentation steps one or more times. In some embodiments, the primary reaction is repeated over 50 hours, 55 hours, 60 hours, 65 hours, or more. For example, the primary reaction can be repeated for about 60 hours to about 72 hours, such as for about 60, 61, 62, 63, 64, 65, 66, 67, 68, 69, 70, 71 or 72 hours. In other examples, the reaction can be performed for no more than 24 hours, no more than 36 hours, no more than 48 hours, no more than 60 hours, no more than 72 hours, no more than 96 hours or no more than 120 hours. In several specific non-limiting examples, the reaction is performed for about 60 hours. The reaction can be performed for 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, or 72 hours. In specific non-limiting examples, the sample is a brain tissue sample or a CSF sample.

In other embodiments, the primary reaction is repeated over 10 hours 15 hours, 20 hours, 25 hours, 30 hours or 35 hours. In other examples, the reaction can be performed for no more than 35 hours, no more than 30 hours, no more than 25 hours, no more than 20 hours, or no more than 15 hours. For example, the primary reaction can be repeated for about 10, 11, 12, 13, 14, 15, 16, 17, 18, 19, 0, 21, 22, 23, 24, 25, 26, 27, 28, 29, 30, 31, 32, 33, 34, or 35 hours. In several specific non-limiting examples, the reaction is performed for about 15 hours or about 25 hours or about 10 hours to about 25 hours. In specific non-limiting examples, the sample is a brain tissue sample or a CSF sample.

In some embodiments, the method is performed without serial amplification, such that substrate bound $T^D$ are retained in a reaction vessel, and that substrate is replenished without removing potential amyloid seeds. For example, amyloid Tau protein can be amplified in a sample, by mixing the sample with purified recombinant Tau protein to make a reaction mix; performing a seeded Tau polymerization assay that includes (i) contacting the biological sample with a purified recombinant truncated Tau protein, wherein the truncated Tau protein comprises three or four microtubule binding domains, and optionally a human Tau-free carrier to form a reaction mixture; (ii) incubating the reaction mixture to permit coaggregation of disease-associated Tau protein ($T^D$) present in the biological sample with the recombinant truncated Tau protein; (iii) maintaining incubation conditions that promote coaggregation of the recombinant truncated Tau protein with the $T^D$ to result in a conversion of the recombinant truncated Tau protein to amyloid Tau protein aggregates while inhibiting development of spontaneously arising ($T^D$-independent) amyloid Tau protein ($rT^{(spon)}$); and agitating amyloid Tau protein aggregates formed during step (iii), wherein the agitating comprises shaking the reaction mixture in a shaking cycle, wherein each shaking cycle comprises a period of rest and a period of shaking.

Detection of amyloid Tau protein in the reaction mix indicates that $T^D$ was present in the sample. Additional recombinant Tau protein can be added during the reaction, such as during the lag phase between the addition of the sample and the detection of amyloid Tau protein formation. However, in some embodiments, a portion of the reaction mix is not removed and incubated with additional recombinant truncated Tau protein. In some embodiments, the recombinant truncated Tau protein can be replenished by adding additional recombinant truncated Tau protein to the reaction mix. In other embodiments, the recombinant truncated Tau protein is not replenished by adding additional recombinant truncated Tau protein to the reaction mix.

In some embodiments, the reaction includes the use of shaking in the absence of sonication. In other embodiments, the reaction uses shaking and sonication In either of these embodiments, the reaction can include cycles of shaking/rest that are 1:10 to 10:1 in duration, such as 1:5 to 5:1 in duration, for example, 1:2 to 2:1 in duration, or about 1:1 in duration. In one non-limiting example, the reaction alternates 60 seconds of shaking and 60 seconds of no shaking (rest). In another non-limiting example, the reaction alternates 30 seconds of shaking and 30 seconds of no shaking (rest). However, the times can be varied, such as 45 seconds of shaking and 45 seconds of no shaking or 70 seconds of shaking and 70 seconds of no shaking. The shaking cycle can be, for example, about 20 to about 180 seconds in length, such as about 30 to about 180 seconds in length, about 40 to about 180– seconds in length, about 50 to about 180 seconds in length, or about 60 to about 180 seconds in length. In some embodiments of these cycle times, the period of rest and the period of shaking are equal. In other embodiments of these cycle times, the period of rest and the period of shaking are unequal.

In some embodiments, the period of rest and the period of shaking are about 120 seconds in length for the total cycle. In other embodiments the total cycle time is about 60 to 180 seconds in length, such as, but not limited to 60, 70, 80, 90, 100, 110, 120, 130, 140, 150, 160, 170, or 180 seconds in length. In non-limiting examples, the period of shaking and rest in each cycle can be equal, as discussed above.

In other embodiments, the period of rest and the period of shaking are unequal. For example, the reaction includes 90 seconds of shaking and 30 seconds of no shaking, or 100 seconds of shaking and 20 seconds of no shaking, or 80 seconds of shaking and 40 seconds of rest. In additional embodiments, the total cycle time is about 60, 70, 80, 90, 100, 110 or 120 seconds in length and includes at least 30 seconds, at least 40, or at least 50, or at least 60 seconds of shaking. In specific non-limiting examples, the total cycle time is 60 to 180 seconds in length, such as, but not limited to 60, 70, 80, 90, 100, 110, 120, 130, 140, 150, 160, 170, or 180 seconds in length.

Reactions can be performed at 25-60° C., for example 25-45° C., such as 25-37° C., such as about 25° C., 37° C., or at about 42° C. to 55° C., such as 42° C. to about 50° C.

In some embodiments, the reaction is performed using a chaotrophic salt. Thus, in some embodiments the reaction is performed using a chaotrophic salt at a concentration of about 50 mM to about 900 mM, such as about 100 to about 700, or about 100 mM to about 500 mM. In additional embodiments, about 100 mM, 200 mM, 300 mM, 400 mM of a chaotropic salt. In other embodiments, the reaction is performed using 200 to 400 mM, such as using 200 mM, of the chaotropic salt. Chaotropic salts are known in the art, and include, but are not limited to, bromide, floride, iodide, and perchlorate salts. Chaotrophic salts also include magnesium, calcium, and guanidinium salts. Exemplary salts include, but are not limited to, sodium bromide, calcium chloride, and guanadinium hydrochloride. Mixtures of these salts can also be use.

In other embodimetns, the reaction is performed using about 100 mM, 200 mM, 300 mM, 400 mM NaCl. In other embodiments, the reaction is performed using 200 to 400 mM NaCl, such as using 200 mM NaCl. sodium chloride (NaCl) at a concentration of about 50 mM to about 900 mM, such as about 100 to about 700, or about 100 mM to about 500 mM NaCl. In additional embodiments, about 100 mM, 200 mM, 300 mM, 400 mM NaCl. In other embodiments, the reaction is performed using 200 to 400 mM NaCl, such as using 200 mM NaCl.

In some embodiments, the reaction does not include an added detergent, such as an anionic, cationic, or zwitterionic detergent. In some examples, the reaction does not include any added detergent. In further embodiments, the reaction does not include added anionic detergent, such as, but not limited to, sodium dodecyl sulfate (SDS). In some embodiments, detergent at a concentration greater than 0.002% is not included in the reaction. The detergent concentration can be, for example, less than 0.001%. The detergent concentration can be, for example, less than 0.005%. In specific non-limiting examples, the detergent is sodium dodecyl sulfate (SDS).

For detection of a 3R, 4R or 3R/4R Tauopathy, the reaction mixture can include heparin and/or polyglutamate. In some embodiments, such as, but not limited to, the detection of Pick disease, PSP, CBD, AGD, or Alzheimer disease, the reaction mixture includes heparin. In other embodiments, such as, but not limited to, the detection of PSP or CBD, the reaction mixture includes polyglutamate, such as poly-L-glutamate and/or poly-D-glutamate. In more embodiments, such as, but not limited to, the detection of PSP and CBD, the reaction mixture includes heparin and polyglutamate, such as poly-L-glutamate and/or poly-D-glutamate.

Polyglutamate is commercially available, and includes forms with weight ranges, for example, of 1,500 to 5,500 confirmed by MALLS. The reaction can include polyglutamate, such as 1-200 µM polyglutamate. In some embodiments, the reaction mixture can include about 1, 5, 10, 20, 30, 40, 50, 60, 70, 80, 90, 100, 110, 120, 130, 140, 150, 16, 170, 180, 190 or 200 µM total concentration of polyglutamate.

In some embodiments the reaction mixture includes 1 to 200 µM total concentration of both heparin and polyglutamate. Thus, the reaction mixture can include about 1, 5, 10, 20, 30, 40, 50, 60, 70, 80, 90, 100, 110, 120, 130, 140, 150, 16, 170, 180, 190 or 200 µM total concentration of heparin and polyglutamate combined. In some embodiments, the reaction mixture includes both heparin and polyglutamate. Exemplary concentrations are 40 µM heparin, 80 µM heparin, 40 µM polyglutamate, and 80 µM polygultamate. In specific non-limiting examples, these reactions can be used to detect PSP, CBD and AGD.

In further embodiments, the reaction mixture includes heparin but not polyglutamate. In some embodiments, the reaction mixture can include about 1, 5, 10, 20, 30, 40, 50, 60, 70, 80, 90, 100, 110, 120, 130, 140, 150, 16, 170, 180, 190 or 200 µM total concentration of heparin, and does not include polyglutamate. Exemplary concentrations are 40 µM heparin, 80 µM heparin, in the absence of polyglutamate. In specific non-limiting examples, these reactions can be used to detect PSP. In other embodiments, these reaction mixtures can be use determine that a sample was from a subject that had PSP, and does not have CBD.

A solid substrate, such as a bead, such as beads can be used in the reaction. The beads can be any solid substrate, and include, but are not limited to, glass, polystyrene, silica, silica/zirconia, or metal beads. In some specific non-limiting examples, glass beads are utilized. The beads can be spherical, and have a diameter of about 0.5 mm to about 3 mm in diameter, such as about 0.5 to about 2 mm in diameter, such as about 0.8 to about 2 mm in diameter. In some non-limiting examples, the beads have a diameter of about 0.8 mm or 1 mm.

The beads can be included in a reaction at a concentration of 1 to 10 beads per 50 microliters (µl), such as 1 to 8 beads per 50 µl, such as 1 to 1 bead per 50 µl of reaction mixture. In some embodiments, the reaction includes 1, 2, 3, 4, 5, 6, 7, 8, 9, or 10 beads per 50 µl of reaction mixture. In some non-limiting examples, the beads are glass.

In yet other embodiments, the reaction mix includes 1 to 10 beads per 50 µl of reaction mixture. In some non-limiting examples, the reaction mix includes 1 glass bead per 50 µl of reaction mixture. In more embodiments, the beads are about 0.5 mm to about 3 mm in diameter, such as about 1 mm in diameter, or about 0.8 mm in diameter. In other non-limiting examples, the beads are glass.

The beads can be included in a reaction at a concentration of 1 to 10 beads per 100 microliters (µl), such as 1 to 8 beads per 50 µl, such as 1 bead per 50 µl of reaction mixture. In some embodiments, the reaction includes 1, 2, 3, 4, 5, 6, 7, 8, 9, or 10 beads per 100 µl of reaction mixture. In some non-limiting examples, the beads are glass.

In yet other embodiments, the reaction mix includes 1 to 10 beads per 100 µl of reaction mixture. In some non-limiting examples, the reaction mix includes 1 glass bead per 100 µl of reaction mixture. In more embodiments, the beads are about 0.5 mm to about 3 mm in diameter, such as about 1 mm in diameter, or about 0.8 mm in diameter. In other non-limiting examples, the beads are glass.

In some embodiments, an effective amount of a human Tau-free carrier, such as a brain homogenate lacking human Tau, is added to the reaction mixture. This carrier does not include any detectable human Tau protein. This embodiment can be used, in some non-limiting examples, when the sample is a brain sample. However, a human Tau-free carrier need not be included in the reaction mixture. In some non-limiting examples, the sample is a CSF sample, and a human Tau-free carrier is not utilized in the reaction mixture.

In some embodiments, the Tau-free carrier is a non-human brain homogenate, such as a murine, porcine, equine, rabbit brain homogenate. The brain homogenate can be from any veterinary animal. In some embodiments, the brain homogenate is murine. In other embodiments, the murine brain homogenate is from a mouse deficient for the use of murine Tau protein. The mouse can be a knock out mouse deficient for murine Tau protein. It should be noted that the carrier need not be a brain homogenate. Other carriers can be used such as milk protein or albumin. In some embodiments 0.1-10% of the Tau-free carrier is added to the reaction mixture, weight to volume. Thus, in a specific non-limiting example, the Tau-free carrier is about 0.5% weight per volume of the total reaction. In some embodiments, about 0.1 to about 1.0% brain homogenate is added to the reaction mixture, such as about 0.5% KO brain homogenate.

In further embodiments, the reaction includes an effective amount of N2. A 100× concentrated solution of N2 includes:

| Components | Molecular Weight | Concentration (mg/L) | mM |
|---|---|---|---|
| Proteins | | | |
| Human Transferrin (Holo) | 10000.0 | 10000.0 | 1.0 |
| Insulin Recombinant Full Chain | 5807.7 | 500.0 | 0.0860926 |
| Other Components | | | |
| Progesterone | 314.47 | 0.63 | 0.0020033708 |
| Putrescine | 161.0 | 1611.0 | 10.006211 |
| Selenite | 173.0 | 0.52 | 0.0030057803 |

Thus, in some embodiments, the reaction mix includes 10× to 0.0001× of N2, such as, but not limited to, 1× to about 0.001× of N2. Exemplary concentrations include, but are not limited to, about 1×, about 0.1×, about 0.01×, or about 0.001× of N2. This embodiment can be used, in some non-limiting examples, when the sample is a brain sample. However, a N2 need not be included in the reaction mixture. In some non-limiting examples, the sample is a CSF sample, and a N2 is not utilized in the reaction mixture.

In an RT-QuIC assay, a reaction product, such as amyloid, is detected in real time (RT). There is generally a lag phase in a QuIC reaction, wherein amyloid cannot be detected. The lag phase is considered to end when a statistically significant amount of amyloid can be detected, as compared to the background level of fluorescence. The length of the lag phase will vary when different substrates are used.

In IP-RT-QuIC, a solid substrate, such as a bead, such as magnetic beads can be used. The beads and any associated amyloid RT-QuIC conversion products tend to cling to the bottom of reaction vessel, such as a well. Thus, the reaction fluid can easily be changed, and the substrate replenished in its pre-RT-QuIC state, without removing many beads or bound reaction products from the well. The recombinant truncated Tau substrate can be replenished preemptively during the lag phase, such as before ThT positivity indicated much consumption by conversion to the amyloid product.

Thus, QuIC reaction can be an RT-QuIC reaction, and thus can include an amyloid-sensing dye, such as thioflavin T (ThT) or thioflavin S (ThS), or any other substrate which allows detection of the amyloid. Exemplary dyes include P-FTAA (quadro-formylthiophene acetic acid), HS-68, HS-67, HS-72, P-HTAA, P-HTAA-Se, P-FTAA-Se, and HS-53. The structure of these dyes is shown in Klingstedt et al., Chemistry 2013 Jul. 29; 19(31):10179-92. doi: 10.1002/chem.201301463, Epub 2013 Jun. 18, which is incorporated herein by reference.

The RT-QuIC assay incorporates recombinant truncated Tau protein as a substrate, intermittent shaking of the reactions such as in multi-well plates, largely detergent-free conditions and, in some embodiments, ThT- or ThS-based fluorescence detection of any resulting amyloid protein generated by the reaction. One advantage of using ThT (or ThS) is that it can be included in the reaction mixture. However, any of the dyes disclosed above can also be utilized.

In some embodiments, ThT is utilized. Thioflavin T is a benzothiazole dye that exhibits enhanced fluorescence upon binding to amyloid fibrils (see Khurana et al., J. Structural Biol. 151: 229-238, 2005), and is commonly used to detect amyloid fibrils.

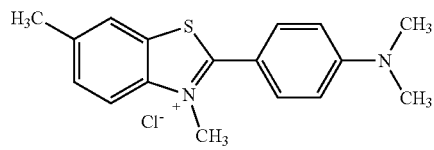

Following amplification, the amyloid Tau protein aggregates in the reaction mix is detected. If ThT is included in the reaction (RT-QuIC), then can be detected using fluorescence at 450+/−10 nm excitation and 480+/−10 nm emission (see for example, Wilham et al., PLOS Pathogens 6(12): 1-15, 2010, incorporated herein by reference.) ThT can be included directly in the amplification mixture.

In some embodiments, the reaction mix does not include chaotropes or detergents. In some embodiments, if ThT is included, the reaction mix does not include chaotropic agents or detergents that can alter the sensitivity of ThT. However, in other embodiments, the reaction mix does not include detergents that can alter the sensitivity of ThT, but incudes chaotrophic salts.

In one non-limiting example, in RT-QuIC reactions the final concentration of ThT in each reaction is 1 mM. In other examples, ThT is used at a final concentration of about 0.001 to 1 mM in the reaction.

Other dyes can be used in place of ThT, such as Thioflavin S, Congo red and congo red-derived fluorescent probe (trans, trans), -1-bromo-2,5-bis-(3-hydroxycarbonyl-4-hydroxy)styrylbenzene (BSB), a Nilsson dye or AMY-LOTRACKER™. One of skill in the art can readily utilize these dyes.

The fluorescent emitted by ThT (or ThS) can be measured in real time (RT). There is usually a lag phase in a RT-QuIC reaction, wherein ThT fluorescence cannot be detected. At some point, a statistically significant amount fluorescence can be measured that is above background fluorescence. The time of initiation of the reaction to the time of appearance of a statistically significant amount of detectable fluorescence, which represents the presence of amyloid Tau protein aggregates, can be measure as the lag phase. The length of the lag phase can vary when different substrates or $T^D$ seed concentrations are used.

If standard QuIC is utilized, amyloid Tau protein aggregates can be detected by means other than ThT fluorescence, for example, using an antibody (see below).

Two types of refolded amyloid protein can be generated in QuIC reactions, one occurring spontaneously without seeding by $T^D$ ($rT^{(spon)}$) and the other initiated by the presence of $T^D$ in the test sample. An unexpectedly superior decrease in the amount of $rT^{(spon)}$ formed is achieved with the QuIC assays disclosed herein. Thus, RT-QuIC (RTQ) (which includes thioflavin T) reactions provide sensitive and specific detection of $T^D$.

IV. Methods for Detecting in the Absence of a Dye

Once amyloid has been generated, the amyloid can be detected in the reaction mixture. Direct and indirect methods can be used for detection of amyloid in a reaction mixture. Detection using a fluorescent dye is described above. However, other methods can be utilized.

A. Western Blot

In some examples, reaction mixtures are then subjected to Western blot for detection of amyloid. Typical Western blot procedures begin with fractionating proteins by sodium dodecyl sulfate-polyacrylamide gel electrophoresis (SDS- PAGE) under reducing conditions. The proteins are then electroblotted onto a membrane, such as nitrocellulose or PVDF and probed, under conditions effective to allow immune complex (antigen/antibody) formation, with an anti-Tau protein antibody. Exemplary antibodies for detection of Tau protein include anti-Tau, anti-Tau (3-repeat isoform RD3), and/or anti-4R Tau antibodies.

Following complex formation, the membrane is washed to remove non-complexed material. An exemplary washing procedure includes washing with a solution such as PBS/Tween, or borate buffer. The immunoreactive bands are visualized by a variety of assays known to those in the art. For example, the enhanced chemoluminesence assay (Amersham, Piscataway, N.J.) can be used.

If desired, Tau protein concentration can be estimated by Western blot followed by densitometric analysis, and comparison to Western blots of samples for which the concentration of Tau protein is known. For example, this can be accomplished by scanning data into a computer followed by analysis with quantitation software. To obtain a reliable and robust quantification, several different dilutions of the sample generally are analyzed in the same gel.

B. ELISA, Immunochromatographic Strip Assay, and Conformation Dependent Immunoassay As described above, immunoassays in their most simple and direct sense are binding assays. Specific non-limiting immunoassays of use include various types of enzyme linked immunosorbent assays (ELISAs), immunochromatographic strip assays, radioimmunoassays (RIA), and specifically conformation-dependent immunoassays.

In one exemplary ELISA, anti-Tau antibodies are immobilized onto a selected surface exhibiting protein affinity, such as a well in a polystyrene microtiter plate. Then, a reaction mixture suspected of containing Tau protein antigen is added to the wells. After binding and washing to remove non-specifically bound immune complexes, the bound Tau protein can be detected. Detection generally is achieved by the addition of another anti-Tau antibody that is linked to a detectable label. This type of ELISA is a simple "sandwich ELISA." Detection also can be achieved by the addition of a second anti-Tau antibody, followed by the addition of a third antibody that has binding affinity for the second antibody, with the third antibody being linked to a detectable label.

In another exemplary ELISA, the reaction mixture suspected of containing the Tau antigen is immobilized onto the well surface and then contacted with the anti-Tau antibodies. After binding and washing to remove non-specifically bound immune complexes, the bound anti-Tau antibodies are detected. Where the initial anti-Tau antibodies are linked to a detectable label, the immune complexes can be detected directly. Again, the immune complexes can be detected using a second antibody that has binding affinity for the first anti-Tau antibody, with the second antibody being linked to a detectable label.

Another ELISA in which protein of the reaction mixture is immobilized involves the use of antibody competition in the detection. In this ELISA, labeled antibodies against Tau protein are added to the wells, allowed to bind, and detected by means of their label. The amount of Tau protein in a given reaction mixture is then determined by mixing it with the labeled antibodies against Tau protein before or during incubation with coated wells. The presence of Tau protein in the sample acts to reduce the amount of antibody against Tau available for binding to the well and thus reduces the ultimate signal. Thus, the amount of Tau protein in the sample can be quantified.

Irrespective of the format employed, ELISAs have certain features in common, such as coating, incubating or binding, washing to remove non-specifically bound species, and detecting the bound immune complexes. These are described below.

In coating a plate with either antigen or antibody, one generally incubates the wells of the plate with a solution of the antigen or antibody, either overnight or for a specified period of hours. The wells of the plate are then washed to remove incompletely adsorbed material. Any remaining available surfaces of the wells are then "coated" with a nonspecific protein that is antigenically neutral with regard to the test antibodies. These include bovine serum albumin, casein, and solutions of milk powder. The coating allows for blocking of nonspecific adsorption sites on the immobilizing surface, and thus reduces the background caused by non-specific binding of antibodies onto the surface.

It is customary to use a secondary or tertiary detection means rather than a direct procedure with ELISAs, though this is not always the case. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, or a secondary binding ligand or antibody in conjunction with a labeled tertiary antibody or third binding ligand.

"Under conditions effective to allow immune complex (antigen/antibody) formation" means that the conditions preferably include diluting the antigens and antibodies with solutions such as BSA, bovine gamma globulin, milk proteins, and phosphate buffered saline (PBS)/Tween. These added agents also tend to assist in the reduction of nonspecific background. "Suitable" conditions also mean that the incubation is at a temperature and for a period of time sufficient to allow effective binding. Incubation steps are typically from about 1 to 2 to 4 hours, at temperatures preferably on the order of 25° C. to 27° C., or can be overnight at about 4° C. or so.

Following all incubation steps in an ELISA, the contacted surface is washed so as to remove non-complexed material. An exemplary washing procedure includes washing with a solution such as PBS/Tween or borate buffer. Following the formation of specific immune complexes between the test sample and the originally bound material, and subsequent washing, the occurrence of even minute amounts of immune complexes can be determined.

To provide a detecting means, the second or third antibody generally will have an associated label to allow detection. In some examples, this is an enzyme that will generate color development upon incubating with an appropriate chromogenic substrate. Thus, for example, the first or second immune complex is contacted and incubated with a urease, glucose oxidase, alkaline phosphatase or hydrogen peroxidase-conjugated antibody for a period of time and under conditions that favor the development of further immune complex formation (for instance, incubation for two hours at room temperature in a PBS-containing solution such as PBS-Tween).

After incubation with the labeled antibody, and subsequent to washing to remove unbound material, the amount of label is quantified, for instance, by incubation with a chromogenic substrate such as urea and bromocresol purple or 2,2'-azino-di-(3-ethyl-benzthiazoline-6-sulfonic acid) and $H_2O_2$, in the case of peroxidase as the enzyme label.

Quantification is then achieved by measuring the degree of color generation, for instance, using a visible spectra spectrophotometer.

C. Recombinant Tau Protein Labeling

In certain embodiments, the recombinant truncated Tau protein can be labeled to enable high sensitivity of detection of protein that is converted into amyloid. For example, the recombinant truncated Tau protein can be radioactively labeled, epitope tagged, or fluorescently labeled. The label can be detected directly or indirectly. Radioactive labels include, but are not limited to $^{125}$I, $^{32}$P, $^{33}$P, and $^{35}$S.

The mixture containing the labeled protein is subjected to a seeded Tau polymerization assay, such as QuIC, and the product detected with high sensitivity by following conversion of the labeled protein to amyloid, and after removal of the unconverted protein. Alternatively, the protein can be labeled in such a way that a signal can be detected upon the conformational changes induced during conversion. An example of this is the use of FRET technology, in which the protein is labeled by two appropriate fluorophores, which upon refolding become close enough to exchange fluorescence energy (see for example U.S. Pat. No. 6,855,503).

In certain other embodiments, the use of a fluorescently-tagged substrate for the reaction is combined with the use an immunochromatographic strip test with an immobilized amyloid specific antibody. Binding of the amyloid to the antibody is then detected with a fluorescence detector.

EXAMPLES

Many neurodegenerative diseases involve the accumulation of self-seeding oligomers and filaments of Tau. The detection of distinctive biomarkers remains a challenging goal in dementia diagnostics, therapeutics and research. Pick disease (PiD) involves language and/or movement dysfunction as well as dementia and preferential accumulation of 3-repeat (3R) Tau isoforms. Using a 3R Tau fragment as a substrate, a seeded polymerization assay (Tau RT-QuIC) was developed for Tau seeds in PiD brain tissue dilutions down to $10^{-7}$-$10^{-9}$. Higher PiD seeding activities were observed in the frontal and temporal lobes compared to the cerebellum. In contrast, the test was $10^3$ to $10^5$-fold less responsive when seeded with brain specimens containing predominant 4-repeat (4R) Tau aggregates from cases of corticobasal degeneration, argyrophilic grain disease, and progressive supranuclear palsy Alzheimer disease brain samples, with 3R+4R Tau deposits, gave variable and weak responses relative to PiD. When applied to cerebrospinal fluid samples, Tau RT-QuIC analyses discriminated PiD from non-PiD cases. These findings demonstrate that abnormal Tau aggregates can be detected with unprecedented sensitivity and specificity in complex tissue or fluid samples, suggesting a novel approach for diagnosing Tauopathies and monitoring therapeutic trials using aggregated Tau itself as a biomarker.

Example 1

Development of Tau RT-QuIC

The goal was to establish assay conditions in high-throughput multi-well plates that maximize the kinetic distinction between reactions initiated with samples from patients with and without significant Tau pathology. Influential parameters were varied such as the sequence and preparation of the recombinant Tau substrate; the polyanionic cofactor (e.g. heparin or polyglutamic acid); temperature; pH; NaCl concentration; shaking speed; detergents; and protein or tissue additives to serve as carriers to reduce non-specific interactions or seed losses.

Figure 1:
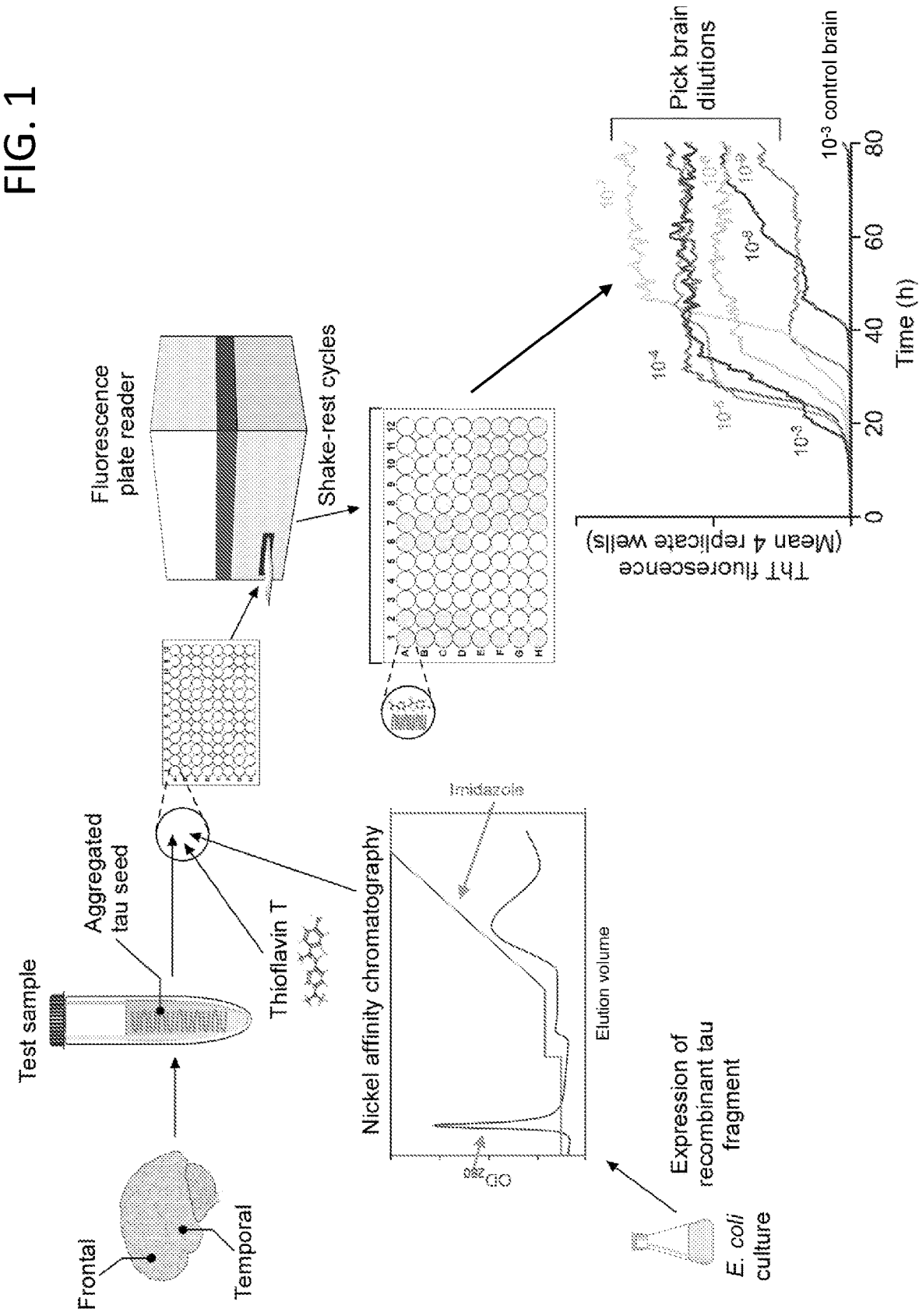
FIG. 1. Flow chart of Tau RT-QuIC assay for Tau seeding activity.

The resulting Tau RT-QuIC test is disclosed herein and outlined in FIG. 1. This assay is based on a synthetic 3R Tau substrate that has been previously named K19 cysteine-free (K19CF) (Dinkel et al., *Biochemistry* 50, 4330-4336 (2011)). The preparation of K19CF was of importance. Previous reports have described the use of cation exchange and size exclusion chromatography steps to purify K19CF (Dinkel et al., *Biochemistry* 50, 4330-4336 (2011)). The yield of the purification was improved by designing a histidine-tagged modification of K19CF (K19CFh) and using a one-step nickel-charged affinity column with imidazole gradient elution. A minor impurity(s) eluting in fractions overlapping the early fractions of the K19CFh peak strongly inhibited seeded polymerization of K19CFh. Therefore the gradient was modified to improve separation at that stage of the elution and discarded the problematic fractions. The K19CFh product was predominantly of the expected ~13-kD size according to SDS-PAGE and MALDI mass spectrometry, however, a smaller fragment that also reacts with Tau antibody was also visible in Coomassie blue stained gels (FIG. 6 and FIG. 21E).

Because the K19CFh is a 3R substrate, initial assay development was based on the detection of natural seeding in the brain of an individual with PiD, a disease that is known to involve preferential accumulation of 3R Tau aggregates (Irwin et al., *Ann. Neurol.* 79, 272-287 (2016)). Under the selected conditions, rapid increases in ThT fluorescence began within 15-25 h in all quadruplicate reactions when seeded with $10^{-3}$ and $10^{-4}$ dilutions of PiD brain homogenate (FIGS. 2A-2B). With $10^{-5}$ and $10^{-7}$ dilutions, all quadruplicate reactions were positive, but with longer lag phases on average (FIGS. 2C-2D). With $10^{-8}$ and $10^{-9}$ dilutions (FIGS. 2F-2G) only a subset of the quadruplicate reactions were positive within 60 h. The analysis was ended at 60 h because after that time-point, reactions seeded with brain homogenate from totally Tau-free knockout (KO) mice began to give rare, Tau seed-independent positive reactions (FIG. 2J). Although it is impossible to ascertain if any particular human brain tissue is totally free of Tau seeds and therefore entirely suitable as a negative control, tissue from a human individual with neuropathological senile changes (SC) but little to no Tau pathology that was visible by immunohistochemical staining was tested. The responses from a $10^{-3}$ dilution of this SC brain only just started giving positive responses at ~60 h (FIG. 2I). This indicated that there was at least ~$10^6$-fold less K19CFh seeding activity in the human SC and mouse Tau KO brains (FIG. 2J) than in the human PiD brain.

Example 2

Tau RT-QuIC Analyses of Brain from Patients with a Broad Spectrum of Tauopathies Seven additional PiD cases were tested, as well as cases of other types of diseases with Tau accumulation, namely AD (n=11), PSP (n=7), CBD (n=4), AGD (n=3), frontotemporal lobar degeneration with TDP 43 (FTD-TDP43, n=4), and frontotemporal dementia with parkinsonism linked to chromosome 17 (FTDP, n=3). While AD is typically associated with deposits containing both 3R and 4R Tau isoforms, the other diseases have preferential accumulation of 4R Tau deposits (William, *Intern. Med. J.* 36, 652-660 (2006)). Although some FTDP cases can have preferential 3R Tau deposits (Williams, *Intern. Med. J.* 36, 652-660 (2006)), the three cases that we analyzed were determined by postmortem analysis to have predominant 4R deposition due to the mutation IVS10+3G>A in the microtubule associated protein Tau (MAPT) (Spillantini et al., *Proc Natl Acad Sci USA* 94, 4113-4118 (1997).). Two additional SC cases were tested, as well as other cases with no immunohistologically detectable Tau pathology with diagnoses of cerebrovascular disease (CVD, n=2), and diffuse Lewy body disease (DLBD, n=4), a synucleinopathy. Table 1 provides patient data as well as results of individual end-point dilution Tau RT-QuIC analyses of all of these cases, using Spearman-Karber analysis to estimate the login concentration of seeding units (or doses) giving positive reactions in 50% of the quadruplicate reactions ($SD_{50}$) per mg brain tissue.

TABLE 1

End-point quantification of Tau seeding activity

| Tauopathy classification | 1° (2°, 3°, 4°) Diagnosis | Brain Region | Sex | AOD | PMI | Brain Weight | Tau-RTQ Seed concentration (log SD50/mg tissue) | | | | | Avg ± SD |
|---|---|---|---|---|---|---|---|---|---|---|---|---|
| | | | | | | | Expt 1 | Expt 2 | Expt 3 | Expt 4 | Expt 5 | |
| 3R | PiD 1 (CVD) | F | M | 56 | 9 | 1032 | 6.7 | 7.0 | 7.2 | 6.7 | 8.5 | 7.3 ± 0.8 |
| | | T | | | | | 6.0 | 8.0 | 8.5 | — | — | 7.5 ± 1.3 |
| | | C | | | | | 5.7 | 7.2 | 5.7 | 5.7 | — | 6.1 ± 0.8 |
| | PiD 2 (β-amyloid pathology, CVD) | F | M | 64 | 3 | 1003 | 8.2 | 8.7 | 8.0 | — | — | 8.3 ± 0.4 |
| | PiD 3 (CVD) | F | F | 67 | 8 | 808 | 9.0 | 8.5 | 7.2 | 7.5 | — | 8.1 ± 0.8 |
| | PID 4 | F | M | 70 | NA | NA | 7.2 | 7.7 | 7.8 | — | — | 7.6 ± 0.3 |
| | PiD 5 (CVD) | F | M | 65 | 13 | 913 | 7.5 | 7.7 | 7.8 | — | — | 7.7 ± 0.2 |
| | PiD 6 (CVD) | F | F | 77 | 9 | 891 | 8.5 | 6.5 | 6.5 | — | — | 7.2 ± 1.2 |
| | PiD 7 (SC, CVD) | F | F | 73 | 24 | 993 | 7.5 | 7.7 | 7.3 | — | — | 7.5 ± 0.2 |
| | PID 8 | F | M | 61 | 25 | 1000 | 6.7 | 7.0 | 7.7 | — | — | 7.1 ± 0.5 |
| 3R/4R | AD 1 | F | M | 58 | 13 | NA | 4.2 | 3.2 | 3.2 | 4.0 | — | 3.7 ± 0.5 |
| | AD 2 | F | F | 80 | 26 | 1007 | 4.2 | 3.2 | 3.0 | — | — | 3.5 ± 0.6 |
| | AD 3 | F | M | 70 | 9 | 1390 | 3.7 | 2.7 | 3.0 | — | — | 3.1 ± 0.5 |
| | AD 4 | Cx | M | 80 | 3 | 1000 | 2.7 | 3.0 | 2.5 | — | — | 2.7 ± 0.3 |
| | AD 5 | Cx | F | 82 | 4 | 932 | 4.2 | 2.7 | 3.0 | 2.5 | — | 3.1 ± 0.8 |
| | AD 6 | Cx | F | 78 | 2 | 750 | 3.2 | 3.2 | 2.7 | — | — | 3.0 ± 0.3 |
| | AD 7 | Cx | F | 89 | 3 | 1048 | <2.2 | 3.0 | 2.5 | — | — | 2.6 ± 0.4 |
| | AD 8 | Cx | F | 68 | 4 | 1074 | <2.2 | 3.0 | <2.2 | — | — | 2.5 ± 0.5 |
| | AD 9 | Cx | M | 85 | 3 | 1085 | <2.2 | 2.7 | 2.5 | — | — | 2.5 ± 0.3 |
| | AD 10 (Vascular pathology) | F | M | 69 | 48 | NA | 2.7 | 3.0 | 2.5 | — | — | 2.7 ± 0.3 |
| | AD 11 | F | F | 79 | 48 | NA | <2.2 | <2.2 | 2.7 | — | — | 2.4 ± 0.3 |
| 4R | PSP 1 | F | M | 86 | 7 | 1530 | 3.2 | 3.2 | 3.5 | 4.2 | — | 3.5 ± 0.5 |
| | PSP 2 (CVD) | F | M | 71 | 13 | 1143 | 3.7 | <2.2 | 3.2 | — | — | 3.0 ± 0.8 |
| | PSP 3 (CVD) | F | M | 65 | 8 | 1175 | 3.0 | 3.0 | 2.7 | — | — | 3.0 ± 0.2 |
| | PSP 4 (SC) | F | M | 67 | 4 | 1480 | 2.7 | 4.2 | 4.7 | — | — | 3.9 ± 1.0 |
| | PSP 5 (CVD) | F | M | 76 | 6 | 1381 | 2.5 | 4.2 | 4.0 | — | — | 3.6 ± 0.9 |
| | PSP 6 | F | F | 71 | 7 | 1043 | <2.2 | 3.0 | 3.0 | — | — | 2.7 ± 0.5 |
| | PSP 7 (Multi-system atrophy) | F | M | 84 | 48 | NA | 2.5 | 3.2 | 3.2 | — | — | 3.0 ± 0.4 |
| | CBD 1 | F | F | 51 | 10 | NA | 2.7 | <2.2 | 2.7 | — | — | 2.5 ± 0.3 |
| | CBD 2 (CV, SC) | F | F | 75 | 51 | 1120 | 3.0 | 3.0 | 3.0 | 2.7 | 3.0 | 2.9 ± 0.1 |
| | CBD 3 (CVD) | F | M | 65 | 17 | 1200 | 4.0 | 3.2 | 3.0 | 2.5 | — | 3.2 ± 0.6 |
| | CBD 4 (CVD, SC) | F | F | 69 | 5 | 1000 | <2.2 | 2.5 | 2.7 | — | — | 2.5 ± 0.3 |
| | AGD 1 | F | F | 82 | 19 | 1049 | <2.2 | <2.2 | 3.5 | — | — | 2.6 ± 0.8 |
| | AGD 2 (CVD) | F | M | 91 | 2 | 1175 | 4.0 | 3.2 | 3.7 | — | — | 3.6 ± 0.4 |
| | AGD 3 (Hippocampal sclerosis) | F | M | 86 | 110 | 1330 | 3.7 | 4.0 | 3.2 | — | — | 3.6 ± 0.4 |
| | FTD-TDP43 1 (CVD) | F | F | 50 | 6 | 754 | 3.7 | 4.7 | 4.2 | 4.0 | — | 4.2 ± 0.4 |
| | FTD-TDP43-Type B 2 (PSP, SC, CVD) | F | F | 73 | 23 | 979 | <2.2 | 3.5 | — | — | — | 2.9 ± 0.9 |
| | FTD-TDP43-Type C 3 (CVD) | F | F | 68 | 15 | 1100 | <2.2 | 3.5 | — | — | — | 2.9 ± 0.9 |
| | FTD-TDP43-Type A 4 (CVD) | F | F | 65 | 5 | 886 | 3.7 | 3.5 | — | — | — | 3.6 ± 0.1 |
| | FTDP 1 | F | M | 54 | 22 | NA | 4.2 | 3.2 | 3.0 | — | — | 3.5 ± 0.6 |
| | FTDP 2 (Status post IVH, CVD) | F | F | 58 | 15 | 1020 | 4.2 | 3.7 | 4.0 | — | — | 4.0 ± 0.3 |
| | FTDP 3 | F | F | 54 | 11 | 1122 | 3.2 | 3.2 | 3.0 | — | — | 3.1 ± 0.1 |
| No/low | SC 1 | F | F | 76 | 4 | 1240 | 2.5 | 2.7 | 3.5 | 2.5 | 2.7 | 2.8 ± 0.4 |
| | | T | | | | | <2.2 | — | — | — | — | |
| | SC 2 (Meningioma) | F | F | 73 | 24 | 975 | 4.2 | 3.0 | 2.7 | 3.2 | 2.7 | 3.2 ± 0.6 |
| | SC 3 | F | F | 81 | 25 | 1100 | 3.5 | 2.7 | <2.2 | <2.2 | 2.7 | 2.7 ± 0.5 |
| | | T | | | | | <2.2 | 2.5 | — | — | — | 2.4 ± 0.2 |
| | CVD 1 | F | F | 53 | 19 | 1192 | <2.2 | 2.5 | 2.7 | <2.2 | <2.2 | 2.4 ± 0.2 |
| | CVD 2 | F | F | 66 | 17 | 1072 | 3.7 | 2.7 | 2.7 | 2.5 | <2.2 | 2.8 ± 0.6 |
| | DLBD 1 (SC, CVD) | F | M | 80 | 12 | 1285 | 4.2 | <2.2 | 2.5 | <2.2 | — | 2.8 ± 1.0 |

TABLE 1-continued

End-point quantification of Tau seeding activity

| | | | | | | | | | | | |
|---|---|---|---|---|---|---|---|---|---|---|---|
| DLBD 2 (SC, CM, CVD) | F | M | 81 | 20 | 1294 | 2.5 | <2.2 | <2.2 | 2.5 | <2.2 | 2.3 ± 0.2 |
| DLBD 3 (SC, CVD) | F | M | 73 | 14 | 1072 | 3.5 | 2.5 | <2.2 | <2.2 | — | 2.6 ± 0.6 |
| DLBD 4 (CVD, SC) | F | M | 71 | 8 | 1395 | <2.2 | 2.5 | 2.5 | <2.2 | 2.5 | 2.4 ± 0.2 |
| Tau KO | Whole | NA | NA | NA | NA | <2.2 | <2.2 | 2.3 | 2.5 | <2.2 | *2.3 ± 0.1 |

| | |
|---|---|
| AGD | Argyrophilic grain disease |
| AD | Alzheimer disease |
| ALS | Amyotrophic lateral sclerosis |
| AOD | Age of death |
| CBD | Corticobasal degeneration |
| CM | Cerebral malformation |
| CVD | Cerebrovascular disease |
| DLBD | Diffuse Lewy body disease |
| FTDP | Frontotemporal dementia with parkinsonism linked to chromosome 17 |
| FTD-TDP43 | Frontotemporal dementia with TDP-43 |
| IVH | Intraventricular hemorrhage |
| NA | Not available |
| PiD | Pick disease |
| PMI | Post-mortem interval |
| PSP | Progressive supranuclear palsy |
| SC | Senile change |
| Tau KO | Human and mouse Tau knockout mouse |

Brain regions: F frontal cortex; T temporal cortex; C cerebellar cortex; Cx cortex
Brain weights in g
*Sixteen more experiments were performed FIG. 3 graphs the mean $SD_{50}$ concentrations for each case. Consistent with the initial PiD case (#3), high K19CFh seeding activities were observed in each of the 7 additional PiD cases, i.e. means of $\geq 10^{7.6}$ $SD_{50}$ per mg brain tissue. In contrast, the seeding activity in the brain of most cases of the other Tauopathies were within ~2 $\log_{10}$ of the detection limit established by the Tau-free KO mouse brain, i.e., $<10^{2.2}$ $SD_{50}$ per mg brain. Primary data from an AD case (AD1) and a PSP case (PSP1) that repeatedly gave readings above the detection limit are shown in FIGS. 4A-4D and FIGS. 4H-4J, respectively. Although these and other cases had K19CFh seeding activities that exceeded that of KO brain, they were ~$10^3$-$10^5$ lower than that seen in PiD brains (Table 1).

Example 3

PiD Seeding Activity in Cerebellum Versus Frontal and Temporal Lobes

Because Tau neuropathology in PiD is more pronounced in the frontal and temporal lobes than in the cerebellum the relative levels of TauRTQ seeding activity in these brain regions was compared. Although seeding activity was detectable in the cerebellum, it was ~100-fold lower than the corresponding frontal and temporal lobes of the same brain (FIGS. 5A-5O, Table 1).

Example 4

Tau RT-QuIC Seeding Activity in Detergent-Insoluble Brain Fractions

It was also determined whether the seeding activity that was observed in crude PiD brain homogenates was present in detergent-insoluble preparations enriched with Tau filaments. As shown in FIGS. 7A-7F, the filament preparation from the PiD case had seeding activity that gave shorter lag phases than comparable preparations from an AD case and, to an even greater extent, a CVD cases. This result is consistent with seeding activity being associated with detergent-insoluble Tau filaments from PiD and AD brains. Confirming the association of seeding activity with Tau filaments, we also detected Tau RT-QuIC seeding activity in synthetic amyloid fibril preparations composed of pure K19CFh Tau.

Example 5

Using CSF to Discriminate PiD and Non-PiD Cases

Figure 2:
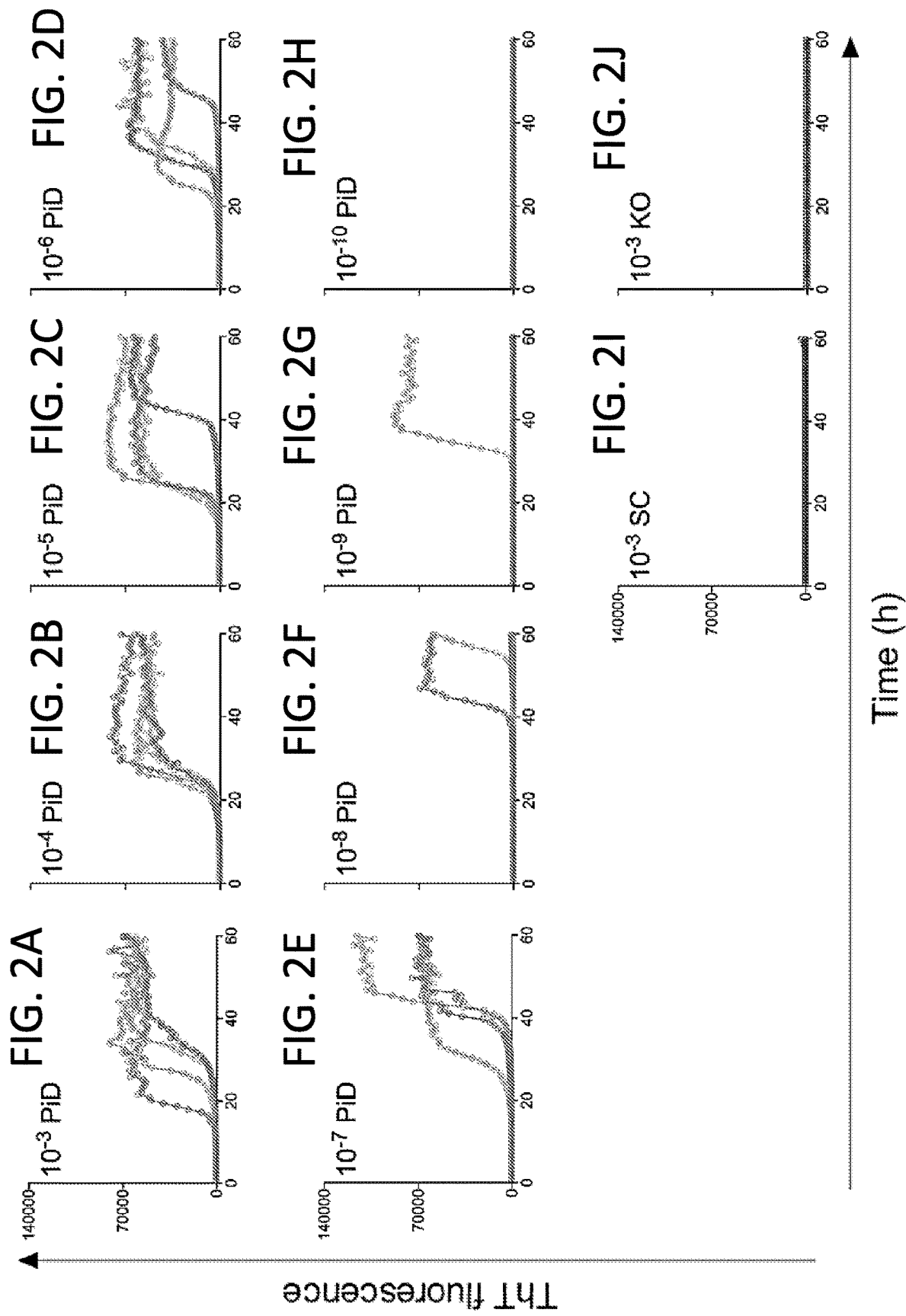
FIGS. 2A-2J. End-point dilution Pick disease-optimized (3R) Tau RT-QuIC analysis of Tau seeding activity in a PiD brain homogenate. Panels
Figure 3:
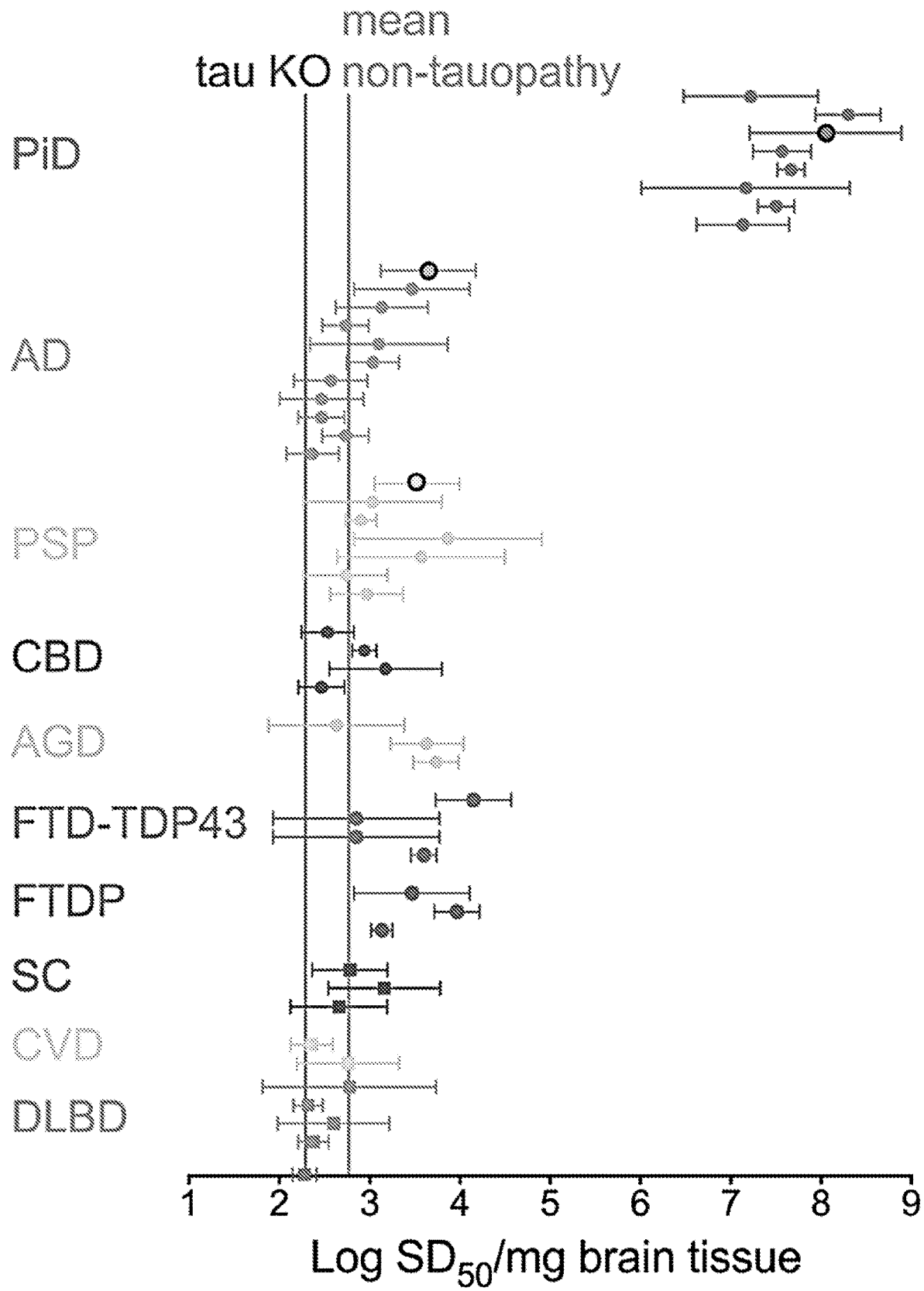
FIG. 3. End-point 3R Tau RT-QuIC quantification of Tau seeding activity in brain tissue from Tauopathy and non-Tauopathy cases. Mean $\log_{10}$ $SD_{50}$/mg brain values are shown for predominantly 3R (PiD), roughly equivalent 3R+4R (AD) and predominantly 4R (PSP, CBD, AGD, FTD-TDP43, and FTDP) Tauopathies. Human brain tissue with senile changes (SC; see FIG. 2 legend), cerebrovascular disease (CVD) and diffuse Lewy body dementia (DLBD) were evaluated as cases with no apparent Tau immunohistopathology. Responses from knockout mouse (KO) brains at a $10^{-3}$ dilution provided Tau-free controls to establish a Tau-negative baseline (grey vertical line). Data points represent the $\log_{10}$ $SD_{50}$/mg brain tissue for each case (as itemized in Table 1) as estimated by Spearman-Karber analysis of a series (if necessary) of 10-fold dilutions, with 4 technical replicate reactions performed at each dilution. When at least 3 independent dilution series were analyzed for a given brain homogenate, error bars indicate the standard deviation of the individual mean $\log_{10}$ $SD_{50}$/mg determinations for the given sample. The vertical blue line indicates the combined mean of the mean $\log_{10}$ $SD_{50}$/mg values from all of the human non-Tauopathy cases. The recombinant truncated Tau substrate was K19CFh.

To examine whether Tau RT-QuIC can detect seeding activity in a specimen that is diagnostically accessible, 5 µl CSF samples were tested from 8 PiD cases and 21 non-PiD cases, the latter including "healthy" controls and cases with other neurological diseases (OND) (Table 2). FIG. 19 shows primary data from the 8 PiD cases and 12 of the non-PiD cases from one experiment. Stronger, faster responses were seen within 15 h from the PiD samples than from the non-PiD samples. End-point dilution analysis of two PiD cases indicated that they had ~1-10 $SD_{50}$ per 5 ul of CSF (FIG. 23), i.e., above, but much closer to the detection limit of the assay than is brain tissue (FIGS. 2 and 3).

Typically, in using RT-QuIC testing for prion disease diagnosis (Atarashi et al., *Nat. Med.* 17, 175-178 (2011); McGuire et al., *Ann. Neurol.* 72, 278-285 (2012); Cramm et al., *Mol. Neurobiol.* 51, 396-405 (2015); Orru et al., *New Engl. J. Med.* 371, 519-529 (2014); McGuire et al., *Ann. Neurol.* 80, 160-165 (2016); Cramm et al., *Mol. Neurobiol.* (2015)), a threshold is chosen to assess whether individual reaction wells are positive within a specific reaction time. This choice is often based on whether, in a particular application, it is more important maximize diagnostic sensitivity or specificity at the margins of the assay. Using a provisional positivity threshold (see below) at the 15-h time point, the fraction of RT-QuIC-positive wells were determined for each CSF specimen in each experiment, and cumulatively through multiple experiments (Table 2). A total of 73/80 (91%) of replicate wells seeded with the PiD samples positive replicate reactions, while only 3/168 (2%)

of the non-PiD reactions were positive. Another criterion that is used in judging whether a CSF specimen is positive in prion RT-QuIC diagnostics is that at least half of the technical replicate wells are positive according to the selected threshold Atarashi et al., *Nat. Med.* 17, 175-178 (2011); McGuire et al., *Ann. Neurol.* 72, 278-285 (2012); Cramm et al., *Mol. Neurobiol.* 51, 396-405 (2015); Orru et al., *New Engl. J. Med.* 371, 519-529 (2014); McGuire et al., *Ann. Neurol.* 80, 160-165 (2016); Cramm et al., *Mol. Neurobiol.* (2015)). Applying this criterion to the CSF data in Table 2, all 8 of the PiD cases would be judged positive in all of the experiments giving 100% sensitivity (the % of PiD cases with positive overall Tau RT-QuIC results). In contrast, in experiments 1, 2, and 4, all of the 21 non-PiD samples were negative, giving 100% specificity (the % of non-PiD cases with negative results). However, in experiment #3, one of the "healthy" controls gave 2/4 positive replicate wells, and thus would be given an overall positive Tau RT-QuIC designation despite being judged negative in the other experiment (#4) in which it was tested. Thus, in experiment #3, the specificity was 15 negative results for 16 total non-PiD cases, giving a specificity of 94%. Collectively, these results suggest that Tau RT-QuIC analysis of CSF is useful for discriminating PiD and non-PiD cases.

Results from experiments analyzing overlapping sets of samples, using 20 µl of CSF samples, are summarized in FIG. 24. Again the data show consistently that the PiD samples caused increased fluorescence within ~15 h while the non-PiD cases gave markedly slower responses (FIGS. 24A, 24B). The greatest discrimination between PiD and the others was observed at ~25 h. At the 25-h time point (FIG. 24C), the differences between the PiD and non-PiD (OND and healthy) responses were highly significant [$p<0.0001$, unpaired t tests], thus it discriminates PiD from non-PiD cases. At the 55-h time point (FIG. 24D), the differences between the healthy and PiD or AD responses were highly significant [$p<0.0001$, unpaired t tests]; further, the differences between the healthy and FTD is also significant [$p<0.01$, an unpaired t test]. Statistical analysis was performed using values from each individual replicate in each experiment.

Thus, it was demonstrated that an assay based on the seeded polymerization of a recombinant Tau-based substrate can sensitively detect and quantitatively distinguish PiD from other Tauopathies. The fact that the seeding activity can be detected in the complex matrix of crude brain homogenate and cerebrospinal fluid attests to the selectivity of the seeded polymerization mechanism under these conditions. The following considerations are consistent with it being comprised of Tau aggregates: 1) PiD involves the accumulation of predominantly 3R Tau filaments; 2) The Tau RT-QuIC seeding activity was also found in Tau filament preparations from brain (FIG. 2, FIG. 3, FIG. 5, FIG. 16 and Table 1) and cerebrospinal fluid (FIG. 19, FIG. 23 and FIG. 24A-24D and Table 2); 3) The reaction substrate is a Tau fragment (K19CFh) that matches the 3R segment of the Tau deposits in PiD; and 4) pure preformed amyloid fibrils of K19CFh have Tau RT-QuIC seeding activity like that found in PiD brain.

The observation that predominantly 3R Tau filaments of PiD have much greater ability to seed K19CFh fibrillization than the 4R filaments of most of the other Tauopathies tested is consistent with a previous report that 3R Tau filaments can seed 3R, but not 4R, Tau substrates (Dinkel et al., *Biochemistry* 50, 4330-4336 (2011)). Surprisingly, AD cases had $10^3$ to $10^5$-fold lower seeding activity than the PiD cases (FIG. 4 and Table 1). In Tau filament preparations from AD brain tissue, 3R Tau isoforms are roughly equivalent to 4R isoforms (Taniguchi et al., *Acta Neuropathol* 131, 267-280 (2016; Hasegawa et al., *Acta Neuropathol* 127, 303-305 (2014)), so it seems unlikely that AD brain contains a $10^5$-fold lower content of 3R Tau-containing filaments. Thus, it is expected that the relative lack of seeding of K19CFh fibrillization by AD samples is due to interference by the presence of the 4R Tau isoforms, and/or a fundamental inability of filaments comprised of both 3R and 4R Tau isoforms to seed the growth of filaments comprised only of K19CFh. The same might be true of many of the other types of non-Pick Tau diseases that, despite having a predominance of 4R Tau deposits, can also accumulate immunochemically detectable 3R isoforms in the brain (reviewed in Williams, *Intern. Med. J.* 36, 652-660 (2006)). This makes it unlikely that AD with both 3R and 4R deposits have separate 3R-only filaments that would presumably be able to seed K19CFh fibrillization without direct interference from 4R Tau isoforms within the same filament. Alternatively, there might be 3R-only filament conformers that are able to grow using natural 3R Tau isoforms, but, unlike the PiD filaments, are unable to accommodate K19CFh monomers, perhaps due to the unnatural lack of cysteines or presence of poly-histidine tags in this substrate construct.

The ability to sensitively detect specific PiD-associated Tau seeds has significant practical applications. In particular, seeds in CSF can serve as a basis for diagnostic testing and disease-specific biomarker detection in neurological patients. Because of the rarity of PiD CSF samples obtained from subjects with a definite diagnosis, only PiD CSF samples were obtained that were collected post-mortem. Tau RT-QuIC permutations using various monomeric recombinant reaction substrates and reaction conditions allows the development of similarly sensitive and specific assays for the other types of Tauopathies.

Currently, the levels of Tau and phospho-Tau in the CSF and positron emission tomography Tau imaging are commonly applied in Alzheimer disease to monitor disease progression and the efficacy of therapeutic compounds in clinical trials (Dani et al., *Eur J Nucl Med Mol Imaging* 43, 1139-1150 (2016)). When a neurodegenerative disorder involving Tau is suspected, the diagnostic sensitivity of Tau imaging and Tau markers is still relatively modest (Hu et al., *Neurology* 81, 1945-1952 (2013); Gold et al., *Neuropsychiatr Dis Treat* 8, 85-93 (2012)). Therefore, identifying specific pathogenic oligomers of Tau represents a novel and promising approach for detection of Tauopathy diagnosis and screening patients for therapeutic trials.

Example 6

Exemplary Materials and Methods

Recombinant Tau protein expression and purification: A 3R K19 construct with a point mutation at residue 322 cysteine to serine is called K19 cysteine-free (K19CF) was used. This mutation prevented inter-molecular disulfide bond formation. A methionine residue was also added to N-terminal residue 244 (using the numbering for full-length human Tau isoform hTau40), and a stop codon was added C-terminal residue 372. The K19CF encoding sequence was designed between two restriction endonuclease enzyme sites NdeI at the 5' and XhoI at the 3' end in a bacterial expression vector pET-28a, consequently, a poly-histidine tag was expressed at the N-terminus yielding K19CFh. Mutated expression cassettes were synthesized and cloned into the bacterial expression vector by GenScript.

K19CFh was expressed in BL21(DE3) strain of *Escherichia coli* following the overnight express autoinduction method (Current Protocols in Protein Science 5.23.1-5.23.18, April 2009) (Studier, *rotein Expr. Purif.* 41, 207-234 (2005)). Bacterial pellets containing expressed Tau were lysed in buffer A (10 mM Tris, pH 8.0, 500 mM NaCl, and 5 mM imidazole) and sonicated for 3 mM (3 cycles of 45 seconds sonication and 15 seconds pulse). The lysate was centrifuged at 10,000×g for 1 h at 4° C. The supernatant was removed, filtered with a 0.45 µm syringe filter and purified over a His-Trap FF (5 ml) column (GE Healthcare 17-5255-01). The expression to purification steps were performed continuously without any freeze-thaw cycles. Before eluting K19CFh, the column was washed with 7 column volumes of 30 mM imidazole in 10 mM Tris, pH 8.0 and 500 mM NaCl and then 5 column volumes of the same buffer with 46 mM imidazole. Protein was eluted with a linear 46-200 mM imidazole gradient over 8 column volumes. Two-ml fractions were collected, and dithiothreitol (DTT) was added to give a final concentration of 2 mM. Fractions were analyzed by SDS-PAGE, pooled according to purity and precipitated in 4 volumes of acetone overnight at 4° C. Pellets were collected by centrifugation for 20 mM at 10,300×g and washed with 5 ml acetone with 2 mM DTT per 2 ml fraction. Pellets were solubilized in 8 M GdnHCl to ensure that proteins were a homogenous pool of monomers. GdnHCl was removed by elution over PD-10 desalting column (GH Healthcare, 17-0851-01) in phosphate-buffered saline (1×PBS, pH 7.4) according to the manufacturer's gravity protocol. Protein concentration was determined by absorbance measurements at 280 nm with a NanoDrop 2000 spectrophotometer. Final protein concentrations were adjusted to ~1 mg/ml with 1×PBS, and aliquots stored at −80° C. Storing protein at greater than ~1 mg/ml tended to cause precipitation during storage.

SDS-PAGE analysis: Samples were prepared in 2× sample loading buffer (125 mM Tris-HCl, pH 6.8, 10% glycerol, 6 mM EDTA, 10% SDS, 0.04% bromophenol blue, 6M urea, 8% β-mercaptoethanol) and boiled for 5 mM. Proteins were separated by gel electrophoresis using 10 or 12% Bis-TrisNuPAGE gels (Invitrogen). For total protein analysis, gels were stained with GelCode Blue Safe Protein Stain (Thermo Scientific, 24594) according to the manufacture protocol.

Preparation of brain homogenate: Frozen frontal and temporal cortex samples from neuropathologically confirmed cases cerebrovascular disease (CVD), diffuse Lewy body disease (DLBD), PiD, PSP, CBD, AGD, AD, frontotemporal lobar degeneration with TDP 43 (FTD-TDP43), and frontotemporal dementia and parkinsonism (FTDP) brains were obtained from the Indiana University School of Medicine. Additional frozen cortex samples from AD brains were obtained. Tau knockout (KO) brains {Tucker, PubMed ID 11135642} and brain lysate (10%) from Tau KO mice were obtained. Brain tissue samples were homogenized at 10% (w/v) in ice-cold PBS pH 7.0 using a multi-bead shocker (Fisher). KO brains were homogenized at 10% (w/v) in ice-cold TBS (25 mM Tris-HCl, 137 mM NaCl, 2.7 mM KCl, pH 7.4 at room temp with EDTA-free protease inhibitor cocktail (Roche)) using a multi-bead shocker (Fisher). After centrifugation at 2,000 g for 2 mM, supernatants were collected and stored at −80° C. until use.

CSF samples: Post-mortem Pick disease samples were obtained. Other neurological disease CSF samples including AD, FTD, rapidly progressive disease (RPD), cognitive decline (CD) and chronic inflammatory demyelinating polyneuropathy (CIDP) also were obtained. Pooled and single donor normal human CSF were purchased.

Tau-Real Time QuIC (Tau RT-QuIC) assay: To avoid contamination, reactions were prepared in a biological safety cabinet using aerosol-resistant tips. To measure Tau seeding activity, 2 µl of each dilution was added to 98 µl of Tau RT-QuIC reaction buffer containing 20 µM K19CFh monomers, 80 µM heparin (Celsus, average MW=4500), 10 mM HEPES pH 7.4, 200 mM NaCl, and 10 µM thioflavin T. To measure Tau seeding activity in CSF samples, 5 µl or 20 µl of CSF was added to 95 µl or 80 µl of the Tau RT-QuIC reaction buffer as described above, respectively. Crude CSF samples were used as a seed without any dilution, unless otherwise indicated in FIGS. 23B, 23C, 23E, and 23F, in which case 10 mM HEPES pH 7.4 was used as the diluent. The K19CFh substrate was thawed immediately before use and filtered with a 100 KDa spin column filter (Pall, OD100C35). Either four or three technical replicate reactions were prepared in a 96-well plate optical black bottom plate (Nunc 265301) to a final total volume of 100 µl. Brain homogenate was diluted in seed dilution buffer containing 10 mM HEPES pH 7.4, ×0.017 N2 supplement (Gibco, 17502-048), 0.5% KO brain homogenate. KO brain homogenate was used to maintain consistent overall biomass in serial dilutions of brain homogenate test samples. Importantly, the KO brain homogenate used for sample dilution was prepared differently than those uses as test samples. Specifically, the KO brain tissue was homogenized in 137 mM NaCl, 2.7 mM KCl, 25 mM Tris-HCl, pH 7.4 at room temperature with an EDTA-free protease inhibitor cocktail (Roche). The presence of KCl and the absence of EDTA helped delay spontaneous, Tauopathy brain-independent, formation of K19CFh fibrillization in RT-QuIC reactions. No KO brain homogenate was used in a preparation or dilution of CSF specimens. The plate was covered with sealing tape (Nunc 236366) and incubated at 37° C. in a plate reader (BMG Labtech POLARstar or FLUOstar Omega) with intermittent shaking, consisting of 60 s of orbital shaking at 500 rpm and no shaking for 60 s, with a 1-min pause to measure the fluorescence. The kinetics of fibril formation was monitored real time by the bottom reading of the fluorescence intensity every 45 min using 450±10-nm excitation and 480±10 nm emission. These plate readers have a fluorescence saturation signal of ~270,000 rfu. Unless otherwise indicated (as in FIGS. 4H-4L), instrument gains were set at 1100 so that no reaction saturated the detector.

Analysis: Tau RT-QuIC data were plotted and analyzed using GraphPad Prism 6. The plate reader measures ThT fluorescence in relative fluorescence units (rfu) with saturation occurring at 270,000. Reactions were judged to be Tau RT-QuIC positive if the ThT fluorescence exceeded a threshold reading; this threshold was chosen as the average of mean baseline readings over the 10-20 h time window in the Tau RT-QuIC traces for the non-Tauopathy samples in the given experiment plus 40 times the standard deviation of those readings, (e.g., 576 +200 =776 rfu). Positive/negative assessments were made at 60-h time point. When the reactions were run longer than 60 h, occasional (i.e., 12 out of >112 reactions running to 80 h) negative control KO samples gave responses exceeding the threshold, suggesting that negative control KO samples can rarely allow spontaneous (Tau aggregate-independent) K19CFh fibrillization after lag phases of >60 h.

For CSF seeds, reactions were also judged to be Tau RT-QuIC positive if the ThT fluorescence exceeded a threshold reading; this threshold was chosen to be 5,000 rfu, which exceeded the average of mean baseline readings over the 3-5 h time window in the Tau RT-QuIC traces for the non-Tauopathy samples in the given experiment plus 100 times the standard deviation of those readings. Positive/negative assessments were made at 15-h time point.

Statistical significance was assessed using GraphPad Prism 6 with unpaired t-tests. A significance level of 0.05 was used to generate the P values. Statistical comparison of percent maximum ThT fluorescence responses at 15 h time point in Pick vs. non-Pick CSF seeded reactions was performed using values from each individual replicate in each experiment.

Sarkosyl extraction of Tau aggregates from brains. Sarkosyl-insoluble Tau was isolated from human brain tissues (Goedert et al., Neuron 8, 159-168 (1992)). Briefly, a 10% (w/v) homogenate was prepared using ice-cold homogenization buffer (H-buffer: 10 mM Tris-HCl, 1 mM EGTA, 0.8 M NaCl, 10% sucrose, pH 7.4) and centrifuged for 20 min at 20,000×g. The supernatant was saved in a clean tube, and pellet was rehomogenized in an additional 5 volumes of H-buffer and centrifuged as described above. Both supernatants were combined and incubated with 1% N-lauroylsarcosinate for 1 h at room temperature with agitation followed by ultracentifugation at 100,000×g for 1 h at 4° C. The sarkosyl insoluble pellet was resuspended in 1×PBS pH 7.0 (0.2 ml per gram of starting material) and stored at −80° C.

An exemplary sensitivity chart is provided below. If a provisional threshold of 5 log $SD_{50}$/mg brain tissue is selected, then the assay would be 100% sensitive (8/8 PiD cases positive) and 100% specific (41/41 non-PiD cases negative) for PiD.

| Tau RT-QuIC sensitivity chart | |
| --- | --- |
| Dilution of seed | Brain tissue (protein mass)/100 µl final reaction |
| $10^{-2}$ | 1 µg |
| $10^{-3}$ | 0.1 µg |
| $10^{-4}$ | 1.01 µg |
| $10^{-5}$ | 1 ng |
| $10^{-6}$ | 0.1 ng |
| $10^{-7}$ | 0.01 ng |
| $10^{-8}$ | 1 pg |
| $10^{-9}$ | 0-1 pg |

Example 7

Application of 4R Tau RT-QuIC to CBD, Sporadic AD, and AGD Brain Tissues

One format of a 4R Tau RT-QuIC assays contains both heparin (H) and poly-L-glutamate (PLG) as polyanionic cofactors; this is called 4R RT-QuIC (H+PLG). Using this assay, as shown in FIG. 25, a representative CBD brain tissue specimen could be diluted out to between $10^{-6}$ and $10^{-7}$ before losing positive responses from individual replicate reactions. In contrast, $10^{-3}$ dilutions of two other types of Tauopathy, i.e., sporadic AD and AGD only gave positive responses in 0-2 out of 4 replicate reactions. Also, a human "senile change" (SC) case with no histologically apparent Tau pathology and at totally Tau-free knock-out (KO) mouse brain were negative in all replicate reactions.

Example 8

Quantitative Comparison of Brain from Multiple Tauopathy and Non-Tauopathy Cases From such end-point dilution analyses, Spearman-Karber analysis was used to calculate the 50% seeding dose ($SD_{50}$) concentrations (see FIG. 25) for brain samples from multiple types of Tauopathy and apparent non-Tauopathy cases (FIG. 26 & FIG. 28 (Table)). In the latter cases, the "non-Tauopathy" designation means that no immunohistological evidence of Tau pathology was seen in the brain tissue, but IHC analysis can be much less sensitive than Tau RT-QuIC (Saijo et al., Acta Neuropath 2017).

In these analyses, all of the CBD cases (n=4) cases have seeding activities that averaged from 250-2,000-fold higher than the detection limit (~$10^{2.2}$ $SD_{50}$/mg) established by the mouse Tau KO brain, and 3 out of 4 of the apparent non-Tauopathy human controls. Three (out of 7) PSP cases gave seed concentrations that were similar to those of the CBD cases; one PSP case (#5) had >$10^9$ $SD_{50}$/mg, i.e., nearly $10^3$ higher than any of the CBD cases; 3 PSP cases had concentrations lower than the CBD cases. AGD cases also varied in their seeding activity, but over a narrower range of <$10^{2.2}$-$10^5$ $SD_{50}$/mg. In contrast, on average, the 5 AD cases had seed concentrations that were at least ~300-fold much lower than the CBD cases. A case of frontotemporal dementia-TDP43 with PSP as a secondary diagnosis (FTD-TDP43-PSP) had a seed concentration between those of AD and CBD. Single cases of senile change (SC), diffuse Lewy body disease (DLBD) and amyotropic lateral sclerosis (ALS) that lacked any immunohistologically apparent Tau lesions were also Tau RT-QuIC-negative, as were brain homogenates from Tau-free (KO) mice. The CVD "control" was positive in 3 of 4 replicate wells at a $10^{-3}$ dilution, and therefore, may contain low concentrations of Tau seeds that were undetectable by IHC.

In summary, the CBD cases consistently had ~$10^{4.2}$-$10^{6.5}$ $SD_{50}$/mg brain tissue, while PSP cases were detected, but were more variable, ranging over ~6 orders of magnitude. The latter result may be related to the "patchy" distribution of Tau pathology in brains of PSP patients together with the fact that only a small sample of tissue was analyzed from each patient.

Different 4R Tau RT-QuIC conditions were tested that contained heparin but no PLG, namely, 4R RT-QuIC (H). These conditions were more selective for PSP over CBD and the other tested Tauopathies (FIGS. 27 and 28). Without being bound by theory, this could be due both to slightly enhanced sensitivity for PSP and less sensitivity for the others, relative to 4R RT-QuIC (H+PLG) conditions. Thus, Tau RT-QuIC reaction conditions can be used to detect many 4R Tauopathies.

Example 9

Increasing Reaction Sensitivity

The 4R Tau RT-QuIC can detect prion seeding activity in cerebrospinal fluid (CSF) from 4R Tauopathy (PSP or CBD) cases. The inclusion of glass beads in reactions containing either heparin or heparin and poly-L-glutamate increased sensitivity.

The effects of 0-12 1 mm glass beads per well was tested. FIGS. 29A-29D show that 6 beads per well provided consistent discrimination 5 µl of CSF (neat) collected postmortem from 4R Tauopathy (PSP; top row) and antemortem from healthy controls (bottom row), with 4/4 replicate wells becoming positive within 16 h with the PSP CSF and 0/4 healthy control reactions becoming positive within 20 h. However, the addition of beads to reactions under these conditions did not allow detection of antemortem CSF from PSP cases, even when seeded at volumes of 20 µl.

FIGS. 30A-30D show that beads also accelerated detection of Tau seeding activity in 5-20 µl CSF samples collected postmortem from a CBD case, as compared to reactions without beads and reactions seeded with the same volumes of healthy control CSF. These reactions used 4R Tau RT-QuIC with heparin and poly-glutamate.

Example 10

RT-QuIC Reactions Using PHF6-378CFh

Alzheimer Disease Brain-Seeded Tau RT-QuIC Reactions Using PHF6-378CFh (Sequence Below) Alone (A & B) or with Different Molar Ratios of K19CFh and/or K18CFh (C-L)

Quadruplicate reactions were given the designated dilutions of brain tissue (in the form of homogenates) from Alzheimer disease (AD) or control decedents, the latter including those derived from mice completely lacking all Tau isoforms (KO), and humans with diffuse Lewy body disease (DLBD), a synucleinopathy, or senile change (SC), with neuropathological lesions but no histologically apparent Tau pathology. Results are shown in FIG. 31. These results demonstrate that under each of these reaction conditions, there are more rapid ThT fluorescence increases in reactions seeded with dilutions of AD brain tissue, in some cases as low as $10^{-5}$-$10^{-6}$, see panels A-L. Assay conditions include 10 mM Hepes pH 7.4, 200 mM NaCl, 80 µM heparin, 10 µM ThT, and either 16 µM of the PHF6-378CFh substrate, 8 µM PHF6-378CFh and 8 µM K19CFh substrate (1:1 K19CFh:PHF6-378CFh), 12 µM K19CFh and 4 µM PHF6-378CFh (3:1 K19CFh:PHF6-378h), 8 µM PHF6-378CFh and 8 µM K18CFh substrate (1:1 K18CFh:PHF6-378CFh), 3.2 µM K19CFh and 3.2 µM K18CFh and 4 µM PHF6-378CFh (0.8:0.8:1 K19CFh:K18CFh:PHF6-378CFh). Reactions were seeded with brain homogenates that are serially diluted in mixtures containing 10 mM Hepes pH7.4, 1× N2 and 0.526% mouse Tau KO brain homogenate.

The substrate molecules and their molar ratios are indicated above each graph. Assay conditions in C-L show nearly comparable results in 96 well (C-F, I-L) or 384 well plates (G&H), the latter containing half the total reaction volume. Each curve shown represents the mean ThT fluorescence of quadruplicate reactions. These results demonstrate that under each of these reaction conditions, there are more rapid ThT fluorescence increases in reactions seeded with dilutions of AD brain tissue, in some cases as low as $10^{-5}$-$10^{-6}$. A positive AD identification resulted in rapid comparative ThT fluorescence as compared to non-tauopathy samples (controls).

The detection of 3R/4R filaments, one of which relates to Alzheimer disease (AD), can be detected using the extended substrates in Tau RT-QuIC assays. For example, [1] a mix of both K19CF-378h and K18CF-378h; [2] PHF6-378CFh only; [3] PHF6-378CFh and K19CF-378h; [4] PHF6-378CFh and K18CF-378h; [5] PHF6-378CFh and K19CFh; [6] PHF6-378CFh and K18CFh; [7] PHF6-378CFh and K18CFh and K19CFh.

Tauopathy can be classified into 3-repeat (3R), 4-repeat (4R) and/or 3R/4R based on the pathological classification of Tau depositions in the brain. For example, Pick disease pathology shows unique 3R Tau deposits called pick bodies in the brain, and the Pick body is only found in individuals with Pick disease. The 3R RT-QuIC assay detects the presence of 3R Tau (inclusive of R1, R3, R4) filaments in brain and CSF samples from Pick disease patients, and does not detect other 4R or 3R/4R Tauopathies. This is indicative of an ultrasensitive, selective assay that can be used to discriminate Pick's disease from other Tauopathies. As the filaments are comprised of different combinations of repeats, or parts thereof, (i.e. 1R, 2R, 3R, 4R), substrates and assay conditions can be designed for a universal detection of Tauopathies or specific detection of a disease-specific filament. The ability of Tau amyloid filaments to faithfully template and propagate new amyloid formation allows different substrate combinations and variations of assay conditions to discriminate Tau filaments from different Tauopathies.

1) 3R Tau RT-QuIC assay can directly detect the presence of Pick-related Tau filaments (e.g. using the K19CFh substrate).

2) 4R Tau RT-QuIC (with Heparin+poly L glutamate) and 4R Tau RT-QuIC (with Heparin) can differentiate PSP from CBD and AGD. (e.g. using mixed ratios of K19CFh and K18CFh substrates).

3) Inclusion of the PHF6-378CFh substrate alone or in mixed ratios with other substrates shows AD-specific increases in ThT fluorescence. The PHF6-378CFh substrate encompasses the protease-resistant amyloid core of AD filaments known to occur based on high resolution cryo-EM structural analysis (Fitzpatrick et al 2017). This indicates evidence for structure-based design of Tau substrates for disease specific detection of Tau filaments. In addition, mixed ratios of K18CF-378h and K19CF-378h substrates are able to discriminate AD brain homogenate samples from non-Tauopathy controls (DLBD) at 10E-4 and 10E-5 dilutions. Thus, substrates including, but not limited to, residues 306-378 has been critical (thus far) for detection of AD-related Tau filaments. Substrates capable of AD detection and discrimination from non-Tauopathy controls include 1) PHF6-378CFh alone, 2) PHF6-378CFh & K19CFh, 3) PHF6-378CFh & K18CFh, 4) PHF6-378CFh & K19CFh & K18CFh, 5) K18CF-378h & K19CF-378h 6) PHF6-378CFh and K19CFh-378 7) PHF6-378CFh & K18CF-378h.

These assays are currently used with heparin and the assay conditions described below. Inclusion of poly-L-glutamate, which prevents spontaneous fibrillization in non-Tauopathy controls without significantly impacting sensitivity, also aids discrimination of Tauopathies (PSP from CBD).

In addition, mixed ratios of K19CFh+PHF6-378CFh allows AD brain homogenates to induce more rapid increases in ThT fluorescence compared to reactions with brain homogenates from 4R Tauopathies, such as PSP and CBD. Different substrates and variations to assay conditions, including heparin, poly-L-glutamate, salts, or combinations thereof, allow preferential detection and discrimination of Tauopathies (e.g. AD versus PSP versus CBD).

| | | Assay type | | | |
|---|---|---|---|---|---|
| | | 3R tau RT-QuIC | 4R tau RT-QuIC | | |
| | | Substrate(s): | | | |
| | | K19CFh | K18CFh | K19CFh & K18CFh | |
| Tau | | | Cofactor: | | |
| classi- | | | | Heparin, | |
| fication | Disease | Heparin | Heparin | Poly Glu | Heparin |
| 3R | Pick | + + + + | NT | NT | NT |
| 4R | PSP | + | + + | + + + | + + + + |

| | | Assay type | | | |
|---|---|---|---|---|---|
| | | 3R tau RT-QuIC | 4R tau RT-QuIC | | |
| | | Substrate(s): | | | |
| | | K19CFh | K18CFh | K19CFh & K18CFh | |
| Tau classification | Disease | Cofactor: | | | |
| | | Heparin | Heparin | Heparin, Poly Glu | Heparin |
| | CBD | Not detected | + + | + + + | + |
| | AGD | Not detected | + + | + | + |
| 3R/4R | AD | + | Not detected | + | + |

| | | Assay type | | | |
|---|---|---|---|---|---|
| | | 3R/4R tau RT-QuIC | | | |
| | | Substrate(s): | | | |
| | | PHF6-378CFh | PHF6-378CFh & K19CFh | PHF6-378CFh & K18CFh | PHF6-378CFh & K18-378CFh |
| Tau classification | Disease | Cofactor: | | | |
| | | Heparin | Heparin | Heparin | Heparin |
| 3R | Pick | NT | Not detected | NT | NT |
| 4R | PSP | NT | Not detected | NT | NT |
| | CBD | NT | Not detected | NT | NT |
| | AGD | NT | Not detected | NT | NT |
| 3R/4R | AD | + + | + + + | + + | + + |

Table. Assay type is indicated with the pertinent substrate(s) and cofactor(s) listed under each assay. The ability to detect and discriminate diseased tissue from non-Tauopathy controls is indicated, with the relative detection sensitivities listed. Samples "not detected" did not give ThT fluorescence increases before the assay cutoff time, which is established by the time at which there are ThT fluorescence increases in non-Tauopathy controls. Diseases not tested under the indicated assay conditions are marked as "NT".

In addition to buffer (typically 10 mM Hepes, pH 7.4). Salts to give 50-500 mM (100-300 mM, NaCl is the most frequently used, but other salts can include NaF, NaI, NaClO$_4$, GdnCl).
- 1-200 µM heparin
- 0-200 µM poly-L-glutamate
- amyloid specific dye (e.g. ThT)
- 1-40 µM final substrate concentration This can include mixed substrate ratios that range from 1:100-100:1 (exemplary 3:1), and can include up to 5 different substrates (such as 3). Ranges include 1:1, 4:1, 3:1, and 3 substrates at ~1:1:1

In view of the many possible embodiments to which the principles of our invention may be applied, it should be recognized that illustrated embodiments are only examples of the invention and should not be considered a limitation on the scope of the invention. Rather, the scope of the invention is defined by the following claims. We therefore claim as our invention all that comes within the scope and spirit of these claims.

The invention claimed is:

1. A method of determining whether a subject has a 3R/4R Tauopathy, comprising:
   (a) performing a seeded Tau polymerization assay on a biological sample from the subject, comprising:
      (i) contacting the biological sample with a purified recombinant truncated Tau protein, wherein the recombinant truncated Tau protein consists of SEQ ID NO: 43 or SEQ ID NO: 44, to form a reaction mixture;
      (ii) incubating the reaction mixture to permit coaggregation of disease-associated Tau protein ($T^D$) present in the biological sample with the recombinant truncated Tau protein;
      (iii) maintaining incubation conditions that promote coaggregation of the recombinant truncated Tau protein with the $T^D$ to result in a conversion of the recombinant truncated Tau protein to amyloid Tau protein aggregates while inhibiting development of spontaneously forming Tau protein aggregates ($rT^{(spon)}$); and
      (iv) agitating amyloid Tau protein aggregates formed during step (iii), wherein the agitating comprises shaking the reaction mixture in a shaking cycle, wherein each shaking cycle comprises a period of rest and a period of shaking; and
   (b) detecting amyloid Tau protein present in the reaction mixture, and wherein detection of amyloid Tau protein in the reaction mixture indicates that the subject has the 3R/4R Tauopathy.

2. The method of claim 1, wherein the biological sample is a brain tissue sample or a cerebral spinal fluid sample.

3. The method of claim 1, wherein the biological sample is a nasal brushing, saliva, blood, serum, plasma, cerebral spinal fluid, feces, urine or tissue sample.

4. The method of claim 1, wherein detecting the presence of Tau amyloid in the biological sample comprises the use of an amyloid-sensing dye.

5. The method of claim 1, wherein agitating aggregates in step (iv) comprises agitating aggregates in the absence of sonication.

6. The method of claim 1, wherein the shaking cycle in step (iv) comprises a period of rest that precedes the period of shaking, and wherein the period of rest and the period of shaking are equal.

7. The method of claim 1, wherein the shaking cycle in step (iv) includes the period of rest and the period of shaking at a ratio of about 1:2 to about 2:1.

8. The method of claim 1, wherein the shaking cycle in step (iv) is 20 to 180 seconds in length.

9. The method of claim 8, shaking cycle in step (iv) is 120 seconds in length.

10. The method of claim 1, wherein the reaction mix includes thioflavin T (ThT), and wherein detecting amyloid Tau protein comprises detecting fluorescence.

11. The method of claim 1, wherein the recombinant truncated Tau protein has an N-terminus or a C-terminus, and the recombinant Tau protein comprises at least six consecutive histidine residues at or near the N-terminus or the C-terminus.

12. The method of claim 11, wherein the recombinant truncated Tau protein is purified using immobilized metal ion affinity chromatography.

13. The method of claim 1, wherein the reaction mix comprises a carrier lacking human Tau.

14. The method of any claim 13, wherein the carrier is a brain homogenate lacking human Tau.

15. The method of claim 14, wherein the human Tau-free brain homogenate is a murine brain homogenate from a mouse deficient for the production of murine Tau protein.

16. The method of claim 1, wherein the reaction mixture further comprises an effective amount of N2.

17. The method of claim 1, wherein steps (a)-(b) are performed in the absence of added anionic detergent.

18. The method of claim 1, wherein agitating amyloid Tau protein aggregates formed during step (iii) is performed for at least about 10 hours.

19. The method of claim 1, wherein agitating amyloid Tau protein aggregates formed during step (iii) is performed for at least about 15 hours.

20. The method of claim 4, wherein the amyloid sensing dye is thioflavin T or thioflavin S.

21. The method of claim 12, wherein the recombinant truncated Tau protein is purified by elution from a column comprising an immobilized metal ion using between about 46 mM and about 200 mM imidazole.

22. The method of claim 1, wherein the reaction mixture comprises 1 to 10 beads per 50 μl or 100 μl of reaction mixture.

23. The method of claim 22, wherein the reaction mixture comprises 1 bead per 50 μl of reaction mixture.

24. The method of claim 22, wherein the beads are about 0.5 mm to about 3 mm in diameter.

25. The method of claim 24, wherein the beads are about 800 μm in diameter.

26. The method of claim 1, wherein the 3R/4R Tauopathy is Alzheimer disease.

27. The method of claim 1, wherein step (i) comprises contacting the biological sample with a first purified recombinant truncated Tau protein consisting of SEQ ID NO: 43 and the reaction mixture further comprises a second purified recombinant truncated Tau protein.

28. The method of claim 27, wherein the second recombinant truncated Tau protein has three microtubule binding domains.

29. The method of claim 28, wherein the second recombinant truncated Tau protein comprises SEQ ID NO: 14.

30. The method of claim 1, wherein the reaction mixture comprises heparin.

31. A method of detecting 3R/4R Tau protein aggregates, comprising:
   (a) performing a seeded Tau polymerization assay on a biological sample from a subject, comprising:
      (i) contacting the biological sample with a purified recombinant truncated Tau protein, wherein the recombinant truncated Tau protein consists of SEQ ID NO: 43 or SEQ ID NO: 44, to form a reaction mixture;
      (ii) incubating the reaction mixture to permit coaggregation of 3R/4R disease-associated Tau protein ($T^D$) present in the biological sample with the recombinant truncated Tau protein;
      (iii) maintaining incubation conditions that promote coaggregation of the recombinant truncated Tau protein with the $T^D$ to result in a conversion of the recombinant truncated Tau protein to amyloid Tau protein aggregates while inhibiting development of spontaneously forming Tau protein aggregates ($rT^{(spon)}$); and
      (iv) agitating amyloid Tau protein aggregates formed during step (iii), wherein the agitating comprises shaking the reaction mixture in a shaking cycle, wherein each shaking cycle comprises a period of rest and a period of shaking; and (b) detecting amyloid Tau protein present in the reaction mixture.

32. The method of claim 31, wherein step (i) comprises contacting the biological sample with a first purified recombinant truncated Tau protein consisting of SEQ ID NO: 43 and the reaction mixture further comprises a second purified recombinant truncated Tau protein.

33. The method of claim 32, wherein the second recombinant truncated Tau protein has three microtubule binding domains.

34. The method of claim 33, wherein the second recombinant truncated Tau protein comprises SEQ ID NO: 14.

35. The method of claim 31, wherein the biological sample comprises a brain tissue sample or a cerebral spinal fluid sample.

* * * * *

SEQUENCE LISTING

```
<160> NUMBER OF SEQ ID NOS: 94

<210> SEQ ID NO 1
<211> LENGTH: 99
<212> TYPE: PRT
<213> ORGANISM: Artificial Sequence
<220> FEATURE:
<223> OTHER INFORMATION: recombinant truncated Tau protein

<400> SEQUENCE: 1

Met Gln Thr Ala Pro Val Pro Met Pro Asp Leu Lys Asn Val Lys Ser
1               5                   10                  15

Lys Ile Gly Ser Thr Glu Asn Leu Lys His Gln Pro Gly Gly Gly Lys
            20                  25                  30

Val Gln Ile Val Tyr Lys Pro Val Asp Leu Ser Lys Val Thr Ser Lys
        35                  40                  45

Ser Gly Ser Leu Gly Asn Ile His His Lys Pro Gly Gly Gly Gln Val
    50                  55                  60
```

Glu Val Lys Ser Glu Lys Leu Asp Phe Lys Asp Arg Val Gln Ser Lys
65                  70                  75                  80

Ile Gly Ser Leu Asp Asn Ile Thr His Val Pro Gly Gly Gly Asn Lys
                85                  90                  95

Lys Ile Glu

<210> SEQ ID NO 2
<211> LENGTH: 99
<212> TYPE: PRT
<213> ORGANISM: Artificial Sequence
<220> FEATURE:
<223> OTHER INFORMATION: recombinant truncated Tau protein

<400> SEQUENCE: 2

Met Gln Thr Ala Pro Val Pro Met Pro Asp Leu Lys Asn Val Lys Ser
1               5                   10                  15

Lys Ile Gly Ser Thr Glu Asn Leu Lys His Gln Pro Gly Gly Gly Lys
                20                  25                  30

Val Gln Ile Val Tyr Lys Pro Val Asp Leu Ser Lys Val Thr Ser Lys
                35                  40                  45

Cys Gly Ser Leu Gly Asn Ile His His Lys Pro Gly Gly Gly Gln Val
        50                  55                  60

Glu Val Lys Ser Glu Lys Leu Asp Phe Lys Asp Arg Val Gln Ser Lys
65                  70                  75                  80

Ile Gly Ser Leu Asp Asn Ile Thr His Val Pro Gly Gly Gly Asn Lys
                85                  90                  95

Lys Ile Glu

<210> SEQ ID NO 3
<211> LENGTH: 130
<212> TYPE: PRT
<213> ORGANISM: Artificial Sequence
<220> FEATURE:
<223> OTHER INFORMATION: recombinant truncated Tau protein

<400> SEQUENCE: 3

Met Gln Thr Ala Pro Val Pro Met Pro Asp Leu Lys Asn Val Lys Ser
1               5                   10                  15

Lys Ile Gly Ser Thr Glu Asn Leu Lys His Gln Pro Gly Gly Gly Lys
                20                  25                  30

Val Gln Ile Ile Asn Lys Lys Leu Asp Leu Ser Asn Val Gln Ser Lys
                35                  40                  45

Ser Gly Ser Lys Asp Asn Ile Lys His Val Pro Gly Gly Gly Ser Val
        50                  55                  60

Gln Ile Val Tyr Lys Pro Val Asp Leu Ser Lys Val Thr Ser Lys Ser
65                  70                  75                  80

Gly Ser Leu Gly Asn Ile His His Lys Pro Gly Gly Gly Gln Val Glu
                85                  90                  95

Val Lys Ser Glu Lys Leu Asp Phe Lys Asp Arg Val Gln Ser Lys Ile
                100                 105                 110

Gly Ser Leu Asp Asn Ile Thr His Val Pro Gly Gly Gly Asn Lys Lys
        115                 120                 125

Ile Glu
    130

<210> SEQ ID NO 4
<211> LENGTH: 130
<212> TYPE: PRT

```
<213> ORGANISM: Artificial Sequence
<220> FEATURE:
<223> OTHER INFORMATION: recombinant truncated Tau protein

<400> SEQUENCE: 4

Met Gln Thr Ala Pro Val Pro Met Pro Asp Leu Lys Asn Val Lys Ser
1               5                   10                  15

Lys Ile Gly Ser Thr Glu Asn Leu Lys His Gln Pro Gly Gly Gly Lys
            20                  25                  30

Val Gln Ile Ile Asn Lys Lys Leu Asp Leu Ser Asn Val Gln Ser Lys
        35                  40                  45

Cys Gly Ser Lys Asp Asn Ile Lys His Val Pro Gly Gly Gly Ser Val
    50                  55                  60

Gln Ile Val Tyr Lys Pro Val Asp Leu Ser Lys Val Thr Ser Lys Cys
65                  70                  75                  80

Gly Ser Leu Gly Asn Ile His His Lys Pro Gly Gly Gly Gln Val Glu
                85                  90                  95

Val Lys Ser Glu Lys Leu Asp Phe Lys Asp Arg Val Gln Ser Lys Ile
            100                 105                 110

Gly Ser Leu Asp Asn Ile Thr His Val Pro Gly Gly Gly Asn Lys Lys
        115                 120                 125

Ile Glu
    130

<210> SEQ ID NO 5
<211> LENGTH: 127
<212> TYPE: PRT
<213> ORGANISM: Artificial Sequence
<220> FEATURE:
<223> OTHER INFORMATION: recombinant truncated Tau protein

<400> SEQUENCE: 5

Met Gln Thr Ala Pro Val Pro Met Pro Asp Leu Lys Asn Val Lys Ser
1               5                   10                  15

Lys Ile Gly Ser Thr Glu Asn Leu Lys His Gln Pro Gly Gly Gly Lys
            20                  25                  30

Val Gln Ile Val Tyr Lys Pro Val Asp Leu Ser Lys Val Thr Ser Lys
        35                  40                  45

Cys Gly Ser Leu Gly Asn Ile His His Lys Pro Gly Gly Gly Gln Val
    50                  55                  60

Glu Val Lys Ser Glu Lys Leu Asp Phe Lys Asp Arg Val Gln Ser Lys
65                  70                  75                  80

Ile Gly Ser Leu Asp Asn Ile Thr His Val Pro Gly Gly Gly Asn Lys
                85                  90                  95

Lys Ile Glu Thr His Lys Leu Thr Phe Arg Glu Asn Ala Lys Ala Lys
            100                 105                 110

Thr Asp His Gly Ala Glu Ile Val Tyr Lys Ser Pro Val Val Ser
        115                 120                 125

<210> SEQ ID NO 6
<211> LENGTH: 127
<212> TYPE: PRT
<213> ORGANISM: Artificial Sequence
<220> FEATURE:
<223> OTHER INFORMATION: recombinant truncated Tau protein

<400> SEQUENCE: 6

Met Gln Thr Ala Pro Val Pro Met Pro Asp Leu Lys Asn Val Lys Ser
1               5                   10                  15
```

```
Lys Ile Gly Ser Thr Glu Asn Leu Lys His Gln Pro Gly Gly Gly Lys
            20                  25                  30

Val Gln Ile Val Tyr Lys Pro Val Asp Leu Ser Lys Val Thr Ser Lys
            35                  40                  45

Ala Gly Ser Leu Gly Asn Ile His His Lys Pro Gly Gly Gly Gln Val
50                  55                  60

Glu Val Lys Ser Glu Lys Leu Asp Phe Lys Asp Arg Val Gln Ser Lys
65                  70                  75                  80

Ile Gly Ser Leu Asp Asn Ile Thr His Val Pro Gly Gly Gly Asn Lys
                85                  90                  95

Lys Ile Glu Thr His Lys Leu Thr Phe Arg Glu Asn Ala Lys Ala Lys
            100                 105                 110

Thr Asp His Gly Ala Glu Ile Val Tyr Lys Ser Pro Val Val Ser
            115                 120                 125

<210> SEQ ID NO 7
<211> LENGTH: 127
<212> TYPE: PRT
<213> ORGANISM: Artificial Sequence
<220> FEATURE:
<223> OTHER INFORMATION: recombinant truncated Tau protein

<400> SEQUENCE: 7

Met Gln Thr Ala Pro Val Pro Met Pro Asp Leu Lys Asn Val Lys Ser
1               5                   10                  15

Lys Ile Gly Ser Thr Glu Asn Leu Lys His Gln Pro Gly Gly Gly Lys
            20                  25                  30

Val Gln Ile Val Tyr Lys Pro Val Asp Leu Ser Lys Val Thr Ser Lys
            35                  40                  45

Ser Gly Ser Leu Gly Asn Ile His His Lys Pro Gly Gly Gly Gln Val
50                  55                  60

Glu Val Lys Ser Glu Lys Leu Asp Phe Lys Asp Arg Val Gln Ser Lys
65                  70                  75                  80

Ile Gly Ser Leu Asp Asn Ile Thr His Val Pro Gly Gly Gly Asn Lys
                85                  90                  95

Lys Ile Glu Thr His Lys Leu Thr Phe Arg Glu Asn Ala Lys Ala Lys
            100                 105                 110

Thr Asp His Gly Ala Glu Ile Val Tyr Lys Ser Pro Val Val Ser
            115                 120                 125

<210> SEQ ID NO 8
<211> LENGTH: 441
<212> TYPE: PRT
<213> ORGANISM: Homo sapiens

<400> SEQUENCE: 8

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
            35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80
```

```
Asp Glu Gly Ala Pro Gly Lys Gln Ala Ala Gln Pro His Thr Glu
                85                  90                  95
Ile Pro Glu Gly Thr Thr Ala Glu Ala Gly Ile Gly Asp Thr Pro
            100                 105                 110
Ser Leu Glu Asp Glu Ala Ala Gly His Val Thr Gln Ala Arg Met Val
        115                 120                 125
Ser Lys Ser Lys Asp Gly Thr Gly Ser Asp Asp Lys Lys Ala Lys Gly
    130                 135                 140
Ala Asp Gly Lys Thr Lys Ile Ala Thr Pro Arg Gly Ala Ala Pro Pro
145                 150                 155                 160
Gly Gln Lys Gly Gln Ala Asn Ala Thr Arg Ile Pro Ala Lys Thr Pro
                165                 170                 175
Pro Ala Pro Lys Thr Pro Pro Ser Ser Gly Glu Pro Pro Lys Ser Gly
            180                 185                 190
Asp Arg Ser Gly Tyr Ser Ser Pro Gly Ser Pro Gly Thr Pro Gly Ser
        195                 200                 205
Arg Ser Arg Thr Pro Ser Leu Pro Thr Pro Pro Thr Arg Glu Pro Lys
    210                 215                 220
Lys Val Ala Val Val Arg Thr Pro Pro Lys Ser Pro Ser Ser Ala Lys
225                 230                 235                 240
Ser Arg Leu Gln Thr Ala Pro Val Pro Met Pro Asp Leu Lys Asn Val
                245                 250                 255
Lys Ser Lys Ile Gly Ser Thr Glu Asn Leu Lys His Gln Pro Gly Gly
            260                 265                 270
Gly Lys Val Gln Ile Ile Asn Lys Lys Leu Asp Leu Ser Asn Val Gln
        275                 280                 285
Ser Lys Cys Gly Ser Lys Asp Asn Ile Lys His Val Pro Gly Gly Gly
    290                 295                 300
Ser Val Gln Ile Val Tyr Lys Pro Val Asp Leu Ser Lys Val Thr Ser
305                 310                 315                 320
Lys Cys Gly Ser Leu Gly Asn Ile His His Lys Pro Gly Gly Gly Gln
                325                 330                 335
Val Glu Val Lys Ser Glu Lys Leu Asp Phe Lys Asp Arg Val Gln Ser
            340                 345                 350
Lys Ile Gly Ser Leu Asp Asn Ile Thr His Val Pro Gly Gly Gly Asn
        355                 360                 365
Lys Lys Ile Glu Thr His Lys Leu Thr Phe Arg Glu Asn Ala Lys Ala
    370                 375                 380
Lys Thr Asp His Gly Ala Glu Ile Val Tyr Lys Ser Pro Val Val Ser
385                 390                 395                 400
Gly Asp Thr Ser Pro Arg His Leu Ser Asn Val Ser Ser Thr Gly Ser
                405                 410                 415
Ile Asp Met Val Asp Ser Pro Gln Leu Ala Thr Leu Ala Asp Glu Val
            420                 425                 430
Ser Ala Ser Leu Ala Lys Gln Gly Leu
        435                 440

<210> SEQ ID NO 9
<211> LENGTH: 412
<212> TYPE: PRT
<213> ORGANISM: Homo sapiens

<400> SEQUENCE: 9

Met Ala Glu Pro Arg Gln Glu Phe Glu Val Met Glu Asp His Ala Gly
1               5                   10                  15
```

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Pro Gly Ser Glu Thr Ser
    50                  55                  60

Asp Ala Lys Ser Thr Pro Thr Ala Glu Asp Glu Glu Ala Gly Ile Gly
65                  70                  75                  80

Asp Thr Pro Ser Leu Glu Asp Glu Ala Ala Gly His Val Thr Gln Ala
                85                  90                  95

Arg Met Val Ser Lys Ser Lys Asp Gly Thr Gly Ser Asp Asp Lys Lys
            100                 105                 110

Ala Lys Gly Ala Asp Gly Lys Thr Lys Ile Ala Thr Pro Arg Gly Ala
        115                 120                 125

Ala Pro Pro Gly Gln Lys Gly Gln Ala Asn Ala Thr Arg Ile Pro Ala
    130                 135                 140

Lys Thr Pro Pro Ala Pro Lys Thr Pro Pro Ser Ser Gly Glu Pro Pro
145                 150                 155                 160

Lys Ser Gly Asp Arg Ser Gly Tyr Ser Ser Pro Gly Ser Pro Gly Thr
                165                 170                 175

Pro Gly Ser Arg Ser Arg Thr Pro Ser Leu Pro Thr Pro Pro Thr Arg
            180                 185                 190

Glu Pro Lys Lys Val Ala Val Val Arg Thr Pro Pro Lys Ser Pro Ser
        195                 200                 205

Ser Ala Lys Ser Arg Leu Gln Thr Ala Pro Val Pro Met Pro Asp Leu
    210                 215                 220

Lys Asn Val Lys Ser Lys Ile Gly Ser Thr Glu Asn Leu Lys His Gln
225                 230                 235                 240

Pro Gly Gly Gly Lys Val Gln Ile Ile Asn Lys Lys Leu Asp Leu Ser
                245                 250                 255

Asn Val Gln Ser Lys Cys Gly Ser Lys Asp Asn Ile Lys His Val Pro
            260                 265                 270

Gly Gly Gly Ser Val Gln Ile Val Tyr Lys Pro Val Asp Leu Ser Lys
        275                 280                 285

Val Thr Ser Lys Cys Gly Ser Leu Gly Asn Ile His His Lys Pro Gly
    290                 295                 300

Gly Gly Gln Val Glu Val Lys Ser Glu Lys Leu Asp Phe Lys Asp Arg
305                 310                 315                 320

Val Gln Ser Lys Ile Gly Ser Leu Asp Asn Ile Thr His Val Pro Gly
                325                 330                 335

Gly Gly Asn Lys Lys Ile Glu Thr His Lys Leu Thr Phe Arg Glu Asn
            340                 345                 350

Ala Lys Ala Lys Thr Asp His Gly Ala Glu Ile Val Tyr Lys Ser Pro
        355                 360                 365

Val Val Ser Gly Asp Thr Ser Pro Arg His Leu Ser Asn Val Ser Ser
    370                 375                 380

Thr Gly Ser Ile Asp Met Val Asp Ser Pro Gln Leu Ala Thr Leu Ala
385                 390                 395                 400

Asp Glu Val Ser Ala Ser Leu Ala Lys Gln Gly Leu
                405                 410

<210> SEQ ID NO 10
<211> LENGTH: 383

```
<212> TYPE: PRT
<213> ORGANISM: Homo sapiens

<400> SEQUENCE: 10

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Ala Glu Glu Ala
        35                  40                  45

Gly Ile Gly Asp Thr Pro Ser Leu Glu Asp Glu Ala Ala Gly His Val
    50                  55                  60

Thr Gln Ala Arg Met Val Ser Lys Ser Lys Asp Gly Thr Gly Ser Asp
65                  70                  75                  80

Asp Lys Lys Ala Lys Gly Ala Asp Gly Lys Thr Lys Ile Ala Thr Pro
                85                  90                  95

Arg Gly Ala Ala Pro Pro Gly Gln Lys Gly Gln Ala Asn Ala Thr Arg
            100                 105                 110

Ile Pro Ala Lys Thr Pro Pro Ala Pro Lys Thr Pro Pro Ser Ser Gly
        115                 120                 125

Glu Pro Pro Lys Ser Gly Asp Arg Ser Gly Tyr Ser Ser Pro Gly Ser
    130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Val Arg Thr Pro Pro Lys
                165                 170                 175

Ser Pro Ser Ser Ala Lys Ser Arg Leu Gln Thr Ala Pro Val Pro Met
            180                 185                 190

Pro Asp Leu Lys Asn Val Lys Ser Lys Ile Gly Ser Thr Glu Asn Leu
        195                 200                 205

Lys His Gln Pro Gly Gly Gly Lys Val Gln Ile Ile Asn Lys Lys Leu
    210                 215                 220

Asp Leu Ser Asn Val Gln Ser Lys Cys Gly Ser Lys Asp Asn Ile Lys
225                 230                 235                 240

His Val Pro Gly Gly Gly Ser Val Gln Ile Val Tyr Lys Pro Val Asp
                245                 250                 255

Leu Ser Lys Val Thr Ser Lys Cys Gly Ser Leu Gly Asn Ile His His
            260                 265                 270

Lys Pro Gly Gly Gly Gln Val Glu Val Lys Ser Glu Lys Leu Asp Phe
        275                 280                 285

Lys Asp Arg Val Gln Ser Lys Ile Gly Ser Leu Asp Asn Ile Thr His
    290                 295                 300

Val Pro Gly Gly Gly Asn Lys Lys Ile Glu Thr His Lys Leu Thr Phe
305                 310                 315                 320

Arg Glu Asn Ala Lys Ala Lys Thr Asp His Gly Ala Glu Ile Val Tyr
                325                 330                 335

Lys Ser Pro Val Val Ser Gly Asp Thr Ser Pro Arg His Leu Ser Asn
            340                 345                 350

Val Ser Ser Thr Gly Ser Ile Asp Met Val Asp Ser Pro Gln Leu Ala
        355                 360                 365

Thr Leu Ala Asp Glu Val Ser Ala Ser Leu Ala Lys Gln Gly Leu
    370                 375                 380

<210> SEQ ID NO 11
```

```
<211> LENGTH: 410
<212> TYPE: PRT
<213> ORGANISM: Homo sapiens

<400> SEQUENCE: 11

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Gln Pro His Thr Glu
            85                  90                  95

Ile Pro Glu Gly Thr Thr Ala Glu Ala Gly Ile Gly Asp Thr Pro
            100                 105                 110

Ser Leu Glu Asp Glu Ala Ala Gly His Val Thr Gln Ala Arg Met Val
            115                 120                 125

Ser Lys Ser Lys Asp Gly Thr Gly Ser Asp Asp Lys Lys Ala Lys Gly
130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
            165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
            195                 200                 205

Arg Ser Arg Thr Pro Ser Leu Pro Thr Pro Pro Thr Arg Glu Pro Lys
210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
            245                 250                 255

Lys Ser Lys Ile Gly Ser Thr Glu Asn Leu Lys His Gln Pro Gly Gly
            260                 265                 270

Gly Lys Val Gln Ile Val Tyr Lys Pro Val Asp Leu Ser Lys Val Thr
            275                 280                 285

Ser Lys Cys Gly Ser Leu Gly Asn Ile His His Lys Pro Gly Gly Gly
290                 295                 300

Gln Val Glu Val Lys Ser Glu Lys Leu Asp Phe Lys Asp Arg Val Gln
305                 310                 315                 320

Ser Lys Ile Gly Ser Leu Asp Asn Ile Thr His Val Pro Gly Gly Gly
            325                 330                 335

Asn Lys Lys Ile Glu Thr His Lys Leu Thr Phe Arg Glu Asn Ala Lys
            340                 345                 350

Ala Lys Thr Asp His Gly Ala Glu Ile Val Tyr Lys Ser Pro Val Val
            355                 360                 365

Ser Gly Asp Thr Ser Pro Arg His Leu Ser Asn Val Ser Ser Thr Gly
            370                 375                 380

Ser Ile Asp Met Val Asp Ser Pro Gln Leu Ala Thr Leu Ala Asp Glu
```

Val Ser Ala Ser Leu Ala Lys Gln Gly Leu
            405                 410

<210> SEQ ID NO 12
<211> LENGTH: 381
<212> TYPE: PRT
<213> ORGANISM: Homo sapiens

<400> SEQUENCE: 12

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Glu Ala Gly Ile Gly
65                  70                  75                  80

Asp Thr Pro Ser Leu Glu Asp Glu Ala Ala Gly His Val Thr Gln Ala
                85                  90                  95

Arg Met Val Ser Lys Ser Lys Asp Gly Thr Gly Ser Asp Asp Lys Lys
            100                 105                 110

Ala Lys Gly Ala Asp Gly Lys Thr Lys Ile Ala Thr Pro Arg Gly Ala
        115                 120                 125

Ala Pro Pro Gly Gln Lys Gly Gln Ala Asn Ala Thr Arg Ile Pro Ala
    130                 135                 140

Lys Thr Pro Pro Ala Pro Lys Thr Pro Pro Ser Ser Gly Glu Pro Pro
145                 150                 155                 160

Lys Ser Gly Asp Arg Ser Gly Tyr Ser Ser Pro Gly Ser Pro Gly Thr
                165                 170                 175

Pro Gly Ser Arg Ser Arg Thr Pro Ser Leu Pro Thr Pro Pro Thr Arg
            180                 185                 190

Glu Pro Lys Lys Val Ala Val Val Arg Thr Pro Pro Lys Ser Pro Ser
        195                 200                 205

Ser Ala Lys Ser Arg Leu Gln Thr Ala Pro Val Pro Met Pro Asp Leu
    210                 215                 220

Lys Asn Val Lys Ser Lys Ile Gly Ser Thr Glu Asn Leu Lys His Gln
225                 230                 235                 240

Pro Gly Gly Gly Lys Val Gln Ile Val Tyr Lys Pro Val Asp Leu Ser
                245                 250                 255

Lys Val Thr Ser Lys Cys Gly Ser Leu Gly Asn Ile His His Lys Pro
            260                 265                 270

Gly Gly Gly Gln Val Glu Val Lys Ser Glu Lys Leu Asp Phe Lys Asp
        275                 280                 285

Arg Val Gln Ser Lys Ile Gly Ser Leu Asp Asn Ile Thr His Val Pro
    290                 295                 300

Gly Gly Gly Asn Lys Lys Ile Glu Thr His Lys Leu Thr Phe Arg Glu
305                 310                 315                 320

Asn Ala Lys Ala Lys Thr Asp His Gly Ala Glu Ile Val Tyr Lys Ser
                325                 330                 335

Pro Val Val Ser Gly Asp Thr Ser Pro Arg His Leu Ser Asn Val Ser
            340                 345                 350

Ser Thr Gly Ser Ile Asp Met Val Asp Ser Pro Gln Leu Ala Thr Leu
            355                 360                 365

Ala Asp Glu Val Ser Ala Ser Leu Ala Lys Gln Gly Leu
370                 375                 380

<210> SEQ ID NO 13
<211> LENGTH: 352
<212> TYPE: PRT
<213> ORGANISM: Homo sapiens

<400> SEQUENCE: 13

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Ala Glu Glu Ala
        35                  40                  45

Gly Ile Gly Asp Thr Pro Ser Leu Glu Asp Glu Ala Ala Gly His Val
    50                  55                  60

Thr Gln Ala Arg Met Val Ser Lys Ser Lys Asp Gly Thr Gly Ser Asp
65                  70                  75                  80

Asp Lys Lys Ala Lys Gly Ala Asp Gly Lys Thr Lys Ile Ala Thr Pro
                85                  90                  95

Arg Gly Ala Ala Pro Pro Gly Gln Lys Gly Gln Ala Asn Ala Thr Arg
            100                 105                 110

Ile Pro Ala Lys Thr Pro Pro Ala Pro Lys Thr Pro Pro Ser Ser Gly
        115                 120                 125

Glu Pro Pro Lys Ser Gly Asp Arg Ser Gly Tyr Ser Ser Pro Gly Ser
130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Val Arg Thr Pro Pro Lys
                165                 170                 175

Ser Pro Ser Ser Ala Lys Ser Arg Leu Gln Thr Ala Pro Val Pro Met
            180                 185                 190

Pro Asp Leu Lys Asn Val Lys Ser Lys Ile Gly Ser Thr Glu Asn Leu
        195                 200                 205

Lys His Gln Pro Gly Gly Gly Lys Val Gln Ile Val Tyr Lys Pro Val
210                 215                 220

Asp Leu Ser Lys Val Thr Ser Lys Cys Gly Ser Leu Gly Asn Ile His
225                 230                 235                 240

His Lys Pro Gly Gly Gly Gln Val Glu Val Lys Ser Glu Lys Leu Asp
                245                 250                 255

Phe Lys Asp Arg Val Gln Ser Lys Ile Gly Ser Leu Asp Asn Ile Thr
            260                 265                 270

His Val Pro Gly Gly Gly Asn Lys Lys Ile Glu Thr His Lys Leu Thr
        275                 280                 285

Phe Arg Glu Asn Ala Lys Ala Lys Thr Asp His Gly Ala Glu Ile Val
290                 295                 300

Tyr Lys Ser Pro Val Val Ser Gly Asp Thr Ser Pro Arg His Leu Ser
305                 310                 315                 320

Asn Val Ser Ser Thr Gly Ser Ile Asp Met Val Asp Ser Pro Gln Leu
                325                 330                 335

Ala Thr Leu Ala Asp Glu Val Ser Ala Ser Leu Ala Lys Gln Gly Leu
            340                 345                 350

<210> SEQ ID NO 14
<211> LENGTH: 119
<212> TYPE: PRT
<213> ORGANISM: Artificial Sequence
<220> FEATURE:
<223> OTHER INFORMATION: recombinant truncated Tau protein

<400> SEQUENCE: 14

```
Met Gly Ser Ser His His His His His Ser Ser Gly Leu Val Pro
1               5                   10                  15

Arg Gly Ser His Met Gln Thr Ala Pro Val Pro Met Pro Asp Leu Lys
            20                  25                  30

Asn Val Lys Ser Lys Ile Gly Ser Thr Glu Asn Leu Lys His Gln Pro
        35                  40                  45

Gly Gly Gly Lys Val Gln Ile Val Tyr Lys Pro Val Asp Leu Ser Lys
    50                  55                  60

Val Thr Ser Lys Ser Gly Ser Leu Gly Asn Ile His His Lys Pro Gly
65                  70                  75                  80

Gly Gly Gln Val Glu Val Lys Ser Glu Lys Leu Asp Phe Lys Asp Arg
                85                  90                  95

Val Gln Ser Lys Ile Gly Ser Leu Asp Asn Ile Thr His Val Pro Gly
            100                 105                 110

Gly Gly Asn Lys Lys Ile Glu
        115
```

<210> SEQ ID NO 15
<211> LENGTH: 119
<212> TYPE: PRT
<213> ORGANISM: Artificial Sequence
<220> FEATURE:
<223> OTHER INFORMATION: recombinant truncated Tau protein

<400> SEQUENCE: 15

```
Met Gly Ser Ser His His His His His Ser Ser Gly Leu Val Pro
1               5                   10                  15

Arg Gly Ser His Met Gln Thr Ala Pro Val Pro Met Pro Asp Leu Lys
            20                  25                  30

Asn Val Lys Ser Lys Ile Gly Ser Thr Glu Asn Leu Lys His Gln Pro
        35                  40                  45

Gly Gly Gly Lys Val Gln Ile Val Tyr Lys Pro Val Asp Leu Ser Lys
    50                  55                  60

Val Thr Ser Lys Cys Gly Ser Leu Gly Asn Ile His His Lys Pro Gly
65                  70                  75                  80

Gly Gly Gln Val Glu Val Lys Ser Glu Lys Leu Asp Phe Lys Asp Arg
                85                  90                  95

Val Gln Ser Lys Ile Gly Ser Leu Asp Asn Ile Thr His Val Pro Gly
            100                 105                 110

Gly Gly Asn Lys Lys Ile Glu
        115
```

<210> SEQ ID NO 16
<211> LENGTH: 150
<212> TYPE: PRT
<213> ORGANISM: Artificial Sequence
<220> FEATURE:
<223> OTHER INFORMATION: recombinant truncated Tau protein

<400> SEQUENCE: 16

```
Met Gly Ser Ser His His His His His Ser Ser Gly Leu Val Pro
1               5                   10                  15

Arg Gly Ser His Met Gln Thr Ala Pro Val Pro Met Pro Asp Leu Lys
            20                  25                  30

Asn Val Lys Ser Lys Ile Gly Ser Thr Glu Asn Leu Lys His Gln Pro
        35                  40                  45

Gly Gly Gly Lys Val Gln Ile Ile Asn Lys Lys Leu Asp Leu Ser Asn
    50                  55                  60

Val Gln Ser Lys Ser Gly Ser Lys Asp Asn Ile Lys His Val Pro Gly
65              70                  75                  80

Gly Gly Ser Val Gln Ile Val Tyr Lys Pro Val Asp Leu Ser Lys Val
            85                  90                  95

Thr Ser Lys Ser Gly Ser Leu Gly Asn Ile His His Lys Pro Gly Gly
            100                 105                 110

Gly Gln Val Glu Val Lys Ser Glu Lys Leu Asp Phe Lys Asp Arg Val
        115                 120                 125

Gln Ser Lys Ile Gly Ser Leu Asp Asn Ile Thr His Val Pro Gly Gly
        130                 135                 140

Gly Asn Lys Lys Ile Glu
145             150

<210> SEQ ID NO 17
<211> LENGTH: 150
<212> TYPE: PRT
<213> ORGANISM: Artificial Sequence
<220> FEATURE:
<223> OTHER INFORMATION: recombinant truncated Tau protein

<400> SEQUENCE: 17

Met Gly Ser Ser His His His His His Ser Ser Gly Leu Val Pro
1               5                   10                  15

Arg Gly Ser His Met Gln Thr Ala Pro Val Pro Met Pro Asp Leu Lys
            20                  25                  30

Asn Val Lys Ser Lys Ile Gly Ser Thr Glu Asn Leu Lys His Gln Pro
        35                  40                  45

Gly Gly Gly Lys Val Gln Ile Ile Asn Lys Lys Leu Asp Leu Ser Asn
    50                  55                  60

Val Gln Ser Lys Cys Gly Ser Lys Asp Asn Ile Lys His Val Pro Gly
65              70                  75                  80

Gly Gly Ser Val Gln Ile Val Tyr Lys Pro Val Asp Leu Ser Lys Val
            85                  90                  95

Thr Ser Lys Cys Gly Ser Leu Gly Asn Ile His His Lys Pro Gly Gly
            100                 105                 110

Gly Gln Val Glu Val Lys Ser Glu Lys Leu Asp Phe Lys Asp Arg Val
        115                 120                 125

Gln Ser Lys Ile Gly Ser Leu Asp Asn Ile Thr His Val Pro Gly Gly
        130                 135                 140

Gly Asn Lys Lys Ile Glu
145             150

<210> SEQ ID NO 18
<211> LENGTH: 147
<212> TYPE: PRT
<213> ORGANISM: Artificial Sequence
<220> FEATURE:
<223> OTHER INFORMATION: recombinant truncated Tau protein

<400> SEQUENCE: 18
```

```
Met Gly Ser Ser His His His His His Ser Ser Gly Leu Val Pro
1               5                   10                  15

Arg Gly Ser His Met Gln Thr Ala Pro Val Pro Met Pro Asp Leu Lys
                20                  25                  30

Asn Val Lys Ser Lys Ile Gly Ser Thr Glu Asn Leu Lys His Gln Pro
            35                  40                  45

Gly Gly Gly Lys Val Gln Ile Val Tyr Lys Pro Val Asp Leu Ser Lys
        50                  55                  60

Val Thr Ser Lys Cys Gly Ser Leu Gly Asn Ile His His Lys Pro Gly
65              70                  75                  80

Gly Gly Gln Val Glu Val Lys Ser Glu Lys Leu Asp Phe Lys Asp Arg
                85                  90                  95

Val Gln Ser Lys Ile Gly Ser Leu Asp Asn Ile Thr His Val Pro Gly
                100                 105                 110

Gly Gly Asn Lys Lys Ile Glu Thr His Lys Leu Thr Phe Arg Glu Asn
            115                 120                 125

Ala Lys Ala Lys Thr Asp His Gly Ala Glu Ile Val Tyr Lys Ser Pro
        130                 135                 140

Val Val Ser
145

<210> SEQ ID NO 19
<211> LENGTH: 147
<212> TYPE: PRT
<213> ORGANISM: Artificial Sequence
<220> FEATURE:
<223> OTHER INFORMATION: recombinant truncated Tau protein

<400> SEQUENCE: 19

Met Gly Ser Ser His His His His His Ser Ser Gly Leu Val Pro
1               5                   10                  15

Arg Gly Ser His Met Gln Thr Ala Pro Val Pro Met Pro Asp Leu Lys
                20                  25                  30

Asn Val Lys Ser Lys Ile Gly Ser Thr Glu Asn Leu Lys His Gln Pro
            35                  40                  45

Gly Gly Gly Lys Val Gln Ile Val Tyr Lys Pro Val Asp Leu Ser Lys
        50                  55                  60

Val Thr Ser Lys Ala Gly Ser Leu Gly Asn Ile His His Lys Pro Gly
65              70                  75                  80

Gly Gly Gln Val Glu Val Lys Ser Glu Lys Leu Asp Phe Lys Asp Arg
                85                  90                  95

Val Gln Ser Lys Ile Gly Ser Leu Asp Asn Ile Thr His Val Pro Gly
                100                 105                 110

Gly Gly Asn Lys Lys Ile Glu Thr His Lys Leu Thr Phe Arg Glu Asn
            115                 120                 125

Ala Lys Ala Lys Thr Asp His Gly Ala Glu Ile Val Tyr Lys Ser Pro
        130                 135                 140

Val Val Ser
145

<210> SEQ ID NO 20
<211> LENGTH: 147
<212> TYPE: PRT
<213> ORGANISM: Artificial Sequence
<220> FEATURE:
<223> OTHER INFORMATION: recombinant truncated Tau protein
```

-continued

```
<400> SEQUENCE: 20

Met Gly Ser Ser His His His His His Ser Ser Gly Leu Val Pro
1               5                   10                  15

Arg Gly Ser His Met Gln Thr Ala Pro Val Pro Met Pro Asp Leu Lys
            20                  25                  30

Asn Val Lys Ser Lys Ile Gly Ser Thr Glu Asn Leu Lys His Gln Pro
        35                  40                  45

Gly Gly Gly Lys Val Gln Ile Val Tyr Lys Pro Val Asp Leu Ser Lys
    50                  55                  60

Val Thr Ser Lys Ser Gly Ser Leu Gly Asn Ile His His Lys Pro Gly
65                  70                  75                  80

Gly Gly Gln Val Glu Val Lys Ser Glu Lys Leu Asp Phe Lys Asp Arg
                85                  90                  95

Val Gln Ser Lys Ile Gly Ser Leu Asp Asn Ile Thr His Val Pro Gly
            100                 105                 110

Gly Gly Asn Lys Lys Ile Glu Thr His Lys Leu Thr Phe Arg Glu Asn
        115                 120                 125

Ala Lys Ala Lys Thr Asp His Gly Ala Glu Ile Val Tyr Lys Ser Pro
    130                 135                 140

Val Val Ser
145

<210> SEQ ID NO 21
<211> LENGTH: 461
<212> TYPE: PRT
<213> ORGANISM: Artificial Sequence
<220> FEATURE:
<223> OTHER INFORMATION: recombinant truncated Tau protein

<400> SEQUENCE: 21

Met Gly Ser Ser His His His His His Ser Ser Gly Leu Val Pro
1               5                   10                  15

Arg Gly Ser His Met Ala Glu Pro Arg Gln Glu Phe Glu Val Met Glu
            20                  25                  30

Asp His Ala Gly Thr Tyr Gly Leu Gly Asp Arg Lys Asp Gln Gly Gly
        35                  40                  45

Tyr Thr Met His Gln Asp Gln Glu Gly Asp Thr Asp Ala Gly Leu Lys
    50                  55                  60

Glu Ser Pro Leu Gln Thr Pro Thr Glu Asp Gly Ser Glu Glu Pro Gly
65                  70                  75                  80

Ser Glu Thr Ser Asp Ala Lys Ser Thr Pro Thr Ala Glu Asp Val Thr
                85                  90                  95

Ala Pro Leu Val Asp Glu Gly Ala Pro Gly Lys Gln Ala Ala Ala Gln
            100                 105                 110

Pro His Thr Glu Ile Pro Glu Gly Thr Thr Ala Glu Glu Ala Gly Ile
        115                 120                 125

Gly Asp Thr Pro Ser Leu Glu Asp Glu Ala Ala Gly His Val Thr Gln
    130                 135                 140

Ala Arg Met Val Ser Lys Ser Lys Asp Gly Thr Gly Ser Asp Asp Lys
145                 150                 155                 160

Lys Ala Lys Gly Ala Asp Gly Lys Thr Lys Ile Ala Thr Pro Arg Gly
                165                 170                 175

Ala Ala Pro Pro Gly Gln Lys Gly Gln Ala Asn Ala Thr Arg Ile Pro
            180                 185                 190

Ala Lys Thr Pro Pro Ala Pro Lys Thr Pro Pro Ser Ser Gly Glu Pro
```

```
                        195                 200                 205
Pro Lys Ser Gly Asp Arg Ser Gly Tyr Ser Pro Gly Ser Pro Gly
    210                 215                 220

Thr Pro Gly Ser Arg Ser Arg Thr Pro Ser Leu Pro Thr Pro Thr
225                 230                 235                 240

Arg Glu Pro Lys Lys Val Ala Val Val Arg Thr Pro Pro Lys Ser Pro
                245                 250                 255

Ser Ser Ala Lys Ser Arg Leu Gln Thr Ala Pro Val Pro Met Pro Asp
            260                 265                 270

Leu Lys Asn Val Lys Ser Lys Ile Gly Ser Thr Glu Asn Leu Lys His
        275                 280                 285

Gln Pro Gly Gly Gly Lys Val Gln Ile Ile Asn Lys Lys Leu Asp Leu
    290                 295                 300

Ser Asn Val Gln Ser Lys Cys Gly Ser Lys Asp Asn Ile Lys His Val
305                 310                 315                 320

Pro Gly Gly Gly Ser Val Gln Ile Val Tyr Lys Pro Val Asp Leu Ser
                325                 330                 335

Lys Val Thr Ser Lys Cys Gly Ser Leu Gly Asn Ile His His Lys Pro
            340                 345                 350

Gly Gly Gly Gln Val Glu Val Lys Ser Glu Lys Leu Asp Phe Lys Asp
        355                 360                 365

Arg Val Gln Ser Lys Ile Gly Ser Leu Asp Asn Ile Thr His Val Pro
    370                 375                 380

Gly Gly Gly Asn Lys Lys Ile Glu Thr His Lys Leu Thr Phe Arg Glu
385                 390                 395                 400

Asn Ala Lys Ala Lys Thr Asp His Gly Ala Glu Ile Val Tyr Lys Ser
                405                 410                 415

Pro Val Val Ser Gly Asp Thr Ser Pro Arg His Leu Ser Asn Val Ser
            420                 425                 430

Ser Thr Gly Ser Ile Asp Met Val Asp Ser Pro Gln Leu Ala Thr Leu
        435                 440                 445

Ala Asp Glu Val Ser Ala Ser Leu Ala Lys Gln Gly Leu
    450                 455                 460

<210> SEQ ID NO 22
<211> LENGTH: 432
<212> TYPE: PRT
<213> ORGANISM: Artificial Sequence
<220> FEATURE:
<223> OTHER INFORMATION: 6XHis human Tau 34

<400> SEQUENCE: 22

Met Gly Ser Ser His His His His His His Ser Ser Gly Leu Val Pro
1               5                   10                  15

Arg Gly Ser His Met Ala Glu Pro Arg Gln Glu Phe Glu Val Met Glu
            20                  25                  30

Asp His Ala Gly Thr Tyr Gly Leu Gly Asp Arg Lys Asp Gln Gly Gly
        35                  40                  45

Tyr Thr Met His Gln Asp Gln Glu Gly Asp Thr Asp Ala Gly Leu Lys
    50                  55                  60

Glu Ser Pro Leu Gln Thr Pro Thr Glu Asp Gly Ser Glu Glu Pro Gly
65                  70                  75                  80

Ser Glu Thr Ser Asp Ala Lys Ser Thr Pro Thr Ala Glu Asp Glu Glu
                85                  90                  95

Ala Gly Ile Gly Asp Thr Pro Ser Leu Glu Asp Glu Ala Ala Gly His
```

```
            100                 105                 110
Val Thr Gln Ala Arg Met Val Ser Lys Ser Lys Asp Gly Thr Gly Ser
            115                 120                 125

Asp Asp Lys Lys Ala Lys Gly Ala Asp Gly Lys Thr Lys Ile Ala Thr
            130                 135                 140

Pro Arg Gly Ala Ala Pro Gly Gln Lys Gly Gln Ala Asn Ala Thr
145                 150                 155                 160

Arg Ile Pro Ala Lys Thr Pro Pro Ala Pro Lys Thr Pro Pro Ser Ser
                165                 170                 175

Gly Glu Pro Pro Lys Ser Gly Asp Arg Ser Gly Tyr Ser Ser Pro Gly
            180                 185                 190

Ser Pro Gly Thr Pro Gly Ser Arg Ser Arg Thr Pro Ser Leu Pro Thr
            195                 200                 205

Pro Pro Thr Arg Glu Pro Lys Lys Val Ala Val Arg Thr Pro Pro
210                 215                 220

Lys Ser Pro Ser Ser Ala Lys Ser Arg Leu Gln Thr Ala Pro Val Pro
225                 230                 235                 240

Met Pro Asp Leu Lys Asn Val Lys Ser Lys Ile Gly Ser Thr Glu Asn
                245                 250                 255

Leu Lys His Gln Pro Gly Gly Gly Lys Val Gln Ile Ile Asn Lys Lys
            260                 265                 270

Leu Asp Leu Ser Asn Val Gln Ser Lys Cys Gly Ser Lys Asp Asn Ile
            275                 280                 285

Lys His Val Pro Gly Gly Gly Ser Val Gln Ile Val Tyr Lys Pro Val
            290                 295                 300

Asp Leu Ser Lys Val Thr Ser Lys Cys Gly Ser Leu Gly Asn Ile His
305                 310                 315                 320

His Lys Pro Gly Gly Gly Gln Val Glu Val Lys Ser Glu Lys Leu Asp
                325                 330                 335

Phe Lys Asp Arg Val Gln Ser Lys Ile Gly Ser Leu Asp Asn Ile Thr
            340                 345                 350

His Val Pro Gly Gly Gly Asn Lys Lys Ile Glu Thr His Lys Leu Thr
            355                 360                 365

Phe Arg Glu Asn Ala Lys Ala Lys Thr Asp His Gly Ala Glu Ile Val
            370                 375                 380

Tyr Lys Ser Pro Val Val Ser Gly Asp Thr Ser Pro Arg His Leu Ser
385                 390                 395                 400

Asn Val Ser Ser Thr Gly Ser Ile Asp Met Val Asp Ser Pro Gln Leu
                405                 410                 415

Ala Thr Leu Ala Asp Glu Val Ser Ala Ser Leu Ala Lys Gln Gly Leu
            420                 425                 430

<210> SEQ ID NO 23
<211> LENGTH: 403
<212> TYPE: PRT
<213> ORGANISM: Artificial Sequence
<220> FEATURE:
<223> OTHER INFORMATION: 6XHis human Tau 24

<400> SEQUENCE: 23

Met Gly Ser Ser His His His His His His Ser Ser Gly Leu Val Pro
1               5                   10                  15

Arg Gly Ser His Met Ala Glu Pro Arg Gln Glu Phe Glu Val Met Glu
            20                  25                  30

Asp His Ala Gly Thr Tyr Gly Leu Gly Asp Arg Lys Asp Gln Gly Gly
```

```
                35                  40                  45
Tyr Thr Met His Gln Asp Gln Glu Gly Asp Thr Asp Ala Gly Leu Lys
 50                  55                  60
Ala Glu Glu Ala Gly Ile Gly Asp Thr Pro Ser Leu Glu Asp Glu Ala
 65                  70                  75                  80
Ala Gly His Val Thr Gln Ala Arg Met Val Ser Lys Ser Lys Asp Gly
                 85                  90                  95
Thr Gly Ser Asp Asp Lys Lys Ala Lys Gly Ala Asp Gly Lys Thr Lys
                100                 105                 110
Ile Ala Thr Pro Arg Gly Ala Ala Pro Pro Gly Gln Lys Gly Gln Ala
            115                 120                 125
Asn Ala Thr Arg Ile Pro Ala Lys Thr Pro Pro Ala Pro Lys Thr Pro
130                 135                 140
Pro Ser Ser Gly Glu Pro Pro Lys Ser Gly Asp Arg Ser Gly Tyr Ser
145                 150                 155                 160
Ser Pro Gly Ser Pro Gly Thr Pro Gly Ser Arg Ser Arg Thr Pro Ser
                165                 170                 175
Leu Pro Thr Pro Pro Thr Arg Glu Pro Lys Lys Val Ala Val Val Arg
            180                 185                 190
Thr Pro Pro Lys Ser Pro Ser Ser Ala Lys Ser Arg Leu Gln Thr Ala
        195                 200                 205
Pro Val Pro Met Pro Asp Leu Lys Asn Val Lys Ser Lys Ile Gly Ser
210                 215                 220
Thr Glu Asn Leu Lys His Gln Pro Gly Gly Gly Lys Val Gln Ile Ile
225                 230                 235                 240
Asn Lys Lys Leu Asp Leu Ser Asn Val Gln Ser Lys Cys Gly Ser Lys
                245                 250                 255
Asp Asn Ile Lys His Val Pro Gly Gly Gly Ser Val Gln Ile Val Tyr
            260                 265                 270
Lys Pro Val Asp Leu Ser Lys Val Thr Ser Lys Cys Gly Ser Leu Gly
        275                 280                 285
Asn Ile His His Lys Pro Gly Gly Gly Gln Val Glu Val Lys Ser Glu
290                 295                 300
Lys Leu Asp Phe Lys Asp Arg Val Gln Ser Lys Ile Gly Ser Leu Asp
305                 310                 315                 320
Asn Ile Thr His Val Pro Gly Gly Gly Asn Lys Lys Ile Glu Thr His
                325                 330                 335
Lys Leu Thr Phe Arg Glu Asn Ala Lys Ala Lys Thr Asp His Gly Ala
            340                 345                 350
Glu Ile Val Tyr Lys Ser Pro Val Val Ser Gly Asp Thr Ser Pro Arg
        355                 360                 365
His Leu Ser Asn Val Ser Ser Thr Gly Ser Ile Asp Met Val Asp Ser
    370                 375                 380
Pro Gln Leu Ala Thr Leu Ala Asp Glu Val Ser Ala Ser Leu Ala Lys
385                 390                 395                 400
Gln Gly Leu
```

<210> SEQ ID NO 24
<211> LENGTH: 430
<212> TYPE: PRT
<213> ORGANISM: Artificial Sequence
<220> FEATURE:
<223> OTHER INFORMATION: 6XHis human Tau 39

<400> SEQUENCE: 24

```
Met Gly Ser Ser His His His His His Ser Ser Gly Leu Val Pro
1               5                   10                  15

Arg Gly Ser His Met Ala Glu Pro Arg Gln Glu Phe Glu Val Met Glu
            20                  25                  30

Asp His Ala Gly Thr Tyr Gly Leu Gly Asp Arg Lys Asp Gln Gly Gly
            35                  40                  45

Tyr Thr Met His Gln Asp Gln Glu Gly Asp Thr Asp Ala Gly Leu Lys
    50                  55                  60

Glu Ser Pro Leu Gln Thr Pro Thr Glu Asp Gly Ser Glu Glu Pro Gly
65                  70                  75                  80

Ser Glu Thr Ser Asp Ala Lys Ser Thr Pro Thr Ala Glu Asp Val Thr
                85                  90                  95

Ala Pro Leu Val Asp Glu Gly Ala Pro Gly Lys Gln Ala Ala Ala Gln
                100                 105                 110

Pro His Thr Glu Ile Pro Glu Gly Thr Thr Ala Glu Glu Ala Gly Ile
            115                 120                 125

Gly Asp Thr Pro Ser Leu Glu Asp Glu Ala Ala Gly His Val Thr Gln
    130                 135                 140

Ala Arg Met Val Ser Lys Ser Lys Asp Gly Thr Gly Ser Asp Asp Lys
145                 150                 155                 160

Lys Ala Lys Gly Ala Asp Gly Lys Thr Lys Ile Ala Thr Pro Arg Gly
                165                 170                 175

Ala Ala Pro Pro Gly Gln Lys Gly Gln Ala Asn Ala Thr Arg Ile Pro
            180                 185                 190

Ala Lys Thr Pro Pro Ala Pro Lys Thr Pro Pro Ser Ser Gly Glu Pro
        195                 200                 205

Pro Lys Ser Gly Asp Arg Ser Gly Tyr Ser Ser Pro Gly Ser Pro Gly
    210                 215                 220

Thr Pro Gly Ser Arg Ser Arg Thr Pro Ser Leu Pro Thr Pro Pro Thr
225                 230                 235                 240

Arg Glu Pro Lys Lys Val Ala Val Val Arg Thr Pro Pro Lys Ser Pro
                245                 250                 255

Ser Ser Ala Lys Ser Arg Leu Gln Thr Ala Pro Val Pro Met Pro Asp
                260                 265                 270

Leu Lys Asn Val Lys Ser Lys Ile Gly Ser Thr Glu Asn Leu Lys His
        275                 280                 285

Gln Pro Gly Gly Gly Lys Val Gln Ile Val Tyr Lys Pro Val Asp Leu
    290                 295                 300

Ser Lys Val Thr Ser Lys Cys Gly Ser Leu Gly Asn Ile His His Lys
305                 310                 315                 320

Pro Gly Gly Gly Gln Val Glu Val Lys Ser Glu Lys Leu Asp Phe Lys
                325                 330                 335

Asp Arg Val Gln Ser Lys Ile Gly Ser Leu Asp Asn Ile Thr His Val
            340                 345                 350

Pro Gly Gly Gly Asn Lys Lys Ile Glu Thr His Lys Leu Thr Phe Arg
    355                 360                 365

Glu Asn Ala Lys Ala Lys Thr Asp His Gly Ala Glu Ile Val Tyr Lys
370                 375                 380

Ser Pro Val Val Ser Gly Asp Thr Ser Pro Arg His Leu Ser Asn Val
385                 390                 395                 400

Ser Ser Thr Gly Ser Ile Asp Met Val Asp Ser Pro Gln Leu Ala Thr
                405                 410                 415
```

```
Leu Ala Asp Glu Val Ser Ala Ser Leu Ala Lys Gln Gly Leu
            420                 425                 430
```

<210> SEQ ID NO 25
<211> LENGTH: 401
<212> TYPE: PRT
<213> ORGANISM: Artificial Sequence
<220> FEATURE:
<223> OTHER INFORMATION: 6XHis human Tau 37

<400> SEQUENCE: 25

```
Met Gly Ser Ser His His His His His Ser Ser Gly Leu Val Pro
1               5                   10                  15

Arg Gly Ser His Met Ala Glu Pro Arg Gln Glu Phe Glu Val Met Glu
                20                  25                  30

Asp His Ala Gly Thr Tyr Gly Leu Gly Asp Arg Lys Asp Gln Gly Gly
            35                  40                  45

Tyr Thr Met His Gln Asp Gln Glu Gly Asp Thr Asp Ala Gly Leu Lys
        50                  55                  60

Glu Ser Pro Leu Gln Thr Pro Thr Glu Asp Gly Ser Glu Glu Pro Gly
65                  70                  75                  80

Ser Glu Thr Ser Asp Ala Lys Ser Thr Pro Thr Ala Glu Asp Glu Glu
                85                  90                  95

Ala Gly Ile Gly Asp Thr Pro Ser Leu Glu Asp Glu Ala Ala Gly His
            100                 105                 110

Val Thr Gln Ala Arg Met Val Ser Lys Ser Lys Asp Gly Thr Gly Ser
        115                 120                 125

Asp Asp Lys Lys Ala Lys Gly Ala Asp Gly Lys Thr Lys Ile Ala Thr
    130                 135                 140

Pro Arg Gly Ala Ala Pro Pro Gly Gln Lys Gly Gln Ala Asn Ala Thr
145                 150                 155                 160

Arg Ile Pro Ala Lys Thr Pro Pro Ala Pro Lys Thr Pro Pro Ser Ser
                165                 170                 175

Gly Glu Pro Pro Lys Ser Gly Asp Arg Ser Gly Tyr Ser Ser Pro Gly
            180                 185                 190

Ser Pro Gly Thr Pro Gly Ser Arg Ser Arg Thr Pro Ser Leu Pro Thr
        195                 200                 205

Pro Pro Thr Arg Glu Pro Lys Lys Val Ala Val Val Arg Thr Pro Pro
    210                 215                 220

Lys Ser Pro Ser Ser Ala Lys Ser Arg Leu Gln Thr Ala Pro Val Pro
225                 230                 235                 240

Met Pro Asp Leu Lys Asn Val Lys Ser Lys Ile Gly Ser Thr Glu Asn
                245                 250                 255

Leu Lys His Gln Pro Gly Gly Gly Lys Val Gln Ile Val Tyr Lys Pro
            260                 265                 270

Val Asp Leu Ser Lys Val Thr Ser Lys Cys Gly Ser Leu Gly Asn Ile
        275                 280                 285

His His Lys Pro Gly Gly Gly Gln Val Glu Val Lys Ser Glu Lys Leu
    290                 295                 300

Asp Phe Lys Asp Arg Val Gln Ser Lys Ile Gly Ser Leu Asp Asn Ile
305                 310                 315                 320

Thr His Val Pro Gly Gly Gly Asn Lys Lys Ile Glu Thr His Lys Leu
                325                 330                 335

Thr Phe Arg Glu Asn Ala Lys Ala Lys Thr Asp His Gly Ala Glu Ile
            340                 345                 350
```

```
Val Tyr Lys Ser Pro Val Val Ser Gly Asp Thr Ser Pro Arg His Leu
            355                 360                 365

Ser Asn Val Ser Ser Thr Gly Ser Ile Asp Met Val Asp Ser Pro Gln
370                 375                 380

Leu Ala Thr Leu Ala Asp Glu Val Ser Ala Ser Leu Ala Lys Gln Gly
385                 390                 395                 400

Leu

<210> SEQ ID NO 26
<211> LENGTH: 372
<212> TYPE: PRT
<213> ORGANISM: Artificial Sequence
<220> FEATURE:
<223> OTHER INFORMATION: 6XHis human Tau 23

<400> SEQUENCE: 26

Met Gly Ser Ser His His His His His His Ser Ser Gly Leu Val Pro
1               5                   10                  15

Arg Gly Ser His Met Ala Glu Pro Arg Gln Glu Phe Glu Val Met Glu
            20                  25                  30

Asp His Ala Gly Thr Tyr Gly Leu Gly Asp Arg Lys Asp Gln Gly Gly
        35                  40                  45

Tyr Thr Met His Gln Asp Gln Glu Gly Asp Thr Asp Ala Gly Leu Lys
50                  55                  60

Ala Glu Glu Ala Gly Ile Gly Asp Thr Pro Ser Leu Glu Asp Glu Ala
65                  70                  75                  80

Ala Gly His Val Thr Gln Ala Arg Met Val Ser Lys Ser Lys Asp Gly
                85                  90                  95

Thr Gly Ser Asp Asp Lys Lys Ala Lys Gly Ala Asp Gly Lys Thr Lys
            100                 105                 110

Ile Ala Thr Pro Arg Gly Ala Ala Pro Pro Gly Gln Lys Gly Gln Ala
        115                 120                 125

Asn Ala Thr Arg Ile Pro Ala Lys Thr Pro Pro Ala Pro Lys Thr Pro
130                 135                 140

Pro Ser Ser Gly Glu Pro Pro Lys Ser Gly Asp Arg Ser Gly Tyr Ser
145                 150                 155                 160

Ser Pro Gly Ser Pro Gly Thr Pro Gly Ser Arg Ser Arg Thr Pro Ser
                165                 170                 175

Leu Pro Thr Pro Pro Thr Arg Glu Pro Lys Lys Val Ala Val Val Arg
            180                 185                 190

Thr Pro Pro Lys Ser Pro Ser Ser Ala Lys Ser Arg Leu Gln Thr Ala
        195                 200                 205

Pro Val Pro Met Pro Asp Leu Lys Asn Val Lys Ser Lys Ile Gly Ser
210                 215                 220

Thr Glu Asn Leu Lys His Gln Pro Gly Gly Gly Lys Val Gln Ile Val
225                 230                 235                 240

Tyr Lys Pro Val Asp Leu Ser Lys Val Thr Ser Lys Cys Gly Ser Leu
                245                 250                 255

Gly Asn Ile His His Lys Pro Gly Gly Gly Gln Val Glu Val Lys Ser
            260                 265                 270

Glu Lys Leu Asp Phe Lys Asp Arg Val Gln Ser Lys Ile Gly Ser Leu
        275                 280                 285

Asp Asn Ile Thr His Val Pro Gly Gly Gly Asn Lys Lys Ile Glu Thr
290                 295                 300

His Lys Leu Thr Phe Arg Glu Asn Ala Lys Ala Lys Thr Asp His Gly
```

```
                    305                 310                 315                 320
Ala Glu Ile Val Tyr Lys Ser Pro Val Val Ser Gly Asp Thr Ser Pro
                325                 330                 335

Arg His Leu Ser Asn Val Ser Ser Thr Gly Ser Ile Asp Met Val Asp
                340                 345                 350

Ser Pro Gln Leu Ala Thr Leu Ala Asp Glu Val Ser Ala Ser Leu Ala
                355                 360                 365

Lys Gln Gly Leu
        370

<210> SEQ ID NO 27
<211> LENGTH: 6
<212> TYPE: PRT
<213> ORGANISM: Artificial Sequence
<220> FEATURE:
<223> OTHER INFORMATION: hexapeptide PHF6

<400> SEQUENCE: 27

Val Gln Ile Val Tyr Lys
1               5

<210> SEQ ID NO 28
<211> LENGTH: 6
<212> TYPE: PRT
<213> ORGANISM: Artificial Sequence
<220> FEATURE:
<223> OTHER INFORMATION: hexapeptide PHF6*

<400> SEQUENCE: 28

Val Gln Ile Ile Asn Lys
1               5

<210> SEQ ID NO 29
<211> LENGTH: 99
<212> TYPE: PRT
<213> ORGANISM: Artificial Sequence
<220> FEATURE:
<223> OTHER INFORMATION: recombinant truncated Tau protein

<400> SEQUENCE: 29

Met Gln Thr Ala Pro Val Pro Met Pro Asp Leu Lys Asn Val Lys Ser
1               5                   10                  15

Lys Ile Gly Ser Thr Glu Asn Leu Lys His Gln Pro Gly Gly Gly Lys
                20                  25                  30

Val Gln Ile Val Tyr Lys Pro Val Asp Leu Ser Lys Val Thr Ser Lys
                35                  40                  45

Ala Gly Ser Leu Gly Asn Ile His His Lys Pro Gly Gly Gly Gln Val
        50                  55                  60

Glu Val Lys Ser Glu Lys Leu Asp Phe Lys Asp Arg Val Gln Ser Lys
65                  70                  75                  80

Ile Gly Ser Leu Asp Asn Ile Thr His Val Pro Gly Gly Gly Asn Lys
                85                  90                  95

Lys Ile Glu

<210> SEQ ID NO 30
<211> LENGTH: 130
<212> TYPE: PRT
<213> ORGANISM: Artificial Sequence
<220> FEATURE:
<223> OTHER INFORMATION: recombinant truncated Tau protein

<400> SEQUENCE: 30
```

```
Met Gln Thr Ala Pro Val Pro Met Pro Asp Leu Lys Asn Val Lys Ser
1               5                   10                  15

Lys Ile Gly Ser Thr Glu Asn Leu Lys His Gln Pro Gly Gly Gly Lys
                20                  25                  30

Val Gln Ile Ile Asn Lys Lys Leu Asp Leu Ser Asn Val Gln Ser Lys
            35                  40                  45

Ala Gly Ser Lys Asp Asn Ile Lys His Val Pro Gly Gly Gly Ser Val
        50                  55                  60

Gln Ile Val Tyr Lys Pro Val Asp Leu Ser Lys Val Thr Ser Lys Ser
65                  70                  75                  80

Gly Ser Leu Gly Asn Ile His His Lys Pro Gly Gly Gly Gln Val Glu
                85                  90                  95

Val Lys Ser Glu Lys Leu Asp Phe Lys Asp Arg Val Gln Ser Lys Ile
                100                 105                 110

Gly Ser Leu Asp Asn Ile Thr His Val Pro Gly Gly Gly Asn Lys Lys
            115                 120                 125

Ile Glu
    130
```

<210> SEQ ID NO 31
<211> LENGTH: 130
<212> TYPE: PRT
<213> ORGANISM: Artificial Sequence
<220> FEATURE:
<223> OTHER INFORMATION: recombinant truncated Tau protein

<400> SEQUENCE: 31

```
Met Gln Thr Ala Pro Val Pro Met Pro Asp Leu Lys Asn Val Lys Ser
1               5                   10                  15

Lys Ile Gly Ser Thr Glu Asn Leu Lys His Gln Pro Gly Gly Gly Lys
                20                  25                  30

Val Gln Ile Ile Asn Lys Lys Leu Asp Leu Ser Asn Val Gln Ser Lys
            35                  40                  45

Ser Gly Ser Lys Asp Asn Ile Lys His Val Pro Gly Gly Gly Ser Val
        50                  55                  60

Gln Ile Val Tyr Lys Pro Val Asp Leu Ser Lys Val Thr Ser Lys Ala
65                  70                  75                  80

Gly Ser Leu Gly Asn Ile His His Lys Pro Gly Gly Gly Gln Val Glu
                85                  90                  95

Val Lys Ser Glu Lys Leu Asp Phe Lys Asp Arg Val Gln Ser Lys Ile
                100                 105                 110

Gly Ser Leu Asp Asn Ile Thr His Val Pro Gly Gly Gly Asn Lys Lys
            115                 120                 125

Ile Glu
    130
```

<210> SEQ ID NO 32
<211> LENGTH: 130
<212> TYPE: PRT
<213> ORGANISM: Artificial Sequence
<220> FEATURE:
<223> OTHER INFORMATION: recombinant truncated Tau protein

<400> SEQUENCE: 32

```
Met Gln Thr Ala Pro Val Pro Met Pro Asp Leu Lys Asn Val Lys Ser
1               5                   10                  15

Lys Ile Gly Ser Thr Glu Asn Leu Lys His Gln Pro Gly Gly Gly Lys
```

```
                    20                  25                  30

Val Gln Ile Ile Asn Lys Lys Leu Asp Leu Ser Asn Val Gln Ser Lys
            35                  40                  45

Ala Gly Ser Lys Asp Asn Ile Lys His Val Pro Gly Gly Gly Ser Val
        50                  55                  60

Gln Ile Val Tyr Lys Pro Val Asp Leu Ser Lys Val Thr Ser Lys Ala
65                  70                  75                  80

Gly Ser Leu Gly Asn Ile His His Lys Pro Gly Gly Gly Gln Val Glu
                85                  90                  95

Val Lys Ser Glu Lys Leu Asp Phe Lys Asp Arg Val Gln Ser Lys Ile
            100                 105                 110

Gly Ser Leu Asp Asn Ile Thr His Val Pro Gly Gly Gly Asn Lys Lys
        115                 120                 125

Ile Glu
    130

<210> SEQ ID NO 33
<211> LENGTH: 119
<212> TYPE: PRT
<213> ORGANISM: Artificial Sequence
<220> FEATURE:
<223> OTHER INFORMATION: recombinant truncated Tau protein

<400> SEQUENCE: 33

Met Gly Ser Ser His His His His His Ser Ser Gly Leu Val Pro
1               5                   10                  15

Arg Gly Ser His Met Gln Thr Ala Pro Val Pro Met Pro Asp Leu Lys
            20                  25                  30

Asn Val Lys Ser Lys Ile Gly Ser Thr Glu Asn Leu Lys His Gln Pro
        35                  40                  45

Gly Gly Gly Lys Val Gln Ile Val Tyr Lys Pro Val Asp Leu Ser Lys
    50                  55                  60

Val Thr Ser Lys Ala Gly Ser Leu Gly Asn Ile His His Lys Pro Gly
65                  70                  75                  80

Gly Gly Gln Val Glu Val Lys Ser Glu Lys Leu Asp Phe Lys Asp Arg
                85                  90                  95

Val Gln Ser Lys Ile Gly Ser Leu Asp Asn Ile Thr His Val Pro Gly
            100                 105                 110

Gly Gly Asn Lys Lys Ile Glu
        115

<210> SEQ ID NO 34
<211> LENGTH: 150
<212> TYPE: PRT
<213> ORGANISM: Artificial Sequence
<220> FEATURE:
<223> OTHER INFORMATION: recombinant truncated Tau protein

<400> SEQUENCE: 34

Met Gly Ser Ser His His His His His Ser Ser Gly Leu Val Pro
1               5                   10                  15

Arg Gly Ser His Met Gln Thr Ala Pro Val Pro Met Pro Asp Leu Lys
            20                  25                  30

Asn Val Lys Ser Lys Ile Gly Ser Thr Glu Asn Leu Lys His Gln Pro
        35                  40                  45

Gly Gly Gly Lys Val Gln Ile Ile Asn Lys Lys Leu Asp Leu Ser Asn
    50                  55                  60
```

```
Val Gln Ser Lys Ala Gly Ser Lys Asp Asn Ile Lys His Val Pro Gly
 65                  70                  75                  80

Gly Gly Ser Val Gln Ile Val Tyr Lys Pro Val Asp Leu Ser Lys Val
                 85                  90                  95

Thr Ser Lys Ser Gly Ser Leu Gly Asn Ile His His Lys Pro Gly Gly
            100                 105                 110

Gly Gln Val Glu Val Lys Ser Glu Lys Leu Asp Phe Lys Asp Arg Val
        115                 120                 125

Gln Ser Lys Ile Gly Ser Leu Asp Asn Ile Thr His Val Pro Gly Gly
    130                 135                 140

Gly Asn Lys Lys Ile Glu
145                 150

<210> SEQ ID NO 35
<211> LENGTH: 150
<212> TYPE: PRT
<213> ORGANISM: Artificial Sequence
<220> FEATURE:
<223> OTHER INFORMATION: recombinant truncated Tau protein

<400> SEQUENCE: 35

Met Gly Ser Ser His His His His His Ser Ser Gly Leu Val Pro
1               5                  10                  15

Arg Gly Ser His Met Gln Thr Ala Pro Val Pro Met Pro Asp Leu Lys
                 20                  25                  30

Asn Val Lys Ser Lys Ile Gly Ser Thr Glu Asn Leu Lys His Gln Pro
            35                  40                  45

Gly Gly Gly Lys Val Gln Ile Ile Asn Lys Lys Leu Asp Leu Ser Asn
        50                  55                  60

Val Gln Ser Lys Ser Gly Ser Lys Asp Asn Ile Lys His Val Pro Gly
 65                  70                  75                  80

Gly Gly Ser Val Gln Ile Val Tyr Lys Pro Val Asp Leu Ser Lys Val
                 85                  90                  95

Thr Ser Lys Ala Gly Ser Leu Gly Asn Ile His His Lys Pro Gly Gly
            100                 105                 110

Gly Gln Val Glu Val Lys Ser Glu Lys Leu Asp Phe Lys Asp Arg Val
        115                 120                 125

Gln Ser Lys Ile Gly Ser Leu Asp Asn Ile Thr His Val Pro Gly Gly
    130                 135                 140

Gly Asn Lys Lys Ile Glu
145                 150

<210> SEQ ID NO 36
<211> LENGTH: 150
<212> TYPE: PRT
<213> ORGANISM: Artificial Sequence
<220> FEATURE:
<223> OTHER INFORMATION: recombinant truncated Tau protein

<400> SEQUENCE: 36

Met Gly Ser Ser His His His His His His Ser Ser Gly Leu Val Pro
1               5                  10                  15

Arg Gly Ser His Met Gln Thr Ala Pro Val Pro Met Pro Asp Leu Lys
                 20                  25                  30

Asn Val Lys Ser Lys Ile Gly Ser Thr Glu Asn Leu Lys His Gln Pro
            35                  40                  45

Gly Gly Gly Lys Val Gln Ile Ile Asn Lys Lys Leu Asp Leu Ser Asn
        50                  55                  60
```

Val Gln Ser Lys Ala Gly Ser Lys Asp Asn Ile Lys His Val Pro Gly
65                  70                  75                  80

Gly Gly Ser Val Gln Ile Val Tyr Lys Pro Val Asp Leu Ser Lys Val
                85                  90                  95

Thr Ser Lys Ala Gly Ser Leu Gly Asn Ile His His Lys Pro Gly Gly
            100                 105                 110

Gly Gln Val Glu Val Lys Ser Glu Lys Leu Asp Phe Lys Asp Arg Val
        115                 120                 125

Gln Ser Lys Ile Gly Ser Leu Asp Asn Ile Thr His Val Pro Gly Gly
    130                 135                 140

Gly Asn Lys Lys Ile Glu
145                 150

<210> SEQ ID NO 37
<211> LENGTH: 127
<212> TYPE: PRT
<213> ORGANISM: Artificial Sequence
<220> FEATURE:
<223> OTHER INFORMATION: microtubule binding domain

<400> SEQUENCE: 37

Gln Thr Ala Pro Val Pro Met Pro Asp Leu Lys Asn Val Lys Ser Lys
1               5                   10                  15

Ile Gly Ser Thr Glu Asn Leu Lys His Gln Pro Gly Gly Gly Lys Val
            20                  25                  30

Gln Ile Ile Asn Lys Lys Leu Asp Leu Ser Asn Val Gln Ser Lys Cys
        35                  40                  45

Gly Ser Lys Asp Asn Ile Lys His Val Pro Gly Gly Gly Ser Val Gln
    50                  55                  60

Ile Val Tyr Lys Pro Val Asp Leu Ser Lys Val Thr Ser Lys Cys Gly
65                  70                  75                  80

Ser Leu Gly Asn Ile His His Lys Pro Gly Gly Gly Gln Val Glu Val
                85                  90                  95

Lys Ser Glu Lys Leu Asp Phe Lys Asp Arg Val Gln Ser Lys Ile Gly
            100                 105                 110

Ser Leu Asp Asn Ile Thr His Val Pro Gly Gly Gly Asn Lys Lys
        115                 120                 125

<210> SEQ ID NO 38
<211> LENGTH: 96
<212> TYPE: PRT
<213> ORGANISM: Artificial Sequence
<220> FEATURE:
<223> OTHER INFORMATION: microtubule binding domain

<400> SEQUENCE: 38

Gln Thr Ala Pro Val Pro Met Pro Asp Leu Lys Asn Val Lys Ser Lys
1               5                   10                  15

Ile Gly Ser Thr Glu Asn Leu Lys His Gln Pro Gly Gly Gly Lys Val
            20                  25                  30

Gln Ile Val Tyr Lys Pro Val Asp Leu Ser Lys Val Thr Ser Lys Cys
        35                  40                  45

Gly Ser Leu Gly Asn Ile His His Lys Pro Gly Gly Gly Gln Val Glu
    50                  55                  60

Val Lys Ser Glu Lys Leu Asp Phe Lys Asp Arg Val Gln Ser Lys Ile
65                  70                  75                  80

Gly Ser Leu Asp Asn Ile Thr His Val Pro Gly Gly Gly Asn Lys Lys

<210> SEQ ID NO 39
<211> LENGTH: 125
<212> TYPE: PRT
<213> ORGANISM: Artificial Sequence
<220> FEATURE:
<223> OTHER INFORMATION: recombinant truncated Tau protein

<400> SEQUENCE: 39

Met Gly Ser Ser His His His His His Ser Ser Gly Leu Val Pro
1               5                   10                  15

Arg Gly Ser His Met Gln Thr Ala Pro Val Pro Met Pro Asp Leu Lys
            20                  25                  30

Asn Val Lys Ser Lys Ile Gly Ser Thr Glu Asn Leu Lys His Gln Pro
        35                  40                  45

Gly Gly Gly Lys Val Gln Ile Val Tyr Lys Pro Val Asp Leu Ser Lys
    50                  55                  60

Val Thr Ser Lys Ser Gly Ser Leu Gly Asn Ile His His Lys Pro Gly
65                  70                  75                  80

Gly Gly Gln Val Glu Val Lys Ser Glu Lys Leu Asp Phe Lys Asp Arg
                85                  90                  95

Val Gln Ser Lys Ile Gly Ser Leu Asp Asn Ile Thr His Val Pro Gly
            100                 105                 110

Gly Gly Asn Lys Lys Ile Glu Thr His Lys Leu Thr Phe
        115                 120                 125

<210> SEQ ID NO 40
<211> LENGTH: 104
<212> TYPE: PRT
<213> ORGANISM: Artificial Sequence
<220> FEATURE:
<223> OTHER INFORMATION: recombinant truncated Tau protein

<400> SEQUENCE: 40

Gln Thr Ala Pro Val Pro Met Pro Asp Leu Lys Asn Val Lys Ser Lys
1               5                   10                  15

Ile Gly Ser Thr Glu Asn Leu Lys His Gln Pro Gly Gly Gly Lys Val
            20                  25                  30

Gln Ile Val Tyr Lys Pro Val Asp Leu Ser Lys Val Thr Ser Lys Ser
        35                  40                  45

Gly Ser Leu Gly Asn Ile His His Lys Pro Gly Gly Gly Gln Val Glu
    50                  55                  60

Val Lys Ser Glu Lys Leu Asp Phe Lys Asp Arg Val Gln Ser Lys Ile
65                  70                  75                  80

Gly Ser Leu Asp Asn Ile Thr His Val Pro Gly Gly Gly Asn Lys Lys
                85                  90                  95

Ile Glu Thr His Lys Leu Thr Phe
            100

<210> SEQ ID NO 41
<211> LENGTH: 156
<212> TYPE: PRT
<213> ORGANISM: Artificial Sequence
<220> FEATURE:
<223> OTHER INFORMATION: recombinant truncated Tau protein

<400> SEQUENCE: 41

Met Gly Ser Ser His His His His His His Ser Ser Gly Leu Val Pro
1               5                   10                  15

```
Arg Gly Ser His Met Gln Thr Ala Pro Val Pro Met Pro Asp Leu Lys
            20                  25                  30

Asn Val Lys Ser Lys Ile Gly Ser Thr Glu Asn Leu Lys His Gln Pro
        35                  40                  45

Gly Gly Gly Lys Val Gln Ile Ile Asn Lys Lys Leu Asp Leu Ser Asn
50                  55                  60

Val Gln Ser Lys Ser Gly Ser Lys Asp Asn Ile Lys His Val Pro Gly
65                  70                  75                  80

Gly Gly Ser Val Gln Ile Val Tyr Lys Pro Val Asp Leu Ser Lys Val
                85                  90                  95

Thr Ser Lys Ser Gly Ser Leu Gly Asn Ile His His Lys Pro Gly Gly
            100                 105                 110

Gly Gln Val Glu Val Lys Ser Glu Lys Leu Asp Phe Lys Asp Arg Val
        115                 120                 125

Gln Ser Lys Ile Gly Ser Leu Asp Asn Ile Thr His Val Pro Gly Gly
    130                 135                 140

Gly Asn Lys Lys Ile Glu Thr His Lys Leu Thr Phe
145                 150                 155

<210> SEQ ID NO 42
<211> LENGTH: 135
<212> TYPE: PRT
<213> ORGANISM: Artificial Sequence
<220> FEATURE:
<223> OTHER INFORMATION: recombinant truncated Tau protein

<400> SEQUENCE: 42

Gln Thr Ala Pro Val Pro Met Pro Asp Leu Lys Asn Val Lys Ser Lys
1               5                   10                  15

Ile Gly Ser Thr Glu Asn Leu Lys His Gln Pro Gly Gly Gly Lys Val
            20                  25                  30

Gln Ile Ile Asn Lys Lys Leu Asp Leu Ser Asn Val Gln Ser Lys Ser
        35                  40                  45

Gly Ser Lys Asp Asn Ile Lys His Val Pro Gly Gly Gly Ser Val Gln
50                  55                  60

Ile Val Tyr Lys Pro Val Asp Leu Ser Lys Val Thr Ser Lys Ser Gly
65                  70                  75                  80

Ser Leu Gly Asn Ile His His Lys Pro Gly Gly Gly Gln Val Glu Val
                85                  90                  95

Lys Ser Glu Lys Leu Asp Phe Lys Asp Arg Val Gln Ser Lys Ile Gly
            100                 105                 110

Ser Leu Asp Asn Ile Thr His Val Pro Gly Gly Gly Asn Lys Lys Ile
        115                 120                 125

Glu Thr His Lys Leu Thr Phe
    130                 135

<210> SEQ ID NO 43
<211> LENGTH: 93
<212> TYPE: PRT
<213> ORGANISM: Artificial Sequence
<220> FEATURE:
<223> OTHER INFORMATION: recombinant truncated Tau protein

<400> SEQUENCE: 43

Met Gly Ser Ser His His His His His His Ser Ser Gly Leu Val Pro
1               5                   10                  15

Arg Gly Ser His Val Gln Ile Val Tyr Lys Pro Val Asp Leu Ser Lys
```

```
                    20                  25                  30
Val Thr Ser Lys Ser Gly Ser Leu Gly Asn Ile His His Lys Pro Gly
                35                  40                  45

Gly Gly Gln Val Glu Val Lys Ser Glu Lys Leu Asp Phe Lys Asp Arg
            50                  55                  60

Val Gln Ser Lys Ile Gly Ser Leu Asp Asn Ile Thr His Val Pro Gly
65                  70                  75                  80

Gly Gly Asn Lys Lys Ile Glu Thr His Lys Leu Thr Phe
                85                  90

<210> SEQ ID NO 44
<211> LENGTH: 73
<212> TYPE: PRT
<213> ORGANISM: Artificial Sequence
<220> FEATURE:
<223> OTHER INFORMATION: recombinant truncated Tau protein

<400> SEQUENCE: 44

Val Gln Ile Val Tyr Lys Pro Val Asp Leu Ser Lys Val Thr Ser Lys
1               5                   10                  15

Ser Gly Ser Leu Gly Asn Ile His His Lys Pro Gly Gly Gly Gln Val
                20                  25                  30

Glu Val Lys Ser Glu Lys Leu Asp Phe Lys Asp Arg Val Gln Ser Lys
            35                  40                  45

Ile Gly Ser Leu Asp Asn Ile Thr His Val Pro Gly Gly Gly Asn Lys
        50                  55                  60

Lys Ile Glu Thr His Lys Leu Thr Phe
65                  70

<210> SEQ ID NO 45
<211> LENGTH: 92
<212> TYPE: PRT
<213> ORGANISM: Artificial Sequence
<220> FEATURE:
<223> OTHER INFORMATION: recombinant truncated Tau protein

<400> SEQUENCE: 45

Met Gly Ser Ser His His His His His His Ser Ser Gly Leu Val Pro
1               5                   10                  15

Arg Gly Ser His Gln Thr Ala Pro Val Pro Met Pro Asp Leu Lys Asn
                20                  25                  30

Val Lys Ser Lys Ile Gly Ser Thr Glu Asn Leu Lys His Gln Pro Gly
            35                  40                  45

Gly Gly Lys Val Gln Ile Val Tyr Lys Pro Val Asp Leu Ser Lys Val
        50                  55                  60

Thr Ser Lys Cys Gly Ser Leu Gly Asn Ile His His Lys Pro Gly Gly
65                  70                  75                  80

Gly Gln Val Glu Val Lys Ser Glu Lys Leu Asp Phe
                85                  90

<210> SEQ ID NO 46
<211> LENGTH: 72
<212> TYPE: PRT
<213> ORGANISM: Artificial Sequence
<220> FEATURE:
<223> OTHER INFORMATION: recombinant truncated Tau protein

<400> SEQUENCE: 46

Gln Thr Ala Pro Val Pro Met Pro Asp Leu Lys Asn Val Lys Ser Lys
1               5                   10                  15
```

```
Ile Gly Ser Thr Glu Asn Leu Lys His Gln Pro Gly Gly Lys Val
            20                  25                  30

Gln Ile Val Tyr Lys Pro Val Asp Leu Ser Lys Val Thr Ser Lys Cys
        35                  40                  45

Gly Ser Leu Gly Asn Ile His His Lys Pro Gly Gly Gly Gln Val Glu
    50                  55                  60

Val Lys Ser Glu Lys Leu Asp Phe
65                  70
```

<210> SEQ ID NO 47
<211> LENGTH: 92
<212> TYPE: PRT
<213> ORGANISM: Artificial Sequence
<220> FEATURE:
<223> OTHER INFORMATION: recombinant truncated Tau protein

<400> SEQUENCE: 47

```
Met Gly Ser Ser His His His His His His Ser Ser Gly Leu Val Pro
1               5                   10                  15

Arg Gly Ser His Gln Thr Ala Pro Val Pro Met Pro Asp Leu Lys Asn
            20                  25                  30

Val Lys Ser Lys Ile Gly Ser Thr Glu Asn Leu Lys His Gln Pro Gly
        35                  40                  45

Gly Gly Lys Val Gln Ile Val Tyr Lys Pro Val Asp Leu Ser Lys Val
    50                  55                  60

Thr Ser Lys Ser Gly Ser Leu Gly Asn Ile His His Lys Pro Gly Gly
65                  70                  75                  80

Gly Gln Val Glu Val Lys Ser Glu Lys Leu Asp Phe
                85                  90
```

<210> SEQ ID NO 48
<211> LENGTH: 72
<212> TYPE: PRT
<213> ORGANISM: Artificial Sequence
<220> FEATURE:
<223> OTHER INFORMATION: recombinant truncated Tau protein

<400> SEQUENCE: 48

```
Gln Thr Ala Pro Val Pro Met Pro Asp Leu Lys Asn Val Lys Ser Lys
1               5                   10                  15

Ile Gly Ser Thr Glu Asn Leu Lys His Gln Pro Gly Gly Gly Lys Val
            20                  25                  30

Gln Ile Val Tyr Lys Pro Val Asp Leu Ser Lys Val Thr Ser Lys Ser
        35                  40                  45

Gly Ser Leu Gly Asn Ile His His Lys Pro Gly Gly Gly Gln Val Glu
    50                  55                  60

Val Lys Ser Glu Lys Leu Asp Phe
65                  70
```

<210> SEQ ID NO 49
<211> LENGTH: 92
<212> TYPE: PRT
<213> ORGANISM: Artificial Sequence
<220> FEATURE:
<223> OTHER INFORMATION: recombinant truncated Tau protein

<400> SEQUENCE: 49

```
Met Gly Ser Ser His His His His His His Ser Ser Gly Leu Val Pro
1               5                   10                  15
```

Arg Gly Ser His Gln Thr Ala Pro Val Pro Met Pro Asp Leu Lys Asn
            20                  25                  30

Val Lys Ser Lys Ile Gly Ser Thr Glu Asn Leu Lys His Gln Pro Gly
        35                  40                  45

Gly Gly Lys Val Gln Ile Ile Asn Lys Lys Leu Asp Leu Ser Asn Val
    50                  55                  60

Gln Ser Lys Cys Gly Ser Lys Asp Asn Ile Lys His Val Pro Gly Gly
65                  70                  75                  80

Gly Ser Val Gln Ile Val Tyr Lys Pro Val Asp Leu
                85                  90

<210> SEQ ID NO 50
<211> LENGTH: 72
<212> TYPE: PRT
<213> ORGANISM: Artificial Sequence
<220> FEATURE:
<223> OTHER INFORMATION: recombinant truncated Tau protein

<400> SEQUENCE: 50

Gln Thr Ala Pro Val Pro Met Pro Asp Leu Lys Asn Val Lys Ser Lys
1               5                   10                  15

Ile Gly Ser Thr Glu Asn Leu Lys His Gln Pro Gly Gly Gly Lys Val
            20                  25                  30

Gln Ile Ile Asn Lys Lys Leu Asp Leu Ser Asn Val Gln Ser Lys Cys
        35                  40                  45

Gly Ser Lys Asp Asn Ile Lys His Val Pro Gly Gly Gly Ser Val Gln
    50                  55                  60

Ile Val Tyr Lys Pro Val Asp Leu
65                  70

<210> SEQ ID NO 51
<211> LENGTH: 92
<212> TYPE: PRT
<213> ORGANISM: Artificial Sequence
<220> FEATURE:
<223> OTHER INFORMATION: recombinant truncated Tau protein

<400> SEQUENCE: 51

Met Gly Ser Ser His His His His His His Ser Ser Gly Leu Val Pro
1               5                   10                  15

Arg Gly Ser His Gln Thr Ala Pro Val Pro Met Pro Asp Leu Lys Asn
            20                  25                  30

Val Lys Ser Lys Ile Gly Ser Thr Glu Asn Leu Lys His Gln Pro Gly
        35                  40                  45

Gly Gly Lys Val Gln Ile Ile Asn Lys Lys Leu Asp Leu Ser Asn Val
    50                  55                  60

Gln Ser Lys Ser Gly Ser Lys Asp Asn Ile Lys His Val Pro Gly Gly
65                  70                  75                  80

Gly Ser Val Gln Ile Val Tyr Lys Pro Val Asp Leu
                85                  90

<210> SEQ ID NO 52
<211> LENGTH: 72
<212> TYPE: PRT
<213> ORGANISM: Artificial Sequence
<220> FEATURE:
<223> OTHER INFORMATION: recombinant truncated Tau protein

<400> SEQUENCE: 52

Gln Thr Ala Pro Val Pro Met Pro Asp Leu Lys Asn Val Lys Ser Lys

```
                1               5                   10                  15
Ile Gly Ser Thr Glu Asn Leu Lys His Gln Pro Gly Gly Lys Val
                20                  25                  30

Gln Ile Ile Asn Lys Lys Leu Asp Leu Ser Asn Val Gln Ser Lys Ser
                35                  40                  45

Gly Ser Lys Asp Asn Ile Lys His Val Pro Gly Gly Ser Val Gln
        50                  55                  60

Ile Val Tyr Lys Pro Val Asp Leu
65                  70
```

<210> SEQ ID NO 53
<211> LENGTH: 92
<212> TYPE: PRT
<213> ORGANISM: Artificial Sequence
<220> FEATURE:
<223> OTHER INFORMATION: recombinant truncated Tau protein

<400> SEQUENCE: 53

```
Met Gly Ser Ser His His His His His His Ser Ser Gly Leu Val Pro
1               5                   10                  15

Arg Gly Ser His Val Gln Ile Ile Asn Lys Lys Leu Asp Leu Ser Asn
                20                  25                  30

Val Gln Ser Lys Cys Gly Ser Lys Asp Asn Ile Lys His Val Pro Gly
                35                  40                  45

Gly Gly Ser Val Gln Ile Val Tyr Lys Pro Val Asp Leu Ser Lys Val
        50                  55                  60

Thr Ser Lys Cys Gly Ser Leu Gly Asn Ile His His Lys Pro Gly Gly
65                  70                  75                  80

Gly Gln Val Glu Val Lys Ser Glu Lys Leu Asp Phe
                85                  90
```

<210> SEQ ID NO 54
<211> LENGTH: 72
<212> TYPE: PRT
<213> ORGANISM: Artificial Sequence
<220> FEATURE:
<223> OTHER INFORMATION: recombinant truncated Tau protein

<400> SEQUENCE: 54

```
Val Gln Ile Ile Asn Lys Lys Leu Asp Leu Ser Asn Val Gln Ser Lys
1               5                   10                  15

Cys Gly Ser Lys Asp Asn Ile Lys His Val Pro Gly Gly Gly Ser Val
                20                  25                  30

Gln Ile Val Tyr Lys Pro Val Asp Leu Ser Lys Val Thr Ser Lys Cys
                35                  40                  45

Gly Ser Leu Gly Asn Ile His His Lys Pro Gly Gly Gly Gln Val Glu
        50                  55                  60

Val Lys Ser Glu Lys Leu Asp Phe
65                  70
```

<210> SEQ ID NO 55
<211> LENGTH: 91
<212> TYPE: PRT
<213> ORGANISM: Artificial Sequence
<220> FEATURE:
<223> OTHER INFORMATION: recombinant truncated Tau protein

<400> SEQUENCE: 55

```
Met Gly Ser Ser His His His His His His Ser Ser Gly Leu Val Pro
1               5                   10                  15
```

Arg Gly Ser His Val Gln Ile Ile Asn Lys Lys Leu Asp Leu Ser Asn
                20                  25                  30

Val Gln Ser Lys Ser Gly Ser Lys Asp Asn Ile Lys His Val Pro Gly
            35                  40                  45

Gly Gly Ser Val Gln Ile Val Tyr Lys Pro Val Asp Leu Ser Lys Val
    50                  55                  60

Thr Ser Lys Ser Gly Ser Leu Gly Asn Ile His His Lys Pro Gly Gly
65                  70                  75                  80

Gly Gln Val Glu Val Lys Ser Glu Lys Leu Asp
                85                  90

<210> SEQ ID NO 56
<211> LENGTH: 72
<212> TYPE: PRT
<213> ORGANISM: Artificial Sequence
<220> FEATURE:
<223> OTHER INFORMATION: recombinant truncated Tau protein

<400> SEQUENCE: 56

Val Gln Ile Ile Asn Lys Lys Leu Asp Leu Ser Asn Val Gln Ser Lys
1               5                   10                  15

Ser Gly Ser Lys Asp Asn Ile Lys His Val Pro Gly Gly Gly Ser Val
            20                  25                  30

Gln Ile Val Tyr Lys Pro Val Asp Leu Ser Lys Val Thr Ser Lys Ser
        35                  40                  45

Gly Ser Leu Gly Asn Ile His His Lys Pro Gly Gly Gly Gln Val Glu
    50                  55                  60

Val Lys Ser Glu Lys Leu Asp Phe
65                  70

<210> SEQ ID NO 57
<211> LENGTH: 114
<212> TYPE: PRT
<213> ORGANISM: Artificial Sequence
<220> FEATURE:
<223> OTHER INFORMATION: recombinant truncated Tau protein

<400> SEQUENCE: 57

Met Gly Ser Ser His His His His His His Ser Ser Gly Leu Val Pro
1               5                   10                  15

Arg Gly Ser His Val Gln Ile Ile Asn Lys Lys Leu Asp Leu Ser Asn
                20                  25                  30

Val Gln Ser Lys Cys Gly Ser Lys Asp Asn Ile Lys His Val Pro Gly
            35                  40                  45

Gly Gly Ser Val Gln Ile Val Tyr Lys Pro Val Asp Leu Ser Lys Val
    50                  55                  60

Thr Ser Lys Cys Gly Ser Leu Gly Asn Ile His His Lys Pro Gly Gly
65                  70                  75                  80

Gly Gln Val Glu Val Lys Ser Glu Lys Leu Asp Phe Lys Asp Arg Val
                85                  90                  95

Gln Ser Lys Ile Gly Ser Leu Asp Asn Ile Thr His Val Pro Gly Gly
            100                 105                 110

Gly Asn

<210> SEQ ID NO 58
<211> LENGTH: 94
<212> TYPE: PRT
<213> ORGANISM: Artificial Sequence
<220> FEATURE:
<223> OTHER INFORMATION: recombinant truncated Tau protein

<400> SEQUENCE: 58

```
Val Gln Ile Ile Asn Lys Lys Leu Asp Leu Ser Asn Val Gln Ser Lys
1               5                   10                  15

Cys Gly Ser Lys Asp Asn Ile Lys His Val Pro Gly Gly Gly Ser Val
            20                  25                  30

Gln Ile Val Tyr Lys Pro Val Asp Leu Ser Lys Val Thr Ser Lys Cys
        35                  40                  45

Gly Ser Leu Gly Asn Ile His His Lys Pro Gly Gly Gly Gln Val Glu
    50                  55                  60

Val Lys Ser Glu Lys Leu Asp Phe Lys Asp Arg Val Gln Ser Lys Ile
65                  70                  75                  80

Gly Ser Leu Asp Asn Ile Thr His Val Pro Gly Gly Gly Asn
            85                  90
```

<210> SEQ ID NO 59
<211> LENGTH: 114
<212> TYPE: PRT
<213> ORGANISM: Artificial Sequence
<220> FEATURE:
<223> OTHER INFORMATION: recombinant truncated Tau protein

<400> SEQUENCE: 59

```
Met Gly Ser Ser His His His His Ser Ser Gly Leu Val Pro
1               5                   10                  15

Arg Gly Ser His Val Gln Ile Ile Asn Lys Lys Leu Asp Leu Ser Asn
            20                  25                  30

Val Gln Ser Lys Ser Gly Ser Lys Asp Asn Ile Lys His Val Pro Gly
        35                  40                  45

Gly Gly Ser Val Gln Ile Val Tyr Lys Pro Val Asp Leu Ser Lys Val
    50                  55                  60

Thr Ser Lys Ser Gly Ser Leu Gly Asn Ile His His Lys Pro Gly Gly
65                  70                  75                  80

Gly Gln Val Glu Val Lys Ser Glu Lys Leu Asp Phe Lys Asp Arg Val
            85                  90                  95

Gln Ser Lys Ile Gly Ser Leu Asp Asn Ile Thr His Val Pro Gly Gly
            100                 105                 110

Gly Asn
```

<210> SEQ ID NO 60
<211> LENGTH: 94
<212> TYPE: PRT
<213> ORGANISM: Artificial Sequence
<220> FEATURE:
<223> OTHER INFORMATION: recombinant truncated Tau protein

<400> SEQUENCE: 60

```
Val Gln Ile Ile Asn Lys Lys Leu Asp Leu Ser Asn Val Gln Ser Lys
1               5                   10                  15

Ser Gly Ser Lys Asp Asn Ile Lys His Val Pro Gly Gly Gly Ser Val
            20                  25                  30

Gln Ile Val Tyr Lys Pro Val Asp Leu Ser Lys Val Thr Ser Lys Ser
        35                  40                  45

Gly Ser Leu Gly Asn Ile His His Lys Pro Gly Gly Gly Gln Val Glu
    50                  55                  60

Val Lys Ser Glu Lys Leu Asp Phe Lys Asp Arg Val Gln Ser Lys Ile
```

```
                65                  70                  75                  80
Gly Ser Leu Asp Asn Ile Thr His Val Pro Gly Gly Gly Asn
                    85                  90
```

<210> SEQ ID NO 61
<211> LENGTH: 86
<212> TYPE: PRT
<213> ORGANISM: Artificial Sequence
<220> FEATURE:
<223> OTHER INFORMATION: recombinant truncated Tau protein

<400> SEQUENCE: 61

```
Met Gly Ser Ser His His His His His Ser Ser Gly Leu Val Pro
1               5                   10                  15

Arg Gly Ser His Gln Thr Ala Pro Val Pro Met Pro Asp Leu Lys Asn
                20                  25                  30

Val Lys Ser Lys Ile Gly Ser Thr Glu Asn Leu Lys His Gln Pro Gly
            35                  40                  45

Gly Gly Lys Val Gln Ile Lys Asp Arg Val Gln Ser Lys Ile Gly Ser
        50                  55                  60

Leu Asp Asn Ile Thr His Val Pro Gly Gly Gly Asn Lys Lys Ile Glu
65                  70                  75                  80

Thr His Lys Leu Thr Phe
                85
```

<210> SEQ ID NO 62
<211> LENGTH: 66
<212> TYPE: PRT
<213> ORGANISM: Artificial Sequence
<220> FEATURE:
<223> OTHER INFORMATION: recombinant truncated Tau protein

<400> SEQUENCE: 62

```
Gln Thr Ala Pro Val Pro Met Pro Asp Leu Lys Asn Val Lys Ser Lys
1               5                   10                  15

Ile Gly Ser Thr Glu Asn Leu Lys His Gln Pro Gly Gly Gly Lys Val
                20                  25                  30

Gln Ile Lys Asp Arg Val Gln Ser Lys Ile Gly Ser Leu Asp Asn Ile
            35                  40                  45

Thr His Val Pro Gly Gly Gly Asn Lys Lys Ile Glu Thr His Lys Leu
        50                  55                  60

Thr Phe
65
```

<210> SEQ ID NO 63
<211> LENGTH: 51
<212> TYPE: PRT
<213> ORGANISM: Artificial Sequence
<220> FEATURE:
<223> OTHER INFORMATION: recombinant truncated Tau protein

<400> SEQUENCE: 63

```
Met Gly Ser Ser His His His His His Ser Ser Gly Leu Val Pro
1               5                   10                  15

Arg Gly Ser His Gln Thr Ala Pro Val Pro Met Pro Asp Leu Lys Asn
                20                  25                  30

Val Lys Ser Lys Ile Gly Ser Thr Glu Asn Leu Lys His Gln Pro Gly
            35                  40                  45

Gly Gly Lys
        50
```

<210> SEQ ID NO 64
<211> LENGTH: 31
<212> TYPE: PRT
<213> ORGANISM: Artificial Sequence
<220> FEATURE:
<223> OTHER INFORMATION: recombinant truncated Tau protein

<400> SEQUENCE: 64

Gln Thr Ala Pro Val Pro Met Pro Asp Leu Lys Asn Val Lys Ser Lys
1               5                   10                  15

Ile Gly Ser Thr Glu Asn Leu Lys His Gln Pro Gly Gly Gly Lys
            20                  25                  30

<210> SEQ ID NO 65
<211> LENGTH: 51
<212> TYPE: PRT
<213> ORGANISM: Artificial Sequence
<220> FEATURE:
<223> OTHER INFORMATION: recombinant truncated Tau protein

<400> SEQUENCE: 65

Met Gly Ser Ser His His His His His His Ser Ser Gly Leu Val Pro
1               5                   10                  15

Arg Gly Ser His Val Gln Ile Ile Asn Lys Lys Leu Asp Leu Ser Asn
            20                  25                  30

Val Gln Ser Lys Cys Gly Ser Lys Asp Asn Ile Lys His Val Pro Gly
        35                  40                  45

Gly Gly Ser
    50

<210> SEQ ID NO 66
<211> LENGTH: 31
<212> TYPE: PRT
<213> ORGANISM: Artificial Sequence
<220> FEATURE:
<223> OTHER INFORMATION: recombinant truncated Tau protein

<400> SEQUENCE: 66

Val Gln Ile Ile Asn Lys Lys Leu Asp Leu Ser Asn Val Gln Ser Lys
1               5                   10                  15

Cys Gly Ser Lys Asp Asn Ile Lys His Val Pro Gly Gly Gly Ser
            20                  25                  30

<210> SEQ ID NO 67
<211> LENGTH: 51
<212> TYPE: PRT
<213> ORGANISM: Artificial Sequence
<220> FEATURE:
<223> OTHER INFORMATION: recombinant truncated Tau protein

<400> SEQUENCE: 67

Met Gly Ser Ser His His His His His His Ser Ser Gly Leu Val Pro
1               5                   10                  15

Arg Gly Ser His Val Gln Ile Ile Asn Lys Lys Leu Asp Leu Ser Asn
            20                  25                  30

Val Gln Ser Lys Ser Gly Ser Lys Asp Asn Ile Lys His Val Pro Gly
        35                  40                  45

Gly Gly Ser
    50

<210> SEQ ID NO 68

```
<211> LENGTH: 31
<212> TYPE: PRT
<213> ORGANISM: Artificial Sequence
<220> FEATURE:
<223> OTHER INFORMATION: recombinant truncated Tau protein

<400> SEQUENCE: 68

Val Gln Ile Ile Asn Lys Lys Leu Asp Leu Ser Asn Val Gln Ser Lys
1               5                   10                  15

Ser Gly Ser Lys Asp Asn Ile Lys His Val Pro Gly Gly Gly Ser
            20                  25                  30

<210> SEQ ID NO 69
<211> LENGTH: 51
<212> TYPE: PRT
<213> ORGANISM: Artificial Sequence
<220> FEATURE:
<223> OTHER INFORMATION: recombinant truncated Tau protein

<400> SEQUENCE: 69

Met Gly Ser Ser His His His His His His Ser Gly Leu Val Pro
1               5                   10                  15

Arg Gly Ser His Val Gln Ile Val Tyr Lys Pro Val Asp Leu Ser Lys
            20                  25                  30

Val Thr Ser Lys Cys Gly Ser Leu Gly Asn Ile His His Lys Pro Gly
        35                  40                  45

Gly Gly Gln
    50

<210> SEQ ID NO 70
<211> LENGTH: 31
<212> TYPE: PRT
<213> ORGANISM: Artificial Sequence
<220> FEATURE:
<223> OTHER INFORMATION: recombinant truncated Tau protein

<400> SEQUENCE: 70

Val Gln Ile Val Tyr Lys Pro Val Asp Leu Ser Lys Val Thr Ser Lys
1               5                   10                  15

Cys Gly Ser Leu Gly Asn Ile His His Lys Pro Gly Gly Gly Gln
            20                  25                  30

<210> SEQ ID NO 71
<211> LENGTH: 51
<212> TYPE: PRT
<213> ORGANISM: Artificial Sequence
<220> FEATURE:
<223> OTHER INFORMATION: recombinant truncated Tau protein

<400> SEQUENCE: 71

Met Gly Ser Ser His His His His His His Ser Gly Leu Val Pro
1               5                   10                  15

Arg Gly Ser His Val Gln Ile Val Tyr Lys Pro Val Asp Leu Ser Lys
            20                  25                  30

Val Thr Ser Lys Ser Gly Ser Leu Gly Asn Ile His His Lys Pro Gly
        35                  40                  45

Gly Gly Gln
    50

<210> SEQ ID NO 72
<211> LENGTH: 31
<212> TYPE: PRT
<213> ORGANISM: Artificial Sequence
```

<220> FEATURE:
<223> OTHER INFORMATION: recombinant truncated Tau protein

<400> SEQUENCE: 72

Val Gln Ile Val Tyr Lys Pro Val Asp Leu Ser Lys Val Thr Ser Lys
1               5                   10                  15

Ser Gly Ser Leu Gly Asn Ile His His Lys Pro Gly Gly Gly Gln
            20                  25                  30

<210> SEQ ID NO 73
<211> LENGTH: 52
<212> TYPE: PRT
<213> ORGANISM: Artificial Sequence
<220> FEATURE:
<223> OTHER INFORMATION: recombinant truncated Tau protein

<400> SEQUENCE: 73

Met Gly Ser Ser His His His His His His Ser Ser Gly Leu Val Pro
1               5                   10                  15

Arg Gly Ser His Val Glu Val Lys Ser Glu Lys Leu Asp Phe Lys Asp
            20                  25                  30

Arg Val Gln Ser Lys Ile Gly Ser Leu Asp Asn Ile Thr His Val Pro
        35                  40                  45

Gly Gly Gly Asn
    50

<210> SEQ ID NO 74
<211> LENGTH: 32
<212> TYPE: PRT
<213> ORGANISM: Artificial Sequence
<220> FEATURE:
<223> OTHER INFORMATION: recombinant truncated Tau protein

<400> SEQUENCE: 74

Val Glu Val Lys Ser Glu Lys Leu Asp Phe Lys Asp Arg Val Gln Ser
1               5                   10                  15

Lys Ile Gly Ser Leu Asp Asn Ile Thr His Val Pro Gly Gly Gly Asn
            20                  25                  30

<210> SEQ ID NO 75
<211> LENGTH: 62
<212> TYPE: PRT
<213> ORGANISM: Artificial Sequence
<220> FEATURE:
<223> OTHER INFORMATION: recombinant truncated Tau protein

<400> SEQUENCE: 75

Met Gly Ser Ser His His His His His His Ser Ser Gly Leu Val Pro
1               5                   10                  15

Arg Gly Ser His Val Glu Val Lys Ser Glu Lys Leu Asp Phe Lys Asp
            20                  25                  30

Arg Val Gln Ser Lys Ile Gly Ser Leu Asp Asn Ile Thr His Val Pro
        35                  40                  45

Gly Gly Gly Asn Lys Lys Ile Glu Thr His Lys Leu Thr Phe
    50                  55                  60

<210> SEQ ID NO 76
<211> LENGTH: 42
<212> TYPE: PRT
<213> ORGANISM: Artificial Sequence
<220> FEATURE:
<223> OTHER INFORMATION: recombinant truncated Tau protein

```
-continued

<400> SEQUENCE: 76

Val Glu Val Lys Ser Glu Lys Leu Asp Phe Lys Asp Arg Val Gln Ser
1               5                   10                  15

Lys Ile Gly Ser Leu Asp Asn Ile Thr His Val Pro Gly Gly Gly Asn
            20                  25                  30

Lys Lys Ile Glu Thr His Lys Leu Thr Phe
        35                  40

<210> SEQ ID NO 77
<211> LENGTH: 6
<212> TYPE: PRT
<213> ORGANISM: Artificial Sequence
<220> FEATURE:
<223> OTHER INFORMATION: Tau 373-378 with N-Terminal Acetylation and
      C-Terminal Amidation

<400> SEQUENCE: 77

Thr His Lys Leu Thr Phe
1               5

<210> SEQ ID NO 78
<211> LENGTH: 11
<212> TYPE: PRT
<213> ORGANISM: Artificial Sequence
<220> FEATURE:
<223> OTHER INFORMATION: Tau 368-378 with N-Terminal Acetylation and
      C-Terminal Amidation

<400> SEQUENCE: 78

Asn Lys Lys Ile Glu Thr His Lys Leu Thr Phe
1               5                   10

<210> SEQ ID NO 79
<211> LENGTH: 15
<212> TYPE: PRT
<213> ORGANISM: Artificial Sequence
<220> FEATURE:
<223> OTHER INFORMATION: Tau 354-369

<400> SEQUENCE: 79

Ile Gly Ser Leu Asp Asn Ile Thr His Val Pro Gly Gly Asn Lys
1               5                   10                  15

<210> SEQ ID NO 80
<211> LENGTH: 124
<212> TYPE: PRT
<213> ORGANISM: Artificial Sequence
<220> FEATURE:
<223> OTHER INFORMATION: recombinant truncated Tau protein

<400> SEQUENCE: 80

Met Gly Ser Ser His His His His His His Ser Gly Leu Val Pro
1               5                   10                  15

Arg Gly Ser His Val Gln Ile Ile Asn Lys Lys Leu Asp Leu Ser Asn
            20                  25                  30

Val Gln Ser Lys Cys Gly Ser Lys Asp Asn Ile Lys His Val Pro Gly
        35                  40                  45

Gly Gly Ser Val Gln Ile Val Tyr Lys Pro Val Asp Leu Ser Lys Val
    50                  55                  60

Thr Ser Lys Cys Gly Ser Leu Gly Asn Ile His His Lys Pro Gly Gly
65                  70                  75                  80

Gly Gln Val Glu Val Lys Ser Glu Lys Leu Asp Phe Lys Asp Arg Val
                85                  90                  95
```

Gln Ser Lys Ile Gly Ser Leu Asp Asn Ile Thr His Val Pro Gly Gly
            100                 105                 110

Gly Asn Lys Lys Ile Glu Thr His Lys Leu Thr Phe
            115                 120

<210> SEQ ID NO 81
<211> LENGTH: 104
<212> TYPE: PRT
<213> ORGANISM: Artificial Sequence
<220> FEATURE:
<223> OTHER INFORMATION: recombinant truncated Tau protein

<400> SEQUENCE: 81

Val Gln Ile Ile Asn Lys Lys Leu Asp Leu Ser Asn Val Gln Ser Lys
1               5                   10                  15

Cys Gly Ser Lys Asp Asn Ile Lys His Val Pro Gly Gly Gly Ser Val
            20                  25                  30

Gln Ile Val Tyr Lys Pro Val Asp Leu Ser Lys Val Thr Ser Lys Cys
            35                  40                  45

Gly Ser Leu Gly Asn Ile His His Lys Pro Gly Gly Gly Gln Val Glu
        50                  55                  60

Val Lys Ser Glu Lys Leu Asp Phe Lys Asp Arg Val Gln Ser Lys Ile
65                  70                  75                  80

Gly Ser Leu Asp Asn Ile Thr His Val Pro Gly Gly Gly Asn Lys Lys
                85                  90                  95

Ile Glu Thr His Lys Leu Thr Phe
            100

<210> SEQ ID NO 82
<211> LENGTH: 124
<212> TYPE: PRT
<213> ORGANISM: Artificial Sequence
<220> FEATURE:
<223> OTHER INFORMATION: recombinant truncated Tau protein

<400> SEQUENCE: 82

Met Gly Ser Ser His His His His His His Ser Ser Gly Leu Val Pro
1               5                   10                  15

Arg Gly Ser His Val Gln Ile Ile Asn Lys Lys Leu Asp Leu Ser Asn
            20                  25                  30

Val Gln Ser Lys Ser Gly Ser Lys Asp Asn Ile Lys His Val Pro Gly
        35                  40                  45

Gly Gly Ser Val Gln Ile Val Tyr Lys Pro Val Asp Leu Ser Lys Val
    50                  55                  60

Thr Ser Lys Ser Gly Ser Leu Gly Asn Ile His His Lys Pro Gly Gly
65                  70                  75                  80

Gly Gln Val Glu Val Lys Ser Glu Lys Leu Asp Phe Lys Asp Arg Val
                85                  90                  95

Gln Ser Lys Ile Gly Ser Leu Asp Asn Ile Thr His Val Pro Gly Gly
            100                 105                 110

Gly Asn Lys Lys Ile Glu Thr His Lys Leu Thr Phe
            115                 120

<210> SEQ ID NO 83
<211> LENGTH: 104
<212> TYPE: PRT
<213> ORGANISM: Artificial Sequence
<220> FEATURE:
<223> OTHER INFORMATION: recombinant truncated Tau protein

<400> SEQUENCE: 83

Val Gln Ile Ile Asn Lys Lys Leu Asp Leu Ser Asn Val Gln Ser Lys
1               5                   10                  15

Ser Gly Ser Lys Asp Asn Ile Lys His Val Pro Gly Gly Gly Ser Val
            20                  25                  30

Gln Ile Val Tyr Lys Pro Val Asp Leu Ser Lys Val Thr Ser Lys Ser
        35                  40                  45

Gly Ser Leu Gly Asn Ile His His Lys Pro Gly Gly Gly Gln Val Glu
    50                  55                  60

Val Lys Ser Glu Lys Leu Asp Phe Lys Asp Arg Val Gln Ser Lys Ile
65                  70                  75                  80

Gly Ser Leu Asp Asn Ile Thr His Val Pro Gly Gly Gly Asn Lys Lys
                85                  90                  95

Ile Glu Thr His Lys Leu Thr Phe
            100

<210> SEQ ID NO 84
<211> LENGTH: 61
<212> TYPE: PRT
<213> ORGANISM: Artificial Sequence
<220> FEATURE:
<223> OTHER INFORMATION: recombinant truncated Tau protein

<400> SEQUENCE: 84

Met Gly Ser Ser His His His His His His Ser Ser Gly Leu Val Pro
1               5                   10                  15

Arg Gly Ser His Val Gln Ile Val Tyr Lys Pro Val Asp Leu Ser Lys
            20                  25                  30

Val Thr Ser Lys Cys Gly Ser Leu Gly Asn Ile His His Lys Pro Gly
        35                  40                  45

Gly Gly Gln Val Glu Val Lys Ser Glu Lys Leu Asp Phe
    50                  55                  60

<210> SEQ ID NO 85
<211> LENGTH: 41
<212> TYPE: PRT
<213> ORGANISM: Artificial Sequence
<220> FEATURE:
<223> OTHER INFORMATION: recombinant truncated Tau protein

<400> SEQUENCE: 85

Val Gln Ile Val Tyr Lys Pro Val Asp Leu Ser Lys Val Thr Ser Lys
1               5                   10                  15

Cys Gly Ser Leu Gly Asn Ile His His Lys Pro Gly Gly Gly Gln Val
            20                  25                  30

Glu Val Lys Ser Glu Lys Leu Asp Phe
        35                  40

<210> SEQ ID NO 86
<211> LENGTH: 61
<212> TYPE: PRT
<213> ORGANISM: Artificial Sequence
<220> FEATURE:
<223> OTHER INFORMATION: recombinant truncated Tau protein

<400> SEQUENCE: 86

Met Gly Ser Ser His His His His His His Ser Ser Gly Leu Val Pro
1               5                   10                  15

Arg Gly Ser His Val Gln Ile Val Tyr Lys Pro Val Asp Leu Ser Lys

```
            20                  25                  30

Val Thr Ser Lys Ser Gly Ser Leu Gly Asn Ile His His Lys Pro Gly
        35                  40                  45

Gly Gly Gln Val Glu Val Lys Ser Glu Lys Leu Asp Phe
    50                  55                  60

<210> SEQ ID NO 87
<211> LENGTH: 41
<212> TYPE: PRT
<213> ORGANISM: Artificial Sequence
<220> FEATURE:
<223> OTHER INFORMATION: recombinant truncated Tau protein

<400> SEQUENCE: 87

Val Gln Ile Val Tyr Lys Pro Val Asp Leu Ser Lys Val Thr Ser Lys
1               5                   10                  15

Ser Gly Ser Leu Gly Asn Ile His His Lys Pro Gly Gly Gly Gln Val
            20                  25                  30

Glu Val Lys Ser Glu Lys Leu Asp Phe
        35                  40

<210> SEQ ID NO 88
<211> LENGTH: 31
<212> TYPE: PRT
<213> ORGANISM: Homo sapiens

<400> SEQUENCE: 88

Gln Thr Ala Pro Val Pro Met Pro Asp Leu Lys Asn Val Lys Ser Lys
1               5                   10                  15

Ile Gly Ser Thr Glu Asn Leu Lys His Gln Pro Gly Gly Gly Lys
            20                  25                  30

<210> SEQ ID NO 89
<211> LENGTH: 31
<212> TYPE: PRT
<213> ORGANISM: Homo sapiens

<400> SEQUENCE: 89

Val Gln Ile Ile Asn Lys Lys Leu Asp Leu Ser Asn Val Gln Ser Lys
1               5                   10                  15

Cys Gly Ser Lys Asp Asn Ile Lys His Val Pro Gly Gly Gly Ser
            20                  25                  30

<210> SEQ ID NO 90
<211> LENGTH: 31
<212> TYPE: PRT
<213> ORGANISM: Homo sapiens

<400> SEQUENCE: 90

Val Gln Ile Val Tyr Lys Pro Val Asp Leu Ser Lys Val Thr Ser Lys
1               5                   10                  15

Cys Gly Ser Leu Gly Asn Ile His His Lys Pro Gly Gly Gly Gln
            20                  25                  30

<210> SEQ ID NO 91
<211> LENGTH: 32
<212> TYPE: PRT
<213> ORGANISM: Homo sapiens

<400> SEQUENCE: 91

Val Glu Val Lys Ser Glu Lys Leu Asp Phe Lys Asp Arg Val Gln Ser
1               5                   10                  15
```

```
Lys Ile Gly Ser Leu Asp Asn Ile Thr His Val Pro Gly Gly Gly Asn
            20                  25                  30
```

<210> SEQ ID NO 92
<211> LENGTH: 93
<212> TYPE: PRT
<213> ORGANISM: Artificial Sequence
<220> FEATURE:
<223> OTHER INFORMATION: recombinant truncated Tau protein

<400> SEQUENCE: 92

```
Met Gly Ser Ser His His His His His His Ser Gly Leu Val Pro
1               5                   10                  15

Arg Gly Ser His Val Gln Ile Val Tyr Lys Pro Val Asp Leu Ser Lys
            20                  25                  30

Val Thr Ser Lys Cys Gly Ser Leu Gly Asn Ile His His Lys Pro Gly
            35                  40                  45

Gly Gly Gln Val Glu Val Lys Ser Glu Lys Leu Asp Phe Lys Asp Arg
        50                  55                  60

Val Gln Ser Lys Ile Gly Ser Leu Asp Asn Ile Thr His Val Pro Gly
65                  70                  75                  80

Gly Gly Asn Lys Lys Ile Glu Thr His Lys Leu Thr Phe
                85                  90
```

<210> SEQ ID NO 93
<211> LENGTH: 73
<212> TYPE: PRT
<213> ORGANISM: Artificial Sequence
<220> FEATURE:
<223> OTHER INFORMATION: recombinant truncated Tau protein

<400> SEQUENCE: 93

```
Val Gln Ile Val Tyr Lys Pro Val Asp Leu Ser Lys Val Thr Ser Lys
1               5                   10                  15

Cys Gly Ser Leu Gly Asn Ile His His Lys Pro Gly Gly Gly Gln Val
            20                  25                  30

Glu Val Lys Ser Glu Lys Leu Asp Phe Lys Asp Arg Val Gln Ser Lys
            35                  40                  45

Ile Gly Ser Leu Asp Asn Ile Thr His Val Pro Gly Gly Gly Asn Lys
        50                  55                  60

Lys Ile Glu Thr His Lys Leu Thr Phe
65                  70
```

<210> SEQ ID NO 94
<211> LENGTH: 4
<212> TYPE: PRT
<213> ORGANISM: Artificial Sequence
<220> FEATURE:
<223> OTHER INFORMATION: Leader amino acid sequence

<400> SEQUENCE: 94

```
Met Gly Ser Ser
1
```